United States Patent
Mueller et al.

(10) Patent No.: US 12,098,192 B2
(45) Date of Patent: *Sep. 24, 2024

(54) COMPOSITION AND METHOD FOR THE DIAGNOSIS AND TREATMENT OF IRON-RELATED DISORDERS

(71) Applicants: AbbVie Deutschland GmbH & Co. KG, Wiesbaden (DE); AbbVie Inc., North Chicago, IL (US)

(72) Inventors: Bernhard Mueller, Ludwigshafen (DE); Andreas Popp, Ludwigshafen (DE); Jennifer M. Perez, North Chicago, IL (US)

(73) Assignees: AbbVie Deutschland Gmbh & Co. KG, Wiesbaden (DE); AbbVie Inc., North Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/638,307

(22) Filed: Apr. 17, 2024

(65) Prior Publication Data

US 2024/0262901 A1    Aug. 8, 2024

Related U.S. Application Data

(63) Continuation of application No. 17/034,454, filed on Sep. 28, 2020, which is a continuation of application No. 16/179,515, filed on Nov. 2, 2018, now Pat. No. 10,822,403, which is a continuation of application No. 13/714,238, filed on Dec. 13, 2012, now Pat. No. 10,118,958.

(60) Provisional application No. 61/570,715, filed on Dec. 14, 2011.

(51) Int. Cl.
  *C07K 16/28* (2006.01)
  *C07K 16/18* (2006.01)
  *G01N 33/566* (2006.01)
  *A61K 39/00* (2006.01)

(52) U.S. Cl.
  CPC ............ *C07K 16/18* (2013.01); *C07K 16/28* (2013.01); *G01N 33/566* (2013.01); *A61K 2039/505* (2013.01); *C07K 2317/24* (2013.01); *C07K 2317/565* (2013.01); *C07K 2317/92* (2013.01)

(58) Field of Classification Search
  None
  See application file for complete search history.

(56) References Cited

U.S. PATENT DOCUMENTS

| | | |
|---|---|---|
| 4,526,938 A | 7/1985 | Churchill et al. |
| 4,554,101 A | 11/1985 | Hopp |
| 4,704,692 A | 11/1987 | Ladner |
| 4,816,567 A | 3/1989 | Cabilly et al. |
| 4,873,316 A | 10/1989 | Meade et al. |
| 4,880,078 A | 11/1989 | Inoue et al. |
| 4,946,778 A | 8/1990 | Ladner et al. |
| 4,980,286 A | 12/1990 | Morgan et al. |
| 5,006,309 A | 4/1991 | Khalil et al. |
| 5,063,081 A | 11/1991 | Cozzette et al. |
| 5,089,424 A | 2/1992 | Khalil et al. |
| 5,128,326 A | 7/1992 | Balazs et al. |
| 5,135,875 A | 8/1992 | Meucci et al. |
| 5,223,409 A | 6/1993 | Ladner et al. |
| 5,225,539 A | 7/1993 | Winter |
| 5,241,070 A | 8/1993 | Law |
| 5,258,498 A | 11/1993 | Huston et al. |
| 5,290,540 A | 3/1994 | Prince et al. |
| 5,294,404 A | 3/1994 | Grandone et al. |
| 5,304,489 A | 4/1994 | Rosen |
| 5,352,803 A | 10/1994 | Mattingly |
| 5,359,093 A | 10/1994 | Adamczyk et al. |
| 5,403,484 A | 4/1995 | Ladner et al. |
| 5,427,908 A | 6/1995 | Dower et al. |
| 5,468,646 A | 11/1995 | Mattingly et al. |
| 5,480,792 A | 1/1996 | Buechler et al. |
| 5,496,925 A | 3/1996 | Mattingly |
| 5,516,637 A | 5/1996 | Huang et al. |
| 5,525,524 A | 6/1996 | Buechler et al. |
| 5,530,101 A | 6/1996 | Queen et al. |
| 5,543,524 A | 8/1996 | Mattingly et al. |
| 5,565,362 A | 10/1996 | Rosen |
| 5,571,698 A | 11/1996 | Ladner et al. |
| 5,573,904 A | 11/1996 | Mattingly |
| 5,580,717 A | 12/1996 | Dower et al. |
| 5,585,089 A | 12/1996 | Queen et al. |
| 5,593,896 A | 1/1997 | Adamczyk et al. |
| 5,627,052 A | 5/1997 | Schrader |
| 5,658,727 A | 8/1997 | Barbas et al. |
| 5,679,377 A | 10/1997 | Bernstein et al. |
| 5,679,526 A | 10/1997 | Buechler et al. |
| 5,693,762 A | 12/1997 | Queen et al. |
| 5,698,426 A | 12/1997 | Huse |
| 5,714,352 A | 2/1998 | Jakobobits et al. |

(Continued)

FOREIGN PATENT DOCUMENTS

| | | |
|---|---|---|
| CN | 1484652 A | 3/2004 |
| CN | 101778864 A | 7/2010 |

(Continued)

OTHER PUBLICATIONS

U.S. Appl. No. 13/714,238, filed Dec. 13, 2012.

(Continued)

*Primary Examiner* — Zachary S Skelding
(74) *Attorney, Agent, or Firm* — Neal, Gerber & Eisenberg LLP

(57) ABSTRACT

Provided herein are methods of using the antibodies that bind to RGMc to treat and diagnose iron-related disorders.

20 Claims, 21 Drawing Sheets

Specification includes a Sequence Listing.

(56) References Cited

U.S. PATENT DOCUMENTS

| | | | |
|---|---|---|---|
| 5,723,323 | A | 3/1998 | Kauffman et al. |
| 5,733,743 | A | 3/1998 | Johnson et al. |
| 5,750,753 | A | 5/1998 | Kimae et al. |
| 5,763,192 | A | 6/1998 | Kauffman et al. |
| 5,766,886 | A | 6/1998 | Studnicka et al. |
| 5,770,429 | A | 6/1998 | Lonberg et al. |
| 5,780,225 | A | 7/1998 | Wigler et al. |
| 5,783,699 | A | 7/1998 | Mattingly et al. |
| 5,814,476 | A | 9/1998 | Kauffman et al. |
| 5,817,483 | A | 10/1998 | Kauffman et al. |
| 5,821,047 | A | 10/1998 | Garrard et al. |
| 5,824,514 | A | 10/1998 | Kauffman et al. |
| 5,824,799 | A | 10/1998 | Buechler et al. |
| 5,827,690 | A | 10/1998 | Meade et al. |
| 5,833,985 | A | 11/1998 | Ball et al. |
| 5,837,243 | A | 11/1998 | Deo et al. |
| 5,849,992 | A | 12/1998 | Meade et al. |
| 5,851,776 | A | 12/1998 | Valkirs |
| 5,855,913 | A | 1/1999 | Hanes et al. |
| 5,874,064 | A | 2/1999 | Edwards et al. |
| 5,885,527 | A | 3/1999 | Buechler |
| 5,912,015 | A | 6/1999 | Bernstein et al. |
| 5,916,597 | A | 6/1999 | Lee et al. |
| 5,916,771 | A | 6/1999 | Hori et al. |
| 5,922,615 | A | 7/1999 | Nowakowski et al. |
| 5,922,845 | A | 7/1999 | Deo et al. |
| 5,934,272 | A | 8/1999 | Lloyd et al. |
| 5,939,272 | A | 8/1999 | Buechler et al. |
| 5,939,598 | A | 8/1999 | Kucherlapati et al. |
| 5,947,124 | A | 9/1999 | Buechler et al. |
| 5,969,108 | A | 10/1999 | Mccafferty et al. |
| 5,976,862 | A | 11/1999 | Kauffman et al. |
| 5,985,309 | A | 11/1999 | Edwards et al. |
| 5,985,320 | A | 11/1999 | Edwards et al. |
| 5,985,579 | A | 11/1999 | Buechler et al. |
| 5,985,615 | A | 11/1999 | Jakobovits et al. |
| 5,989,463 | A | 11/1999 | Tracy et al. |
| 5,994,616 | A | 11/1999 | Rosen |
| 5,998,209 | A | 12/1999 | Jokobovits et al. |
| 6,017,517 | A | 1/2000 | Park |
| 6,019,944 | A | 2/2000 | Buechler |
| 6,019,968 | A | 2/2000 | Platz et al. |
| 6,075,181 | A | 6/2000 | Kucherlapati et al. |
| 6,091,001 | A | 7/2000 | Jakobovits et al. |
| 6,096,311 | A | 8/2000 | Fanger et al. |
| 6,111,166 | A | 8/2000 | van de Winkel |
| 6,113,855 | A | 9/2000 | Buechler |
| 6,114,598 | A | 9/2000 | Kucherlapati et al. |
| 6,130,364 | A | 10/2000 | Jakobovits et al. |
| 6,143,576 | A | 11/2000 | Buechler |
| 6,180,370 | B1 | 1/2001 | Queen et al. |
| 6,204,023 | B1 | 3/2001 | Robinson et al. |
| 6,270,765 | B1 | 8/2001 | Deo et al. |
| 6,303,755 | B1 | 10/2001 | Deo et al. |
| 6,365,116 | B1 | 4/2002 | Barham et al. |
| 6,410,690 | B1 | 6/2002 | Deo et al. |
| 6,632,926 | B1 | 10/2003 | Chen et al. |
| 6,660,843 | B1 | 12/2003 | Feige et al. |
| 6,682,928 | B2 | 1/2004 | Keler et al. |
| 6,699,658 | B1 | 3/2004 | Wittrup et al. |
| 6,890,763 | B2 | 5/2005 | Jackowski et al. |
| 6,914,128 | B1 | 7/2005 | Salfeld et al. |
| 6,925,389 | B2 | 8/2005 | Hitt et al. |
| 6,984,720 | B1 | 1/2006 | Korman et al. |
| 6,989,100 | B2 | 1/2006 | Norton |
| 7,612,181 | B2 | 11/2009 | Wu et al. |
| 7,906,293 | B2 | 3/2011 | Mattingly et al. |
| 8,445,199 | B2 | 5/2013 | Collier et al. |
| 2003/0170881 | A1 | 9/2003 | Davis et al. |
| 2003/0186374 | A1 | 10/2003 | Hufton et al. |
| 2004/0018577 | A1 | 1/2004 | Emerson et al. |
| 2005/0042664 | A1 | 2/2005 | Wu et al. |
| 2005/0054078 | A1 | 3/2005 | Miller et al. |
| 2006/0104968 | A1 | 5/2006 | Bookbinder et al. |
| 2006/0160164 | A1 | 7/2006 | Miller et al. |
| 2007/0004618 | A1 | 1/2007 | Ganz et al. |
| 2008/0020401 | A1 | 1/2008 | Grenier et al. |
| 2010/0028340 | A1 | 2/2010 | Mueller et al. |
| 2011/0085973 | A1 | 4/2011 | Kao et al. |
| 2011/0135664 | A1 | 6/2011 | Mueller et al. |
| 2011/0293526 | A1 | 12/2011 | Plikus et al. |
| 2022/0372135 | A1 | 11/2022 | Quisel et al. |
| 2022/0372136 | A1 | 11/2022 | Quisel et al. |
| 2023/0174645 | A1 | 6/2023 | Beconi et al. |
| 2023/0183339 | A1 | 6/2023 | Beconi et al. |

FOREIGN PATENT DOCUMENTS

| | | | |
|---|---|---|---|
| EP | 0404097 | A2 | 12/1990 |
| EP | 0471293 | A2 | 2/1992 |
| WO | WO-9002809 | A1 | 3/1990 |
| WO | WO-9105548 | A1 | 5/1991 |
| WO | WO-9110737 | A1 | 7/1991 |
| WO | WO-9110741 | A1 | 7/1991 |
| WO | WO-9117271 | A1 | 11/1991 |
| WO | WO-9201047 | A1 | 1/1992 |
| WO | WO-9202551 | A1 | 2/1992 |
| WO | WO-9209690 | A2 | 6/1992 |
| WO | WO-9215679 | A1 | 9/1992 |
| WO | WO-9218619 | A1 | 10/1992 |
| WO | WO-9219244 | A2 | 11/1992 |
| WO | WO-9220791 | A1 | 11/1992 |
| WO | WO-9222324 | A1 | 12/1992 |
| WO | WO-9301288 | A1 | 1/1993 |
| WO | WO-9311161 | A1 | 6/1993 |
| WO | WO-9311236 | A1 | 6/1993 |
| WO | WO-9402602 | A1 | 2/1994 |
| WO | WO-9515982 | A2 | 6/1995 |
| WO | WO-9520401 | A1 | 8/1995 |
| WO | WO-9620698 | A2 | 7/1996 |
| WO | WO-9633735 | A1 | 10/1996 |
| WO | WO-9634096 | A1 | 10/1996 |
| WO | WO-9729131 | A1 | 8/1997 |
| WO | WO-9732572 | A2 | 9/1997 |
| WO | WO-9744013 | A1 | 11/1997 |
| WO | WO-9816654 | A1 | 4/1998 |
| WO | WO-9824893 | A2 | 6/1998 |
| WO | WO-9831346 | A1 | 7/1998 |
| WO | WO-9831700 | A1 | 7/1998 |
| WO | WO-9850433 | A2 | 11/1998 |
| WO | WO-9915154 | A1 | 4/1999 |
| WO | WO-9920253 | A1 | 4/1999 |
| WO | WO-9925044 | A1 | 5/1999 |
| WO | WO-9945031 | A2 | 9/1999 |
| WO | WO-9953049 | A1 | 10/1999 |
| WO | WO-9966903 | A2 | 12/1999 |
| WO | WO-0009560 | A2 | 2/2000 |
| WO | WO-0037504 | A2 | 6/2000 |
| WO | WO-0056772 | A1 | 9/2000 |
| WO | WO-0158956 | A2 | 8/2001 |
| WO | WO-0202773 | A2 | 1/2002 |
| WO | WO-0216436 | | 2/2002 |
| WO | WO-2004078140 | A2 | 9/2004 |
| WO | WO-2006088972 | A2 | 8/2006 |
| WO | WO-2007024715 | A2 | 3/2007 |
| WO | WO-2009030500 | A1 | 3/2009 |
| WO | WO-2007024715 | A9 | 4/2009 |
| WO | WO-2009106356 | A1 | 9/2009 |
| WO | WO-2010056981 | A2 | 5/2010 |
| WO | WO-2011070045 | A1 | 6/2011 |
| WO | WO-2012150973 | A1 | 11/2012 |
| WO | WO-2021062163 | A1 | 4/2021 |
| WO | WO-2021231798 | A1 | 11/2021 |
| WO | WO-2021231800 | A1 | 11/2021 |
| WO | WO-2023091968 | A1 | 5/2023 |
| WO | WO-2021062171 | A1 | 4/2024 |

OTHER PUBLICATIONS

U.S. Appl. No. 16/179,515, filed Nov. 2, 2018.
U.S. Appl. No. 17/034,454, filed Sep. 28, 2020.
Adamczyk M., et al., "Chemiluminescence Quenching of Pteroic Aacid-N-sulfonyl-acridinium-9-carboxamide Conjugates by Folate

(56) References Cited

OTHER PUBLICATIONS

Binding Protein," Bioorganic and Medicinal Chemistry Letters, 2004, vol. 14 (9), pp. 2313-2317.
Adamczyk M., et al., "Chemiluminescent Acridinium-9-Carboxamide Boronic Acid Probes: Application to a Homogeneous Glycated Hemoglobin Assay," Bioorganic & Medicinal Chemistry Letters, 2006, vol. 16 (5), pp. 1324-1328.
Adamczyk M., et al., "Chemiluminescent N-Sulfonylacridinium-9-Carboxamides and Their Application in Clinical Assays ," Luminescence Biotechnology: Instruments and Applications , 2002, pp. 77-105.
Adamczyk M., et al., "Homogeneous Chemiluminescent Assays for Free Choline in Human Plasma and Whole Blood ," Analytica Chimica Acta, 2006, vol. 579 (1), pp. 61-67.
Adamczyk M., et al., "Intrinsic Factor-Mediated Modulation of Cyanocobalamin-N-sulfonyl-acridinium-9-carboxamide Chemiluminescence," Bioorganic and Medicinal Chemistry Letters, 2004, vol. 14 (15), pp. 3917-3921.
Adamczyk M., et al., "Linker-Medicated Modulation of the Cheiluminescent Signal from N10-(3-Sulfopropyl)-N-Sulfonylacridinium-9-carboxamide Tracers," Bioconjugate Chemistry, 2000, vol. 11 (5), pp. 714-724.
Adamczyk M., et al., "Modulation of the Chemiluminescent Signal from N10-(3-Sulfopropyl)-N-Sulfonylacridinium-9-carboxamides ," Tetrahedron, 1999, vol. 55, pp. 10899-10914.
Adamczyk M., et al., "Neopentyl 3-Triflyloxypropanesulfaonate Areactive Sulfopropylation Reagent for the Preparation of Chemiluminescent Labels ," Journal of Organic Chemistry, 1998, vol. 63, pp. 5636-5639.
Adamczyk M., et al., "Regiodependent Luminescence Quenching of Biotinylated N-Sulfonyl-acridinium-9-carboxamides by Avidin ," Organic Letters, 2003, vol. 5 (21), pp. 3779-3782.
Adamczyk M., et al., "Synthesis of a Chemiluminescent Acridinium Hydroxylamine (AHA) for the Direct Detection of Abasic Sites in DNA," Organic Letters , 1999, vol. 1 (5), pp. 779-781.
Ames R.S., et al., "Conversion of Murine Fabs Isolated from a Combinatorial Phage Display Library to Full Length Immunoglobulins," Journal of Immunological Methods , 1995, vol. 184 (2), pp. 177-186.
Andriopoulos B. Jr., "BMP6 is a Key Endogenous Regulator of Hepcidin Expression and Iron Metabolism," Nature Genetics, 2009, vol. 41 (4), pp. 482-487.
Anonymous: "SA1170801 SEQ ID No. 17-19 HCDR1-3", XP055231665, [online], [retrieved on Nov. 26, 2015]. Retrieved from the Internet: URL:http://ibis.internal.epo.org/exam/jobResult?id=357938.
Anonymous: "SA1170801 SEQ ID No. 20-22, LDCR1-3", XP055231667, [online], [retrieved on Nov. 26, 2015]. Retrieved from the Internet: URL:http://ibis.internal.epo.org/exam/jobResult?id=357939.
Ausubel et al., Current Protocols in Molecular Biology, John Wiley &Sons, NY, 1993, Table of Contents.
Ausubel F.M., et al., eds., Current Protocols in Molecular Biology, vol. 1, Green Publishing Associates, Inc., and John Wiley & Sons, Inc., 1989, p. 6.3.1-6.3.6 and 2.10.3.
Babcook U.S., et al., "A Novel Strategy for Generating Monoclonal Antibodies from Single, Isolated Lymphocytes Producing Antibodies of Defined Specificities," Proceedings of the National Academy of Sciences, 1996, vol. 93 (15), pp. 7843-7848.
Barbas C.F., et al., "In Vitro Evolution of a Neutralizing Human Antibody to Human Immunodeficiency Virus Type 1 to Enhance Affinity and Broaden Strain Cross-Reactivity," Proceedings of the National Academy of Sciences, 1994, vol. 91 (9), pp. 3809-3813.
Barbas C.F., et al., "Assembly of Combinatorial Antibody Libraries on Phage Surfaces: The Gene III Site," Proceedings of the National Academy of Sciences, 1991, vol. 88 (18), pp. 7978-7982.
Better M., et al. "*Escherichia coli* Secretion of an Active Chimeric Antibody Fragment," Science, 1988, vol. 240 (4855), pp. 1041-1043.

Bird R.E., et al., "Single-Chain Antigen-Binding Proteins," Science, 1988, vol. 242 (4877), pp. 423-426.
Bodanszky M., et al., "Active Esters and Resins in Peptide Synthesis," Chemistry and Industry, 1966, vol. 38, pp. 1597-1598.
Boser P., et al., "Anti-Repulsive Guidance Molecule C (RGMc) Antibodies Increases Serum Iron in Rats and Cynomolgus Monkeys by Hepcidin Downregulation," The AAPS Journal, 2015, vol. 17 (4), pp. 930-938.
Brasse-Lagnel C., et al., "Immunoassay for Human Serum Hemojuvelin.," Haematologica, 2010, vol. 95 (12), pp. 2031-2037.
Brinkmann U., et al., "Phage Display of Disulfide-stabilized Fv Fragments," Journal of Immunological Methods , 1995, vol. 182 (1), pp. 41-50.
Brissot P., et al., "Current Approach to Hemochromatosis," Blood Reviews, 2008, vol. 22 (4), pp. 195-210.
Browne S.A., et al., "Potential Role of Bone Morphogenetic Protein (BMP) Signalling as a Potential Therapeutic Target for Modification of Iron Balance," Nephrol Dial Transplant, Jan. 2009, vol. 24 (1), pp. 28-30.
Buchwald H., et al., "Long-term, Continuous Intravenous Heparin Administration by an Implantable Infusion Pump in Ambulatory Patients with Recurrent Venous Thrombosis," Surgery, 1980, vol. 88 (4), pp. 507-516.
Burton D.R., et al. , "Human Antibodies from Combinatorial Libraries," Advances in Immunology, 1994, vol. 57, pp. 191-280.
Casadevall A., et al., "Immunoglobulin Isotype Influences Affinity and Specificity," Proceedings of the National Academy of Sciences, 2012, vol. 109 (31), pp. 12272-12273.
Casset, F., et al., "A Peptie Mimetic of an Anti-CD4 Monoclonal Antibody by Rational Design," Biochemical and Biophysical Research Communications, 2003, vol. 307 (1), pp. 198-205.
Chen W., et al., "A Novel Validated Enzyme-linked Immunosorbent Assay to Quantify Soluble Hemojuvelin in Mouse Serum," Haematologica, 2013, vol. 98 (2), pp. 296-304.
Cheng P.P., et al., "Hepcidin Expression in Anemia of Chronic Disease and Concomitant Iron-deficiency Anemia," Clinical and Experimental Medicine, 2011, vol. 11 (1), pp. 33-42.
Chothia C., et al., "Canonical Structures for the Hypervariable Regions of Immunoglobulins," Journal of Molecular Biology , 1987, vol. 196 (4), pp. 901-917.
Chothia C., et al., "Conformations of Immunoglobulin Hypervariable Regions," Nature, 1989, vol. 342 (6252), pp. 877-883.
Clackson T., et al., "Making Antibody Fragments Using Phage Display Libraries," Nature, 1991, vol. 352 (6336), pp. 624-628.
Cleek R.L., et al., "Biodegradable Polymeric Carriers for a bFGF Antibody for Cardiovascular Application," Proc. Intl. Symp. Control. Rel. Bioact. Mater., 1997, vol. 24, pp. 853-854.
Conrad U., et al., "Compartment-specific Accumulation of Recombinant Immunoglobulins in Plant Cells: An Essential Tool for Antibody Production and Immunomodulation of Physiological Functions and Pathogen Activity," Plant Molecular Biology, 1998, vol. 38 (1-2), pp. 101-109.
Co-pending U.S. Appl. No. 09/428,082, filed Oct. 22, 1999.
Co-pending U.S. Appl. No. 11/697,835, filed Apr. 9, 2007.
Co-pending U.S. Appl. No. 61/142,048, filed Dec. 31, 2008.
Coyne D.W., "Hepcidin: Clinical Utility as a Diagnostic Tool and Therapeutic Target," Kidney International, Aug. 2011, vol. 80 (3), pp. 240-244.
Cramer C.L., et al., "Transgenic Plants for Therapeutic Proteins: Linking Upstream and Downstream Strategies," Current Topics in Microbiology and Immunology, 1999, vol. 240, pp. 95-118.
De Pascalis R., et al., "Grafting of "Abbreviated" Complementarity-Determining Regions Containing Specificity-Determining Residues Essential for Ligand Contact to Engineer a Less Immunogenic Humanized Monoclonal Antibody," Journal of Immunological Methods, 2002, vol. 169 (6), pp. 3076-3084.
During M. J., et al., "Controlled Release of Dopamine from a Polymeric Brain Implant: In Vivo Characterization," Annals of Neurology, 1989, vol. 25 (4), pp. 351-356.
Eleftheriadis T., et al., "The Role of Hepcidin in Iron Homeostasis and Anemia in Hemodialysis Patients," Seminars in Dialysis, Feb. 2009, vol. 22 (1), pp. 70-77.

(56) References Cited

OTHER PUBLICATIONS

Eren R., et al., "Human Monoclonal Antibodies Specific to Hepatitis B Virus Generated in a Human/mouse Radiation Chimera: the Trimera System," Immunology, 1998, vol. 93 (2), pp. 154-161.
European Search Report for Application No. EP12806834, mailed on Aug. 8, 2017, 8 pages.
Fuchs P., et al., "Targeting Recombinant Antibodies to the Surface of *Escherichia coli*: Fusion to a Peptidoglycan Associated Lipoprotein," BioTechnology, 1991, vol. 9 (12), pp. 1369-1372.
Ganz T., "Hepcidin and Iron Regulation, 10 Years Later," Blood, 2011, vol. 117 (17), pp. 4425-4433.
Garrard L.J., et al., "Fab Assembly and Enrichment in a Monovalent Phage Display System," BioTechnology, 1991, vol. 9 (12), pp. 1373-1377.
Gennaro A.R., ed., Remington, The Science and Practice of Pharmacy, 19th Edition, Mack Publishing, 1995, Table of Contents.
Gisin., "The Preparation of Merrifield-Resins through Total Esterification with Cesium Salts," Helvetica Chimica Acta, 1973, vol. 56, pp. 1476-1482.
Goldspiel B.R., et al., "Human Gene therapy," Clinical Pharmacy, 1993, vol. 12 (7), pp. 488-505.
Goodson J.M., "Dental Applications" in: Medical Applications of Controlled Release, vol. 2, Chapter 6, Langer R.S., et al., eds., CRC Press, 1984, pp. 115-138.
Gram H., et al., "In Vitro Selection and Affinity Maturation of Antibodies from a Naïve Combinatorial Immunoglobulin Library," Proceedings of the National Academy of Sciences, 1992, vol. 89 (8), pp. 3576-3580.
Gray F., et al., "Secretion Capture and Report Web: use of Affinity Derivatized Agarose Microdroplets for the Selection of Hybridoma Cells," Journal of Immunological Methods, 1995, vol. 182 (2), pp. 155-163.
Green L. L., et al., "Regulation of B Cell Development by Variable Gene Complexity in Mice Reconstituted with Human Immunoglobulin Yeast Artificial Chromosomes," Journal of Experimental Medicine, 1998, vol. 188 (3), pp. 483-495.
Green L.L., et al., "Antigen-Specific Human Monoclonal Antibodies from Mice Engineered with Human Ig Heavy and Light Chain YACs," Nature Genetics, 1994, vol. 7 (1), pp. 13-21.
Griffiths A.D., et al., "Human Anti-Self Antibodies with High Specificity from Phage Display Libraries," European Molecular Biology Organization, 1993, vol. 12 (2), pp. 725-734.
Haematologica, Editorials and Perspectives, Dec. 1, 2001, vol. 95 (12). Table of Contents.
Hammerling G.J., et al., Eds., Monoclonal Antibodies and T-Cell Hybridomas : Perspectives and Technical Advances, Elsevier/North-Holland Biomedical Press, 1981, Appendix, pp. 563-587.
Hanes J., et al., "In Vitro Selection and Evolution of Functional Proteins by using Ribosome Display," Proceedings of the National Academy of Sciences, 1997, vol. 94 (10), pp. 4937-4942.
Hanes J., et al., "Ribosome Display Efficiently Selects and Evolves High-Affinity Antibodies in Vitro from Immune Libraries," Proceedings of the National Academy of Sciences, 1998, vol. 95 (24), pp. 14130-14135.
Harlow E., et al., "Antibodies: A Laboratory Manual", Cold Spring Harbor Laboratory, 1988, Table of Contents.
Harlow E., et al., Antibodies: A Laboratory Manual, Cold Spring Harbor Laboratory Press, 1988, pp. 555-561, 578-582 and 591-592.
Haugland, et al., Handbook of Fluorescent Probes and Research Chemicals, Molecular Probes, 1996, Table of Contents.
Hawkins R.E., et al., "Selection of Phage Antibodies by Binding Affinity Mimicking Affinity Maturation," Journal of Molecular Biology, 1992, vol. 226 (3), pp. 889-896.
Hay B.N., et al., "Bacteriophage Cloning and *Escherichia coli* Expression of a Human IgM Fab," Human Antibodies and Hybridomas, 1992, vol. 3 (2), pp. 81-85.
Hentze M.W., et al., "Two to Tango: Regulation of Mammalian Iron Metabolism," Cell, 2010, vol. 142 (1), pp. 24-38.

Holliger P., et al., ""Diabodies": Small Bivalent and Bispecific Antibody Fragments," Proceedings of the National Academy of Sciences, 1993, vol. 90 (14), pp. 6444-6448.
Hood E.E., et al., "Molecular Farming of Industrial Proteins from Transgenic Maize," Advances in Experimental Medicine and Biology, 1999, vol. 464, pp. 127-147.
Hoogenboom H.R., et al., "Multi-Subunit Proteins on the Surface of Filamentous Phage: Methodologies for Displaying Antibody (Fab) Heavy and Light Chains," Nucleic Acids Research, 1991, vol. 19 (15), pp. 4133-4137.
Howard M.A., et al., "Intracerebral Drug Delivery in Rats with Lesion-Induced Memory Deficits," Journal of Neurosurgery, 1989, vol. 71 (1), pp. 105-112.
Huse W.D., et al., "Generation of a Large Combinatorial Library of the Immunoglobulin Repertoire in Phage Lambda," Science, 1989, vol. 246 (4935), pp. 1275-1281.
Huston J.S., et al., "Protein Engineering of Antibody Binding Sites: Recovery of Specific Activity in an Anti-Digoxin Single-Chain Fv Analogue Produced in *Escherichia coli*," Proceedings of the National Academy of Sciences, 1988, vol. 85 (16), pp. 5879-5883.
Huston J.S., et al., "Protein Engineering of Single-Chain Fv Analogs and Fusion Proteins," Methods in Enzymology, 1991, vol. 203, pp. 46-88.
International Search Report and Written Opinion for Application No. PCT/US2012/069584, mailed on Jul. 11, 2013, 24 pages.
International Search Report and Written Opinion for Application No. PCT/US2012/069586, mailed on Jul. 31, 2013, 24 pages.
Jackson J.R., et al., "In Vitro Antibody Maturation Improvement of a High Affinity, Neutralizing Antibody Against IL-1ß," The Journal of Immunology, 1995, vol. 154 (7), pp. 3310-3319.
Joliot A., et al., "Antennapedia Homeobox Peptide Regulates Neural Morphogenesis," Proceedings of the National Academy of Sciences, 1991, vol. 88 (5), pp. 1864-1868.
Kabat E.A., et al., "Accession No. PS91-192898, Sequences of Proteins of Immunological Interest," 5th Edition, National Institutes of Health Publication No. 91-3242, 1991, Table of Contents.
Kabat E.A., et al., in: Sequence of Proteins of Immunological Interest, 4th Edition, 1987, Table of Contents.
Kaufman R.J., et al., "Amplification and Expression of Sequences Cotransfected with a Modular Dihydrofolate Reductase Complementary DNA Gene," Journal of Molecular Biology, 1982, vol. 159 (4), pp. 601-621.
Kenney J.S., et al., "Production of Monoclonal Antibodies using a Secretion Capture Report Web," Biotechnology, 1995, vol. 13 (8), pp. 787-790.
Kettleborough C.A., et al., "Isolation of Tumor Cell-specific Single-chain Fv from Immunized Mice using Phage-antibody Libraries and the Re-construction of Whole Antibodies from these Antibody Fragments," European Journal of Immunology, 1994, vol. 24 (4), pp. 952-958.
Kohler G., et al., "Continuous Cultures of Fused Cells Secreting Antibody of Predefined Specificity ," Nature, 1975, vol. 256 (5517), pp. 495-497.
Korchynskyi O., et al., "Identification and Functional Characterization of Distinct Critically Important Bone Morphogenetic Protein-Specific Response Elements in the Id1 Promoter," Journal of Biological Chemistry, 2002, vol. 277 (7), pp. 4883-4891.
Kriegler M., Gene Transfer and Expression: A Laboratory Manual, Stockton Press, 1990, Table of Contents.
Kroot J.J., et al., "Second Round Robin for Plasma Hepcidin Methods: First Steps Toward Harmonization," American Journal of Hematology, 2012, vol. 87 (10), pp. 977-983.
Kroot J.J., et al., "Hepcidin in Human Iron Disorders: Diagnostic Implications," Clinical Chemistry, 2011, vol. 57 (12), pp. 1650-1669.
Kuninger D., et al., "Complex Biosynthesis of the Muscle-enriched Iron Regulator RGMc," Journal of Cell Science, 2006, vol. 119 (Pt 16), pp. 3273-3283.
Kuns-Hashimotod R., et al., "Selective Binding of RGMc/hemojuvelin, a Key Protein in Systemic Iron Metabolism, to BMP-2 and Neogenin," American journal of physiology, 2008, vol. 294 (4), pp. C994-C1003.

(56) References Cited

OTHER PUBLICATIONS

Kyte J., et al., "A Simple Method for Displaying the Hydropathic Character of a Protein," Journal of Molecular Biology, 1982, vol. 157 (1), pp. 105-132.
Lam X.M., et al., "Microencapsulation of Recombinant Humanized Monoclonal Antibody for Local Delivery," Proceedings of the 24th International Symposium on Controlled Release of Bioactive Materials, 1997, vol. 24, pp. 759-760.
Langer R., et al., "Chemical and Physical Structure of Polymers as Carriers for Controlled Rlease of Bioactive Agents: A Review," Journal of Macromolecular Science—Reviews in Macromolecular Chemistry & Physics, 1983, vol. C23 (1), pp. 61-126.
Langer R., "New Methods of Drug Delivery," Science, 1990, vol. 249 (4976), pp. 1527-1533.
Lee D.H., et al., "Neogenin Inhibits HJV Secretion and Regulates BMP-induced hepcidin expression and iron homeostasis," Blood, 2010, vol. 115 (15), pp. 3136-3145.
Levy R.D., et al., "Inhibition of Calcification of Bioprosthetic Heart Valves by Local Controlled-Release Diphosphonate," Science, 1985, vol. 228 (4696), pp. 190-192.
Li J., et al., "Potential Prognostic Value of Repulsive Guidance Molecules in Breast Cancer," Anticancer Research, 2011, vol. 31 (5), pp. 1703-1711.
Maccallum R.M., et al., "Antibody-Antigen Interactions: Contact Analysis and Binding Site Topography," Journal of Molecular Biology, 1996, vol. 262 (5), pp. 732-745.
Marks J.D., et al., "By-Passing Immunization: Building High Affinity Human Antibodies by Chain Shuffling," Biotechnology, 1992, vol. 10 (7), pp. 779-783.
Masuda K., et al., "The Role of Interface Framework Residues in Determining Antibody V(H)/V(L) Interaction Strength and Antigen-Binding Affinity," FEBS Journal, May 2006, vol. 273 (10), pp. 2184-2194.
Mattingly P.G., "Chemiluminescent 10-Methyl-Acridinium-9(N-Sulphonylcarboxamide) Salts. Synthesis and Kinetics of Light Emission," Journal of Bioluminescence and Chemiluminescence, 1991, vol. 6 (2), pp. 107-114.
Mattingly P.G., et al., In Instruments and Applications Luminescence: Instruments and Applications, Dyke K.V., Ed., CRC Press, 2002, pp. 77-105.
Mccafferty J., et al., "Phage Antibodies: Filamentous Phage Displaying Antibody Variable Domains," Nature, 1990, vol. 348 (6301), pp. 552-554.
Mccapra F., et al., "Chemiluminescence Involving Peroxide Decompositions," Photochemistry and Photobiology, 1965, vol. 4 (6), pp. 1111-1121.
Mendez M.J., et al., "Functional Transplant of Megabase Human Immunoglobulin Loci Recapitulates Human Antibody Response in Mice," Nature Genetics, 1997, vol. 15 (2), pp. 146-156.
Merrifield R.B., et al., "Solid Phase Peptide Synthesis. I. The Synthesis of a Tetrapeptide," Journal of the American Chemical Society, 1963, vol. 85, pp. 2149-2154.
Milstein C., et al., "Hybrid Hybridomas and their use in Immunohistochemistry," Nature, 1983, vol. 305 (5934), pp. 537-540.
Morgan R.A., et al., "Human Gene Therapy," Annual Review of Biochemistry, 1993, vol. 62, 191-217.
Mueller B.K., et al., "The Role of Repulsive Guidance Molecules in the Embryonic and Adult Vertebrate Central Nervous System," Philosophical Transactions of the Royal Society, 2006, vol. 361 (1473), pp. 1513-1529.
Mulligan R.C., "The Basic Science of Gene Therapy," Science, 1993, vol. 260 (5110), pp. 926-932.
Mullinax R.L., et al., "Expressoin of a Heterodimeric Fab Antibody Protein in One Cloning Step," Bio Techniques,, 1992, vol. 12 (6), pp. 864-869.
Nguyen H., et al., "Production of Human Monoclonal Antibodies in SCID Mouse," Microbiology and Immunology, 1997, vol. 41 (12), pp. 901-907.
Nili M., et al., "Soluble Repulsive Guidance Molecule c/hemojuvelin is a Broad Spectrum Bone Morphogenetic Protein (BMP) Antagonist and Inhibits both BMP2- and BMP6-mediated Signaling and Gene Expression," The Journal of Biological Chemistry, 2010, vol. 285 (32), pp. 24783-24792.
Ning S., et al., "Intratumoral Radioimmunotherapy of a Human Colon Cancer Xenograft Using a Sustained-Release Gel," Radiotherapy & Oncology: The Journal of the European Society for Therapeutic Radiology and Oncology, 1996, vol. 39 (2), pp. 179-189.
Padlan E.A., et al., "Identification of Specificity-determining Residues in Antibodies," FASEB Journal, 1995, vol. 9 (1), pp. 133-139.
Panka D.J., et al., "Variable Region Framework Differences Result in Decreased or Increased Affinity of Variant Anti-Digoxin Antibodies.," Immunology, 1988, vol. 85 (9), pp. 3080-3084.
Paul W.E., Ed., "Structure and Function of Immunoglobulins," in: Fundamental Immunology, 1993, 3rd Edition and Chapter 9, Raven Press Ltd., New York, pp. 292-295.
Persic L., et al., "An Integrated Vector System for the Eukaryotic Expression of Antibodies or their Fragments After Selection from Phage Display Libraries," Gene, 1997, vol. 187 (1), pp. 9-18.
Pietrangelo A., "Hepcidin in Human Iron Disorders: Therapeutic Implications," Journal of Hepatology, 2011, vol. 54 (1), pp. 173-181.
Pietta P.G., et al., "Amide Protection and Amide Supports in Solid-phase Peptide Synthesis," Chemical Communications, 1970, pp. 650-651.
Polak J.M., et al., Introduction to Immunocytochemistry, 2nd Edition, Springer-Verlag, 1997, Table of Contents.
Powell K.T., et al., "Gel Microdroplets and Flow Cytometry Rapid Determination of Antibody Secretion by Individual Cells within a Cell Population," Biotechnology, 1990, vol. 8 (4), pp. 333-337.
Rajpal A., et al., "A General Method for Greatly Improving the Affinity of Antibodies by Using Combinatorial Libraries," National Academy of Science, Apr. 29, 2005, vol. 102 (24), pp. 8466-8471.
Razavi Z., et al., "Stable and Versatile Active Acridinium Esters I ," Luminescence, 2000, vol. 15 (4), pp. 239-244.
Razavi Z., et al., "Stable and Versatile Active Acridinium Esters II," Luminescence, 2000, vol. 15, pp. 245-249.
Roberts R.W., et al., "RNA-peptide Fusions for the in Vitro Selection of Peptides and Proteins," Proceedings of the National Academy of Sciences, 1997, vol. 94 (23), pp. 12297-12302.
Robinson C., "Gene Therapy—Proceeding from Laboratory to Clinic," Trends in Biotechnology, 1993, vol. 11 (5), pp. 155-215.
Robinson J.R., Sustained and Controlled Release Drug Delivery Systems, Marcel Dekker, Inc., 1978, Table of Contents.
Rudikoff S., et al., "Single Amino Acid Substitution Altering Antigen-Binding Specificity," PNAS, Proceedings of the National Academy of Sciences, 1982, vol. 79 (6), pp. 1979-1983.
Rudnick S., et al., "Affinity and Avidity in Antibody-Based Tumor Targeting," Cancer Biotherapy and Radiopharmaceuticals, 2009, vol. 24 (2), pp. 155-161.
Saeed O., et al., "Pharmacological Suppression of Hepcidin Increases Macrophage Cholesterol Efflux and Reduces Foam Cell Formation and Atherosclerosis," Arteriosclerosis, Thrombosis, and Vascular Biology, 2012, vol. 32 (2), pp. 299-307.
Sandhu J.S., et al., "The use of SCID Mice in Biotechnology and as a Model for Human Disease," Critical Reviews in Biotechnology, 1996, vol. 16 (1), pp. 95-118.
Saudek C.D., et al., "A Preliminary Trial of the Programmable Implantable Medication System for Insulin Delivery," The New England Journal of Medicine, 1989, vol. 321 (9), pp. 574-579.
Sawai H., et al., "Direct Production of the Fab Fragment Derived from the Sperm Immobilizing Antibody using Polymerase Chain Reaction and Cdna Expression Vectors," American Journal of Reproductive Immunology, 1995, vol. 34 (1), pp. 26-34.
Schier R., et al., "Identification of Functional and Structural Amino-Acid Residues by Parsimonious Mutagenesis," Gene, 1996, vol. 169 (2), 147-155.
Seed B., "An LFA-3 cDNA Encodes a Phospholipid-Linked Membrane Protein Homologous to its Receptor CD2," Nature, 1997, vol. 329 (6142), pp. 840-842.

(56) References Cited

OTHER PUBLICATIONS

Sefton M.V., et al., "Implantable Pumps," Critical Reviews in Biomedical Engineering, 1987, vol. 14 (3), pp. 201-240.
Severyn C.J., et al., "Molecular Biology, Genetics and Biochemistry of the Repulsive Guidance Molecule Family," Biochemical Journal, 2009, vol. 422 (3), pp. 393-403.
Severyn C.J., et al., "Molecular Biology Genetics and Biochemistry of the Repulsive Guidance Molecule Family," The Biochemical journal, 2009, vol. 422 (3), pp. 393-403.
Shaw S.Y., et al., "A Spontaneous Variant of an Antidigoxin Hybridoma Antibody with Increased Affinity Arises from a Heavy Chain Signal Peptide Mutation," Molecular Immunology, 1992, vol. 29 (4), pp. 525-529.
Shu L., et al., "Secretion of a Single-Gene-Encoded Immunoglobulin from Myeloma Cells," Proceedings of the National Academy of Sciences, 1993, vol. 90 (17), pp. 7995-7999.
Skerra A., et al., "Assembly of a Functional Immunoglobulin Fv Fragment in *Escherichia coli*," Science, 1988, vol. 240 (4855), pp. 1038-1041.
Smolen V.F., et al., eds., Controlled Drug Bioavailability: Drug Product Design and Performance, vol. 1, John Wiley & Sons, 1984, Table of Contents.
Song Y.K., et al., "Antibody Mediated Lung Targeting of Long-Circulating Emulsions," PDA Journal of Pharmaceutical Science & Technology, 1995, vol. 50 (6), pp. 372-377.
Staerz U.D., et al., "Hybrid Antibodies Can Target Sites for Attack by T Cells," Nature, 1985, vol. 314 (6012), pp. 628-631.
Steenbakkers P.G., et al., "Efficient Generation of Monoclonal Antibodies from Preselected Antigen-Specific B Cells. Efficient Immortalization of Preselected B Cells," Molecular Biology Reports, 1994, vol. 19 (2), pp. 125-134.
Stewart J.M., et al., Solid-Phase Peptide Synthesis, 2nd Edition, Pierce Chemical Company, 1984, Table of Contents.
Theurl I., et al., "Pharmacologic Inhibition of Hepcidin Expression Reverses Anemia of Chronic Inflammation in Rats," Blood, 2011, vol. 118 (18), pp. 4977-4984.
Tian C., et al., "Repulsive Guidance Molecules (RGMs) and Neogenin in Bone Morphogenetic Protein (BMP) Signaling," Molecular Reproduction and Development, 2013, vol. 80 (9), pp. 700-717.
Tolstoshev P., "Gene Therapy, Concepts, Current Trials and Future Directions," Annual Review of Pharmacology and Toxicology, 1993, vol. 33, pp. 573-596.
Tsuchiya H., et al., "Iron State in Association with Retinoid Metabolism in Non-Alcoholic Fatty Liver Disease," Hepatology Research, 2010, vol. 40 (12), pp. 1227-1238.
Uniprot: "Alignment of human RGMa and RGMc," Oct. 20, 2015 (Oct. 20, 2015), XP055222407, Retrieved from the Internet URL:http://www.uniprot.org/align/A20151020759YX4NR2V [retrieved on Oct. 20, 2015], 2 pages.
Urlaub G., et al., "Isolation of Chinese Hamster Cell Mutants Deficient in Dihydrofolate Reductase Activity," Proceedings of the National Academy of Sciences, 1980, vol. 77 (7), pp. 4216-4220.
Wallemacq P.E., et al., "Evaluation of the New AxSYM Cyclosporine Assay: Comparison with TDx Monoclonal Whole Blood and Emit Cyclosporine Assays," Clinical Chemistry, 1999, vol. 45 (3), pp. 432-435.
Wells D.A., et al., "High Throughput Bioanalytical Sample Preparation Methods and Automation Strategies", Progress in Pharmaceutical and Biomedical Analysis, 2003, Table of Contents.
Wen L., et al., "Limiting Dilution Assay for Human B Cells Based on their Activation by Mutant EL4 Thymoma Cells: Total and Antimalaria Responder B Cell Frequencies," European Journal of Immunology, 1987, vol. 17 (6), pp. 887-892.
Wilbur W.J., et al., "Rapid Similarity Searches of Nucleic Acid and Protein Data Banks," Proceedings of the National Academy of Sciences, 1983, vol. 80 (3), pp. 726-730.
Winnaker E.L., From Genes to Clones: Introduction to Gene Technology, VCH Publishers, 1987, Table of Contents.
Wu C., et al., "Simultaneous Targeting of Multiple Disease Mediators by a Dual-Variable-Domain Immunoglobulin," Nature Biotechnology, 2007, vol. 25 (11), pp. 1290-1297.
Wu G., et al., "Delivery Systems for Gene Therapy," Biotherapy, 1991, vol. 3 (1), pp. 87-95.
Wu G.Y., et al., "Receptor-mediated in Vitro Gene Transformation by a Soluble DNA Carrier System," Journal of Biological Chemistry, 1987, vol. 262 (10), pp. 4429-4432.
Yatscoff R.W., et al., "Abbott TDx Monoclonal Antibody Assay Evaluated for Measuring Cyclosporine in Whole Blood," Clinical Chemistry, 1990, vol. 36 (11), pp. 1969-1973.
Yelton D.E., et al., "Affinity Maturation of the BR96 Anti-Carcinoma Antibody by Codon-Based Mutagenesis," The Journal of Immunology, 1995, vol. 155 (4), pp. 1994-2004.
Zapata G., et al., "Engineering Linear F(ab')2 Fragments for Efficient Production in *Escherichia coli* and Enhanced Antiproliferative Activity," Protein Engineering, 1995, vol. 8 (10), pp. 1057-1062.
Zhang A.S., "Control of Systemic Iron Homeostasis by the Hemojuvelin-Hepcidin Axis," Advances in Nutrition, 2010, vol. 1 (1), pp. 38-45.
Zhang A.S., et al., "The Role of Hepatocyte Hemojuvelin in the Regulation of Bone Morphogenic Protein-6 and Hepcidin Expression in Vivo," The Journal of Biological Chemistry, 2010, vol. 285 (22), pp. 16416-16423.
Sullivan, Arterioscler Thromb Vasc Biol. 2005;25: 1532-1535. (Year: 2005).
Preza et al. (J Clin Invest. 2011;121 (12):4880-4888). (Year: 2011).

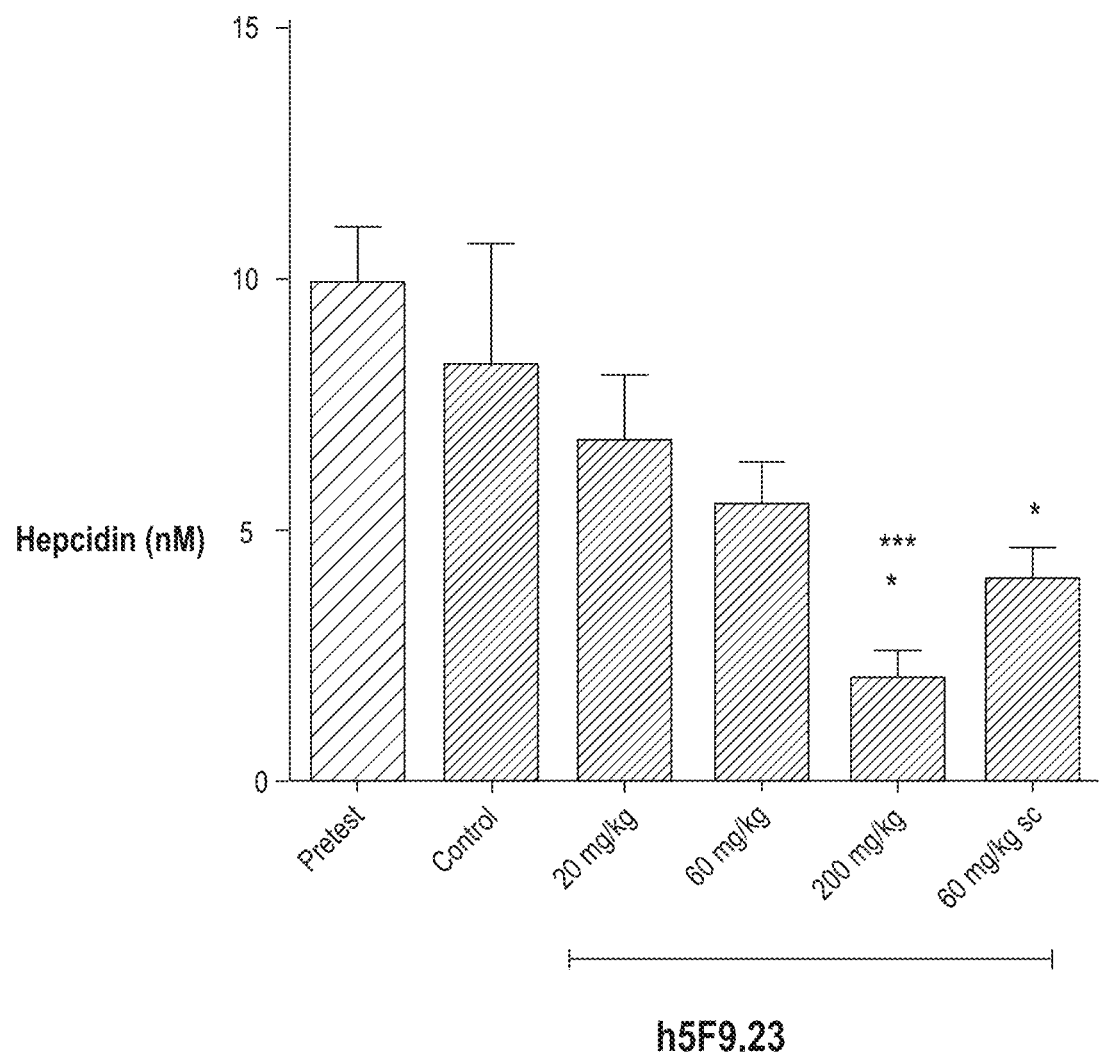

COMPOSITION AND METHOD FOR THE DIAGNOSIS AND TREATMENT OF IRON-RELATED DISORDERS

RELATED APPLICATION INFORMATION

This application is a continuation of U.S. patent Ser. No. 17/034,454, filed on Sep. 28, 2020, which is a continuation of U.S. patent application Ser. No. 16/179,515, filed on Nov. 2, 2018, now U.S. Pat. No. 10,822,403, which is a continuation of U.S. patent application Ser. No. 13/714,238, filed Dec. 13, 2012, now U.S. Pat. No. 10,118,958, which claims the benefit of U.S. Provisional Patent Application No. 61/570,715 filed on Dec. 14, 2011, the contents of which are herein fully incorporated by reference.

SEQUENCE LISTING

The computer-readable Sequence Listing submitted on Apr. 17, 2024 and identified as follows: 260,520 bytes ST.26 XML document file named "11386USC3 Sequence Listing.xml," created Apr. 11, 2024, is incorporated herein by reference in its entirety.

FIELD OF THE INVENTION

The present invention relates to antibodies and methods of using the antibodies to treat and diagnose iron-related disorders.

BACKGROUND

Iron homeostasis is critical for the normal function of the body. Because iron is central to hemoglobin production, deficient levels of iron result in iron-deficient anemia. Iron overload can also upset the balance of iron by inappropriately increasing intestinal iron absorption. This increase often results in the deposition of iron in the liver, pancreas, heart, pituitary, and other organs, leading to tissue damage and impairment of normal function of those organs.

A variety of iron-related diseases can be attributed, at least in part, to the mis-regulation of iron and can be difficult to diagnose and treat. Such disorders include liver disease, hypogonadism, diabetes, cirrhosis, cardiomyopathy, iron-deficient anemia, and anemia of chronic disease ("ACD"), which is characterized by a maldistribution of iron that is associated with infection, malignancy and/or chronic inflammation. Because symptoms related to iron-related disorders are often vague and the resultant effects tend not to appear immediately, current procedures often fail to properly diagnose and treat an iron disorder. These difficulties can cause delays in administering the appropriate therapy.

Accordingly, there is a need for reliable methods of diagnosis and treatment for iron-related disorders. Current treatment options for iron-related disorders, including anemia of chronic disease, include the administration of erythropoetic agents, such as epoetin alpha, epoetin beta, and darbepoetin. Further treatments include oral or parental iron therapy and/or blood transfusions. Iron therapies however have limited efficacy and are usually not recommended for ACD subjects. In addition, blood transfusions have the ongoing issue of multiorgan failure and increased mortality in critical care patients. Accordingly, there exists a need for a new method of treatment for iron-related diseases that is highly specific, well-tolerated, and can serve as a useful therapy for those subjects that do not respond to epoetin and its related analogs in a sufficient manner.

SUMMARY OF THE INVENTION

In one aspect, the present invention is directed to an isolated antibody or antibody fragment thereof which binds to Repulsive Guidance Molecule c ("RGMc"). The antibody comprises a domain or region selected from the group consisting of: (a) a variable heavy domain region comprising the amino acid sequence of SEQ ID NO:3, (b) a variable light domain region comprising the amino acid sequence of SEQ ID NO:4, (c) a variably heavy domain region comprising the amino acid sequence of SEQ ID NO:5, (d) a variable light domain region comprising the amino acid sequence of SEQ ID NO:6, (e) a variably heavy domain region comprising the amino acid sequence of SEQ ID NO:7, (f) a variable light domain region comprising the amino acid sequence of SEQ ID NO:8, (g) a variably heavy domain region comprising the amino acid sequence of SEQ ID NO:9, (h) a variable light domain region comprising the amino acid sequence of SEQ ID NO: 10, (i) a variable heavy chain comprising a complementarity determining region (CDR)1 comprising the amino acid sequence of SEQ ID NO:11, a CDR2 comprising the amino acid sequence of SEQ ID NO:12, and a CDR3 comprising the amino acid sequence of SEQ ID NO:13, (j) a variable light chain comprising a CDR1 comprising the amino acid sequence of SEQ ID NO: 14, a CDR2 comprising the amino acid sequence of SEQ ID NO: 15, and a CDR3 comprising the amino acid sequence of SEQ ID NO:16, (k) a variable heavy chain comprising a CDR1 comprising the amino acid sequence of SEQ ID NO:17, a CDR2 comprising the amino acid sequence of SEQ ID NO: 18, and a CDR3 comprising the amino acid sequence of SEQ ID NO: 19, (l) a variable light chain comprising a CDR1 comprising the amino acid sequence of SEQ ID NO:20, a CDR2 comprising the amino acid sequence of SEQ ID NO:21, and a CDR3 comprising the amino acid sequence of SEQ ID NO:22, (m) a variable heavy chain comprising a CDR1 comprising the amino acid sequence of SEQ ID NO:23, a CDR2 comprising the amino acid sequence of SEQ ID NO:24, and a CDR3 comprising the amino acid sequence of SEQ ID NO:25, (n) a variable light chain comprising a CDR1 comprising the amino acid sequence of SEQ ID NO:26, a CDR2 comprising the amino acid sequence of SEQ ID NO:27, and a CDR3 comprising the amino acid sequence of SEQ ID NO:28, (o) a variable heavy chain comprising a CDR1 comprising the amino acid sequence of SEQ ID NO:29, a CDR2 comprising the amino acid sequence of SEQ ID NO:30, and a CDR3 comprising the amino acid sequence of SEQ ID NO:31, (p) a variable light chain comprising a CDR1 comprising the amino acid sequence of SEQ ID NO:32, a CDR2 comprising the amino acid sequence of SEQ ID NO:33, and a CDR3 comprising the amino acid sequence of SEQ ID NO:34, (q) a variable heavy chain comprising CDR1 comprising the amino acid sequence of SEQ ID NO:11, a CDR2 comprising the amino acid sequence of SEQ ID NO: 12, and a CDR3 comprising the amino acid sequence of SEQ ID NO: 13 and a variable light chain comprising a CDR1 comprising the amino acid sequence of SEQ ID NO: 14, a CDR2 comprising the amino acid sequence of SEQ ID NO: 15, and a CDR3 comprising the amino acid sequence of SEQ ID NO:16, (r) a variable heavy chain comprising a CDR1 comprising the amino acid sequence of SEQ ID NO:17, a CDR2 comprising the amino acid sequence of SEQ ID NO:18, and a CDR3 comprising the amino acid sequence of SEQ ID NO: 19 and a variable light chain comprising a CDR1 comprising the amino acid sequence of SEQ ID NO:20, a CDR2 comprising the amino acid sequence of SEQ ID NO:21, and a CDR3 comprising the amino acid sequence of SEQ ID NO:22, (s) a variable heavy chain comprising a CDR1 comprising the amino acid sequence of SEQ ID NO:23, a CDR2 comprising the amino acid sequence of SEQ ID NO:24, and a CDR3 comprising the amino acid sequence of SEQ ID NO:25 and a variable light chain comprising a CDR1 comprising the amino acid sequence of SEQ ID NO:26, a CDR2 comprising the amino acid sequence of SEQ ID NO:27, and a CDR3 comprising the amino acid sequence of SEQ ID NO:28, (t) a variable heavy chain comprising a CDR1 comprising the amino acid sequence of SEQ ID NO:29, a CDR2 comprising the amino acid sequence of SEQ ID NO:30, and a CDR3 comprising the amino acid sequence of SEQ ID NO:31 and a variable light chain comprising a CDR1 comprising the amino acid sequence of SEQ ID NO:32, a CDR2 comprising the amino acid sequence of SEQ ID NO:33, and a CDR3 comprising the amino acid sequence of SEQ ID NO:34. The antibody may be an immunoglobulin molecule, a disulfide linked Fv, an affinity matured antibody, a scFv, a chimeric antibody, a single domain antibody, a CDR-grafted antibody, a diabody, a humanized antibody, a human antibody, a multispecific antibody, a Fab, a dual specific antibody, a DVD, a Fab', a bispecific antibody, a F(ab')2, and a Fv. The isolated antibody or antibody fragment of claim 2, wherein the antibody or antibody fragment is a monoclonal antibody, a humanized antibody or a human antibody. The antibody or antibody fragment comprises a heavy chain immunoglobulin constant domain selected from the group consisting of a human IgM constant domain, a human IgG4 constant domain, a human IgG1 constant domain, a human IgE constant domain, a human IgG2 constant domain, a human IgG3 constant domain, and a human IgA constant domain.

The isolated antibody or antibody fragment may comprise a variable heavy domain region comprising the amino acid sequence of SEQ ID NO:3, a variably heavy domain region comprising the amino acid sequence of SEQ ID NO:5, a variably heavy domain region comprising the amino acid sequence of SEQ ID NO:7, or a variably heavy domain region comprising the amino acid sequence of SEQ ID NO:9. The antibody may comprise a variable light domain region comprising the amino acid sequence of SEQ ID NO:4, a variable light domain region comprising the amino acid sequence of SEQ ID NO:6, a variable light domain region comprising the amino acid sequence of SEQ ID NO:8, or a variable light domain region comprising the amino acid sequence of SEQ ID NO: 10. The antibody may comprise a variably heavy domain region comprising the amino acid sequence of SEQ ID NO:3 and a variable light domain region comprising the amino acid sequence of SEQ ID NO:4.

The antibody may comprise a variably heavy domain region comprising the amino acid sequence of SEQ ID NO:5 and a variable light domain region comprising the amino acid sequence of SEQ ID NO:6. The antibody may comprise a variably heavy domain region comprising the amino acid sequence of SEQ ID NO:7 and a variable light domain region comprising the amino acid sequence of SEQ ID NO:8. The antibody may comprise a variably heavy domain region comprising the amino acid sequence of SEQ ID NO:9 and a variable light domain region comprising the amino acid sequence of SEQ ID NO: 10. The antibody may comprise a variable heavy chain comprising a complementarity determining region (CDR)1 comprising the amino acid sequence of SEQ ID NO:11, a CDR2 comprising the amino acid sequence of SEQ ID NO: 12, and a CDR3 comprising the amino acid sequence of SEQ ID NO:13.

The antibody may comprise a variable light chain comprising a CDR1 comprising the amino acid sequence of SEQ ID NO: 14, a CDR2 comprising the amino acid sequence of SEQ ID NO:15, and a CDR3 comprising the amino acid sequence of SEQ ID NO:16. The antibody may comprise a variable heavy chain comprising a CDR1 comprising the amino acid sequence of SEQ ID NO:17, a CDR2 comprising the amino acid sequence of SEQ ID NO: 18, and a CDR3 comprising the amino acid sequence of SEQ ID NO: 19.

The antibody may comprise a variable light chain comprising a CDR1 comprising the amino acid sequence of SEQ ID NO:20, a CDR2 comprising the amino acid sequence of SEQ ID NO:21, and a CDR3 comprising the amino acid sequence of SEQ ID NO:22.

The antibody may comprise a variable heavy chain comprising a CDR1 comprising the amino acid sequence of SEQ ID NO:23, a CDR2 comprising the amino acid sequence of SEQ ID NO:24, and a CDR3 comprising the amino acid sequence of SEQ ID NO:25. The antibody may comprise a variable light chain comprising a CDR1 comprising the amino acid sequence of SEQ ID NO:26, a CDR2 comprising the amino acid sequence of SEQ ID NO:27, and a CDR3 comprising the amino acid sequence of SEQ ID NO:28. The antibody may comprise a variable heavy chain comprising a CDR1 comprising the amino acid sequence of SEQ ID NO:29, a CDR2 comprising the amino acid sequence of SEQ ID NO:30, and a CDR3 comprising the amino acid sequence of SEQ ID NO:31. The antibody may comprise a variable light chain comprising a CDR1 comprising the amino acid sequence of SEQ ID NO:32, a CDR2 comprising the amino acid sequence of SEQ ID NO:33, and a CDR3 comprising the amino acid sequence of SEQ ID NO:34. The antibody may comprise a variable heavy chain comprising a complementarity determining region (CDR)1 comprising the amino acid sequence of SEQ ID NO:11, a CDR2 comprising the amino acid sequence of SEQ ID NO: 12, and a CDR3 comprising the amino acid sequence of SEQ ID NO: 13 and a variable light chain comprising a CDR1 comprising the amino acid sequence of SEQ ID NO: 14, a CDR2 comprising the amino acid sequence of SEQ ID NO: 15, and a CDR3 comprising the amino acid sequence of SEQ ID NO:16.

The antibody may comprise a variable heavy chain comprising a CDR1 comprising the amino acid sequence of SEQ ID NO: 17, a CDR2 comprising the amino acid sequence of SEQ ID NO:18, and a CDR3 comprising the amino acid sequence of SEQ ID NO: 19 and a variable light chain comprising a CDR1 comprising the amino acid sequence of SEQ ID NO:20, a CDR2 comprising the amino acid sequence of SEQ ID NO:21, and a CDR3 comprising the amino acid sequence of SEQ ID NO:22.

The antibody may comprise a variable heavy chain comprising a CDR1 comprising the amino acid sequence of SEQ ID NO:23, a CDR2 comprising the amino acid sequence of SEQ ID NO:24, and a CDR3 comprising the amino acid sequence of SEQ ID NO:25 and a variable light chain comprising a CDR1 comprising the amino acid sequence of SEQ ID NO:26, a CDR2 comprising the amino acid sequence of SEQ ID NO:27, and a CDR3 comprising the amino acid sequence of SEQ ID NO:28.

The antibody may comprise a variable heavy chain comprising a CDR1 comprising the amino acid sequence of SEQ ID NO:29, a CDR2 comprising the amino acid sequence of SEQ ID NO:30, and a CDR3 comprising the amino acid sequence of SEQ ID NO:31 and a variable light chain comprising a CDR1 comprising the amino acid sequence of SEQ ID NO:32, a CDR2 comprising the amino acid sequence of SEQ ID NO:33, and a CDR3 comprising the amino acid sequence of SEQ ID NO:34. The antibody or antibody fragment may further comprise an agent selected from the group consisting of: an immunoadhesion molecule, an imaging agent, and a therapeutic agent. The imaging agent may be a radiolabel, an enzyme, a fluorescent label, a luminescent label, a bioluminescent label, a magnetic label, or biotin. The radiolabel may be 3H, 14C, 35S, 90Y, 99Tc, 111 In, 125I, 131I, 177Lu, 166Ho, or 153Sm.

In another aspect, the present invention is also directed to an isolated nucleic acid encoding any one of the antibodies, or fragments thereof, described herein. The present disclosure is also directed to pharmaceutical compositions that comprise the herein described antibody, antibody fragment, mixture or derivative thereof.

In another aspect, the present invention is also directed to a method of treating a disease of iron metabolism. The method comprises the steps of administering to a subject in need thereof a therapeutically or prophylactically effective amount of an antibody, wherein the antibody comprises a domain or region selected from the group consisting of: (a) a variable heavy domain region comprising the amino acid sequence of SEQ ID NO:3, (b) a variable light domain region comprising the amino acid sequence of SEQ ID NO:4, (c) a variably heavy domain region comprising the amino acid sequence of SEQ ID NO:5, (d) a variable light domain region comprising the amino acid sequence of SEQ ID NO:6, (e) a variably heavy domain region comprising the amino acid sequence of SEQ ID NO:7, (f) a variable light domain region comprising the amino acid sequence of SEQ ID NO:8, (g) a variably heavy domain region comprising the amino acid sequence of SEQ ID NO:9, (h) a variable light domain region comprising the amino acid sequence of SEQ ID NO: 10, (i) a variable heavy chain comprising a complementarity determining region (CDR)1 comprising the amino acid sequence of SEQ ID NO:11, a CDR2 comprising the amino acid sequence of SEQ ID NO: 12, and a CDR3 comprising the amino acid sequence of SEQ ID NO:13, (j) a variable light chain comprising a CDR1 comprising the amino acid sequence of SEQ ID NO: 14, a CDR2 comprising the amino acid sequence of SEQ ID NO: 15, and a CDR3 comprising the amino acid sequence of SEQ ID NO:16, (k) a variable heavy chain comprising a CDR1 comprising the amino acid sequence of SEQ ID NO:17, a CDR2 comprising the amino acid sequence of SEQ ID NO:18, and a CDR3 comprising the amino acid sequence of SEQ ID NO: 19, (l) a variable light chain comprising a CDR1 comprising the amino acid sequence of SEQ ID NO:20, a CDR2 comprising the amino acid sequence of SEQ ID NO:21, and a CDR3 comprising the amino acid sequence of SEQ ID NO:22, (m) a variable heavy chain comprising a CDR1 comprising the amino acid sequence of SEQ ID NO:23, a CDR2 comprising the amino acid sequence of SEQ ID NO:24, and a CDR3 comprising the amino acid sequence of SEQ ID NO:25, (n) a variable light chain comprising a CDR1 comprising the amino acid sequence of SEQ ID NO:26, a CDR2 comprising the amino acid sequence of SEQ ID NO:27, and a CDR3 comprising the amino acid sequence of SEQ ID NO:28, (o) a variable heavy chain comprising a CDR1 comprising the amino acid sequence of SEQ ID NO:29, a CDR2 comprising the amino acid sequence of SEQ ID NO:30, and a CDR3 comprising the amino acid sequence of SEQ ID NO:31, (p) a variable light chain comprising a CDR1 comprising the amino acid sequence of SEQ ID NO:32, a CDR2 comprising the amino acid sequence of SEQ ID NO:33, and a CDR3 comprising the amino acid sequence of SEQ ID NO:34, (q) a variable heavy chain comprising a complementarity determining region (CDR)1 comprising the amino acid sequence of SEQ ID NO: 11, a CDR2 comprising the amino acid sequence of SEQ ID NO: 12, and a CDR3 comprising the amino acid sequence of SEQ ID NO: 13 and a variable light chain comprising a CDR1 comprising the amino acid sequence of SEQ ID NO:14, a CDR2 comprising the amino acid sequence of SEQ ID NO: 15, and a CDR3 comprising the amino acid sequence of SEQ ID NO:16, (r) a variable heavy chain comprising a CDR1 comprising the amino acid sequence of SEQ ID NO: 17, a CDR2 comprising the amino acid sequence of SEQ ID NO: 18, and a CDR3 comprising the amino acid sequence of SEQ ID NO:19 and a variable light chain comprising a CDR1 comprising the amino acid sequence of SEQ ID NO:20, a CDR2 comprising the amino acid sequence of SEQ ID NO:21, and a CDR3 comprising the amino acid sequence of SEQ ID NO:22, (s) a variable heavy chain comprising a CDR1 comprising the amino acid sequence of SEQ ID NO:23, a CDR2 comprising the amino acid sequence of SEQ ID NO:24, and a CDR3 comprising the amino acid sequence of SEQ ID NO:25 and a variable light chain comprising a CDR1 comprising the amino acid sequence of SEQ ID NO:26, a CDR2 comprising the amino acid sequence of SEQ ID NO:27, and a CDR3 comprising the amino acid sequence of SEQ ID NO:28, and (t) a variable heavy chain comprising a CDR1 comprising the amino acid sequence of SEQ ID NO:29, a CDR2 comprising the amino acid sequence of SEQ ID NO:30, and a CDR3 comprising the amino acid sequence of SEQ ID NO:31 and a variable light chain comprising a CDR1 comprising the amino acid sequence of SEQ ID NO:32, a CDR2 comprising the amino acid sequence of SEQ ID NO:33, and a CDR3 comprising the amino acid sequence of SEQ ID NO:34, (u) a variable heavy domain region comprising the amino acid sequence of SEQ ID NO:43, (v) a variable light domain region comprising the amino acid sequence of SEQ ID NO:44, (w) a variably heavy domain region comprising the amino acid sequence of SEQ ID NO:51, (x) a variable light domain region comprising the amino acid sequence of SEQ ID NO:52, (y) a variably heavy domain region comprising the amino acid sequence of SEQ ID NO:53, (z) a variable light domain region comprising the amino acid sequence of SEQ ID NO:54, (aa) a variably heavy domain region comprising the amino acid sequence of SEQ ID NO:57, (bb) a variable light domain region comprising the amino acid sequence of SEQ ID NO:58, (cc) a variably heavy domain region comprising the amino acid sequence of SEQ ID NO:69, (dd) a variable light domain region comprising the amino acid sequence of SEQ ID NO:70, (ee) a variable heavy chain comprising a complementarity determining region (CDR)1 comprising the amino acid sequence of SEQ ID NO:95, a CDR2 comprising the amino acid sequence of SEQ ID NO:96, and a CDR3 comprising the amino acid sequence of SEQ ID NO:97, (ff) a variable light chain comprising a CDR1 comprising the amino acid sequence of SEQ ID NO:98, a CDR2 comprising the amino acid sequence of SEQ ID NO:99, and a CDR3 comprising the amino acid sequence of SEQ ID NO: 100, (gg) a variable heavy chain comprising a CDR1 comprising the amino acid sequence of SEQ ID NO:119, a CDR2 comprising the amino acid sequence of SEQ ID NO:120, and a CDR3 comprising the amino acid sequence of SEQ ID NO:121, (hh) a variable light chain comprising a CDR1 comprising the amino acid sequence of SEQ ID NO: 122, a CDR2 comprising the amino acid sequence of SEQ ID NO: 123, and a CDR3 comprising the amino acid sequence of SEQ ID NO:124, (ii)

a variable heavy chain comprising a CDR1 comprising the amino acid sequence of SEQ ID NO: 125, a CDR2 comprising the amino acid sequence of SEQ ID NO:126, and a CDR3 comprising the amino acid sequence of SEQ ID NO: 127, (jj) a variable light chain comprising a CDR1 comprising the amino acid sequence of SEQ ID NO:128, a CDR2 comprising the amino acid sequence of SEQ ID NO:129, and a CDR3 comprising the amino acid sequence of SEQ ID NO:130, (kk) a variable heavy chain comprising a CDR1 comprising the amino acid sequence of SEQ ID NO:137, a CDR2 comprising the amino acid sequence of SEQ ID NO:138, and a CDR3 comprising the amino acid sequence of SEQ ID NO:139, (ll) a variable light chain comprising a CDR1 comprising the amino acid sequence of SEQ ID NO: 140, a CDR2 comprising the amino acid sequence of SEQ ID NO: 141, and a CDR3 comprising the amino acid sequence of SEQ ID NO:142, (mm) a variable heavy chain comprising a CDR1 comprising the amino acid sequence of SEQ ID NO:173, a CDR2 comprising the amino acid sequence of SEQ ID NO: 174, and a CDR3 comprising the amino acid sequence of SEQ ID NO:175, (nn) a variable light chain comprising a CDR1 comprising the amino acid sequence of SEQ ID NO: 176, a CDR2 comprising the amino acid sequence of SEQ ID NO: 177, and a CDR3 comprising the amino acid sequence of SEQ ID NO:178, (oo) a variable heavy chain comprising a complementarity determining region (CDR)1 comprising the amino acid sequence of SEQ ID NO:95, a CDR2 comprising the amino acid sequence of SEQ ID NO:96, and a CDR3 comprising the amino acid sequence of SEQ ID NO:97 and a variable light chain comprising a CDR1 comprising the amino acid sequence of SEQ ID NO:98, a CDR2 comprising the amino acid sequence of SEQ ID NO:99, and a CDR3 comprising the amino acid sequence of SEQ ID NO: 100, (pp) a variable heavy chain comprising a CDR1 comprising the amino acid sequence of SEQ ID NO:119, a CDR2 comprising the amino acid sequence of SEQ ID NO: 120, and a CDR3 comprising the amino acid sequence of SEQ ID NO:121 and a variable light chain comprising a CDR1 comprising the amino acid sequence of SEQ ID NO: 122, a CDR2 comprising the amino acid sequence of SEQ ID NO:123, and a CDR3 comprising the amino acid sequence of SEQ ID NO:124, (qq) a variable heavy chain comprising a CDR1 comprising the amino acid sequence of SEQ ID NO:125, a CDR2 comprising the amino acid sequence of SEQ ID NO: 126, and a CDR3 comprising the amino acid sequence of SEQ ID NO: 127 and a variable light chain comprising a CDR1 comprising the amino acid sequence of SEQ ID NO:128, a CDR2 comprising the amino acid sequence of SEQ ID NO: 129, and a CDR3 comprising the amino acid sequence of SEQ ID NO:130, (rr) a variable heavy chain comprising a CDR1 comprising the amino acid sequence of SEQ ID NO:137, a CDR2 comprising the amino acid sequence of SEQ ID NO: 138, and a CDR3 comprising the amino acid sequence of SEQ ID NO:139 and a variable light chain comprising a CDR1 comprising the amino acid sequence of SEQ ID NO:140, a CDR2 comprising the amino acid sequence of SEQ ID NO: 141, and a CDR3 comprising the amino acid sequence of SEQ ID NO:142, (ss) a variable heavy chain comprising a CDR1 comprising the amino acid sequence of SEQ ID NO:173, a CDR2 comprising the amino acid sequence of SEQ ID NO:174, and a CDR3 comprising the amino acid sequence of SEQ ID NO: 175 and a variable light chain comprising a CDR1 comprising the amino acid sequence of SEQ ID NO:176, a CDR2 comprising the amino acid sequence of SEQ ID NO: 177, and a CDR3 comprising the amino acid sequence of SEQ ID NO:178, wherein a disease of iron metabolism in the subject is treated therapeutically or prophylactically. For example, the disease of iron metabolism treated in the method can be selected from the group consisting of Anemia of Chronic Disease (ACD), iron-refractory iron-deficiency anemia, anemia of chronic kidney disease, resistance to erythropoiesis stimulating agents, and β-thalassemia.

In another aspect, the present invention also relates to a method for determining whether a subject has an iron-related disorder. The method comprises the steps of:
  a. measuring the level of membrane-associated or soluble RGMc in a sample from the subject; and
  b. comparing the level of RGMc in the sample with the RGMc level of a normal control or calibrator, wherein an altered level of RGMc indicates that the subject has an iron-related disorder; and
  c. diagnosing the subject as having an iron-related disorder. An altered level of RGMc as compared to the control may indicate that the subject has an iron-related disorder. In the above method, a decreased level of membrane-associated RGMc as compared to the RGMc level of a normal control, indicates that the subject has an iron-related disorder related to iron overload. In the above method, a decreased level of membrane-associated RGMc as compared to the RGMc level of a normal control, indicates that the subject has an iron-related disorder related to iron overload. In the above method, an increased level of membrane-associated RGMc as compared to the RGMc level of a normal control, indicates that the subject has an iron-related disorder related to iron deficiency. In the above method, a decreased level of soluble RGMc as compared to the RGMc level of a normal control, indicates that the subject has an iron-related disorder related to iron deficiency. In the above method, an increased level of soluble RGMc as compared to the RGMc level of a normal control, indicates that the subject has an iron-related disorder related to iron overload. In the above method, the subject has been or may have been previously diagnosed with a disorder selected from the group consisting of cancer, acute infection, chronic infection, autoimmune disease, liver disease, and chronic kidney disease. In the above method, the sample can be selected from the group consisting of a blood sample and a serum sample. In the above method, step a) is an immunoassay, such as an enzyme-linked immunosorbent assay (ELISA).

Specifically, the ELISA may be a sandwich ELISA. In the above method, the level of membrane-associated RGMc or soluble RGMc in a sample can be determined using any of the isolated antibodies described above.

In another aspect, the present invention also relates to a method of determining the presence, amount or concentration of RGMc or a fragment thereof in a test sample. The method comprises the steps of assaying the test sample for RGMc (or a fragment thereof) by an immunoassay employing at least one antibody and at least one detectable label and comprising comparing a signal generated by the detectable label as a direct or indirect indication of the presence, amount or concentration of RGMc in the test sample to a signal generated as a direct or indirect indication of the presence, amount or concentration of RGMc in a control or calibrator, wherein one of the at least one antibody is an isolated antibody, which specifically binds to RGMc or a fragment thereof, and wherein the antibody comprises a domain or region selected from the group consisting of: (a) a variable heavy domain region comprising the amino acid sequence of SEQ ID NO:3, (b) a variable light domain region comprising the amino acid sequence of SEQ ID NO:4, (c) a variably heavy domain region comprising the amino acid sequence of SEQ ID NO:5, (d) a variable light domain region comprising the amino acid sequence of SEQ ID NO:6, (e) a variably heavy domain region comprising the amino acid sequence of SEQ ID NO:7, (f) a variable light domain region comprising the amino acid sequence of SEQ ID NO:8, (g) a variably heavy domain region comprising the amino acid sequence of SEQ ID NO:9, (h) a variable light domain region comprising the amino acid sequence of SEQ ID NO:10, (i) a variable heavy chain comprising a complementarity determining region (CDR)1 comprising the amino acid sequence of SEQ ID NO:11, a CDR2 comprising the amino acid sequence of SEQ ID NO: 12, and a CDR3 comprising the amino acid sequence of SEQ ID NO:13, (j) a variable light chain comprising a CDR1 comprising the amino acid sequence of SEQ ID NO: 14, a CDR2 comprising the amino acid sequence of SEQ ID NO:15, and a CDR3 comprising the amino acid sequence of SEQ ID NO: 16, (k) a variable heavy chain comprising a CDR1 comprising the amino acid sequence of SEQ ID NO:17, a CDR2 comprising the amino acid sequence of SEQ ID NO: 18, and a CDR3 comprising the amino acid sequence of SEQ ID NO:19, (l) a variable light chain comprising a CDR1 comprising the amino acid sequence of SEQ ID NO:20, a CDR2 comprising the amino acid sequence of SEQ ID NO:21, and a CDR3 comprising the amino acid sequence of SEQ ID NO:22, (m) a variable heavy chain comprising a CDR1 comprising the amino acid sequence of SEQ ID NO:23, a CDR2 comprising the amino acid sequence of SEQ ID NO:24, and a CDR3 comprising the amino acid sequence of SEQ ID NO:25, (n) a variable light chain comprising a CDR1 comprising the amino acid sequence of SEQ ID NO:26, a CDR2 comprising the amino acid sequence of SEQ ID NO:27, and a CDR3 comprising the amino acid sequence of SEQ ID NO:28, (o) a variable heavy chain comprising a CDR1 comprising the amino acid sequence of SEQ ID NO:29, a CDR2 comprising the amino acid sequence of SEQ ID NO:30, and a CDR3 comprising the amino acid sequence of SEQ ID NO:31, (p) a variable light chain comprising a CDR1 comprising the amino acid sequence of SEQ ID NO:32, a CDR2 comprising the amino acid sequence of SEQ ID NO:33, and a CDR3 comprising the amino acid sequence of SEQ ID NO:34, (q) a variable heavy chain comprising a complementarity determining region (CDR)1 comprising the amino acid sequence of SEQ ID NO: 11, a CDR2 comprising the amino acid sequence of SEQ ID NO: 12, and a CDR3 comprising the amino acid sequence of SEQ ID NO: 13 and a variable light chain comprising a CDR1 comprising the amino acid sequence of SEQ ID NO:14, a CDR2 comprising the amino acid sequence of SEQ ID NO: 15, and a CDR3 comprising the amino acid sequence of SEQ ID NO: 16, (r) a variable heavy chain comprising a CDR1 comprising the amino acid sequence of SEQ ID NO: 17, a CDR2 comprising the amino acid sequence of SEQ ID NO: 18, and a CDR3 comprising the amino acid sequence of SEQ ID NO:19 and a variable light chain comprising a CDR1 comprising the amino acid sequence of SEQ ID NO:20, a CDR2 comprising the amino acid sequence of SEQ ID NO:21, and a CDR3 comprising the amino acid sequence of SEQ ID NO:22, (s) a variable heavy chain comprising a CDR1 comprising the amino acid sequence of SEQ ID NO:23, a CDR2 comprising the amino acid sequence of SEQ ID NO:24, and a CDR3 comprising the amino acid sequence of SEQ ID NO:25 and a variable light chain comprising a CDR1 comprising the amino acid sequence of SEQ ID NO:26, a CDR2 comprising the amino acid sequence of SEQ ID NO:27, and a CDR3 comprising the amino acid sequence of SEQ ID NO:28, (t) a variable heavy chain comprising a CDR1 comprising the amino acid sequence of SEQ ID NO:29, a CDR2 comprising the amino acid sequence of SEQ ID NO:30, and a CDR3 comprising the amino acid sequence of SEQ ID NO:31 and a variable light chain comprising a CDR1 comprising the amino acid sequence of SEQ ID NO:32, a CDR2 comprising the amino acid sequence of SEQ ID NO:33, and a CDR3 comprising the amino acid sequence of SEQ ID NO:34, (u) a variable heavy domain region comprising the amino acid sequence of SEQ ID NO:43, (v) a variable light domain region comprising the amino acid sequence of SEQ ID NO:44, (w) a variably heavy domain region comprising the amino acid sequence of SEQ ID NO:51, (x) a variable light domain region comprising the amino acid sequence of SEQ ID NO:52, (y) a variably heavy domain region comprising the amino acid sequence of SEQ ID NO:53, (z) a variable light domain region comprising the amino acid sequence of SEQ ID NO:54, (aa) a variably heavy domain region comprising the amino acid sequence of SEQ ID NO:57, (bb) a variable light domain region comprising the amino acid sequence of SEQ ID NO:58, (cc) a variably heavy domain region comprising the amino acid sequence of SEQ ID NO:69, (dd) a variable light domain region comprising the amino acid sequence of SEQ ID NO:70, (ee) a variable heavy chain comprising a complementarity determining region (CDR)1 comprising the amino acid sequence of SEQ ID NO:95, a CDR2 comprising the amino acid sequence of SEQ ID NO:96, and a CDR3 comprising the amino acid sequence of SEQ ID NO:97, (ff) a variable light chain comprising a CDR1 comprising the amino acid sequence of SEQ ID NO:98, a CDR2 comprising the amino acid sequence of SEQ ID NO:99, and a CDR3 comprising the amino acid sequence of SEQ ID NO: 100, (gg) a variable heavy chain comprising a CDR1 comprising the amino acid sequence of SEQ ID NO:119, a CDR2 comprising the amino acid sequence of SEQ ID NO:120, and a CDR3 comprising the amino acid sequence of SEQ ID NO: 121, (hh) a variable light chain comprising a CDR1 comprising the amino acid sequence of SEQ ID NO: 122, a CDR2 comprising the amino acid sequence of SEQ ID NO: 123, and a CDR3 comprising the amino acid sequence of SEQ ID NO:124, (ii) a variable heavy chain comprising a CDR1 comprising the amino acid sequence of SEQ ID NO:125, a CDR2 comprising the amino acid sequence of SEQ ID NO: 126, and a CDR3 comprising the amino acid sequence of SEQ ID NO: 127, (jj) a variable light chain comprising a CDR1 comprising the amino acid sequence of SEQ ID NO: 128, a CDR2 comprising the amino acid sequence of SEQ ID NO:129, and a CDR3 comprising the amino acid sequence of SEQ ID NO:130, (kk) a variable heavy chain comprising a CDR1 comprising the amino acid sequence of SEQ ID NO:137, a CDR2 comprising the amino acid sequence of SEQ ID NO: 138, and a CDR3 comprising the amino acid sequence of SEQ ID NO: 139, (ll) a variable light chain comprising a CDR1 comprising the amino acid sequence of SEQ ID NO: 140, a CDR2 comprising the amino acid sequence of SEQ ID NO:141, and a CDR3 comprising the amino acid sequence of SEQ ID NO:142, (mm) a variable heavy chain comprising a CDR1 comprising the amino acid sequence of SEQ ID NO: 173, a CDR2 comprising the amino acid sequence of SEQ ID NO: 174, and a CDR3 comprising the amino acid sequence of SEQ ID NO:175, (nn) a variable light chain comprising a CDR1 comprising the amino acid sequence of SEQ ID NO: 176, a CDR2 comprising the amino acid sequence of SEQ ID NO: 177, and a CDR3 comprising the amino acid sequence of SEQ ID NO:178, (oo) a variable heavy chain comprising a complementarity determining region (CDR)1 comprising the amino acid sequence of SEQ ID NO:95, a CDR2 comprising the amino acid sequence of SEQ ID NO:96, and a CDR3 comprising the amino acid sequence of SEQ ID NO:97 and a variable light chain comprising a CDR1 comprising the amino acid sequence of SEQ ID NO:98, a CDR2 comprising the amino acid sequence of SEQ ID NO:99, and a CDR3 comprising the amino acid sequence of SEQ ID NO: 100, (pp) a variable heavy chain comprising a CDR1 comprising the amino acid sequence of SEQ ID NO:119, a CDR2 comprising the amino acid sequence of SEQ ID NO: 120, and a CDR3 comprising the amino acid sequence of SEQ ID NO: 121 and a variable light chain comprising a CDR1 comprising the amino acid sequence of SEQ ID NO: 122, a CDR2 comprising the amino acid sequence of SEQ ID NO: 123, and a CDR3 comprising the amino acid sequence of SEQ ID NO:124, (qq) a variable heavy chain comprising a CDR1 comprising the amino acid sequence of SEQ ID NO:125, a CDR2 comprising the amino acid sequence of SEQ ID NO: 126, and a CDR3 comprising the amino acid sequence of SEQ ID NO: 127 and a variable light chain comprising a CDR1 comprising the amino acid sequence of SEQ ID NO: 128, a CDR2 comprising the amino acid sequence of SEQ ID NO: 129, and a CDR3 comprising the amino acid sequence of SEQ ID NO:130, (rr) a variable heavy chain comprising a CDR1 comprising the amino acid sequence of SEQ ID NO:137, a CDR2 comprising the amino acid sequence of SEQ ID NO:138, and a CDR3 comprising the amino acid sequence of SEQ ID NO: 139 and a variable light chain comprising a CDR1 comprising the amino acid sequence of SEQ ID NO:140, a CDR2 comprising the amino acid sequence of SEQ ID NO:141, and a CDR3 comprising the amino acid sequence of SEQ ID NO:142, (ss) a variable heavy chain comprising a CDR1 comprising the amino acid sequence of SEQ ID NO:173, a CDR2 comprising the amino acid sequence of SEQ ID NO: 174, and a CDR3 comprising the amino acid sequence of SEQ ID NO: 175 and a variable light chain comprising a CDR1 comprising the amino acid sequence of SEQ ID NO:176, a CDR2 comprising the amino acid sequence of SEQ ID NO: 177, and a CDR3 comprising the amino acid sequence of SEQ ID NO:178, whereupon the presence, amount or concentration of RGMc or a fragment thereof in a test sample is determined.

In the above method, the presence, amount or concentration of RGMc or a fragment thereof in a test sample is used to determine or assess whether a subject has or is at risk of developing an iron-related disorder. In the above method, the RGMc is membrane-associated RGMc or soluble RGMc. In the above method, a decreased level of membrane-associated RGMc as compared to the RGMc level of a normal control indicates that the subject has an iron-related disorder related to iron overload. In the above method, an increased level of membrane-associated RGMc as compared to the RGMc level of a normal control indicates that the subject has an iron-related disorder related to iron deficiency. In the above method, a decreased level of soluble RGMc as compared to the RGMc level of a normal control indicates that the subject has an iron-related disorder related to iron deficiency. In the above method, an increased level of soluble RGMc as compared to the RGMc level of a normal control indicates that the subject has an iron-related disorder related to iron overload. In the above method, the iron-related disorder is selected from the group consisting of cancer, acute infection, chronic infection, autoimmune disease, liver disease, and chronic kidney disease. Additionally, the above method can further comprise the following steps:

a. contacting the test sample with at least one capture antibody, which binds to an epitope on RGMc (or a fragment thereof) so as to form a capture antibody/RGMc (or a fragment thereof) complex, b. contacting the capture antibody/RGMc (or a fragment thereof) complex with at least one detection antibody, which comprises a detectable label and binds to an epitope on RGMc (or a fragment thereof) that is not bound by the capture antibody, to form a capture antibody/RGMc (or a fragment thereof)/detection antibody complex, and c. determining the presence, amount or concentration of RGMc (or a fragment thereof) in the test sample based on the signal generated by the detectable label in the capture antibody/RGMc (or a fragment thereof)/detection antibody complex formed in (b), whereupon the presence, amount or concentration of RGMc (or a fragment thereof) in the test sample is determined.

Alternatively, the above method can further comprise the following steps:

a. contacting the test sample with at least one capture antibody, which binds to an epitope on RGMc (or a fragment thereof) so as to form a capture antibody/RGMc (or a fragment thereof) complex, and simultaneously or sequentially, in either order, contacting the test sample with detectably labeled RGMc (or a fragment thereof), which can compete with any RGMc (or a fragment thereof) in the test sample for binding to the at least one capture antibody, wherein any RGMc (or a fragment thereof) present in the test sample and the detectably labeled RGMc compete with each other to form a capture antibody/RGMc (or a fragment thereof) complex and a capture antibody/detectably labeled RGMc (or a fragment thereof) complex, respectively, and b. determining the presence, amount or concentration of RGMc in the test sample based on the signal generated by the detectable label in the capture antibody/detectably labeled RGMc (or a fragment thereof) complex formed in (b), wherein the signal generated by the detectable label in the capture antibody/detectably labeled RGMc (or a fragment thereof) complex is inversely proportional to the amount or concentration of RGMc in the test sample, whereupon the presence, amount or concentration of RGMc in the test sample is determined. The above method can further comprise assaying the test sample for hepcidin.

In another aspect, the present invention also relates to a method for determining whether a subject has an iron-related disorder. The method comprises the steps of:

a. measuring the level of membrane-associated or soluble RGMc in a first sample from the subject;

b. measuring the level of hepcidin in a second sample from the subject;

c. comparing the level of RGMc in the first sample with the level of RGMc in a normal control or calibrator, and d. comparing the level of hepcidin in the second sample with the level of hepcidin in a normal control or calibrator, wherein an altered level of each RGMc and hepcidin indicates that the subject has an iron-related disorder; and e. diagnosing the subject as having an iron-related disorder.

In the above method, a decreased level of membrane-associated RGMc as compared to the level of membrane-associated RGMc in a normal control, indicates that the subject has an iron-related disorder related to iron overload. In the above method, an increased level of membrane-associated RGMc as compared to the level of membrane-associated RGMc in a normal control, indicates that the subject has an iron-related disorder related to iron deficiency. In the above method, a decreased level of soluble RGMc as compared to the level of soluble RGMc in a normal control indicates that the subject has an iron-related disorder related to iron deficiency. In the above method, an increased level of soluble RGMc as compared to the level of soluble RGMc in a normal control indicates that the subject has an iron-related disorder related to iron overload. In the above method, a decreased level of hepcidin as compared to the level of hepcidin in a normal control indicates that the subject has an iron-related disorder related to iron overload. In the above method, an increased level of hepcidin as compared to the level of hepcidin in a normal control indicates that the subject has an iron-related disorder related to iron deficiency.

In the above method, a subject has been diagnosed with a disorder selected from the group consisting of cancer, acute infection, chronic infection, autoimmune disease, liver disease, and chronic kidney disease. In the above method, the level of membrane-associated or soluble RGMc and the level of hepcidin in each of the first and second samples are determined sequentially. In the above method, the level of membrane-associated or soluble RGMc and the level of hepcidin in each of the first and second samples are determined simulatenously.

In the above method, the sample is selected from the group consisting of a blood sample and a serum sample. In the above method, step a) is an enzyme-linked immunosorbent assay (ELISA). For example, the ELISA is a sandwich ELISA. In the above method, the level membrane-associated RGMc or soluble RGMc in a sample is determined using any of the above described isolated antibodies.

Any assay for RGMc (such as membrane-associated RGMc, soluble RGMc, fragments of membrane-associated RGMc, fragments of soluble RGMc, variants of RGMc (membrane-associated or soluble RGMc) or any combinations thereof) and hepcidin can be simultaneous or sequential, in either order, using the same type of methodology or different methodology and using the same test sample or a different test sample obtained from the same source, such as the same patient. Alternatively, the method may also comprise using data obtained from the assay of a test sample obtained from the same source, such as the same patient, but either assayed or obtained and assayed for hepcidin at a different point in time.

In another aspect, the present invention also relates to a kit for assaying a test sample for RGMc (or a fragment thereof). The kit can comprise at least one component for assaying the test sample for RGMc (or a fragment thereof) and instructions for assaying the test sample for RGMc (or a fragment thereof), wherein the at least one component includes at least one composition comprising an isolated antibody that specifically binds to RGMc (or a fragment thereof), wherein the antibody comprises a domain or region selected from the group consisting of: (a) a variable heavy domain region comprising the amino acid sequence of SEQ ID NO:3, (b) a variable light domain region comprising the amino acid sequence of SEQ ID NO:4, (c) a variably heavy domain region comprising the amino acid sequence of SEQ ID NO:5, (d) a variable light domain region comprising the amino acid sequence of SEQ ID NO:6, (e) a variably heavy domain region comprising the amino acid sequence of SEQ ID NO:7, (f) a variable light domain region comprising the amino acid sequence of SEQ ID NO:8, (g) a variably heavy domain region comprising the amino acid sequence of SEQ ID NO:9, (h) a variable light domain region comprising the amino acid sequence of SEQ ID NO: 10, (i) a variable heavy chain comprising a complementarity determining region (CDR)1 comprising the amino acid sequence of SEQ ID NO:11, a CDR2 comprising the amino acid sequence of SEQ ID NO: 12, and a CDR3 comprising the amino acid sequence of SEQ ID NO: 13, (j) a variable light chain comprising a CDR1 comprising the amino acid sequence of SEQ ID NO: 14, a CDR2 comprising the amino acid sequence of SEQ ID NO: 15, and a CDR3 comprising the amino acid sequence of SEQ ID NO:16, (k) a variable heavy chain comprising a CDR1 comprising the amino acid sequence of SEQ ID NO:17, a CDR2 comprising the amino acid sequence of SEQ ID NO: 18, and a CDR3 comprising the amino acid sequence of SEQ ID NO: 19, (l) a variable light chain comprising a CDR1 comprising the amino acid sequence of SEQ ID NO:20, a CDR2 comprising the amino acid sequence of SEQ ID NO:21, and a CDR3 comprising the amino acid sequence of SEQ ID NO:22, (m) a variable heavy chain comprising a CDR1 comprising the amino acid sequence of SEQ ID NO:23, a CDR2 comprising the amino acid sequence of SEQ ID NO:24, and a CDR3 comprising the amino acid sequence of SEQ ID NO:25, (n) a variable light chain comprising a CDR1 comprising the amino acid sequence of SEQ ID NO:26, a CDR2 comprising the amino acid sequence of SEQ ID NO:27, and a CDR3 comprising the amino acid sequence of SEQ ID NO:28, (o) a variable heavy chain comprising a CDR1 comprising the amino acid sequence of SEQ ID NO:29, a CDR2 comprising the amino acid sequence of SEQ ID NO:30, and a CDR3 comprising the amino acid sequence of SEQ ID NO:31, (p) a variable light chain comprising a CDR1 comprising the amino acid sequence of SEQ ID NO:32, a CDR2 comprising the amino acid sequence of SEQ ID NO:33, and a CDR3 comprising the amino acid sequence of SEQ ID NO:34, (q) a variable heavy chain comprising a complementarity determining region (CDR)1 comprising the amino acid sequence of SEQ ID NO: 11, a CDR2 comprising the amino acid sequence of SEQ ID NO: 12, and a CDR3 comprising the amino acid sequence of SEQ ID NO: 13 and a variable light chain comprising a CDR1 comprising the amino acid sequence of SEQ ID NO:14, a CDR2 comprising the amino acid sequence of SEQ ID NO: 15, and a CDR3 comprising the amino acid sequence of SEQ ID NO: 16, (r) a variable heavy chain comprising a CDR1 comprising the amino acid sequence of SEQ ID NO: 17, a CDR2 comprising the amino acid sequence of SEQ ID NO: 18, and a CDR3 comprising the amino acid sequence of SEQ ID NO: 19 and a variable light chain comprising a CDR1 comprising the amino acid sequence of SEQ ID NO:20, a CDR2 comprising the amino acid sequence of SEQ ID NO:21, and a CDR3 comprising the amino acid sequence of SEQ ID NO:22, (s) a variable heavy chain comprising a CDR1 comprising the amino acid sequence of SEQ ID NO:23, a CDR2 comprising the amino acid sequence of SEQ ID NO:24, and a CDR3 comprising the amino acid sequence of SEQ ID NO:25 and a variable light chain comprising a CDR1 comprising the amino acid sequence of SEQ ID NO:26, a CDR2 comprising the amino acid sequence of SEQ ID NO:27, and a CDR3 comprising the amino acid sequence of SEQ ID NO:28, (t) a variable heavy chain comprising a CDR1 comprising the amino acid sequence of SEQ ID NO:29, a CDR2 comprising the amino acid sequence of SEQ ID NO:30, and a CDR3 comprising the amino acid sequence of SEQ ID NO:31 and a variable light chain comprising a CDR1 comprising the amino acid sequence of SEQ ID NO:32, a CDR2 comprising the amino acid sequence of SEQ ID NO:33, and a CDR3 comprising the amino acid sequence of SEQ ID NO:34, (u) a variable heavy domain region comprising the amino acid sequence of SEQ ID NO:43, (v) a variable light domain region comprising the amino acid sequence of SEQ ID NO:44, (w) a variably heavy domain region comprising the amino acid sequence of SEQ ID NO:51, (x) a variable light domain region comprising the amino acid sequence of SEQ ID NO:52, (y) a variably heavy domain region comprising the amino acid sequence of SEQ ID NO:53, (z) a variable light domain region comprising the amino acid sequence of SEQ ID NO:54, (aa) a variably heavy domain region comprising the amino acid sequence of SEQ ID NO:57, (bb) a variable light domain region comprising the amino acid sequence of SEQ ID NO:58, (cc) a variably heavy domain region comprising the amino acid sequence of SEQ ID NO:69, (dd) a variable light domain region comprising the amino acid sequence of SEQ ID NO:70, (ee) a variable heavy chain comprising a complementarity determining region (CDR)1 comprising the amino acid sequence of SEQ ID NO:95, a CDR2 comprising the amino acid sequence of SEQ ID NO:96, and a CDR3 comprising the amino acid sequence of SEQ ID NO:97, (ff) a variable light chain comprising a CDR1 comprising the amino acid sequence of SEQ ID NO:98, a CDR2 comprising the amino acid sequence of SEQ ID NO:99, and a CDR3 comprising the amino acid sequence of SEQ ID NO:100, (gg) a variable heavy chain comprising a CDR1 comprising the amino acid sequence of SEQ ID NO:119, a CDR2 comprising the amino acid sequence of SEQ ID NO:120, and a CDR3 comprising the amino acid sequence of SEQ ID NO: 121, (hh) a variable light chain comprising a CDR1 comprising the amino acid sequence of SEQ ID NO: 122, a CDR2 comprising the amino acid sequence of SEQ ID NO: 123, and a CDR3 comprising the amino acid sequence of SEQ ID NO:124, (ii) a variable heavy chain comprising a CDR1 comprising the amino acid sequence of SEQ ID NO: 125, a CDR2 comprising the amino acid sequence of SEQ ID NO: 126, and a CDR3 comprising the amino acid sequence of SEQ ID NO: 127, (jj) a variable light chain comprising a CDR1 comprising the amino acid sequence of SEQ ID NO:128, a CDR2 comprising the amino acid sequence of SEQ ID NO: 129, and a CDR3 comprising the amino acid sequence of SEQ ID NO:130, (kk) a variable heavy chain comprising a CDR1 comprising the amino acid sequence of SEQ ID NO: 137, a CDR2 comprising the amino acid sequence of SEQ ID NO: 138, and a CDR3 comprising the amino acid sequence of SEQ ID NO:139, (ll) a variable light chain comprising a CDR1 comprising the amino acid sequence of SEQ ID NO: 140, a CDR2 comprising the amino acid sequence of SEQ ID NO: 141, and a CDR3 comprising the amino acid sequence of SEQ ID NO:142, (mm) a variable heavy chain comprising a CDR1 comprising the amino acid sequence of SEQ ID NO: 173, a CDR2 comprising the amino acid sequence of SEQ ID NO:174, and a CDR3 comprising the amino acid sequence of SEQ ID NO:175, (nn) a variable light chain comprising a CDR1 comprising the amino acid sequence of SEQ ID NO: 176, a CDR2 comprising the amino acid sequence of SEQ ID NO: 177, and a CDR3 comprising the amino acid sequence of SEQ ID NO:178, (oo) a variable heavy chain comprising a complementarity determining region (CDR)1 comprising the amino acid sequence of SEQ ID NO:95, a CDR2 comprising the amino acid sequence of SEQ ID NO:96, and a CDR3 comprising the amino acid sequence of SEQ ID NO:97 and a variable light chain comprising a CDR1 comprising the amino acid sequence of SEQ ID NO:98, a CDR2 comprising the amino acid sequence of SEQ ID NO:99, and a CDR3 comprising the amino acid sequence of SEQ ID NO: 100, (pp) a variable heavy chain comprising a CDR1 comprising the amino acid sequence of SEQ ID NO:119, a CDR2 comprising the amino acid sequence of SEQ ID NO: 120, and a CDR3 comprising the amino acid sequence of SEQ ID NO: 121 and a variable light chain comprising a CDR1 comprising the amino acid sequence of SEQ ID NO: 122, a CDR2 comprising the amino acid sequence of SEQ ID NO: 123, and a CDR3 comprising the amino acid sequence of SEQ ID NO:124, (qq) a variable heavy chain comprising a CDR1 comprising the amino acid sequence of SEQ ID NO:125, a CDR2 comprising the amino acid sequence of SEQ ID NO:126, and a CDR3 comprising the amino acid sequence of SEQ ID NO: 127 and a variable light chain comprising a CDR1 comprising the amino acid sequence of SEQ ID NO: 128, a CDR2 comprising the amino acid sequence of SEQ ID NO: 129, and a CDR3 comprising the amino acid sequence of SEQ ID NO:130, (rr) a variable heavy chain comprising a CDR1 comprising the amino acid sequence of SEQ ID NO:137, a CDR2 comprising the amino acid sequence of SEQ ID NO:138, and a CDR3 comprising the amino acid sequence of SEQ ID NO: 139 and a variable light chain comprising a CDR1 comprising the amino acid sequence of SEQ ID NO: 140, a CDR2 comprising the amino acid sequence of SEQ ID NO: 141, and a CDR3 comprising the amino acid sequence of SEQ ID NO:142, (ss) a variable heavy chain comprising a CDR1 comprising the amino acid sequence of SEQ ID NO:173, a CDR2 comprising the amino acid sequence of SEQ ID NO: 174, and a CDR3 comprising the amino acid sequence of SEQ ID NO: 175 and a variable light chain comprising a CDR1 comprising the amino acid sequence of SEQ ID NO:176, a CDR2 comprising the amino acid sequence of SEQ ID NO: 177, and a CDR3 comprising the amino acid sequence of SEQ ID NO:178, wherein the antibody is optionally detectably labeled. In the above kit, the RGMc or a fragment thereof assayed in the test sample is used to determine or assess whether a subject has or is at risk of developing an iron-related disorder. Additionally, the RGMc assayed is RGMc is membrane-associated RGMc or soluble RGMc. The kit can further comprise at least one component for assaying a test sample for hepcidin and instructions for assaying the test sample for hepcidin.

BRIEF DESCRIPTION OF THE DRAWINGS

FIG. 3 shows the data from rats treated once weekly by intravenous injection of 0, 20, 60 or 200 mg/kg. Blood iron levels were significantly increased at all h5F9.23 doses used (significance: P<0.01; *P<0.001). This data shows that h5F9.23 increases blood iron levels in rats.

(FIG. 11A) Schematic of RGM-mediated BMP reporter assay. (FIG. 11B) The rat hybridoma mAb 5F9, h5F9.23 and its affinity matured Abs inhibited RGMc-mediated luc activity in a dose-dependent manner. The IC50 values are shown next to the legend. The Y axis represents luciferase activity as relative light units (RLU).

FIG. 12 is a histogram that shows the results in Example 5 where female cyno monkeys were treated with different doses of humanized antibody 5F9.23 (h5F9.23). Monkeys were injected subcutaneously, subcutaneously with 60 mg/kg (sc) or intraveneously with 20, 60, 200 mg/kg (iv) once per week for 4 weeks. At day 22 primate serum blood was collected at 0.5 hours, 4 hours, 24 hours post antibody application (4th dose). Hepcidin was measured using a mass spectrometric method. ***p<0.001: significance versus pretest, *p<0.05: significance versus pretest, p<0.05: significance versus control.

FIG. 16A shows that the control antibody hIgG does not change significantly the low hemoglobin level of the anemic rats on days 41, 47 and 51. *p<0.05: significance versus DO hemoglobin level. FIG. 16B shows that humanized monoclonal antibody that was selective for RGM A does not change significantly the low haemoglobin level of the anemic rates on days 41, 47 and 51. *p<0.05, p<0.01, significance versus DO hemoglobin level. FIG. 16C shows that antibody h5F9.AM8 significantly increases the low hemoglobin level (D24) of the anemic rats on days 41, 47 and 51. *p<0.001, significance versus Day 0 (DO) hemoglobin level. D41: *p<0.05 significance versus D24, D47/55: *p<0.05 significance versus D24. FIG. 16D shows that antibody h5F9.23, increases the low hemoglobin level (day 24 (D24) of the anemic rats on days 41, 47 and 51.*p<0.05; **p<0.001, significance versus DO hemoglobin level at day 41: *p<0.05 significance versus days 24, 47 and 51: p<0.05 significance versus day.

DETAILED DESCRIPTION

Figure 1:
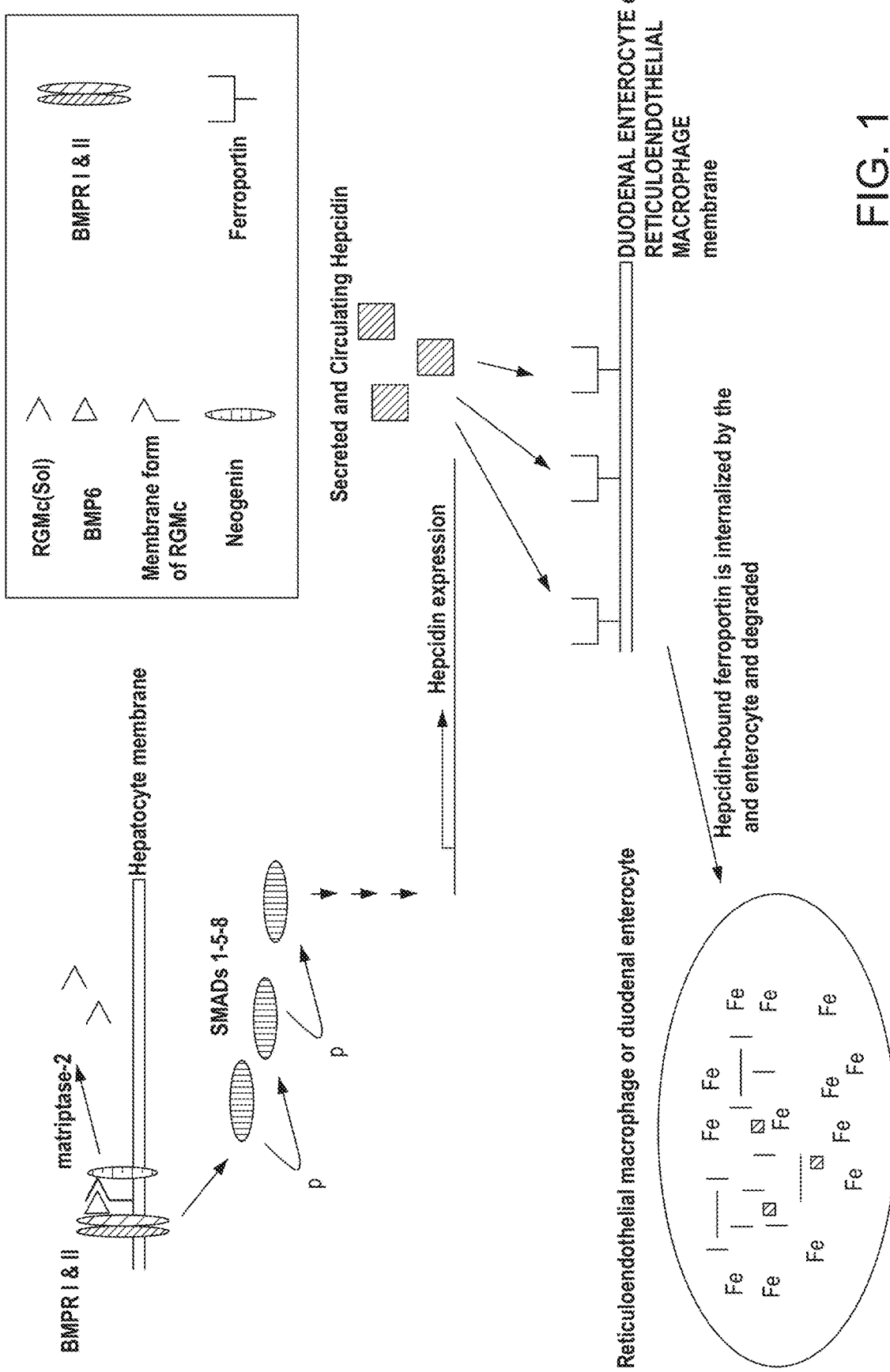
FIG. 1 shows a simplified schematic of a signaling pathway related to iron homeostasis.
Figure 2:
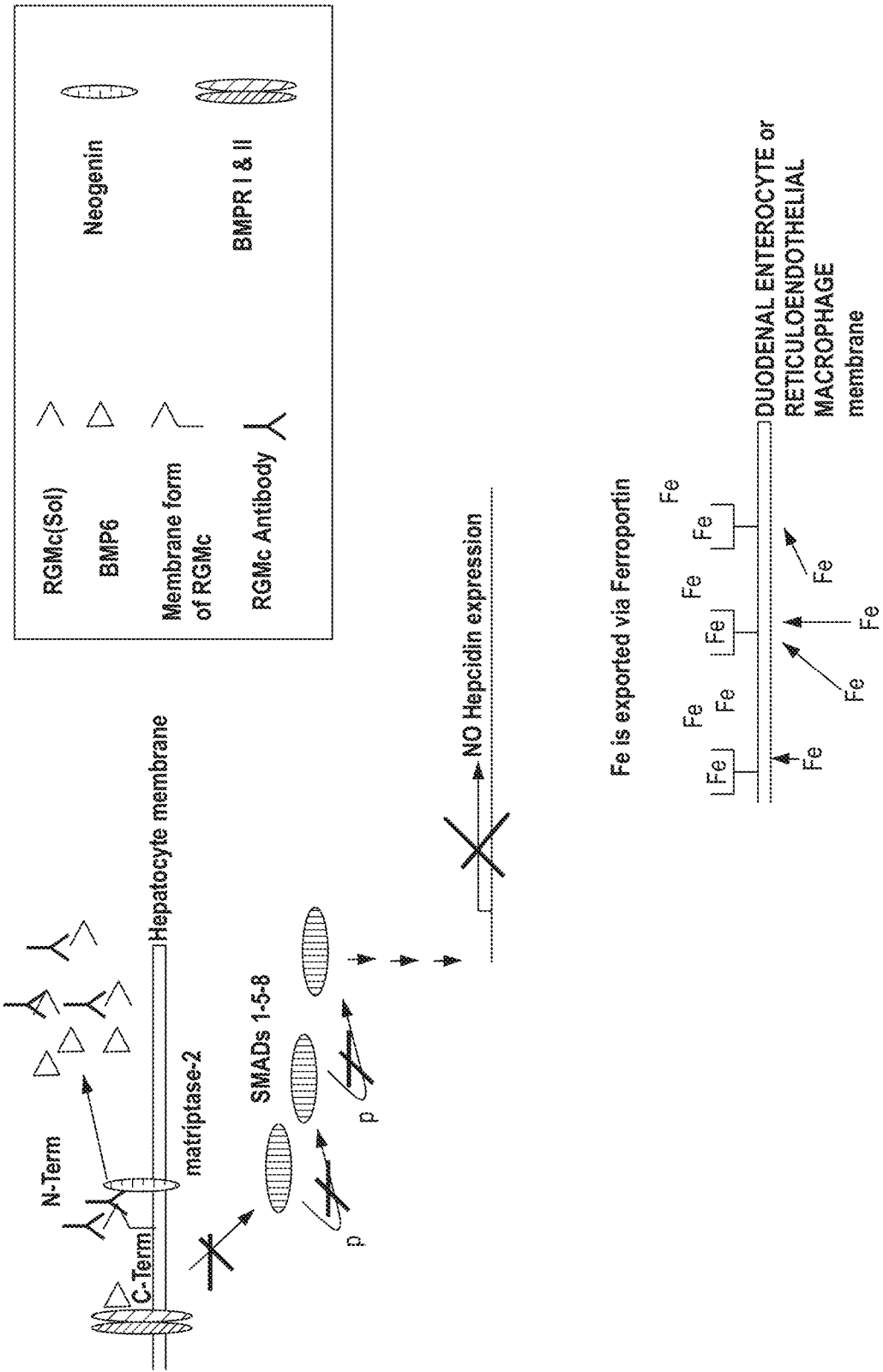
FIG. 2 shows another simplified schematic of a signaling pathway related to iron homeostasis.

RGMc is a glycosylphosphatidylinositol ("GPI") anchored membrane protein expressed in muscle, the retina and periportal hepatocytes. RGMc works in conjunction with hepcidin via signaling proteins to maintain iron homeostasis in the body. See, for example, Severyn et al., Biochem. J., 422:393-403 (2009) and Pietrangelo, J. Hepatology, 54:173-181 (2011). Cell membrane RGMc binds to neogenin and facilitates signaling through bone morphogenetic proteins (BMPs), which trigger intracellular signaling through downstream effectors to promote hepcidin gene expression. See again, for example, Pietrangelo, J. Hepatology, 54:173-181 (2011). Soluble RGMc is released by cleavage of membrane bound RGMc by a serine protease, matriptase-2 (TMPRSS6). The release of soluble RGMc is induced by decreasing extracellular concentrations of iron and, conversely, inhibited by increased extracellular concentrations of iron. See again, for example, Severyn et al., Biochem. J., 422:393-403 (2009) and FIG. 1. The soluble form of RGMc sequesters BMP6 from membrane bound RGMc, thereby preventing the induction of hepcidin expression. See FIG. 2.

Upon BMP binding to BMP receptors I and II, a membrane associated complex is formed with neogenin, BMP6 and RGMc. This complex, along with intracellular proteins, called Smads (Smads 1, 5 and 8), transduce extracellular signals thereby initiating a signaling pathway that governs hepcidin expression and, ultimately, systemic iron metabolism. See again, for example, Pietrangelo, J. Hepatology, 54:173-181 (2011) and FIG. 1. Hepcidin binds to ferroportin, the exclusive iron exporter of mammals. Upon hepcidin binding to ferroportin, ferroportin is internalized by macrophages and duodenal enterocytes where it is degraded, thereby shutting down the iron export pathway. See, for example, Hentz et al, Cell, 142:24-38 (2010) and Cheng et al., Clin. Exp. Med., 11:33-42 (2011).

Both macrophages and duodenal enterocytes express ferroportin; at high hepcidin levels, the hepcidin-induced degradation of ferroportin shuts down the only available iron export pathway. As a consequence, both macrophages and duodenal enterocytes accumulate large amounts of intracellular iron. See FIG. 1. Anemia of chronic disease ("ACD") is a common consequence, as these cells are no longer able to release iron into the blood. See again, for example, Cheng et al., Clin. Exp. Med., 11:33-42 (2011).

RGMc-specific antibodies interrupt the normal expression of hepcidin, which directly regulates iron concentration in the plasma and the distribution of iron to a variety of tissues. The antibodies may prevent binding between BMPs and RGMc. The antibodies may prevent binding between BMPs and the N-terminus of RGMc. A consequence of this action, is the decreased, or inhibited, expression of hepcidin. As hepcidin levels decrease, the ferroportin-dependent export of iron is increased because hepcidin no longer available to bind ferroportin and induce its internalization and degradation. See FIG. 2.

The inventors have made the surprising discovery that antibodies, which bind to Repulsive Guidance Molecule c ("RGMc"), may be used to regulate iron metabolism. Provided herein are antibodies that interrupt the normal expression of hepcidin, which directly regulates iron concentration in plasma and the distribution of iron to a variety of tissues. Excess levels of hepcidin causes iron-restricted anemia. For example, pronounced increases in hepcidin levels have been reported in patients suffering from ACD and in patients suffering with acute inflammation (AI). Slightly increased hepcidin levels were observed in patients suffering from ACD and iron-deficiency anemia (ACD-IDA). Patients suffering only from iron deficiency anemia (IDA) showed a trend towards lower serum hepcidin levels. For example, serum hepcidin levels have been shown to be 177.58 µg/l (+/−119.84) in healthy controls, 434.83 µg//l (+/−217) in ACD patients, 410.08 µg/l (+/−299.96) in AI patients, 238.32 µg/l (+/−93.85) in ACD-IDA patients and a slightly decreased serum hepcidiin level in IDA patients 110.79 µg/l (+/−19.22). In contrast, hemochromatosis is characterized by low serum hepcidin levels. In addition, β-thalassaemia is a disease where hepcidin levels may be low.

The antibodies disclosed herein are useful in the treatment of diseases of iron metabolism. In addition, the antibodies disclosed herein are use in diagnostic assays for determining whether a subject has an iron-related disorder.

1. Definitions

The terminology used herein is for the purpose of describing particular embodiments only and is not intended to be limiting. As used in the specification and the appended claims, the singular forms "a," "and" and "the" include plural references unless the context clearly dictates otherwise.

a. About

"About" as used herein may refer to approximately a +/−10% variation from the stated value. It is to be understood that such a variation is always included in any given value provided herein, whether or not specific reference is made to it.

b. Affinity Matured Antibody

"Affinity Matured Antibody" is used herein to refer to an antibody with one or more alterations in one or more CDRs, which result in an improvement in the affinity (i.e. $K_D$, $k_d$ or $k_a$) of the antibody for a target antigen compared to a parent antibody, which does not possess the alteration(s). Exemplary affinity matured antibodies will have nanomolar or even picomolar affinities for the target antigen. A variety of procedures for producing affinity matured antibodies are known in the art, including the screening of a combinatory antibody library that has been prepared using bio-display. For example, Marks et al., BioTechnology, 10: 779-783 (1992) describes affinity maturation by VH and VL domain shuffling. Random mutagenesis of CDR and/or framework residues is described by Barbas et al., Proc. Nat. Acad. Sci. USA, 91: 3809-3813 (1994); Schier et al., Gene, 169: 147-155 (1995); Yelton et al., J. Immunol., 155: 1994-2004 (1995); Jackson et al., J. Immunol., 154(7): 3310-3319 (1995); and Hawkins et al, J. Mol. Biol., 226: 889-896 (1992). Selective mutation at selective mutagenesis positions and at contact or hypermutation positions with an activity-enhancing amino acid residue is described in U.S. Pat. No. 6,914,128 B1.

c. Antibody and Antibodies

"Antibody" and "antibodies" as used herein refers to monoclonal antibodies, multispecific antibodies, human antibodies, humanized antibodies (fully or partially humanized), animal antibodies (such as, but not limited to, a bird (for example, a duck or a goose), a shark, a whale, and a mammal, including a non-primate (for example, a cow, a pig, a camel, a llama, a horse, a goat, a rabbit, a sheep, a hamster, a guinea pig, a cat, a dog, a rat, a mouse, etc.) or a non-human primate (for example, a monkey, a chimpanzee, etc.), recombinant antibodies, chimeric antibodies, single-chain Fvs ("scFv"), single chain antibodies, single domain antibodies, Fab fragments, F(ab') fragments, F(ab')$_2$ fragments, disulfide-linked Fvs ("sdFv"), and anti-idiotypic ("anti-Id") antibodies, dual-domain antibodies, dual variable domain (DVD) or triple variable domain (TVD) antibodies (dual-variable domain immunoglobulins and methods for making them are described in Wu, C., et al., Nature Biotechnology, 25(11): 1290-1297 (2007) and PCT International Application WO 2001/058956, the contents of each of which are herein incorporated by reference), and functionally active epitope-binding fragments of any of the above. In particular, antibodies include immunoglobulin molecules and immunologically active fragments of immunoglobulin molecules, namely, molecules that contain an analyte-binding site. Immunoglobulin molecules can be of any type (for example, IgG, IgE, IgM, IgD, IgA and IgY), class (for example, IgG1, IgG2, IgG3, IgG4, IgA1 and IgA2) or subclass. For simplicity sake, an antibody against an analyte is frequently referred to herein as being either an "anti-analyte antibody," or merely an "analyte antibody" (e.g., an anti-RGMc antibody or an RGMc antibody).

d. Antibody Fragment

"Antibody fragment" as used herein refers to a portion of an intact antibody comprising the antigen-binding site or variable region. The portion does not include the constant heavy chain domains (i.e. CH2, CH3 or CH4, depending on the antibody isotype) of the Fc region of the intact antibody. Examples of antibody fragments include, but are not limited to, Fab fragments, Fab' fragments, Fab'-SH fragments, F(ab')2 fragments, Fd fragments, Fv fragments, diabodies, single-chain Fv (scFv) molecules, single-chain polypeptides containing only one light chain variable domain, single-chain polypeptides containing the three CDRs of the light-chain variable domain, single-chain polypeptides containing only one heavy chain variable region, and single-chain polypeptides containing the three CDRs of the heavy chain variable region.

e. Binding Constants

"Binding Constants" are described herein. The term "association rate constant," "$k_{on}$" or "$k_a$" as used herein, refers to the value indicating the binding rate of an antibody to its target antigen or the rate of complex formation between an antibody and antigen as shown by the equation below:

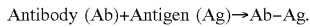

Antibody (Ab)+Antigen (Ag)→Ab–Ag.

The term "dissociation rate constant," "$k_{off}$" or "$k_d$" as used interchangeably herein, refers to the value indicating the dissociation rate of an antibody form its target antigen or separation of Ab–Ag complex over time into free antibody and antigen as shown by the equation below:

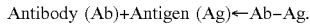

Antibody (Ab)+Antigen (Ag)←Ab–Ag.

Methods for determining association and dissociation rate constants are well known in the art. Using fluorescence-based techniques offers high sensitivity and the ability to examine samples in physiological buffers at equilibrium. Other experimental approaches and instruments such as a BIAcore® (biomolecular interaction analysis) assay can be used (e.g., instrument available from BIAcore International AB, a GE Healthcare company, Uppsala, Sweden). Additionally, a KinExA® (Kinetic Exclusion Assay) assay, available from Sapidyne Instruments (Boise, Idaho) can also be used.

The term "equilibrium dissociation constant" or "$K_D$" as used interchangeably, herein, refers to the value obtained by dividing the dissociation rate ($k_{off}$) by the association rate ($k_{on}$). The association rate, the dissociation rate and the equilibrium dissociation constant are used to represent the binding affinity of an antibody to an antigen.

f. Binding Protein

"Binding Protein" is used herein to refer to a monomeric or multimeric protein that binds to and forms a complex with a binding partner, such as, for example, a polypeptide, an antigen, a chemical compound or other molecule, or a substrate of any kind. A binding protein specifically binds a binding partner. Binding proteins include antibodies, as well as antigen-binding fragments thereof and other various forms and derivatives thereof as are known in the art and described herein below, and other molecules comprising one or more antigen-binding domains that bind to an antigen molecule or a particular site (epitope) on the antigen molecule. Accordingly, a binding protein includes, but is not limited to, an antibody a tetrameric immunoglobulin, an IgG molecule, an IgG$_1$ molecule, a monoclonal antibody, a chimeric antibody, a CDR-grafted antibody, a humanized antibody, an affinity matured antibody, and fragments of any such antibodies that retain the ability to bind to an antigen.

g. Bispecific Antibody

"Bispecific antibody" is used herein to refer to a full-length antibody that is generated by quadroma technology (see Milstein et al., Nature, 305(5934): 537-540 (1983)), by chemical conjugation of two different monoclonal antibodies (see, Staerz et al., Nature, 314(6012): 628-631 (1985)), or by knob-into-hole or similar approaches, which introduce mutations in the Fc region (see Holliger et al., Proc. Natl. Acad. Sci. USA, 90(14): 6444-6448 (1993)), resulting in multiple different immunoglobulin species of which only one is the functional bispecific antibody. A bispecific antibody binds one antigen (or epitope) on one of its two binding arms (one pair of HC/LC), and binds a different antigen (or epitope) on its second arm (a different pair of HC/LC). By this definition, a bispecific antibody has two distinct antigen-binding arms (in both specificity and CDR sequences), and is monovalent for each antigen to which it binds to.

h. CDR

"CDR" is used herein to refer to the "complementarity determining region" within an antibody variable sequence. There are three CDRs in each of the variable regions of the heavy chain and the light chain, which are designated "CDR1", "CDR2", and "CDR3", for each of the variable regions. The term "CDR set" as used herein refers to a group of three CDRs that occur in a single variable region that binds the antigen. The exact boundaries of these CDRs have been defined differently according to different systems. The system described by Kabat (Kabat et al., Sequences of Proteins of Immunological Interest (National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as "Kabat CDRs". Chothia and coworkers (Chothia and Lesk, J. Mol. Biol., 196: 901-917 (1987); and Chothia et al., Nature, 342: 877-883 (1989)) found that certain sub-portions within Kabat CDRs adopt nearly identical peptide backbone conformations, despite having great diversity at the level of amino acid sequence. These sub-portions were designated as "L1", "L2", and "L3", or "H1", "H2", and "H3", where the "L" and the "H" designate the light chain and the heavy chain regions, respectively. These regions may be referred to as "Chothia CDRs", which have boundaries that overlap with Kabat CDRs. Other boundaries defining CDRs overlapping with the Kabat CDRs have been described by Padlan, FASEB J., 9: 133-139 (1995), and MacCallum, J. Mol. Biol., 262(5): 732-745 (1996). Still other CDR boundary definitions may not strictly follow one of the herein systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although certain embodiments use Kabat- or Chothia-defined CDRs.

i. Component or Components

"Component," "components," or "at least one component," refer generally to a capture antibody, a detection or conjugate a calibrator, a control, a sensitivity panel, a container, a buffer, a diluent, a salt, an enzyme, a co-factor for an enzyme, a detection reagent, a pretreatment reagent/solution, a substrate (e.g., as a solution), a stop solution, and the like that can be included in a kit for assay of a test sample, such as a patient urine, serum or plasma sample, in accordance with the methods described herein and other methods known in the art. Some components can be in solution or lyophilized for reconstitution for use in an assay.

j. Consensus or Consensus Sequence

"Consensus" or "Consensus Sequence" as used herein refers to a synthetic nucleic acid sequence, or corresponding polypeptide sequence, constructed based on analysis of an alignment of multiple subtypes of a particular antigen. The sequence may be used to induce broad immunity against multiple subtypes or sertypes of a particular antigen. Synthetic antigens, such as fusion proteins, may be manipulated to consensus sequences (or consensus antigens).

k. Control

"Control" as used herein refers to a composition known to not contain an analyte of interest ("negative"), e.g., RGMc (such as membrane-associated RGMc, soluble RGMc, fragments of membrane-associated RGMc, fragments of soluble RGMc, variants of RGMc (membrane-associated or soluble RGMc) or any combinations thereof), or to contain an analyte of interest ("positive control"), e.g., RGMc (such as membrane-associated RGMc, soluble RGMc, fragments of membrane-associated RGMc, fragments of soluble RGMc, variants of RGMc (membrane-associated or soluble RGMc) or any combinations thereof). A positive control can comprise a known concentration of RGMc. "Control," "positive control," and "calibrator" may be used interchangeably herein to refer to a composition comprising a known concentration of RGMc. A "positive control" can be used to establish assay performance characteristics and is a useful indicator of the integrity of reagents (e.g., analytes). A "normal control" may refer to a sample or a subject that is free from an iron-related disease or disorder.

l. Derivative

"Derivative" of an antibody as used herein may refer to an antibody having one or more modifications to its amino acid sequence when compared to a genuine or parent antibody and exhibit a modified domain structure. The derivative may still be able to adopt the typical domain configuration found in native antibodies, as well as an amino acid sequence, which is able to bind to targets (antigens) with specificity. Typical examples of antibody derivatives are antibodies coupled to other polypeptides, rearranged antibody domains or fragments of antibodies. The derivative may also comprise at least one further compound, e.g. a protein domain, said protein domain being linked by covalent or non-covalent bonds. The linkage can be based on genetic fusion according to the methods known in the art. The additional domain present in the fusion protein comprising the antibody employed in accordance with the invention may preferably be linked by a flexible linker, advantageously a peptide linker, wherein said peptide linker comprises plural, hydrophilic, peptide-bonded amino acids of a length sufficient to span the distance between the C-terminal end of the further protein domain and the N-terminal end of the antibody or vice versa. The antibody may be linked to an effector molecule having a conformation suitable for biological activity or selective binding to a solid support, a biologically active substance (e.g. a cytokine or growth hormone), a chemical agent, a peptide, a protein or a drug, for example.

m. Dual-Specific Antibody

"Dual-specific antibody" is used herein to refer to a full-length antibody that can bind two two different antigens (or epitopes) in each of its two binding arms (a pair of HC/LC) (see PCT publication WO 02/02773). Accordingly a dual-specific binding protein has two identical antigen binding arms, with identical specificity and identical CDR sequences, and is bivalent for each antigen to which it binds.

n. Dual Variable Domain

"Dual variable domain" is used herein to refer to two or more antigen binding sites on a binding protein, which may be divalent (two antigen binding sites), tetravalent (four antigen binding sites), or multivalent binding proteins. DVDs may be monospecific, i.e., capable of binding one antigen (or one specific epitope), or multispecific, i.e., capable of binding two or more antigens (i.e., two or more epitopes of the same target antigen molecule or two or more epitopes of different target antigens). A preferred DVD binding protein comprises two heavy chain DVD polypeptides and two light chain DVD polypeptides and is referred to as a "DVD immunoglobulin" or "DVD-Ig". Such a DVD-Ig binding protein is thus tetrameric and reminiscent of an IgG molecule, but provides more antigen binding sites than an IgG molecule. Thus, each half of a tetrameric DVD-Ig molecule is reminiscent of one half of an IgG molecule and comprises a heavy chain DVD polypeptide and a light chain DVD polypeptide, but unlike a pair of heavy and light chains of an IgG molecule that provides a single antigen binding domain, a pair of heavy and light chains of a DVD-Ig provide two or more antigen binding sites.

Each antigen binding site of a DVD-Ig binding protein may be derived from a donor ("parental") monoclonal antibody and thus comprises a heavy chain variable domain (VH) and a light chain variable domain (VL) with a total of six CDRs involved in antigen binding per antigen binding site. Accordingly, a DVD-Ig binding protein that binds two different epitopes (i.e., two different epitopes of two different antigen molecules or two different epitopes of the same antigen molecule) comprises an antigen binding site derived from a first parental monoclonal antibody and an antigen binding site of a second parental monoclonal antibody.

A description of the design, expression, and characterization of DVD-Ig binding molecules is provided in PCT Publication No. WO 2007/024715, U.S. Pat. No. 7,612,181, and Wu et al., Nature Biotech., 25: 1290-1297 (2007). A preferred example of such DVD-Ig molecules comprises a heavy chain that comprises the structural formula VD1-(X1)n-VD2-C-(X2)n, wherein VD1 is a first heavy chain variable domain, VD2 is a second heavy chain variable domain, C is a heavy chain constant domain, X1 is a linker with the proviso that it is not CH1, X2 is an Fc region, and n is 0 or 1, but preferably 1; and a light chain that comprises the structural formula VD1-(X1)n-VD2-C-(X2)n, wherein VD1 is a first light chain variable domain, VD2 is a second light chain variable domain, C is a light chain constant domain, X1 is a linker with the proviso that it is not CH1, and X2 does not comprise an Fc region; and n is 0 or 1, but preferably 1. Such a DVD-Ig may comprise two such heavy chains and two such light chains, wherein each chain comprises variable domains linked in tandem without an intervening constant region between variable regions, wherein a heavy chain and a light chain associate to form tandem functional antigen binding sites, and a pair of heavy and light chains may associate with another pair of heavy and light chains to form a tetrameric binding protein with four functional antigen binding sites. In another example, a DVD-Ig molecule may comprise heavy and light chains that each comprise three variable domains (VD1, VD2, VD3) linked in tandem without an intervening constant region between variable domains, wherein a pair of heavy and light chains may associate to form three antigen binding sites, and wherein a pair of heavy and light chains may associate with another pair of heavy and light chains to form a tetrameric binding protein with six antigen binding sites.

In a preferred embodiment, a DVD-Ig binding protein according to the invention not only binds the same target molecules bound by its parental monoclonal antibodies, but also possesses one or more desirable properties of one or more of its parental monoclonal antibodies. Preferably, such an additional property is an antibody parameter of one or more of the parental monoclonal antibodies. Antibody parameters that may be contributed to a DVD-Ig binding protein from one or more of its parental monoclonal antibodies include, but are not limited to, antigen specificity, antigen affinity, potency, biological function, epitope recognition, protein stability, protein solubility, production efficiency, immunogenicity, pharmacokinetics, bioavailability, tissue cross reactivity, and orthologous antigen binding.

A DVD-Ig binding protein binds at least one epitope of a RGMc. Non-limiting examples of a DVD-Ig binding protein include a DVD-Ig binding protein that binds one or more epitopes of RGMc, a DVD-Ig binding protein that binds an epitope of a human RGMc and an epitope of a RGMc of another species (for example, mouse), and a DVD-Ig binding protein that binds an epitope of a human RGMc and an epitope of another target molecule (for example, VEGFR2 or VEGFR1).

o. Epitope or Epitopes

"Epitope," or "epitopes," or "epitopes of interest" refer to a site(s) on any molecule that is recognized and can bind to a complementary site(s) on its specific binding partner. The molecule and specific binding partner are part of a specific binding pair. For example, an epitope can be on a polypeptide, a protein, a hapten, a carbohydrate antigen (such as, but not limited to, glycolipids, glycoproteins or lipopolysaccharides), or a polysaccharide. Its specific binding partner can be, but is not limited to, an antibody.

p. Framework or Framework Sequence

"Framework" (FR) or "Framework sequence" as used herein may mean the remaining sequences of a variable region minus the CDRs. Because the exact definition of a CDR sequence can be determined by different systems (for example, see above), the meaning of a framework sequence is subject to correspondingly different interpretations. The six CDRs (CDR-L1, -L2, and -L3 of light chain and CDR-H1, -H2, and -H3 of heavy chain) also divide the framework regions on the light chain and the heavy chain into four sub-regions (FR1, FR2, FR3, and FR4) on each chain, in which CDR1 is positioned between FR1 and FR2, CDR2 between FR2 and FR3, and CDR3 between FR3 and FR4. Without specifying the particular sub-regions as FR1, FR2, FR3, or FR4, a framework region, as referred by others, represents the combined FRs within the variable region of a single, naturally occurring immunoglobulin chain. As used herein, a FR represents one of the four sub-regions, and FRs represents two or more of the four sub-regions constituting a framework region.

Human heavy chain and light chain FR sequences are known in the art that can be used as heavy chain and light chain "acceptor" framework sequences (or simply, "acceptor" sequences) to humanize a non-human antibody using techniques known in the art. In one embodiment, human heavy chain and light chain acceptor sequences are selected from the framework sequences listed in publicly available databases such as V-base (hypertext transfer protocol:// vbase.mrc-cpe.cam.ac.uk/) or in the international ImMuno-GeneTics® (IMGT®) information system (hypertext transfer protocol://imgt.cines.fr/texts/IMGTrepertoire/LocusGenes/).

q. Functional Antigen Binding Site

"Functional antigen binding site" as used herein may mean a site on a binding protein (e.g. an antibody) that is capable of binding a target antigen. The antigen binding affinity of the antigen binding site may not be as strong as the parent binding protein, e.g., parent antibody, from which the antigen binding site is derived, but the ability to bind antigen must be measurable using any one of a variety of methods known for evaluating protein, e.g., antibody, binding to an antigen. Moreover, the antigen binding affinity of each of the antigen binding sites of a multivalent protein, e.g., multivalent antibody, herein need not be quantitatively the same.

r. Humanized Antibody

"Humanized antibody" is used herein to describe an antibody that comprises heavy and light chain variable region sequences from a non-human species (e.g. a mouse) but in which at least a portion of the VH and/or VL sequence has been altered to be more "human-like," i.e., more similar to human germline variable sequences. A "humanized antibody" is an antibody or a variant, derivative, analog, or fragment thereof, which immunospecifically binds to an antigen of interest and which comprises a framework (FR) region having substantially the amino acid sequence of a human antibody and a complementary determining region (CDR) having substantially the amino acid sequence of a non-human antibody. As used herein, the term "substantially" in the context of a CDR refers to a CDR having an amino acid sequence at least 80%, at least 85%, at least 90%, at least 95%, at least 98% or at least 99% identical to the amino acid sequence of a non-human antibody CDR. A humanized antibody comprises substantially all of at least one, and typically two, variable domains (Fab, Fab', F(ab')$_2$, FabC, Fv) in which all or substantially all of the CDR regions correspond to those of a non-human immunoglobulin (i.e., donor antibody) and all or substantially all of the framework regions are those of a human immunoglobulin consensus sequence. In an embodiment, a humanized antibody also comprises at least a portion of an immunoglobulin constant region (Fc), typically that of a human immunoglobulin. In some embodiments, a humanized antibody contains the light chain as well as at least the variable domain of a heavy chain. The antibody also may include the CH1, hinge, CH2, CH3, and CH4 regions of the heavy chain. In some embodiments, a humanized antibody only contains a humanized light chain. In some embodiments, a humanized antibody only contains a humanized heavy chain. In specific embodiments, a humanized antibody only contains a humanized variable domain of a light chain and/or humanized heavy chain.

A humanized antibody can be selected from any class of immunoglobulins, including IgM, IgG, IgD, IgA, and IgE, and any isotype, including without limitation IgG1, IgG2, IgG3, and IgG4. A humanized antibody may comprise sequences from more than one class or isotype, and particular constant domains may be selected to optimize desired effector functions using techniques well-known in the art.

The framework regions and CDRs of a humanized antibody need not correspond precisely to the parental sequences, e.g., the donor antibody CDR or the consensus framework may be mutagenized by substitution, insertion, and/or deletion of at least one amino acid residue so that the CDR or framework residue at that site does not correspond to either the donor antibody or the consensus framework. In a preferred embodiment, such mutations, however, will not be extensive. Usually, at least 80%, preferably at least 85%, more preferably at least 90%, and most preferably at least 95% of the humanized antibody residues will correspond to those of the parental FR and CDR sequences. As used herein, the term "consensus framework" refers to the framework region in the consensus immunoglobulin sequence. As used herein, the term "consensus immunoglobulin sequence" refers to the sequence formed from the most frequently occurring amino acids (or nucleotides) in a family of related immunoglobulin sequences (see, e.g., Winnaker, From Genes to Clones (Verlagsgesellschaft, Weinheim, 1987)). A "consensus immunoglobulin sequence" may thus comprise a "consensus framework region(s)" and/or a "consensus CDR(s)". In a family of immunoglobulins, each position in the consensus sequence is occupied by the amino acid occurring most frequently at that position in the family. If two amino acids occur equally frequently, either can be included in the consensus sequence.

s. Identical or Identity

"Identical" or "identity," as used herein in the context of two or more polypeptide or polynucleotide sequences, can mean that the sequences have a specified percentage of residues that are the same over a specified region. The percentage can be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of the single sequence are included in the denominator but not the numerator of the calculation.

t. Isolated Polynucleotide

"Isolated polynucleotide" as used herein may mean a polynucleotide (e.g. of genomic, cDNA, or synthetic origin, or a combination thereof) that, by virtue of its origin, the isolated polynucleotide is not associated with all or a portion of a polynucleotide with which the "isolated polynucleotide" is found in nature; is operably linked to a polynucleotide that it is not linked to in nature; or does not occur in nature as part of a larger sequence.

u. Label and Detectable Label

"Label" and "detectable label" as used herein refer to a moiety attached to an antibody or an analyte to render the reaction between the antibody and the analyte detectable, and the antibody or analyte so labeled is referred to as "detectably labeled." A label can produce a signal that is detectable by visual or instrumental means. Various labels include signal-producing substances, such as chromogens, fluorescent compounds, chemiluminescent compounds, radioactive compounds, and the like. Representative examples of labels include moieties that produce light, e.g., acridinium compounds, and moieties that produce fluorescence, e.g., fluorescein. Other labels are described herein. In this regard, the moiety, itself, may not be detectable but may become detectable upon reaction with yet another moiety. Use of the term "detectably labeled" is intended to encompass such labeling.

Any suitable detectable label as is known in the art can be used. For example, the detectable label can be a radioactive label (such as $^3H$, $^{125}I$, $^{35}S$, $^{14}C$, $^{32}P$, and $^{33}P$), an enzymatic label (such as horseradish peroxidase, alkaline peroxidase, glucose 6-phosphate dehydrogenase, and the like), a chemiluminescent label (such as acridinium esters, thioesters, or sulfonamides; luminol, isoluminol, phenanthridinium esters, and the like), a fluorescent label (such as fluorescein (e.g., 5-fluorescein, 6-carboxyfluorescein, 3'6-carboxyfluorescein, 5(6)-carboxyfluorescein, 6-hexachloro-fluorescein, 6-tetrachlorofluorescein, fluorescein isothiocyanate, and the like)), rhodamine, phycobiliproteins, R-phycoerythrin, quantum dots (e.g., zinc sulfide-capped cadmium selenide), a thermometric label, or an immuno-polymerase chain reaction label. An introduction to labels, labeling procedures and detection of labels is found in Polak and Van Noorden, *Introduction to Immunocytochemistry*, 2$^{nd}$ ed., Springer Verlag, N.Y. (1997), and in Haugland, *Handbook of Fluorescent Probes and Research Chemicals* (1996), which is a combined handbook and catalogue published by Molecular Probes, Inc., Eugene, Oregon. A fluorescent label can be used in FPIA (see, e.g., U.S. Pat. Nos. 5,593,896, 5,573,904, 5,496,925, 5,359,093, and 5,352,803, which are hereby incorporated by reference in their entireties). An acridinium compound can be used as a detectable label in a homogeneous chemiluminescent assay (see, e.g., Adamczyk et al., Bioorg. Med. Chem. Lett. 16: 1324-1328 (2006); Adamczyk et al., Bioorg. Med. Chem. Lett. 4: 2313-2317 (2004); Adamczyk et al., Biorg. Med. Chem. Lett. 14: 3917-3921 (2004); and Adamczyk et al., *Org. Lett.* 5: 3779-3782 (2003)).

In one aspect, the acridinium compound is an acridinium-9-carboxamide. Methods for preparing acridinium 9-carboxamides are described in Mattingly, J. Biolumin. Chemilumin. 6: 107-114 (1991); Adamczyk et al., *J. Org. Chem.* 63: 5636-5639 (1998); Adamczyk et al., Tetrahedron 55: 10899-10914 (1999); Adamczyk et al., Org. Lett. 1: 779-781 (1999); Adamczyk et al., Bioconjugate Chem. 11: 714-724 (2000); Mattingly et al., In *Luminescence Biotechnology: Instruments and Applications*; Dyke, K. V. Ed.; CRC Press: Boca Raton, pp. 77-105 (2002); Adamczyk et al., Org. Lett. 5: 3779-3782 (2003); and U.S. Pat. Nos. 5,468,646, 5,543,524 and 5,783,699 (each of which is incorporated herein by reference in its entirety for its teachings regarding same).

Another example of an acridinium compound is an acridinium-9-carboxylate aryl ester. An example of an acridinium-9-carboxylate aryl ester of formula II is 10-methyl-9-(phenoxycarbonyl)acridinium fluorosulfonate (available from Cayman Chemical, Ann Arbor, MI). Methods for preparing acridinium 9-carboxylate aryl esters are described in McCapra et al., Photochem. Photobiol. 4: 1111-21 (1965); Razavi et al., Luminescence 15: 245-249 (2000); Razavi et al., Luminescence 15: 239-244 (2000); and U.S. Pat. No. 5,241,070 (each of which is incorporated herein by reference in its entirety for its teachings regarding same). Such acridinium-9-carboxylate aryl esters are efficient chemiluminescent indicators for hydrogen peroxide produced in the oxidation of an analyte by at least one oxidase in terms of the intensity of the signal and/or the rapidity of the signal. The course of the chemiluminescent emission for the acridinium-9-carboxylate aryl ester is completed rapidly, i.e., in under 1 second, while the acridinium-9-carboxamide chemiluminescent emission extends over 2 seconds. Acridinium-9-carboxylate aryl ester, however, loses its chemiluminescent properties in the presence of protein. Therefore, its use requires the absence of protein during signal generation and detection. Methods for separating or removing proteins in the sample are well-known to those skilled in the art and include, but are not limited to, ultrafiltration, extraction, precipitation, dialysis, chromatography, and/or digestion (see, e.g., Wells, *High Throughput Bioanalytical Sample Preparation. Methods and Automation Strategies*, Elsevier (2003)). The amount of protein removed or separated from the test sample can be about 40%, about 45%, about 50%, about 55%, about 60%, about 65%, about 70%, about 75%, about 80%, about 85%, about 90%, or about 95%. Further details regarding acridinium-9-carboxylate aryl ester and its use are set forth in U.S. patent application Ser. No. 11/697,835, filed Apr. 9, 2007. Acridinium-9-carboxylate aryl esters can be dissolved in any suitable solvent, such as degassed anhydrous N,N-dimethylformamide (DMF) or aqueous sodium cholate.

v. Linking Sequence and Linking Peptide Sequence

"Linking sequence" or "linking peptide sequence" refers to a natural or artificial polypeptide sequence that is connected to one or more polypeptide sequences of interest (e.g., full-length, fragments, etc.). The term "connected" refers to the joining of the linking sequence to the polypeptide sequence of interest. Such polypeptide sequences are preferably joined by one or more peptide bonds. Linking sequences can have a length of from about 4 to about 50 amino acids. Preferably, the length of the linking sequence is from about 6 to about 30 amino acids. Natural linking sequences can be modified by amino acid substitutions, additions, or deletions to create artificial linking sequences. Exemplary linking sequences include, but are not limited to: (i) Histidine (His) tags, such as a 6× His tag, which has an amino acid sequence of HHHHHH (SEQ ID NO:83), are useful as linking sequences to facilitate the isolation and purification of polypeptides and antibodies of interest; (ii) Enterokinase cleavage sites, like His tags, are used in the isolation and purification of proteins and antibodies of interest. Often, enterokinase cleavage sites are used together with His tags in the isolation and purification of proteins and antibodies of interest. Various enterokinase cleavage sites are known in the art. Examples of enterokinase cleavage sites include, but are not limited to, the amino acid sequence of DDDDK (SEQ ID NO:84) and derivatives thereof (e.g., ADDDDK (SEQ ID NO:85), etc.); (iii) Miscellaneous sequences can be used to link or connect the light and/or heavy chain variable regions of single chain variable region fragments. Examples of other linking sequences can be found in Bird et al., Science 242: 423-426 (1988); Huston et al., PNAS USA 85: 5879-5883 (1988); and McCafferty et al., Nature 348: 552-554 (1990). Linking sequences also can be modified for additional functions, such as attachment of drugs or attachment to solid supports. In the context of the present disclosure, the monoclonal antibody, for example, can contain a linking sequence, such as a His tag, an enterokinase cleavage site, or both.

w. Multivalent Binding Protein

"Multivalent binding protein" is used herein to refer to a binding protein comprising two or more antigen binding sites (also referred to herein as "antigen binding domains"). A multivalent binding protein is preferably engineered to have three or more antigen binding sites, and is generally not a naturally occurring antibody. The term "multispecific binding protein" refers to a binding protein that can bind two or more related or unrelated targets, including a binding protein capable of binding two or more different epitopes of the same target molecule.

x. Predetermined Cutoff and Predetermined Level

"Predetermined cutoff" and "predetermined level" refer generally to an assay cutoff value that is used to assess diagnostic/prognostic/therapeutic efficacy results by comparing the assay results against the predetermined cutoff/level, where the predetermined cutoff/level already has been linked or associated with various clinical parameters (e.g., severity of disease, progression/nonprogression/improvement, etc.). The present disclosure provides exemplary predetermined levels. However, it is well-known that cutoff values may vary depending on the nature of the immunoassay (e.g., antibodies employed, etc.). It further is well within the ordinary skill of one in the art to adapt the disclosure herein for other immunoassays to obtain immunoassay-specific cutoff values for those other immunoassays based on this disclosure. Whereas the precise value of the predetermined cutoff/level may vary between assays, the correlations as described herein should be generally applicable.

y. Pretreatment Reagent

"Pretreatment reagent," e.g., lysis, precipitation and/or solubilization reagent, as used in a diagnostic assay as described herein is one that lyses any cells and/or solubilizes any analyte that is/are present in a test sample. Pretreatment is not necessary for all samples, as described further herein. Among other things, solubilizing the analyte (i.e., RGMc (such as membrane-associated RGMc, soluble RGMc, fragments of membrane-associated RGMc, fragments of soluble RGMc, variants of RGMc (membrane-associated or soluble RGMc) or any combinations thereof)) entails release of the analyte from any endogenous binding proteins present in the sample. A pretreatment reagent may be homogeneous (not requiring a separation step) or heterogeneous (requiring a separation step). With use of a heterogeneous pretreatment reagent there is removal of any precipitated analyte binding proteins from the test sample prior to proceeding to the next step of the assay. The pretreatment reagent optionally can comprise: (a) one or more solvents and salt, (b) one or more solvents, salt and detergent, (c) detergent, (d) detergent and salt, or (e) any reagent or combination of reagents appropriate for cell lysis and/or solubilization of analyte.

z. Quality Control Reagents

"Quality control reagents" in the context of immunoassays and kits described herein, include, but are not limited to, calibrators, controls, and sensitivity panels. A "calibrator" or "standard" typically is used (e.g., one or more, such as a plurality) in order to establish calibration (standard) curves for interpolation of the concentration of an analyte, such as an antibody or an analyte. Alternatively, a single calibrator, which is near a predetermined positive/negative cutoff, can be used. Multiple calibrators (i.e., more than one calibrator or a varying amount of calibrator(s)) can be used in conjunction so as to comprise a "sensitivity panel."

aa. Recombinant Antibody and Recombinant Antibodies

"Recombinant antibody" and "recombinant antibodies" refer to antibodies prepared by one or more steps, including cloning nucleic acid sequences encoding all or a part of one or more monoclonal antibodies into an appropriate expression vector by recombinant techniques and subsequently expressing the antibody in an appropriate host cell. The terms include, but are not limited to, recombinantly produced monoclonal antibodies, chimeric antibodies, humanized antibodies (fully or partially humanized), multi-specific or multi-valent structures formed from antibody fragments, bifunctional antibodies, heteroconjugate Abs, DVD-Ig®s, and other antibodies as described in (i) herein. (Dual-variable domain immunoglobulins and methods for making them are described in Wu, C., et al., Nature Biotechnology, 25:1290-1297 (2007)). The term "bifunctional antibody," as used herein, refers to an antibody that comprises a first arm having a specificity for one antigenic site and a second arm having a specificity for a different antigenic site, i.e., the bifunctional antibodies have a dual specificity.

bb. Sample, Test Sample, and Patient Sample

"Sample," "test sample," and "patient sample" may be used interchangeably herein. The sample, such as a sample of urine, serum, plasma, amniotic fluid, cerebrospinal fluid, placental cells or tissue, endothelial cells, leukocytes, or monocytes, can be used directly as obtained from a patient or can be pre-treated, such as by filtration, distillation, extraction, concentration, centrifugation, inactivation of interfering components, addition of reagents, and the like, to modify the character of the sample in some manner as discussed herein or otherwise as is known in the art.

cc. Series of Calibrating Compositions

"Series of calibrating compositions" refers to a plurality of compositions comprising a known concentration of Cys-RGMcC, wherein each of the compositions differs from the other compositions in the series by the concentration of Cys-CRGMc.

dd. Solid Phase

"Solid phase" refers to any material that is insoluble, or can be made insoluble by a subsequent reaction. The solid phase can be chosen for its intrinsic ability to attract and immobilize a capture agent. Alternatively, the solid phase can have affixed thereto a linking agent that has the ability to attract and immobilize the capture agent. The linking agent can, for example, include a charged substance that is oppositely charged with respect to the capture agent itself or to a charged substance conjugated to the capture agent. In general, the linking agent can be any binding partner (preferably specific) that is immobilized on (attached to) the solid phase and that has the ability to immobilize the capture agent through a binding reaction. The linking agent enables the indirect binding of the capture agent to a solid phase material before the performance of the assay or during the performance of the assay. The solid phase can, for example, be plastic, derivatized plastic, magnetic or non-magnetic metal, glass or silicon, including, for example, a test tube, microtiter well, sheet, bead, microparticle, chip, and other configurations known to those of ordinary skill in the art.

ee. Specific Binding

"Specific binding" or "specifically binding" as used herein may refer to the interaction of an antibody, a protein, or a peptide with a second chemical species, wherein the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

ff. Specific Binding Partner

"Specific binding partner" is a member of a specific binding pair. A specific binding pair comprises two different molecules, which specifically bind to each other through chemical or physical means. Therefore, in addition to antigen and antibody specific binding pairs of common immunoassays, other specific binding pairs can include biotin and avidin (or streptavidin), carbohydrates and lectins, complementary nucleotide sequences, effector and receptor molecules, cofactors and enzymes, enzymes and enzyme inhibitors, and the like. Furthermore, specific binding pairs can include members that are analogs of the original specific binding members, for example, an analyte-analog. Immunoreactive specific binding members include antigens, antigen fragments, and antibodies, including monoclonal and polyclonal antibodies as well as complexes and fragments thereof, whether isolated or recombinantly produced.

gg. Stringent Conditions

"Stringent conditions" is used herein to describe hybridization to filter-bound DNA in 6× sodium chloride/sodium citrate (SSC) at about 45° C. followed by one or more washes in 0.2×SSC/0.1% SDS at about 50-65° C. The term "under highly stringent conditions", refers to hybridization to filter-bound nucleic acid in 6×SSC at about 45° C. followed by one or more washes in 0.1×SSC/0.2% SDS at about 68° C., or under other stringent hybridization conditions. See, for example, Ausubel, F. M. et al., eds., 1989, Current Protocols in Molecular Biology, Vol. I, Green Publishing Associates, Inc. and John Wiley & Sons, Inc., New York at pages 6.3.1-6.3.6 and 2.10.3.

hh. Treat, Treating or Treatment

"Treat", "treating" or "treatment" are each used interchangeably herein to describe reversing, alleviating, or inhibiting the progress of a disease, or one or more symptoms of such disease, to which such term applies. Depending on the condition of the subject, the term also refers to preventing a disease, and includes preventing the onset of a disease, or preventing the symptoms associated with a disease. A treatment may be either performed in an acute or chronic way. The term also refers to reducing the severity of a disease or symptoms associated with such disease prior to affliction with the disease. Such prevention or reduction of the severity of a disease prior to affliction refers to administration of a antibodies or pharmaceutical composition of the present invention to a subject that is not at the time of administration afflicted with the disease. "Preventing" also refers to preventing the recurrence of a disease or of one or more symptoms associated with such disease. "Treatment" and "therapeutically," refer to the act of treating, as "treating" is defined above.

ii. Tracer

"Tracer" as used herein refers to an analyte or analyte fragment conjugated to a label, such as Cys-CRGMc conjugated to a fluorescein moiety, wherein the analyte conjugated to the label can effectively compete with the analyte for sites on an antibody specific for the analyte.

jj. Variant

"Variant" is used herein to describe a peptide or polypeptide that differs in amino acid sequence by the insertion, deletion, or conservative substitution of amino acids, but retain at least one biological activity. Representative examples of "biological activity" include the ability to be bound by a specific antibody or to promote an immune response. Variant is also used herein to describe a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyte et al., J. Mol. Biol. 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of +2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554,101, incorporated fully herein by reference. Substitution of amino acids having similar hydrophilicity values can result in peptides retaining biological activity, for example immunogenicity, as is understood in the art. Substitutions may be performed with amino acids having hydrophilicity values within +2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties. "Variant" also can be used to refer to an antigenically reactive fragment of an anti-RGMc antibody that differs from the corresponding fragment of anti-RGMc antibody in amino acid sequence but is still antigenically reactive and can compete with the corresponding fragment of anti-RGMc antibody for binding with RGMc. "Variant" also can be used to describe a polypeptide or a fragment thereof that has been differentially processed, such as by proteolysis, phosphorylation, or other post-translational modification, yet retains its antigen reactivity.

kk. Vector

"Vector" is used herein to describe a nucleic acid molecule that can transport another nucleic acid to which it has been linked. One type of vector is a "plasmid", which refers to a circular double-stranded DNA loop into which additional DNA segments may be ligated. Another type of vector is a viral vector, wherein additional DNA segments may be ligated into the viral genome. Certain vectors can replicate autonomously in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. "Plasmid" and "vector" may be used interchangeably as the plasmid is the most commonly used form of vector. However, other forms of expression vectors, such as viral vectors (e.g., replication defective retroviruses, adenoviruses and adeno-associated viruses), which serve equivalent functions, can be used. In this regard, RNA versions of vectors (including RNA viral vectors) may also find use in the context of the present disclosure.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

2. Anti-RGMc Antibodies

Provided herein are antibodies that bind to RGMc and interrupt the normal expression of hepcidin, which directly regulates iron concentration in plasma and the distribution of iron to a variety of tissues.

a. RGMc

As discussed previously herein, RGMc is a glycosylphosphatidylinositol ("GPI") anchored membrane protein expressed in muscle, the retina and periportal hepatocytes. RGMc works in conjunction with hepcidin via signaling proteins to maintain iron homeostasis in the body. Hepcidin is a small peptide (20-25 amino acids) that regulates systemic iron metabolism by binding to ferroportin, the exclusive iron exporter of mammals. Anemia of chronic disease ("ACD") is a common consequence, as these cells are no longer able to release iron into the blood. Hepcidin induced degradation of ferroportin may occur at a level of greater than 300 mg/l of hepcidin, of greater than 325 mg/l of hepcidin, of greater than 350 mg/l of hepcidin, of greater than 375 mg/l of hepcidin, of greater than 400 mg/l of hepcidin, of greater than 425 mg/l of hepcidin, of greater than 450 mg/l of hepcidin, or of greater than 475 mg/l of hepcidin.

Human RGMc, a 426 amino acid protein with a predicted N-terminal signal peptide of 31 amino acids and a C-terminal GPI-attachment signal of 45 amino acids, was first proposed to be involved in systemic iron metabolism when mutations in the human gene were linked to a severe iron overload disorder, juvenile hemochromatosis. Hepcidin expression is controlled by membrane-bound RGMc expressed on the surface of hepatocytes and by soluble RGMc present at a concentration of approximately 1 µg/ml in human blood. Soluble RGMc is produced by cleavage of membrane-bound RGMc by matriptase-2 (TMPRSS6). The soluble form of RGMc binds to and sequesters BMP-6, thereby preventing the induction of hepcidin expression. The membrane form of RGMc has an opposite effect: it increases hepcidin expression.

Human RGMc may have the following amino acid sequence:

```
                                          (SEQ ID NO: 1)
MGEPGQSPSPRSSHGSPPTLSTLTLLLLLCGHAHSQCKILRCNAEYVSST

LSLRGGGSSGALRGGGGGRGGGVGSGGLCRALRSYALCTRRTARTCRGD

LAFHSAVHGIEDLMIQHNCSRQGPTAPPPPRGPALPGAGSGLPAPDPCDY

EGRFSRLHGRPPGFLHCASFGDPHVRSFHHHFHTCRVQGAWPLLDNDFLF

VQATSSPMALGANATATRKLTIIFKNMQECIDQKVYQAEVDNLPVAFEDG

SINGGDRPGGSSLSIQTANPGNHVEIQAAYIGTTIIIRQTAGQLSFSIKV

AEDVAMAFSAEQDLQLCVGGCPPSQRLSRSERNRRGAITIDTARRLCKEG

LPVEDAYFHSCVFDVLISGDPNFTVAAQAALEDARAFLPDLEKLHLFPSD

AGVPLSSATLLAPLLSGLFVLWLCIQ. The human RGMc may be a fragment or a variant of SEQ ID NO: 1.
```

The human RGMc may be a fragment or a variant of SEQ ID NO:1.

The fragment of RGMc may be between about 5 and about 425 amino acids, between about 10 and about 400 amino acids, between about 50 and about 350 amino acids, between about 100 and about 300 amino acids, between about 150 and about 250 amino acids, between about 200 and about 300 amino acids, or between about 75 and about 150 amino acids in length. The fragment may comprise a contiguous number of amino acids from RGMc.

The fragment of RGMc may have the following amino acid sequence:

```
                                          (SEQ ID NO: 2)
AHSQCKILRCNAEYVSSTLSLRGGGSSGALRGGGGGRGGGVGSGGLCRA

LRSYALCTRRTARTCRGDLAFHSAVHGIEDLMIQHNCSRQGPTAPPPPRG

PALPGAGSGLPAPDPCDYEGRFSRLHGRPPGFLHCASFGDPHVRSFEIRH

FHTCRVQGAWPLLDNDFLFVQATSSPMALGANATATRKLTIIFKNMQECI

DQKVYQAEVDNLPVAFEDGSINGGDRPGGSSLSIQTANPGNHVEIQAAYI

GTTIIIRQTAGQLSFSIKVAEDVAMAFSAEQDLQLCVGGCPPSQRLSRSE

RNRRGAITIDTARRLCKEGLPVEDAYFHSCVFDVLISGDPNFTVAAQAAL

EDARAFLPDL.
```

The RGMc fragment may be a variant of SEQ ID NO:2.

b. RGMc-Recognizing Antibody

The antibody is an antibody that binds to human RGMc (such as membrane-associated RGMc, soluble RGMc, fragments of membrane-associated RGMc, fragments of soluble RGMc, variants of RGMc (membrane-associated or soluble RGMc) or any combinations thereof). The antibody may be a fragment of the anti-RGMc antibody or a variant or a derivative thereof. The antibody may be a polyclonal antibody or monoclonal antibody. The antibody may be a chimeric antibody, a single chain antibody, a humanized antibody, a fully human antibody or an antibody fragment, such as a Fab fragment, or a mixture thereof. The antibody may be an immunoglobulin molecule, a disulfide linked Fv, an affinity matured antibody, a scFv, a chimeric antibody, a single domain antibody, a CDR-grafted antibody, a diabody, a humanized antibody, a fully human antibody, a multispecific antibody, a Fab, a dual specific antibody, a DVD, a Fab', a bispecific antibody, a F(ab')$_2$, or a Fv. Antibody fragments or derivatives may comprise F(ab')$_2$, Fv or scFv fragments. The antibody derivatives can be produced by peptidomimetics. Further, techniques described for the production of single chain antibodies can be adapted in accordance with methods known in the art to produce single chain antibodies. Also, transgenic animals may be used to express humanized or fully human antibodies.

The antibody may recognize and specifically bind an epitope present on a RGMc polypeptide or a variant as described above (e.g., an epitope contained in SEQ ID NO:1 or a variant of SEQ ID NO:1). The epitope may be an epitope contained in SEQ ID NO:2 or a variant of SEQ ID NO:2.

The antibody is distinguishable from known anti-RGMc antibodies, preferably by possession of different biological function(s) from anti-RGMc antibodies known in the art. For example, in addition to recognizing and binding to membrane-bound RGMc, the antibody preferably has an additional biological activity, for example, the ability to increase or decrease hepcidin expression. Additionally, or alternatively, the antibody has the ability to block RGMc-neogenin interaction and/or RGMc-BMP-6 (bone morphogenetic protein 6) interaction.

(1) Antibody Binding Characteristics

The antibody may immunospecifically bind to RGMc (membrane-associated RGMc, soluble RGMc or combinations thereof), a fragment thereof, or a variant thereof and has a $k_{off}$ (or $k_d$) of at least about $1.0\times10^{-3}$ s$^{-1}$, of at least about $1.0\times10^{-4}$ s$^{-1}$, of at least about $1.0\times10^{-5}$ s$^{-1}$, of at least about $1.0\times10^{-6}$ s$^{-1}$ or has a $k_{off}$ (or $k_d$) ranging from about $1.0\times10^{-3}$ s$^{-1}$ to about $1.0\times10^{-6}$ s$^{-1}$, from about $1.0\times10^{-3}$ s$^{-1}$ to about $1.0\times10^{-5}$ s$^{-1}$ or from about $1.0\times10^{-3}$ s$^{-1}$ to about $1.0\times10^{-4}$ s$^{-1}$. The fragment may be SEQ ID NO:2.

The antibody may immunospecifically bind to RGMc (membrane-associated RGMc, soluble RGMc or a combination thereof), a fragment thereof, or a variant thereof and has a $k_{on}$ (or $k_a$) of at least about $2.4\times10^4$ M$^{-1}$s$^{-1}$, of at least about $2.5\times10^4$ M$^{-1}$s$^{-1}$, of at least about $3.3\times10^4$ M$^{-1}$s$^{-1}$, of at least about $5.0\times10^4$ M$^{-1}$s$^{-1}$, of at least about $1.25\times10^7$ M$^{-1}$s$^{-1}$ of at least about $1.35\times10^7$ M$^{-1}$s$^{-1}$, of at least about $1.0\times10^8$ M$^{-1}$s$^{-1}$, of at least about $1.0\times10^9$ M$^{-1}$s$^{-1}$, or has a $k_{on}$ (or $k_a$) ranging from about $5.0\times10^4$ M$^{-1}$s$^{-1}$ to about $1.0\times10^8$ M$^{-1}$s$^{-1}$, from about $3.3\times10^4$ M$^{-1}$s$^{-1}$ to about $1.0\times10^9$ M$^{-1}$s$^{-1}$, from about $2.5\times10^4$ M$^{-1}$s$^{-1}$ to about $1.25\times10^7$ M$^{-1}$s$^{-1}$, from about $2.4\times10^4$ M$^{-1}$s$^{-1}$ to about $1.35\times10^7$ M$^{-1}$s$^{-1}$. The fragment may be SEQ ID NO:2.

(2) Antibody Structure (a) Variable Heavy and Light Chain Regions and Heavy and Light Chain CDRs The antibody may immunospecifically bind to RGMc, a fragment thereof, or a variant thereof and comprise a variable heavy chain and/or variable light chain shown in Table 1. The antibody may immunospecifically bind to RGMc, a fragment thereof, or a variant thereof and comprise one or more of the heavy chain or light chain CDR sequences also shown in Table 1 and/or Table 2.

TABLE 1

List of Amino Acid Sequences of VH and VL Regions of Humanized Anti-RGMc Antibodies

| PROTEIN REGION | SEQ ID NO. | SEQUENCE |
| --- | --- | --- |
| h5F9.AM4 (VH) | 3 | EVQLVESGGGLVQPGGSLRLSCAASGFTFS NYGMNWIRQAPGKGLEWIGMIYYDSSEKHY ADSVKGRFTISRDNSKNTLYLQMNSLRAED TAVYYCAKGTTPDYWGQGTMVTVSS |
| h5F9.AM4 (VL) | 4 | DVVLTQSPLSLPVTLGQPASISCRSSQSLE SSDGDTFLEWFQQRPGQSPRLLIYDVSTRF SGVPDRFSGSGSGTDFTLKISRVEAEDVGV YYCFQVTHDPVTFGQGTKLEIK |
| h5F9.AM8 (VH) | 5 | EVQLVESGGGLVQPGGSLRLSCAASGFTFS NYGMNWIRQAPGKGLEWIGMIYYDSSEKHY ADSVKGRFTISRDNSKNTLYLQMNSLRAED TAVYYCAKGTTPDYWGQGTMVTVSS |
| h5F9.AM8 (VL) | 6 | DVVLTQSPLSLPVTLGQPASISCRSSQS LEESDGYTFLHWFQQRPGQSPRLLIYE VSTRFSGVPDRFSGSGSGTDFTLKISRV EAEDVGVYYCFQATHDPLTFGQGTKLEIK |
| h5F9.AM9 (VH) | 7 | EVQLVESGGGVVQPGRSLRLSCAASGFTFS NYGMNWVRQAPGKGLEWVAMIYYDSSEKHY ADSVKGRFTISRDNSKNTLYLQMNSLRAED TAVYYCARGTTPDYWGQGTMVTVSS |
| h5F9.AM9 (VL) | 8 | DVVLTQSPLSLPVTLGQPASISCRSSQ SLADSDGDTFLHWFQQRPGQSPRLLIY AVSHRFSGVPDRFSGSGSGTDFTLKISR VEAEDVGVYYCFQATHDPVTFGQGTKLEIK |
| h5F9.AM11 (VH) | 9 | EVQLVESGGGLVQPGGSLRLSCAASGFTFS NYGMNWVRQAPGKGLEWVSMIYYDSSEKHY ADSVKGRFTISRDNSKNTLYLQMNSLRAED TAVYYCAKGTTPDYWGQGTMVTVSS |
| h5F9.AM11 (VL) | 10 | DVVLTQSPLSLPVTLGQPASISCRSSQ SLEDSDGGTFLEWFQQRPGQSPRLLI YDVSSRFSGVPDRFSGSGSGTDFTLKISR VEAEDVGVYYCFQATHDPLSFGQGTKLEIK |
| h5F9.AM4 (VH) CDR-H1 | 11 | NYGMN |
| h5F9.AM4 (VH) CDR-H2 | 12 | MIYYDSSEKHYADSVKG |
| h5F9.AM4 (VH) CDR-H3 | 13 | GTTPDY |
| h5F9.AM4 (VL) CDR-L1 | 14 | RSSQSLESSDGDTFLE |
| h5F9.AM4 (VL) CDR-L2 | 15 | DVSTRFS |
| h5F9.AM4 (VL) CDR-L3 | 16 | FQVTHDPVT |
| h5F9.AM8 (VH) CDR-H1 | 17 | NYGMN |
| h5F9.AM8 (VH) CDR-H2 | 18 | MIYYDSSEKHYADSVKG |
| h5F9.AM8 (VH) CDR-H3 | 19 | GTTPDY |

TABLE 1-continued

List of Amino Acid Sequences of VH and VL
Regions of Humanized Anti-RGMc Antibodies

| PROTEIN REGION | SEQ ID NO. | SEQUENCE |
|---|---|---|
| h5F9.AM8 (VL) CDR-L1 | 20 | RSSQSLEESDGYTFLH |
| h5F9.AM8 (VL) CDR-L2 | 21 | EVSTRFS |
| h5F9.AM8 (VL) CDR-L3 | 22 | FQATHDPLT |
| 5F9.AM9 (VH) CDR-H1 | 23 | NYGMN |
| h5F9.AM9 (VH) CDR-H2 | 24 | MIYYDSSEKHYADSVKG |
| h5F9.AM9 (VH) CDR-H3 | 25 | GTTPDY |
| h5F9.AM9 (VL) CDR-L1 | 26 | RSSQSLADSDGDTFLH |
| h5F9.AM9 (VL) CDR-L2 | 27 | AVSHRFS |
| h5F9.AM9 (VL) CDR-L3 | 28 | FQATHDPVT |
| h5F9.AM11 (VH) CDR-H1 | 29 | NYGMN |
| (AM) h5F9.AM11 (VH) CDR-H2 | 30 | MIYYDSSEKHYADSVKG |
| h5F9.AM11 (VH) CDR-H3 | 31 | GTTPDY |
| h5F9.AM11 (VL) CDR-L1 | 32 | RSSQSLEDSDGGTFLE |
| h5F9.AM11 (VL) CDR-L2 | 33 | DVSSRFS |
| h5F9.AM11 (VL) CDR-L3 | 34 | FQATHDPLS |

TABLE 2

List of Amino Acid Sequences of VH and VL
Regions of Humanized Anti-RGMc Antibodies

| PROTEIN REGION | SEQ ID NO. | SEQUENCE |
|---|---|---|
| VH h5F9.1 | 37 | EVQLVESGGGVVQPGRSLRLSCAASGFTFSNYGMNWVRQAPGKGLEWVAMIYYDSSEKHYADSVKGRFTISRDNSKNTLYLQMNSLRAEDTAVYYCARGTTPDYWGQGTMVTVSS |
| VL h5F9.1 | 38 | DIVMTQTPLSLSVTPGQPASISCRSSQSLEYSDGYTFLEWYLQKPGQSPQLLIYEVSNRFSGVPDRFSGSGSGTDFTLKISRVEAEDVGVYYCFQATHDPLTFGQGTKLEIKR |
| VH h5F9.2 | 39 | EVQLVESGGGVVQPGRSLRLSCAASGFTFSNYGMNWIRQAPGKGLEWIGMIYYDSSEKHYADSVKGRFTISRDNSKNTLYLQMNSLRAEDTAVYYCAKGTTPDYWGQGTMVTVSS |
| VL h5F9.2 | 40 | DIVMTQTPLSLSVTPGQPASISCRSSQSLEYSDGYTFLEWYLQKPGQSPQLLIYEVSNRFSGVPDRFSGSGSGTDFTLKISRVEAEDVGVYYCFQATHDPLTFGQGTKLEIKR |
| VH h5F9.3 | 41 | EVQLVESGGGLVQPGGSLRLSCAASGFTFSNYGMNWVRQAPGKGLEWVSMIYYDSSEKHYADSVKGRFTISRDNSKNTLYLQMNSLRAEDTAVYYCAKGTTPDYWGQGTMVTVSS |
| VL h5F9.3 | 42 | DIVMTQTPLSLSVTPGQPASISCRSSQSLEYSDGYTFLEWYLQKPGQSPQLLIYEVSNRFSGVPDRFSGSGSGTDFTLKISRVEAEDVGVYYCFQATHDPLTFGQGTKLEIKR |
| VH h5F9.4 | 43 | EVQLVESGGGLVQPGGSLRLSCAASGFTFSNYGMNWIRQAPGKGLEWIGMIYYDSSEKHYADSVKGRFTISRDNSKNTLYLQMNSLRAEDTAVYYCAKGTTPDYWGQGTMVTVSS |

TABLE 2-continued

List of Amino Acid Sequences of VH and VL
Regions of Humanized Anti-RGMc Antibodies

| PROTEIN REGION | SEQ ID NO. | SEQUENCE |
|---|---|---|
| VL h5F9.4 | 44 | DIVMTQTPLSLSVTPGQPASISCRSSQSLEYSDGYTFLEWYLQKPGQSPQLLIYEVSNRFSGVPDRFSGSGSGTDFTLKISRVEAEDVGVYYCFQATHDPLTFGQGTKLEIKR |
| VH h5F9.5 | 45 | EVQLVESGGGVVQPGRSLRLSCAASGFTFSNYGMNWVRQAPGKGLEWVAMIYYDSSEKHYADSVKGRFTISRDNSKNTLYLQMNSLRAEDTAVYYCARGTTPDYWGQGTMVTVSS |
| VL h5F9.5 | 46 | DVVMTQSPLSLPVTLGQPASISCRSSQSLEYSDGYTFLEWFQQRPGQSPRRLIYEVSNRFSGVPDRFSGSGSGTDFTLKISRVEAEDVGVYYCFQATHDPLTFGQGTKLEIKR |
| VH h5F9.6 | 47 | EVQLVESGGGVVQPGRSLRLSCAASGFTFSNYGMNWIRQAPGKGLEWIGMIYYDSSEKHYADSVKGRFTISRDNSKNTLYLQMNSLRAEDTAVYYCAKGTTPDYWGQGTMVTVSS |
| VL h5F9.6 | 48 | DVVMTQSPLSLPVTLGQPASISCRSSQSLEYSDGYTFLEWFQQRPGQSPRRLIYEVSNRFSGVPDRFSGSGSGTDFTLKISRVEAEDVGVYYCFQATHDPLTFGQGTKLEIKR |
| VH h5F9.7 | 49 | EVQLVESGGGLVQPGGSLRLSCAASGFTFSNYGMNWVRQAPGKGLEWVSMIYYDS SEKHYADSVKGRFTISRDNSKNTLYLQMNSLRAEDTAVYYCAKGTTPDYWGQGTMVTVSS |
| VL h5F9.7 | 50 | DVVMTQSPLSLPVTLGQPASISCRSSQSLEYSDGYTFLEWFQQRPGQSPRRLIYEVSNRFSGVPDRFSGSGSGTDFTLKISRVEAEDVGVYYCFQATHDPLTFGQGTKLEIKR |
| VH h5F9.8 | 51 | EVQLVESGGGLVQPGGSLRLSCAASGFTFSNYGMNWIRQAPGKGLEWIGMIYYDSSEKHYADSVKGRFTISRDNSKNTLYLQMNSLRAEDTAVYYCAKGTTPDYWGQGTMVTVSS |
| VL h5F9.8 | 52 | DVVMTQSPLSLPVTLGQPASISCRSSQSLEYSDGYTFLEWFQQRPGQSPRRLIYEVSNRFSGVPDRFSGSGSGTDFTLKISRVEAEDVGVYYCFQATHDPLTFGQGTKLEIKR |
| VH h5F9.9 | 53 | EVQLVESGGGVVQPGRSLRLSCAASGFTFSNYGMNWVRQAPGKGLEWVAMIYYDSSEKHYADSVKGRFTISRDNSKNTLYLQMNSLRAEDTAVYYCARGTTPDYWGQGTMVTVSS |
| VL h5F9.9 | 54 | DVVMTQSPLSLPVTLGQPASISCRSSQSLEYSDGYTFLEWYLQKPGQSPQLLIYEVSNRFSGVPDRFSGSGSGTDFTLKISRVEAEDVGVYYCFQATHDPLTFGQGTKLEIKR |
| VH h5F9.10 | 55 | EVQLVESGGGVVQPGRSLRLSCAASGFTFSNYGMNWIRQAPGKGLEWIGMIYYDSSEKHYADSVKGRFTISRDNSKNTLYLQMNSLRAEDTAVYYCAKGTTPDYWGQGTMVTVSS |
| VL h5F9.10 | 56 | DVVMTQSPLSLPVTLGQPASISCRSSQSLEYSDGYTFLEWYLQKPGQSPQLLIYEVSNRFSGVPDRFSGSGSGTDFTLKISRVEAEDVGVYYCFQATHDPLTFGQGTKLEIKR |

TABLE 2-continued

List of Amino Acid Sequences of VH and VL
Regions of Humanized Anti-RGMc Antibodies

| PROTEIN REGION | SEQ ID NO. | SEQUENCE |
| --- | --- | --- |
| VH h5F9.11 | 57 | EVQLVESGGGLVQPGGSLRLSCAASGFTF SNYGMNWVRQAPGKGLEWVSMIYYDSS EKHYADSVKGRFTISRDNSKNTLYLQM NSLRAEDTAVYYCAKGTTPDYWGQGT MVTVSS |
| VL h5F9.11 | 58 | DVVMTQSPLSLPVTLGQPASISCRSSQSLE YSDGYTFLEWYLQKPGQSPQLLIYEVSNR FSGVPDRFSGSGSGTDFTLKISRVEAEDVG VYYCFQATHDPLTFGQGTKLEIKR |
| VH h5F9.12 | 59 | EVQLVESGGGLVQPGGSLRLSCAASGFTFSN YGMNWIRQAPGKGLEWIGMIYYDSSEKHYA DSVKGRFTISRDNSKNTLYLQMNSLRAEDTA VYYCAKGTTPDYWGQGTMVTVSS |
| VL h5F9.12 | 60 | DVVMTQSPLSLPVTLGQPASISCRSSQSLEYSD GYTFLEWYLQKPGQSPQLLIYEVSNRFSGVPD RFSGSGSGTDFTLKISRVEAEDVGVYYCFQAT HDPLTFGQGTKLEIKR |
| VH h5F9.19 | 61 | EVQLVESGGGVVQPGRSLRLSCAASGFTFSNY GMNWIRQAPGKGLEWIGMIYYDSSEKHYADS VKGRFTISRDNSKNTLYLQMNSLRAEDTAVY YCAKGTTPDYWGQGTMVTVSS |
| VL h5F9.19 | 62 | DVVLTQSPLSLPVTLGQPASISCRSSQSLEYSD GYTFLEWFQQRPGQSPRLLIYEVSNRFSGVPD RFSGSGSGTDFTLKISRVEAEDVGVYYCFQAT HDPLTFGQGTKLEIKR |
| VH h5F9.20 | 63 | EVQLVESGGGVVQPGRSLRLSCAASGFTFSNY GMNWIRQAPGKGLEWIGMIYYDSSEKHYADS VKGRFTISRDNSKNTLYLQMNSLRAEDTAVYY CAKGTTPDYWGQGTMVTVSS |
| VL h5F9.20 | 64 | DVVLTQSPLSLPVTLGQPASISCRSSQSLEYS DGYTFLEWFQQRPGQSPRRLIYEVSNRFSGV PDRFSGSGSGTDFTLKISRVEAEDVGVYYCF QATHDPLTFGQGTKLEIKR |
| VH h5F9.21 | 65 | EVQLVESGGGVVQPGRSLRLSCAASGFTFSN YGMNWIRQAPGKGLEWIGMIYYDSSEKH YADSVKGRFTISRDNSKNTLYLQMNSLR AEDTAVYYCAKGTTPDYWGQGTMVTVSS |
| VL h5F9.21 | 66 | DVVLTQSPLSLPVTLGQPASISCRSSQSLE YSDGYTFLEWFLQKPGQSPQLLIYEVSNR FSGVPDRFSGSGSGTDFTLKISRVEAEDVG VYYCFQATHDPLTFGQGTKLEIKR |
| VH h5F9.22 | 67 | EVQLVESGGGVVQPGRSLRLSCAASGFTF SNYGMNWIRQAPGKGLEWIGMIYYDSSE KHYADSVKGRFTISRDNSKNTLYLQMNSL RAEDTAVYYCAKGTTPDYWGQGTMVTVSS |
| VL h5F9.22 | 68 | DVVLTQSPLSLPVTLGQPASISCRSSQSLEY SDGYTFLEWYLQKPGQSPQLLIYEVSNRFS GVPDRFSGSGSGTDFTLKISRVEAEDVGVY YCFQATHDPLTFGQGTKLEIKR |
| VH h5F9.23 | 69 | EVQLVESGGGLVQPGGSLRLSCAASGFTFS NYGMNWIRQAPGKGLEWIGMIYYDSSEKHYA DSVKGRFTISRDNSKNTLYLQMNSLRAEDTAV YYCAKGTTPDYWGQGTMVTVSS |
| VL h5F9.23 | 70 | DVVLTQSPLSLPVTLGQPASISCRSSQSLEY SDGYTFLEWFQQRPGQSPRLLIYEVSNRF SG VPDRFSGSGSGTDFTLKISRVEAEDVGVYY CFQATHDPLTFGQGTKLEIKR |
| VH h5F9.24 | 71 | EVQLVESGGGLVQPGGSLRLSCAASGFTFSN YGMNWIRQAPGKGLEWIGMIYYDSSEKHYA DSVKGRFTISRDNSKNTLYLQMNSLRAEDTA VYYCAKGTTPDYWGQGTMVTVSS |

TABLE 2-continued

List of Amino Acid Sequences of VH and VL
Regions of Humanized Anti-RGMc Antibodies

| PROTEIN REGION | SEQ ID NO. | SEQUENCE |
|---|---|---|
| VL h5F9.24 | 72 | DVVLTQSPLSLPVTLGQPASISCRSSQSLEYSDGYTFLEWFQQRPGQSPRRLIYEVSNRFSGVPDRFSGSGSGTDFTLKISRVEAEDVGVYYCFQATHDPLTFGQGTKLEIKR |
| VH h5F9.25 | 73 | EVQLVESGGGLVQPGGSLRLSCAASGFTFSNYGMNWIRQAPGKGLEWIGMIYYDSSEKHYADSVKGRFTISRDNSKNTLYLQMNSLRAEDTAVYYCAKGTTPDYWGQGTMVTVSS |
| VL h5F9.25 | 74 | DVVLTQSPLSLPVTLGQPASISCRSSQSLEYSDGYTFLEWFLQKPGQSPQLLIYEVSNRFSGVPDRFSGSGSGTDFTLKISRVEAEDVGVYYCFQATHDPLTFGQGTKLEIKR |
| VH h5F9.26 | 75 | EVQLVESGGGLVQPGGSLRLSCAASGFTFSNYGMNWIRQAPGKGLEWIGMIYYDSSEKHYADSVKGRFTISRDNSKNTLYLQMNSLRAEDTAVYYCAKGTTPDYWGQGTMVTVSS |
| VL h5F9.26 | 76 | DVVLTQSPLSLPVTLGQPASISCRSSQSLEYSDGYTFLEWYLQKPGQSPQLLIYEVSNRFSGVPDRFSGSGSGTDFTLKISRVEAEDVGVYYCFQATHDPLTFGQGTKLEIKR |
| VH h5F9.1 CDR-H1 | 77 | NYGMN |
| VH h5F9.1 CDR-H2 | 78 | MIYYDSSEKHYADSVKG |
| VH h5F9.1 CDR-H3 | 79 | GTTPDY |
| VL h5F9.1 CDR-L1 | 80 | RSSQSLEYSDGYTFLE |
| VL h5F9.1 CDR-L2 | 81 | EVSNRFS |
| VL h5F9.1 CDR-L3 | 82 | FQATHDPLT |
| VH h5F9.2 CDR-H1 | 83 | NYGMN |
| VH h5F9.2 CDR-H2 | 84 | MIYYDSSEKHYADSVKG |
| VH h5F9.2 CDR-H3 | 85 | GTTPDY |
| VL h5F9.2 CDR-L1 | 86 | RSSQSLEYSDGYTFLE |
| VL h5F9.2 CDR-L2 | 87 | EVSNRFS |
| VL h5F9.2 CDR-L3 | 88 | FQATHDPLT |
| VH h5F9.3 CDR-H1 | 89 | NYGMN |
| VH h5F9.3 CDR-H2 | 90 | MIYYDSSEKHYADSVKG |
| VH h5F9.3 CDR-H3 | 91 | GTTPDY |
| VL h5F9.3 CDR-L1 | 92 | RSSQSLEYSDGYTFLE |
| VL h5F9.3 CDR-L2 | 93 | EVSNRFS |
| VL h5F9.3 CDR-L3 | 94 | FQATHDPLT |
| VH h5F9.4 CDR-H1 | 95 | NYGMN |
| VH h5F9.4 CDR-H2 | 96 | MIYYDSSEKHYADSVKG |
| VH h5F9.4 CDR-H3 | 97 | GTTPDY |
| VL h5F9.4 CDR-L1 | 98 | RSSQSLEYSDGYTFLE |
| VL h5F9.4 CDR-L2 | 99 | EVSNRFS |
| VL h5F9.4 CDR-L3 | 100 | FQATHDPLT |
| VH h5F9.5 CDR-H1 | 101 | NYGMN |

TABLE 2-continued

List of Amino Acid Sequences of VH and VL
Regions of Humanized Anti-RGMc Antibodies

| PROTEIN REGION | SEQ ID NO. | SEQUENCE |
| --- | --- | --- |
| VH h5F9.5 CDR-H2 | 102 | MIYYDSSEKHYADSVKG |
| VH h5F9.5 CDR-H3 | 103 | GTTPDY |
| VL h5F9.5 CDR-L1 | 104 | RSSQSLEYSDGYTFLE |
| VL h5F9.5 CDR-L2 | 105 | EVSNRFS |
| VL h5F9.5 CDR-L3 | 106 | FQATHDPLT |
| VH h5F9.6 CDR-H1 | 107 | NYGMN |
| VH h5F9.6 CDR-H2 | 108 | MIYYDSSEKHYADSVKG |
| VH h5F9.6 CDR-H3 | 109 | GTTPDY |
| VL h5F9.6 CDR-L1 | 110 | RSSQSLEYSDGYTFLE |
| VL h5F9.6 CDR-L2 | 111 | EVSNRFS |
| VL h5F9.6 CDR-L3 | 112 | FQATHDPLT |
| VH h5F9.7 CDR-H1 | 113 | NYGMN |
| VH h5F9.7 CDR-H2 | 114 | MIYYDSSEKHYADSVKG |
| VH h5F9.7 CDR-H3 | 115 | GTTPDY |
| VL h5F9.7 CDR-L1 | 116 | RSSQSLEYSDGYTFLE |
| VL h5F9.7 CDR-L2 | 117 | EVSNRFS |
| VL h5F9.7 CDR-L3 | 118 | FQATHDPLT |
| VH h5F9.8 CDR-H1 | 119 | NYGMN |
| VH h5F9.8 CDR-H2 | 120 | MIYYDSSEKHYADSVKG |
| VH h5F9.8 CDR-H3 | 121 | GTTPDY |
| VL h5F9.8 CDR-L1 | 122 | RSSQSLEYSDGYTFLE |
| VL h5F9.8 CDR-L2 | 123 | EVSNRFS |
| VL h5F9.8 CDR-L3 | 124 | FQATHDPLT |
| VH h5F9.9 CDR-H1 | 125 | NYGMN |
| VH h5F9.9 CDR-H2 | 126 | MIYYDSSEKHYADSVKG |
| VH h5F9.9 CDR-H3 | 127 | GTTPDY |
| VL h5F9.9 CDR-L1 | 128 | RSSQSLEYSDGYTFLE |
| VL h5F9.9 CDR-L2 | 129 | EVSNRFS |
| VL h5F9.9 CDR-L3 | 130 | FQATHDPLT |
| VH h5F9.10 CDR-H1 | 131 | NYGMN |
| VH h5F9.10 CDR-H2 | 132 | MIYYDSSEKHYADSVKG |
| VH h5F9.10 CDR-H3 | 133 | GTTPDY |
| VL h5F9.10 CDR-L1 | 134 | RSSQSLEYSDGYTFLE |
| VL h5F9.10 CDR-L2 | 135 | EVSNRFS |
| VL h5F9.10 CDR-L3 | 136 | FQATHDPLT |
| VH h5F9.11 CDR-H1 | 137 | NYGMN |
| VH h5F9.11 CDR-H2 | 138 | MIYYDSSEKHYADSVKG |

TABLE 2-continued

List of Amino Acid Sequences of VH and VL
Regions of Humanized Anti-RGMc Antibodies

| PROTEIN REGION | SEQ ID NO. | SEQUENCE |
|---|---|---|
| VH h5F9.11 CDR-H3 | 139 | GTTPDY |
| VL h5F9.11 CDR-L1 | 140 | RSSQSLEYSDGYTFLE |
| VL h5F9.11 CDR-L2 | 141 | EVSNRFS |
| VL h5F9.11 CDR-L3 | 142 | FQATHDPLT |
| VH h5F9.12 CDR-H1 | 143 | NYGMN |
| VH h5F9.12 CDR-H2 | 144 | MIYYDSSEKHYADSVKG |
| VH h5F9.12 CDR-H3 | 145 | GTTPDY |
| VL h5F9.12 CDR-L1 | 146 | RSSQSLEYSDGYTFLE |
| VL h5F9.12 CDR-L2 | 147 | EVSNRFS |
| VL h5F9.12 CDR-L3 | 148 | FQATHDPLT |
| VH h5F9.19 CDR-H1 | 149 | NYGMN |
| VH h5F9.19 CDR-H2 | 150 | MIYYDSSEKHYADSVKG |
| VH h5F9.19 CDR-H3 | 151 | GTTPDY |
| VL h5F9.19 CDR-L1 | 152 | RSSQSLEYSDGYTFLE |
| VL h5F9.19 CDR-L2 | 153 | EVSNRFS |
| VL h5F9.19 CDR-L3 | 154 | FQATHDPLT |
| VH h5F9.20 CDR-H1 | 155 | NYGMN |
| VH h5F9.20 CDR-H2 | 156 | MIYYDSSEKHYADSVKG |
| VH h5F9.20 CDR-H3 | 157 | GTTPDY |
| VL h5F9.20 CDR-L1 | 158 | RSSQSLEYSDGYTFLE |
| VL h5F9.20 CDR-L2 | 159 | EVSNRF |
| VL h5F9.20 CDR-L3 | 160 | FQATHDPLT |
| VH h5F9.21 CDR-H1 | 161 | NYGMN |
| VH h5F9.21 CDR-H2 | 162 | MIYYDSSEKHYADSVKG |
| VH h5F9.21 CDR-H3 | 163 | GTTPDY |
| VL h5F9.21 CDR-L1 | 164 | RSSQSLEYSDGYTFLE |
| VL h5F9.21 CDR-L2 | 165 | EVSNRFS |
| VL h5F9.21 CDR-L3 | 166 | FQATHDPLT |
| VH h5F9.22 CDR-H1 | 167 | NYGMN |
| VH h5F9.22 CDR-H2 | 168 | MIYYDSSEKHYADSVKG |
| VH h5F9.22 CDR-H3 | 169 | GTTPDY |
| VL h5F9.22 CDR-L1 | 170 | RSSQSLEYSDGYTFLE |
| VL h5F9.22 CDR-L2 | 171 | EVSNRFS |
| VL h5F9.22 CDR-L3 | 172 | FQATHDPLT |
| VH h5F9.23 CDR-H1 | 173 | NYGMN |
| VH h5F9.23 CDR-H2 | 174 | MIYYDSSEKHYADSVKG |
| VH h5F9.23 CDR-H3 | 175 | GTTPDY |
| VL h5F9.23 CDR-L1 | 176 | RSSQSLEYSDGYTFLE |

TABLE 2-continued

List of Amino Acid Sequences of VH and VL Regions of Humanized Anti-RGMc Antibodies

| PROTEIN REGION | SEQ ID NO. | SEQUENCE |
|---|---|---|
| VL h5F9.23 CDR-L2 | 177 | EVSNRFS |
| VL h5F9.23 CDR-L3 | 178 | FQATHDPLT |
| VH h5F9.24 CDR-H1 | 179 | NYGMN |
| VH h5F9.24 CDR-H2 | 180 | MIYYDSSEKHYADSVKG |
| VH h5F9.24 CDR-H3 | 181 | GTTPDY |
| VL h5F9.24 CDR-L1 | 182 | RSSQSLEYSDGYTFLE |
| VL h5F9.24 CDR-L2 | 183 | EVSNRFS |
| VL h5F9.24 CDR-L3 | 184 | FQATHDPLT |
| VH h5F9.25 CDR-H1 | 185 | NYGMN |
| VH h5F9.25 CDR-H2 | 186 | MIYYDSSEKHYADSVKG |
| VH h5F9.25 CDR-H3 | 187 | GTTPDY |
| VL h5F9.25 CDR-L1 | 188 | RSSQSLEYSDGYTFLE |
| VL h5F9.25 CDR-L2 | 189 | EVSNRFS |
| VL h5F9.25 CDR-L3 | 190 | FQATHDPLT |
| VH h5F9.26 CDR-H1 | 191 | NYGMN |
| VH h5F9.26 CDR-H2 | 192 | MIYYDSSEKHYADSVKG |
| VH h5F9.26 CDR-H3 | 193 | GTTPDY |
| VL h5F9.26 CDR-L1 | 194 | RSSQSLEYSDGYTFLE |
| VL h5F9.26 CDR-L2 | 195 | EVSNRFS |
| VL h5F9.26 CDR-L3 | 196 | FQATHDPLT |

The humanized antibodies described above in Table 2 and methods for making them are described in U.S. Patent Publication No. 2010/0028340, the contents of which are herein incorporated by reference.

As shown in Table 2, the variable region (VH and VL) CDR-H1 domains are all identical in sequence. Also, each of the CDR-H2, CDR-H3, CDR-L1, CDR-L2, and CDR-L3 domains are respectively identical in sequence (i.e. the CDR-H2 domain of the VH h5F9.1 region is identical to the CDR-H2 domain of the VH h5F9.2 region is identical to the CDR-H2 domain of the VH h5F9.3 region, etc. The CDR-H3 domain of the VH h5F9.1 region is identical to the CDR-H3 domain of the VH h5F9.2 region is identical to the CDR-H3 domain of the VH h5F9.3 region, etc. . . . ).

An isolated antibody that specifically binds to RGMc (or fragment thereof) of the present disclosure can have a region or domain selected from the group consisting of: (a) a variable heavy domain region comprising the amino acid sequence of SEQ ID NO:3, (b) a variable light domain region comprising the amino acid sequence of SEQ ID NO:4, (c) a variably heavy domain region comprising the amino acid sequence of SEQ ID NO:5, (d) a variable light domain region comprising the amino acid sequence of SEQ ID NO:6, (e) a variably heavy domain region comprising the amino acid sequence of SEQ ID NO:7, (f) a variable light domain region comprising the amino acid sequence of SEQ ID NO:8, (g) a variably heavy domain region comprising the amino acid sequence of SEQ ID NO:9, (h) a variable light domain region comprising the amino acid sequence of SEQ ID NO: 10, (i) a variable heavy chain comprising a complementarity determining region (CDR)1 comprising the amino acid sequence of SEQ ID NO:11, a CDR2 comprising the amino acid sequence of SEQ ID NO:12, and a CDR3 comprising the amino acid sequence of SEQ ID NO:13, (j) a variable light chain comprising a CDR1 comprising the amino acid sequence of SEQ ID NO: 14, a CDR2 comprising the amino acid sequence of SEQ ID NO: 15, and a CDR3 comprising the amino acid sequence of SEQ ID NO:16, (k) a variable heavy chain comprising a CDR1 comprising the amino acid sequence of SEQ ID NO:17, a CDR2 comprising the amino acid sequence of SEQ ID NO: 18, and a CDR3 comprising the amino acid sequence of SEQ ID NO: 19, (l) a variable light chain comprising a CDR1 comprising the amino acid sequence of SEQ ID NO:20, a CDR2 comprising the amino acid sequence of SEQ ID NO:21, and a CDR3 comprising the amino acid sequence of SEQ ID NO:22, (m) a variable heavy chain comprising a CDR1 comprising the amino acid sequence of SEQ ID NO:23, a CDR2 comprising the amino acid sequence of SEQ ID NO:24, and a CDR3 comprising the amino acid sequence of SEQ ID NO:25, (n) a variable light chain comprising a CDR1 comprising the amino acid sequence of SEQ ID NO:26, a CDR2 comprising the amino acid sequence of SEQ ID NO:27, and a CDR3 comprising the amino acid sequence of SEQ ID NO:28, (o) a variable heavy chain comprising a CDR1 comprising the amino acid sequence of SEQ ID NO:29, a CDR2 comprising the amino acid sequence of SEQ ID NO:30, and a CDR3 comprising the amino acid sequence of SEQ ID NO:31, (p) a variable light chain comprising a CDR1 comprising the amino acid sequence of SEQ ID NO:32, a CDR2 comprising the amino acid sequence of SEQ ID NO:33, and a CDR3 comprising the amino acid sequence of SEQ ID NO:34, (q) a variable heavy chain comprising a complementarity determining region (CDR)1 comprising the amino acid sequence of SEQ ID NO: 11, a CDR2 comprising the amino acid sequence of SEQ ID NO: 12, and a CDR3 comprising the amino acid sequence of SEQ ID NO:13 and a variable light chain comprising a CDR1 comprising the amino acid sequence of SEQ ID NO:14, a CDR2 comprising the amino acid sequence of SEQ ID NO: 15, and a CDR3 comprising the amino acid sequence of SEQ ID NO: 16, (r) a variable heavy chain comprising a CDR1 comprising the amino acid sequence of SEQ ID NO: 17, a CDR2 comprising the amino acid sequence of SEQ ID NO: 18, and a CDR3 comprising the amino acid sequence of SEQ ID NO:19 and a variable light chain comprising a CDR1 comprising the amino acid sequence of SEQ ID NO:20, a CDR2 comprising the amino acid sequence of SEQ ID NO:21, and a CDR3 comprising the amino acid sequence of SEQ ID NO:22, (s) a variable heavy chain comprising a CDR1 comprising the amino acid sequence of SEQ ID NO:23, a CDR2 comprising the amino acid sequence of SEQ ID NO:24, and a CDR3 comprising the amino acid sequence of SEQ ID NO:25 and a variable light chain comprising a CDR1 comprising the amino acid sequence of SEQ ID NO:26, a CDR2 comprising the amino acid sequence of SEQ ID NO:27, and a CDR3 comprising the amino acid sequence of SEQ ID NO:28, (t) a variable heavy chain comprising a CDR1 comprising the amino acid sequence of SEQ ID NO:29, a CDR2 comprising the amino acid sequence of SEQ ID NO:30, and a CDR3 comprising the amino acid sequence of SEQ ID NO:31 and a variable light chain comprising a CDR1 comprising the amino acid sequence of SEQ ID NO:32, a CDR2 comprising the amino acid sequence of SEQ ID NO:33, and a CDR3 comprising the amino acid sequence of SEQ ID NO:34.

The antibody, a fragment thereof, a variant or a derivative thereof may contain one or more amino acid sequences that are equal to or have greater than about 95%, about 90%, about about 85%, about 80%, about 75%, about 70%, about 65%, about 60%, about 55%, or about 50% identity to one or more of SEQ ID NOs:3-34. The antibody or variant or derivative thereof may be encoded by one or more nucleic acid sequences that are equal to or have greater than about 95%, about 90%, about 85%, about 80%, about 75%, about 70%, about 65%, about 60%, about 55%, or about 50% identity to one or more nucleic acid sequences that encode one or more of SEQ ID NOs:3-34. Polypeptide identity and homology can be determined, for example, by the algorithm described in the report: Wilbur, W. J. and Lipman, D. J. Proc. Natl. Acad. Sci. USA 80, 726-730 (1983). The herein described antibody, fragment thereof, variant thereof or a derivative thereof may be encoded by a nucleic acid that hybridizes under stringent conditions with the complement of one or more nucleic acid sequences that encode one or more of SEQ ID NOs:3-34. The herein described antibody, fragment thereof, variant thereof, or derivative thereof may be encoded by a nucleic acid that hybridizes under highly stringent conditions with the complement of one or more of nucleic acid sequences that encode one or more of SEQ ID NOs:3-34.

c. Antibody Preparation/Production

Antibodies may be prepared by any of a variety of techniques. In general, antibodies can be produced by cell culture techniques, including the generation of monoclonal antibodies via conventional techniques, or via transfection of antibody genes, heavy chains and/or light chains into suitable bacterial or mammalian cell hosts, in order to allow for the production of antibodies, wherein the antibodies may be recombinant. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is possible to express the antibodies of the invention in either prokaryotic or eukaryotic host cells, expression of antibodies in eukaryotic cells is preferable, and most preferable in mammalian host cells, because such eukaryotic cells (and in particular mammalian cells) are more likely than prokaryotic cells to assemble and secrete a properly folded and immunologically active antibody.

Exemplary mammalian host cells for expressing the recombinant antibodies of the invention include Chinese Hamster Ovary (CHO cells) (including dhfr-CHO cells, described in Urlaub and Chasin, Proc. Natl. Acad. Sci. USA, 77: 4216-4220 (1980), used with a DHFR selectable marker, e.g., as described in Kaufman and Sharp, J. Mol. Biol., 159: 601-621 (1982), NS0 myeloma cells, COS cells, and SP2 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Host cells can also be used to produce functional antibody fragments, such as Fab fragments or scFv molecules. It will be understood that variations on the above procedure are within the scope of the present invention. For example, it may be desirable to transfect a host cell with DNA encoding functional fragments of either the light chain and/or the heavy chain of an antibody of this invention. Recombinant DNA technology may also be used to remove some, or all, of the DNA encoding either or both of the light and heavy chains that is not necessary for binding to the antigens of interest. The molecules expressed from such truncated DNA molecules are also encompassed by the antibodies of the invention. In addition, bifunctional antibodies may be produced in which one heavy and one light chain are an antibody of the invention (i.e., binds human RGMc) and the other heavy and light chain are specific for an antigen other than human RGMc by crosslinking an antibody of the invention to a second antibody by standard chemical cross-linking methods.

In a preferred system for recombinant expression of an antibody, or antigen-binding portion thereof, of the invention, a recombinant expression vector encoding both the antibody heavy chain and the antibody light chain is introduced into dhfr-CHO cells by calcium phosphate-mediated transfection. Within the recombinant expression vector, the antibody heavy and light chain genes are each operatively linked to CMV enhancer/AdMLP promoter regulatory elements to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium. Still further the invention provides a method of synthesizing a recombinant antibody of the invention by culturing a host cell of the invention in a suitable culture medium until a recombinant antibody of the invention is synthesized. The method can further comprise isolating the recombinant antibody from the culture medium.

Methods of preparing monoclonal antibodies involve the preparation of immortal cell lines capable of producing antibodies having the desired specificity. Such cell lines may be produced from spleen cells obtained from an immunized animal. The animal may be immunized with RGMc or a fragment and/or variant thereof. For example, any of SEQ ID NO:1, SEQ ID NO:2, a fragment of SEQ ID NO: 1 or SEQ ID NO:2, or a variant of SEQ ID NO: 1 or SEQ ID NO:2 may be used to immunize the animal. The animal may be immunized with RGMa or a fragment and/or variant thereof. For example, any of SEQ ID NO:35, SEQ ID NO:36, a fragment of SEQ ID NO:35 or SEQ ID NO:36, or a variant of SEQ ID NO:35 or SEQ ID NO:36 may be used to immunize the animal. RGMa may have the following amino acid sequence:

```
                                            (SEQ ID NO: 35)
MGMGRGAGRS ALGFWPTLAF LLCSFPAATS PCKILKCNSE

FWSATSGSHA PASDDTPEFC AALRSYALCT RRTARTCRGD

LAYHSAVHGI EDLMSQHNCS KDGPTSQPRL RTLPPAGDSQ

ERSDSPEICH YEKSFHKHSA TPNYTHCGLF GDPHLRTFTD

RFQTCKVQGA WPLIDNNYLN VQVTNTPVLP GSAATATSKL

TIIFKNFQEC VDQKVYQAEM DELPAAFVDG SKNGGDKHGA

NSLKITEKVS GQHVEIQAKY IGTTIVVRQV GRYLTFAVRM

PEEVVNAVED WDSQGLYLCL RGCPLNQQID FQAFHTNAEG

TGARRLAAAS PAPTAPETFP YETAVAKCKE KLPVEDLYYQ

ACVFDLLTTG DVNFTLAAYY ALEDVKMLHS NKDKLHLYER

TRDLPGRAAA GLPLAPRPLL GALVPLLALL PVFC.
```

The RGMa may be a fragment or variant of SEQ ID NO:35.

The fragment of may be between 5 and 425 amino acids, between 10 and 400 amino acids, between 50 and 350 amino acids, between 100 and 300 amino acids, between 150 and 250 amino acids, between 200 and 300 amino acids, or between 75 and 150 amino acids in length. The fragment may comprise a contiguous number of amino acids from SEQ ID NO:35.

The fragment of RGMa may have the following amino acid sequence:

```
                                            (SEQ ID NO: 66)
MGMGRGAGRS ALGFWPTLAF LLCSFPAATS PCKILKCNSE

FWSATSGSHA PASDDTPEFC AALRSYALCT RRTARTCRGD

LAYHSAVHGI EDLMSQHNCS KDGPTSQPRL RTLPPAGDSQ

ERSDSPEICH YEKSFHKHSA TPNYTHCGLF GDPHLRTFTD

RFQTCKVQGA WPLIDNNYLN VQVTNTPVLP GSAATATSKL.
```

The RGMa fragment may be a fragment of SEQ ID NO:36. The RGMa fragment may be a variant of SEQ ID NO:36.

The peptide used to immunize the animal may comprise amino acids encoding human Fc, for example the fragment crystallizable region or tail region of human antibody. The spleen cells may then be immortalized by, for example, fusion with a myeloma cell fusion partner. A variety of fusion techniques may be employed. For example, the spleen cells and myeloma cells may be combined with a nonionic detergent for a few minutes and then plated at low density on a selective medium that supports that growth of hybrid cells, but not myeloma cells. One such technique uses hypoxanthine, aminopterin, thymidine (HAT) selection. After a sufficient time, usually about 1 to 2 weeks, colonies of hybrids are observed. Single colonies are selected and their culture supernatants tested for binding activity against the polypeptide. Hybridomas having high reactivity and specificity may be used.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. Affinity chromatography is an example of a method that can be used in a process to purify the antibodies.

The proteolytic enzyme papain preferentially cleaves IgG molecules to yield several fragments, two of which (the F(ab) fragments) each comprise a covalent heterodimer that includes an intact antigen-binding site. The enzyme pepsin is able to cleave IgG molecules to provide several fragments, including the F(ab')$_2$ fragment, which comprises both antigen-binding sites.

The Fv fragment can be produced by preferential proteolytic cleavage of an IgM, and on rare occasions IgG or IgA immunoglobulin molecules. The Fv fragment may be derived using recombinant techniques. The Fv fragment includes a non-covalent VH::VL heterodimer including an antigen-binding site which retains much of the antigen recognition and binding capabilities of the native antibody molecule.

The antibody, antibody fragment, or derivative may comprise a heavy chain and a light chain complementarity determining region ("CDR") set, respectively interposed between a heavy chain and a light chain framework ("FR") set which provide support to the CDRs and define the spatial relationship of the CDRs relative to each other. The CDR set may contain three hypervariable regions of a heavy or light chain V region. Proceeding from the N-terminus of a heavy or light chain, these regions are denoted as "CDR1," "CDR2," and "CDR3," respectively. An antigen-binding site, therefore, may include six CDRs, comprising the CDR set from each of a heavy and a light chain V region. A polypeptide comprising a single CDR, (e.g., a CDR1, CDR2 or CDR3) may be referred to as a "molecular recognition unit." Crystallographic analyses of antigen-antibody complexes have demonstrated that the amino acid residues of CDRs from extensive contact with bound antigen, wherein the most extensive antigen contact is with the heavy chain CDR3. Thus, the molecular recognition units may be primarily responsible for the specificity of an antigen-binding site. In general, the CDR residues are directly and most substantially involved in influencing antigen binding.

The humanized antibody may be designed to minimize unwanted immunological response toward rodent anti-human antibodies, which limits the duration and effectiveness of therapeutic applications of those moieties in human recipients. The humanized antibody may have one or more amino acid residues introduced into it from a source that is non-human. These non-human residues are often referred to as "import" residues, which are typically taken from a variable domain. Humanization may be performed by substituting hypervariable region sequences for the corresponding sequences of a human antibody. Accordingly, such "humanized" antibodies are chimeric antibodies wherein substantially less than an intact human variable domain has been substituted by the corresponding sequence from a non-human species. For example, see U.S. Pat. No. 4,816, 567, the contents of which are herein incorporated by reference. The humanized antibody may be a human antibody in which some hypervariable region residues, and possibly some FR residues are substituted by residues from analogous sites in rodent antibodies. Humanization or engineering of antibodies of the present invention can be performed using any known method, such as but not limited to those described in U.S. Pat. Nos. 5,723,323, 5,976,862, 5,824,514, 5,817,483, 5,814,476, 5,763,192, 5,723,323, 5,766,886, 5,714,352, 6,204,023, 6,180,370, 5,693,762, 5,530,101, 5,585,089, 5,225,539; and 4,816,567.

The humanized antibody may retain high affinity for RGMc and other favorable biological properties. The humanized antibody may be prepared by a process of analysis of the parental sequences and various conceptual humanized products using three-dimensional models of the parental and humanized sequences. Three-dimensional immunoglobulin models are commonly available. Computer programs are available that illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined form the recipient and import sequences so that the desired antibody characteristics, such as increased affinity for RGMc, is achieved. In general, the hypervariable region residues may be directly and most substantially involved in influencing antigen binding.

As an alternative to humanization, human antibodies (also referred to herein as "fully human antibodies") can be generated. For example, it is possible to produce transgenic animals (e.g. mice that are capable, upon immunization, of producing a full repertoire of human antibodies in the absence of endogenous immunoglobulin production. For example, the homozygous deletion of the antibody heavy-chain joining region ($J_H$) gene in chimeric and germline mutant mice results in complete inhibition of endogenous antibody production. Transfer of the human germline immunoglobulin gene array in such germline mutant mice will result in the production of human antibodies upon antigen challenge. The humanized or fully human antibodies may be prepared according to the methods described in U.S. Pat. Nos. 5,770,429; 5,833,985; 5,837,243; 5,922,845; 6,017, 517; 6,096,311; 6,111,166; 6,270,765; 6,303,755; 6,365, 116; 6,410,690; 6,682,928; and 6,984,720, the contents each of which are herein incorporated by reference.

Other suitable methods of producing or isolating antibodies of the requisite specificity can be used, including, but not limited to, methods that select recombinant antibody from a peptide or protein library (e.g., but not limited to, a bacteriophage, ribosome, oligonucleotide, RNA, cDNA, or the like, display library; e.g., as available from various commercial vendors such as Cambridge Antibody Technologies (Cambridgeshire, UK), MorphoSys (Martinsreid/Planegg, Del.), Biovation (Aberdeen, Scotland, UK) BioInvent (Lund, Sweden), using methods known in the art. See U.S. Pat. Nos. 4,704,692; 5,723,323; 5,763,192; 5,814,476; 5,817,483; 5,824,514; 5,976,862. Alternative methods rely upon immunization of transgenic animals (e.g., SCID mice, Nguyen et al. (1977) Microbiol. Immunol. 41:901-907 (1997); Sandhu et al. (1996) Crit. Rev. Biotechnol. 16:95-118; Eren et al. (1998) Immunol. 93:154-161 that are capable of producing a repertoire of human antibodies, as known in the art and/or as described herein. Such techniques, include, but are not limited to, ribosome display (Hanes et al. (1997) Proc. Natl. Acad. Sci. USA, 94:4937-4942; Hanes et al. (1998) Proc. Natl. Acad. Sci. USA, 95:14130-14135); single cell antibody producing technologies (e.g., selected lymphocyte antibody method ("SLAM") (U.S. Pat. No. 5,627,052, Wen et al. (1987) J. Immunol. 17:887-892; Babcook et al. (1996) Proc. Natl. Acad. Sci. USA 93:7843-7848); gel microdroplet and flow cytometry (Powell et al. (1990) Biotechnol. 8:333-337; One Cell Systems, (Cambridge, Mass.).; Gray et al. (1995) J. Imm. Meth. 182:155-163; Kenny et al. (1995) Bio/Technol. 13:787-790); B-cell selection (Steenbakkers et al. (1994) Molec. Biol. Reports 19:125-134 (1994).

An affinity matured antibody may be produced by any one of a number of procedures that are known in the art. For example, see Marks et al., BioTechnology, 10: 779-783 (1992) describes affinity maturation by VH and VL domain shuffling. Random mutagenesis of CDR and/or framework residues is described by Barbas et al., Proc. Nat. Acad. Sci. USA, 91: 3809-3813 (1994); Schier et al., Gene, 169: 147-155 (1995); Yelton et al., J. Immunol., 155: 1994-2004 (1995); Jackson et al., J. Immunol., 154(7): 3310-3319 (1995); Hawkins et al, J. Mol. Biol., 226: 889-896 (1992). Selective mutation at selective mutagenesis positions and at contact or hypermutation positions with an activity enhancing amino acid residue is described in U.S. Pat. No. 6,914, 128 B1.

Antibody variants of the present invention can also be prepared using delivering a polynucleotide encoding an antibody of this invention to a suitable host such as to provide transgenic animals or mammals, such as goats, cows, horses, sheep, and the like, that produce such antibodies in their milk. These methods are known in the art and are described for example in U.S. Pat. Nos. 5,827,690; 5,849,992; 4,873,316; 5,849,992; 5,994,616; 5,565,362; and 5,304,489.

Antibody variants also can be prepared by delivering a polynucleotide of this invention to provide transgenic plants and cultured plant cells (e.g., but not limited to tobacco, maize, and duckweed) that produce such antibodies, specified portions or variants in the plant parts or in cells cultured therefrom. For example, Cramer et al. (1999) Curr. Top. Microbol. Immunol. 240:95-118 and references cited therein, describe the production of transgenic tobacco leaves expressing large amounts of recombinant proteins, e.g., using an inducible promoter. Transgenic maize have been used to express mammalian proteins at commercial production levels, with biological activities equivalent to those produced in other recombinant systems or purified from natural sources. See, e.g., Hood et al., Adv. Exp. Med. Biol. (1999) 464: 127-147 and references cited therein. Antibody variants have also been produced in large amounts from transgenic plant seeds including antibody fragments, such as single chain antibodies (scFv's), including tobacco seeds and potato tubers. See, e.g., Conrad et al. (1998) Plant Mol. Biol. 38:101-109 and reference cited therein. Thus, antibodies of the present invention can also be produced using transgenic plants, according to know methods.

Antibody derivatives can be produced, for example, by adding exogenous sequences to modify immunogenicity or reduce, enhance or modify binding, affinity, on-rate, off-rate, avidity, specificity, half-life, or any other suitable characteristic. Generally part or all of the non-human or human CDR sequences are maintained while the non-human sequences of the variable and constant regions are replaced with human or other amino acids.

Small antibody fragments may be diabodies having two antigen-binding sites, wherein fragments comprise a heavy chain variable domain ($V_H$) connected to a light chain variable domain ($V_L$) in the same polypeptide chain ($V_H$ $V_L$). See for example, EP 404,097; WO 93/11161; and Hollinger et al., (1993) Proc. Natl. Acad. Sci. USA 90:6444-6448. By using a linker that is too short to allow pairing between the two domains on the same chain, the domains are forced to pair with the complementary domains of another chain and create two antigen-binding sites. See also, U.S. Pat. No. 6,632,926 to Chen et al. which is hereby incorporated by reference in its entirety and discloses antibody variants that have one or more amino acids inserted into a hypervariable region of the parent antibody and a binding affinity for a target antigen which is at least about two fold stronger than the binding affinity of the parent antibody for the antigen.

The antibody may be a linear antibody. The procedure for making a linear antibody is known in the art and described in Zapata et al. (1995) Protein Eng. 8(10):1057-1062. Briefly, these antibodies comprise a pair of tandem Fd segments ($V_H$-$C_{H1}$-$V_H$-$C_{H1}$) which form a pair of antigen binding regions. Linear antibodies can be bispecific or monospecific.

The antibodies may be recovered and purified from recombinant cell cultures by known methods including, but not limited to, protein A purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography ("HPLC") can also be used for purification.

It may be useful to detectably or therapeutically label the antibody. Methods for conjugating antibodies to these agents are known in the art. For the purpose of illustration only, antibodies can be labeled with a detectable moiety such as a radioactive atom, a chromophore, a fluorophore, or the like. Such labeled antibodies can be used for diagnostic techniques, either in vivo, or in an isolated test sample. Antibodies can also be conjugated, for example, to a pharmaceutical agent, such as chemotherapeutic drug or a toxin. They can be linked to a cytokine, to a ligand, to another antibody. Suitable agents for coupling to antibodies to achieve an anti-tumor effect include cytokines, such as interleukin 2 (IL-2) and Tumor Necrosis Factor (TNF); photosensitizers, for use in photodynamic therapy, including aluminum (III) phthalocyanine tetrasulfonate, hematoporphyrin, and phthalocyanine; radionuclides, such as iodine-131 ($^{131}$I), yttrium-90 ($^{90}$Y), bismuth-212 ($^{212}$Bi), bismuth-213 ($^{213}$Bi), technetium-99m ($^{99m}$Tc), rhenium-186 ($^{186}$Re), and rhenium-188 ($^{188}$Re); antibiotics, such as doxorubicin, adriamycin, daunorubicin, methotrexate, daunomycin, neocarzinostatin, and carboplatin; bacterial, plant, and other toxins, such as diphtheria toxin, pseudomonas exotoxin A, staphylococcal enterotoxin A, abrin-A toxin, ricin A (deglycosylated ricin A and native ricin A), TGF-alpha toxin, cytotoxin from chinese cobra (naja naja atra), and gelonin (a plant toxin); ribosome inactivating proteins from plants, bacteria and fungi, such as restrictocin (a ribosome inactivating protein produced by *Aspergillus restrictus*), saporin (a ribosome inactivating protein from *Saponaria officinalis*), and RNase; tyrosine kinase inhibitors; ly207702 (a difluorinated purine nucleoside); liposomes containing anti cystic agents (e.g., antisense oligonucleotides, plasmids which encode for toxins, methotrexate, etc.); and other antibodies or antibody fragments, such as F(ab).

The antibodies can be sequenced and replicated by recombinant or synthetic means. They also can be further sequenced down to the linear sequence of nucleotides that encode them. Accordingly, this invention provides these polynucleotides, alone or in combination with a carrier, vector or host cell as described above, that encode a sequence of an antibody of this invention.

Antibody production via the use of hybridoma technology, the selected lymphocyte antibody method (SLAM), transgenic animals, and recombinant antibody libraries is described in more detail below.

(1) Anti-RGMc Monoclonal Antibodies Using Hybridoma Technology

As described above, monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, second edition, (Cold Spring Harbor Laboratory Press, Cold Spring Harbor, 1988); Hammerling, et al., In Monoclonal Antibodies and T-Cell Hybridomas, (Elsevier, N.Y., 1981). It is also noted that the term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

In an embodiment, provided are methods of generating monoclonal antibodies as well as antibodies produced by the method comprising culturing a hybridoma cell secreting an antibody wherein, preferably, the hybridoma is generated by fusing splenocytes isolated from an animal, e.g., a rat or a mouse, immunized with RGMc with myeloma cells and then screening the hybridomas resulting from the fusion for hybridoma clones that secrete an antibody that can bind to RGMc (or a fragment or a variant thereof). Briefly, rats can be immunized with an RGMc antigen (see, Examples, below). In a preferred embodiment, the RGMc antigen is administered with an adjuvant to stimulate the immune response. Such adjuvants include complete or incomplete Freund's adjuvant, RIBI (muramyl dipeptides) or ISCOM (immunostimulating complexes). Such adjuvants may protect the polypeptide from rapid dispersal by sequestering it in a local deposit, or they may contain substances that stimulate the host to secrete factors that are chemotactic for macrophages and other components of the immune system. Preferably, if a polypeptide is being administered, the immunization schedule will involve two or more administrations of the polypeptide, spread out over several weeks; however, a single administration of the polypeptide may also be used.

After immunization of an animal with an RGMc antigen, antibodies and/or antibody-producing cells may be obtained from the animal. An anti-RGMc antibody-containing serum is obtained from the animal by bleeding or sacrificing the animal. The serum may be used as it is obtained from the animal, an immunoglobulin fraction may be obtained from the serum, or the anti-RGMc antibodies may be purified from the serum. Serum or immunoglobulins obtained in this manner are polyclonal, thus having a heterogeneous array of properties.

Once an immune response is detected, e.g., antibodies specific for the antigen RGMc are detected in the rat serum, the rat spleen is harvested and splenocytes isolated. The splenocytes are then fused by well-known techniques to any suitable myeloma cells, for example cells from cell line SP20 available from the American Type Culture Collection (ATCC, Manassas, Va., US). Hybridomas are selected and cloned by limited dilution. The hybridoma clones are then assayed by methods known in the art for cells that secrete antibodies that can bind RGMc (or a fragment or a variant thereof). Ascites fluid, which generally contains high levels of antibodies, can be generated by immunizing rats with positive hybridoma clones.

In another embodiment, antibody-producing immortalized hybridomas may be prepared from the immunized animal. After immunization, the animal is sacrificed and the splenic B cells are fused to immortalized myeloma cells as is well-known in the art. See, e.g., Harlow and Lane, supra. In a preferred embodiment, the myeloma cells do not secrete immunoglobulin polypeptides (a non-secretory cell line). After fusion and antibiotic selection, the hybridomas are screened using RGMc, or a fragment or a variant thereof, or a cell expressing RGMc (or a fragment or a variant thereof). In a preferred embodiment, the initial screening is performed using an enzyme-linked immunosorbent assay (ELISA) or a radioimmunoassay (RIA), preferably an ELISA. An example of ELISA screening is provided in PCT Publication No. WO 00/37504.

Anti-RGMc antibody-producing hybridomas are selected, cloned, and further screened for desirable characteristics, including robust hybridoma growth, high antibody production, and desirable antibody characteristics, as discussed further below. Hybridomas may be cultured and expanded in vivo in syngeneic animals, in animals that lack an immune system, e.g., nude mice, or in cell culture in vitro. Methods of selecting, cloning and expanding hybridomas are well-known to those of ordinary skill in the art.

In a preferred embodiment, hybridomas are rat hybridomas, as described herein. In another embodiment, hybridomas are produced in a non-human, non-rat species such as mice, sheep, pigs, goats, cattle, or horses. In yet another preferred embodiment, the hybridomas are human hybridomas, in which a human non-secretory myeloma is fused with a human cell expressing an anti-RGMc antibody.

Antibody fragments that recognize specific epitopes may be generated by known techniques. For example, Fab and F(ab')$_2$ fragments may be produced by proteolytic cleavage of immunoglobulin molecules, using enzymes such as papain (to produce two identical Fab fragments) or pepsin (to produce a F(ab')$_2$ fragment). A F(ab')$_2$ fragment of an IgG molecule retains the two antigen-binding sites of the larger ("parent") IgG molecule, including both light chains (containing the variable light chain and constant light chain regions), the CH1 domains of the heavy chains, and a disulfide-forming hinge region of the parent IgG molecule. Accordingly, a F(ab')$_2$ fragment can crosslink antigen molecules like the parent IgG molecule.

(2) Anti-RGMc Monoclonal Antibodies Using SLAM.

Recombinant antibodies can be generated from single, isolated lymphocytes using a procedure referred to in the art as the selected lymphocyte antibody method (SLAM), as described in U.S. Pat. No. 5,627,052; PCT Publication No. WO 92/02551; and Babcook et al., Proc. Natl. Acad. Sci. USA, 93: 7843-7848 (1996). In this method, single cells secreting antibodies of interest, e.g., lymphocytes derived from any one of the immunized animals described in Section I.A.1 (above), are screened using an antigen-specific hemolytic plaque assay, wherein the antigen RGMc, a subunit of RGMc, or a fragment thereof, is coupled to sheep red blood cells using a linker, such as biotin, and used to identify single cells that secrete antibodies with specificity for RGMc. Following identification of antibody-secreting cells of interest, heavy- and light-chain variable region cDNAs are rescued from the cells by reverse transcriptase-PCR (RT-PCR) and these variable regions can then be expressed, in the context of appropriate immunoglobulin constant regions (e.g., human constant regions), in mammalian host cells, such as COS or CHO cells. The host cells transfected with the amplified immunoglobulin sequences, derived from in vivo-selected lymphocytes, can then undergo further analysis and selection in vitro, for example, by panning the transfected cells to isolate cells expressing antibodies to RGMc. The amplified immunoglobulin sequences further can be manipulated in vitro, such as by in vitro affinity maturation method. See, for example, PCT Publication No. WO 97/29131 and PCT Publication No. WO 00/56772.

(3) Anti-RGMc Monoclonal Antibodies Using Transgenic Animals.

Antibodies also can be produced by immunizing a non-human animal comprising some, or all, of the human immunoglobulin locus with a RGMc antigen. In an embodiment, the non-human animal is a XENOMOUSE® transgenic mouse, an engineered mouse strain that comprises large fragments of the human immunoglobulin locus and is deficient in mouse antibody production. See, e.g., Green et al., Nature Genetics, 7: 13-21 (1994) and U.S. Pat. Nos. 5,916, 771; 5,939,598; 5,985,615; 5,998,209; 6,075,181; 6,091, 001; 6,114,598; and 6,130,364. See also PCT Publication Nos. WO 91/10741; WO 94/02602; WO 96/34096; WO 96/33735; WO 98/16654; WO 98/24893; WO 98/50433; WO 99/45031; WO 99/53049; WO 00/09560; and WO 00/37504. The XENOMOUSE® transgenic mouse produces an adult-like human repertoire of fully human antibodies, and generates antigen-specific human monoclonal antibodies. The XENOMOUSE® transgenic mouse contains approximately 80% of the human antibody repertoire through introduction of megabase-sized, germline configuration YAC fragments of the human heavy chain loci and x light chain loci. See Mendez et al., Nature Genetics, 15: 146-156 (1997), Green and Jakobovits, J. Exp. Med., 188: 483-495 (1998), the disclosures of which are hereby incorporated by reference.

(4) Anti-RGMc Monoclonal Antibodies Using Recombinant Antibody Libraries.

In vitro methods also can be used to make the antibodies, wherein an antibody library is screened to identify an antibody having the desired RGMc-binding specificity. Methods for such screening of recombinant antibody libraries are well-known in the art and include methods described in, for example, U.S. Pat. No. 5,223,409 (Ladner et al.); PCT Publication No. WO 92/18619 (Kang et al.); PCT Publication No. WO 91/17271 (Dower et al.); PCT Publication No. WO 92/20791 (Winter et al.); PCT Publication No. WO 92/15679 (Markland et al.); PCT Publication No. WO 93/01288 (Breitling et al.); PCT Publication No. WO 92/01047 (McCafferty et al.); PCT Publication No. WO 92/09690 (Garrard et al.); Fuchs et al., Bio/Technology, 9: 1369-1372 (1991); Hay et al., Hum. Antibod. Hybridomas, 3: 81-85 (1992); Huse et al., Science, 246: 1275-1281 (1989); McCafferty et al., Nature, 348: 552-554 (1990); Griffiths et al., EMBO J., 12: 725-734 (1993); Hawkins et al., J. Mol. Biol., 226: 889-896 (1992); Clackson et al., Nature, 352: 624-628 (1991); Gram et al., Proc. Natl. Acad. Sci. USA, 89: 3576-3580 (1992); Garrard et al., Bio/Technology, 9: 1373-1377 (1991); Hoogenboom et al., Nucl. Acids Res., 19: 4133-4137 (1991); Barbas et al., Proc. Natl. Acad. Sci. USA, 88: 7978-7982 (1991); US Patent Application Publication No. 2003/0186374; and PCT Publication No. WO 97/29131, the contents of each of which are incorporated herein by reference.

The recombinant antibody library may be from a subject immunized with RGMc, or a portion of RGMc. Alternatively, the recombinant antibody library may be from a naive subject, i.e., one who has not been immunized with RGMc, such as a human antibody library from a human subject who has not been immunized with human RGMc. Antibodies are selected by screening the recombinant antibody library with the peptide comprising human RGMc to select those antibodies that recognize RGMc. Methods for conducting such screening and selection are well-known in the art, such as described in the references in the preceding paragraph. To select antibodies having particular binding affinities for RGMc, such as those that dissociate from human RGMc with a particular $K_{off}$ rate constant, the art-known method of surface plasmon resonance can be used to select antibodies having the desired $K_{off}$ rate constant. To select antibodies having a particular neutralizing activity for hRGMc, such as those with a particular $IC_{50}$, standard methods known in the art for assessing the inhibition of RGMc activity may be used.

In one aspect, the isolated antibody, or an antigen-binding portion thereof, that binds human RGMc. Preferably, the antibody is a neutralizing antibody. In various embodiments, the antibody is a recombinant antibody or a monoclonal antibody.

For example, antibodies can also be generated using various phage display methods known in the art. In phage display methods, functional antibody domains are displayed on the surface of phage particles which carry the polynucleotide sequences encoding them. Such phage can be utilized to display antigen-binding domains expressed from a repertoire or combinatorial antibody library (e.g., human or murine). Phage expressing an antigen-binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv, or disulfide stabilized Fv antibody domains recombinantly fused to either the phage gene III or gene VIII protein. Examples of phage display methods that can be used to make the antibodies include those disclosed in Brinkmann et al., J. Immunol. Methods, 182: 41-50 (1995); Ames et al., J. Immunol. Methods, 184:177-186 (1995); Kettleborough et al., Eur. J. Immunol., 24: 952-958 (1994); Persic et al., Gene, 187: 9-18 (1997); Burton et al., Advances in Immunology, 57: 191-280 (1994); PCT Publication Nos. WO 92/01047; WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743; and 5,969,108.

As described in the above references, after phage selection, the antibody-coding regions from the phage can be isolated and used to generate whole antibodies including human antibodies or any other desired antigen-binding fragment, and expressed in any desired host, including mammalian cells, insect cells, plant cells, yeast, and bacteria, e.g., as described in detail below. For example, techniques to recombinantly produce Fab, Fab', and F(ab')$_2$ fragments can also be employed using methods known in the art such as those disclosed in PCT publication No. WO 92/22324; Mullinax et al., BioTechniques, 12(6): 864-869 (1992); Sawai et al., Am. J. Reprod. Immunol., 34: 26-34 (1995); and Better et al., Science, 240: 1041-1043 (1988). Examples of techniques which can be used to produce single-chain Fvs and antibodies include those described in U.S. Pat. Nos. 4,946,778 and 5,258,498; Huston et al., Methods in Enzymology, 203: 46-88 (1991); Shu et al., Proc. Natl. Acad. Sci. USA, 90: 7995-7999 (1993); and Skerra et al., Science, 240: 1038-1041 (1988).

Alternative to screening of recombinant antibody libraries by phage display, other methodologies known in the art for screening large combinatorial libraries can be applied to the identification of antibodies. One type of alternative expression system is one in which the recombinant antibody library is expressed as RNA-protein fusions, as described in PCT Publication No. WO 98/31700 (Szostak and Roberts), and in Roberts and Szostak, Proc. Natl. Acad. Sci. USA, 94: 12297-12302 (1997). In this system, a covalent fusion is created between an mRNA and the peptide or protein that it encodes by in vitro translation of synthetic mRNAs that carry puromycin, a peptidyl acceptor antibiotic, at their 3' end. Thus, a specific mRNA can be enriched from a complex mixture of mRNAs (e.g., a combinatorial library) based on the properties of the encoded peptide or protein, e.g., antibody, or portion thereof, such as binding of the antibody, or portion thereof, to the dual specificity antigen. Nucleic acid sequences encoding antibodies, or portions thereof, recovered from screening of such libraries can be expressed by recombinant means as described above (e.g., in mammalian host cells) and, moreover, can be subjected to further affinity maturation by either additional rounds of screening of mRNA-peptide fusions in which mutations have been introduced into the originally selected sequence(s), or by other methods for affinity maturation in vitro of recombinant antibodies, as described above. A preferred example of this methodology is PROfusion display technology.

In another approach the antibodies can also be generated using yeast display methods known in the art. In yeast display methods, genetic methods are used to tether antibody domains to the yeast cell wall and display them on the surface of yeast. In particular, such yeast can be utilized to display antigen-binding domains expressed from a repertoire or combinatorial antibody library (e.g., human or murine). Examples of yeast display methods that can be used to make the antibodies include those disclosed in U.S. Pat. No. 6,699,658 (Wittrup et al.), which is incorporated herein by reference.

(5) Synthetic Production

Once sequenced, polypeptides, such as a monoclonal antibody (or a fragment thereof), which specifically binds to RGMc, can be synthesized using methods known in the art, such as, for example, exclusive solid phase synthesis, partial solid phase synthesis, fragment condensation, and classical solution synthesis. See, e.g., Merrifield, J. Am. Chem. Soc. 85: 2149 (1963). On solid phase, the synthesis typically begins from the C-terminal end of the peptide using an alpha-amino protected resin. A suitable starting material can be prepared, for instance, by attaching the required alpha-amino acid to a chloromethylated resin, a hydroxymethyl resin, or a benzhydrylamine resin. One such chloromethylated resin is sold under the tradename BIO-BEADS SX-1 by Bio Rad Laboratories (Richmond, CA), and the preparation of the hydroxymethyl resin is described by Bodonszky et al., Chem. Ind. (London) 38: 1597 (1966). The benzhydrylamine (BHA) resin has been described by Pietta and Marshall, Chem. Comm. 650 (1970) and is commercially available from Beckman Instruments, Inc. (Palo Alto, CA) in the hydrochloride form. Automated peptide synthesizers are commercially available, as are services that make peptides to order.

Thus, the polypeptides can be prepared by coupling an alpha-amino protected amino acid to the chloromethylated resin with the aid of, for example, cesium bicarbonate catalyst, according to the method described by Gisin, Helv. Chim. Acta. 56: 1467 (1973). After the initial coupling, the alpha-amino protecting group is removed by a choice of reagents including trifluoroacetic acid (TFA) or hydrochloric acid (HCl) solutions in organic solvents at room temperature.

Suitable alpha-amino protecting groups include those known to be useful in the art of stepwise synthesis of peptides. Examples of alpha-amino protecting groups are: acyl type protecting groups (e.g., formyl, trifluoroacetyl, and acetyl), aromatic urethane type protecting groups (e.g., benzyloxycarbonyl (Cbz) and substituted Cbz), aliphatic urethane protecting groups (e.g., t-butyloxycarbonyl (Boc), isopropyloxycarbonyl, and cyclohexyloxycarbonyl), and alkyl type protecting groups (e.g., benzyl and triphenylmethyl). Boc and Fmoc are preferred protecting groups. The side chain protecting group remains intact during coupling and is not split off during the deprotection of the amino-terminus protecting group or during coupling. The side chain protecting group must be removable upon the completion of the synthesis of the final peptide and under reaction conditions that will not alter the target peptide.

After removal of the alpha-amino protecting group, the remaining protected amino acids are coupled stepwise in the desired order. An excess of each protected amino acid is generally used with an appropriate carboxyl group activator such as dicyclohexylcarbodiimide (DCC) in solution, for example, in methylene chloride and dimethyl formamide (DMF) mixtures.

After the desired amino acid sequence has been completed, the desired peptide is decoupled from the resin support by treatment with a reagent, such as TFA or hydrogen fluoride (HF), which not only cleaves the peptide from the resin, but also cleaves all remaining side chain protecting groups. When the chloromethylated resin is used, HF treatment results in the formation of the free peptide acids. When the benzhydrylamine resin is used, HF treatment results directly in the free peptide amide. Alternatively, when the chloromethylated resin is employed, the side chain protected peptide can be decoupled by treatment of the peptide resin with ammonia to give the desired side chain protected amide or with an alkylamine to give a side chain protected alkyl-amide or dialkylamide. Side chain protection is then removed in the usual fashion by treatment with hydrogen fluoride to give the free amides, alkylamides, or dialkylamides.

These and other solid phase peptide synthesis procedures are well-known in the art. Such procedures are also described by Stewart and Young in Solid Phase Peptide Syntheses (2nd Ed., Pierce Chemical Company, 1984).

3. Pharmaceutical Composition

The antibodies can be incorporated into pharmaceutical compositions suitable for administration to a subject (such as a patient, which can be a human or non-human). Typically, the pharmaceutical composition comprises an antibody and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate-buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the antibody.

In a further embodiment, the pharmaceutical composition comprises at least one additional therapeutic agent for treating, preventing, modulating or attenuating a disorder as disclosed herein. The additional therapeutic agent may be an erythropoietin or other erythropoiesis-stimulating agent (ESA). The additional therapeutic agent may be one or more other antibodies that activate the EPO receptor, such as a bispecific antibody or a dual variable antibody, and/or that bind to IL-6, BMP-2, BMP-4, and or BMP-6. Other therapeutic agents, such as hepcidin-lowering compounds may be used. Examples of hepcidin-lowering compounds include spiegelmere NOX-H94 and/or Dorsomorphin.

Various delivery systems are known and can be used to administer one or more antibodies or the combination of one or more antibodies and a prophylactic agent or therapeutic agent useful for treating or ameliorating a disorder or one or more symptoms thereof, e.g., encapsulation in liposomes, microparticles, microcapsules, recombinant cells that can express the antibody or antibody fragment, receptor mediated endocytosis (see, e.g., Wu and Wu, J. Biol. Chem. 262:4429-4432 (1987)), construction of a nucleic acid as part of a retroviral or other vector, etc. Methods of administering a prophylactic or therapeutic agent include, but are not limited to, parenteral administration (e.g., intradermal, intramuscular, intraperitoneal, intravenous and subcutaneous), epidural administration, intratumoral administration, and mucosal administration (e.g., intranasal and oral routes). In addition, pulmonary administration can be employed, e.g., by use of an inhaler or nebulizer, and formulation with an aerosolizing agent. See, e.g., U.S. Pat. Nos. 6,019,968, 5,985,320, 5,985,309, 5,934,272, 5,874,064, 5,855,913, 5,290,540, and 4,880,078; and PCT Publication Nos. WO 92/19244, WO97/32572, WO97/44013, WO98/31346, and WO99/66903, each of which is incorporated herein by reference in its entirety. In one embodiment, an antibody, combination therapy, or a composition is administered using Alkermes AIR® pulmonary drug delivery technology (Alkermes, Inc., Cambridge, Mass.). In a specific embodiment, prophylactic or therapeutic agents are administered intramuscularly, intravenously, intratumorally, orally, intranasally, pulmonary, or subcutaneously. The prophylactic or therapeutic agents may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

In a specific embodiment, it may be desirable to administer the antibodies locally to the area in need of treatment; this may be achieved by, for example, and not by way of limitation, local infusion, by injection, or by means of an implant, said implant being of a porous or non-porous material, including membranes and matrices, such as sialastic membranes, polymers, fibrous matrices (e.g., Tissuel®), or collagen matrices. In one embodiment, an effective amount of one or more antibodies is administered locally to the affected area to a subject to prevent, treat, manage, and/or ameliorate a disorder or a symptom thereof. In another embodiment, an effective amount of one or more antibodies is administered locally to the affected area in combination with an effective amount of one or more therapies (e.g., one or more prophylactic or therapeutic agents) other than an antibody of the invention of a subject to prevent, treat, manage, and/or ameliorate a disorder or one or more symptoms thereof.

In another embodiment, the antibody can be delivered in a controlled release or sustained release system. In one embodiment, a pump may be used to achieve controlled or sustained release (see Langer, supra; Sefton, 1987, CRC Crit. Ref. Biomed. Eng. 14:20; Buchwald et al., 1980, Surgery 88:507; Saudek et al., 1989, N. Engl. J. Med. 321:574). In another embodiment, polymeric materials can be used to achieve controlled or sustained release of the therapies (see e.g., Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, J., Macromol. Sci. Rev. Macromol. Chem. 23:61; see also Levy et al., 1985, Science 228:190; During et al., 1989, Ann. Neurol. 25:351; Howard et al., 1989, J. Neurosurg. 7 1:105); U.S. Pat. Nos. 5,679,377; 5,916,597; 5,912,015; 5,989,463; 5,128,326; PCT Publication No. WO99/15154; and PCT Publication No. WO99/20253. Examples of polymers used in sustained release formulations include, but are not limited to, poly(2-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In a particular embodiment, the polymer used in a sustained-release formulation is inert, free of leachable impurities, stable on storage, sterile, and biodegradable. In yet another embodiment, a controlled or sustained-release system can be placed in proximity of the prophylactic or therapeutic target, thus requiring only a fraction of the systemic dose (see, e.g., Goodson, in Medical Applications of Controlled Release, supra, vol. 2, pp. 115-138 (1984)).

Controlled-release systems are discussed in the review by Langer (1990, Science 249:1527-1533). Any technique known to one of skill in the art can be used to produce sustained-release formulations comprising one or more antibodies. See, e.g., U.S. Pat. No. 4,526,938, PCT publication WO91/05548, PCT publication WO96/20698, Ning et al., 1996, "Intratumoral Radioimmunotherapy of a Human Colon Cancer Xenograft Using a Sustained-Release Gel," Radiotherapy & Oncology 39:179-189, Song et al., 1995, "Antibody Mediated Lung Targeting of Long-Circulating Emulsions," PDA Journal of Pharmaceutical Science & Technology 50:372-397, Cleek et al., 1997, "Biodegradable Polymeric Carriers for a bFGF Antibody for Cardiovascular Application," Pro. Int'l. Symp. Control. Rel. Bioact. Mater. 24:853-854, and Lam et al., 1997, "Microencapsulation of Recombinant Humanized Monoclonal Antibody for Local Delivery," Proc. Int'l. Symp. Control Rel. Bioact. Mater. 24:759-760, each of which is incorporated herein by reference in its entirety.

In a specific embodiment, where the composition is a nucleic acid encoding an antibody, the nucleic acid can be administered in vivo to promote expression of its encoded antibody, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see, e.g., Joliot et al., 1991, Proc. Natl. Acad. Sci. USA 88:1864-1868). Alternatively, a nucleic acid can be introduced intracellularly and incorporated within host cell DNA for expression by homologous recombination.

A pharmaceutical composition is formulated to be compatible with its intended route of administration. Examples of routes of administration include, but are not limited to, parenteral, e.g., intravenous, intradermal, subcutaneous, oral, intranasal (e.g., inhalation), transdermal (e.g., topical), transmucosal, and rectal administration. In a specific embodiment, the composition is formulated in accordance with routine procedures as a pharmaceutical composition adapted for intravenous, subcutaneous, intramuscular, oral, intranasal, or topical administration to human beings. Typically, compositions for intravenous administration are solutions in sterile isotonic aqueous buffer. Where necessary, the composition may also include a solubilizing agent and a local anesthetic such as lignocaine to ease pain at the site of the injection.

If the compositions are to be administered topically, the compositions can be formulated in the form of an ointment, cream, transdermal patch, lotion, gel, shampoo, spray, aerosol, solution, emulsion, or other form well-known to one of skill in the art. See, e.g., Remington's Pharmaceutical Sciences and Introduction to Pharmaceutical Dosage Forms, 19th ed., Mack Pub. Co., Easton, Pa. (1995). For nonsprayable topical dosage forms, viscous to semi-solid or solid forms comprising a carrier or one or more excipients compatible with topical application and having a dynamic viscosity greater than water are typically employed. Suitable formulations include, without limitation, solutions, suspensions, emulsions, creams, ointments, powders, liniments, salves, and the like, which are, if desired, sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations wherein the active ingredient, for example in combination with a solid or liquid inert carrier, is packaged in a mixture with a pressurized volatile (e.g., a gaseous propellant, such as freon) or in a squeeze bottle. Moisturizers or humectants can also be added to pharmaceutical compositions and dosage forms if desired. Examples of such additional ingredients are well-known in the art.

If the method comprises intranasal administration of a composition, the composition can be formulated in an aerosol form, spray, mist or in the form of drops. In particular, prophylactic or therapeutic agents for use according to the present invention can be conveniently delivered in the form of an aerosol spray presentation from pressurized packs or a nebuliser, with the use of a suitable propellant (e.g., dichlorodifluoromethane, trichlorofluoromethane, dichlorotetrafluoroethane, carbon dioxide or other suitable gas). In the case of a pressurized aerosol the dosage unit may be determined by providing a valve to deliver a metered amount. Capsules and cartridges (composed of, e.g., gelatin) for use in an inhaler or insufflator may be formulated containing a powder mix of the compound and a suitable powder base such as lactose or starch.

If the method comprises oral administration, compositions can be formulated orally in the form of tablets, capsules, cachets, gelcaps, solutions, suspensions, and the like. Tablets or capsules can be prepared by conventional means with pharmaceutically acceptable excipients such as binding agents (e.g., pregelatinised maize starch, polyvinylpyrrolidone, or hydroxypropyl methylcellulose); fillers (e.g., lactose, microcrystalline cellulose, or calcium hydrogen phosphate); lubricants (e.g., magnesium stearate, talc, or silica); disintegrants (e.g., potato starch or sodium starch glycolate); or wetting agents (e.g., sodium lauryl sulphate). The tablets may be coated by methods well-known in the art. Liquid preparations for oral administration may take the form of, but not limited to, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives, or hydrogenated edible fats); emulsifying agents (e.g., lecithin or acacia); non-aqueous vehicles (e.g., almond oil, oily esters, ethyl alcohol, or fractionated vegetable oils); and preservatives (e.g., methyl or propyl-p-hydroxybenzoates or sorbic acid). The preparations may also contain buffer salts, flavoring, coloring, and sweetening agents as appropriate. Preparations for oral administration may be suitably formulated for slow release, controlled release, or sustained release of a prophylactic or therapeutic agent(s).

The method may comprise pulmonary administration, e.g., by use of an inhaler or nebulizer, of a composition formulated with an aerosolizing agent. See, e.g., U.S. Pat. Nos. 6,019,968, 5,985, 320, 5, 985,309, 5,934,272, 5,874, 064, 5,855,913, 5,290,540, and 4,880,078; and PCT Publication Nos. WO 92/19244, WO 97/32572, WO 97/44013, WO 98/31346, and WO 99/66903, each of which is incorporated herein by reference their entireties. In a specific embodiment, an antibody, combination therapy, and/or composition is administered using Alkermes AIR® pulmonary drug delivery technology (Alkermes, Inc., Cambridge, Mass.).

The method may comprise administration of a composition formulated for parenteral administration by injection (e.g., by bolus injection or continuous infusion). Formulations for injection may be presented in unit dosage form (e.g., in ampoules or in multi-dose containers) with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle (e.g., sterile pyrogen-free water) before use. The methods may additionally comprise of administration of compositions formulated as depot preparations. Such long-acting formulations may be administered by implantation (e.g., subcutaneously or intramuscularly) or by intramuscular injection. Thus, for example, the compositions may be formulated with suitable polymeric or hydrophobic materials (e.g., as an emulsion in an acceptable oil) or ion exchange resins, or as sparingly soluble derivatives (e.g., as a sparingly soluble salt).

The methods encompass administration of compositions formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

Generally, the ingredients of compositions are supplied either separately or mixed together in unit dosage form, for example, as a dry lyophilized powder or water-free concentrate in a hermetically sealed container such as an ampoule or sachette indicating the quantity of active agent. Where the mode of administration is infusion, the composition can be dispensed with an infusion bottle containing sterile pharmaceutical grade water or saline. Where the mode of administration is by injection, an ampoule of sterile water for injection or saline can be provided so that the ingredients may be mixed prior to administration.

In particular, one or more of the antibodies, or pharmaceutical compositions, can be packaged in a hermetically sealed container such as an ampoule or sachette indicating the quantity of the antibody. In one embodiment, one or more of the antibodies, or pharmaceutical compositions is/are supplied as a dry sterilized lyophilized powder or water-free concentrate in a hermetically sealed container and can be reconstituted (e.g., with water or saline) to the appropriate concentration for administration to a subject. In one embodiment, one or more of the antibodies or pharmaceutical compositions is supplied as a dry, sterile, lyophilized powder in a hermetically sealed container at a unit dosage of at least 5 mg, for example at least 10 mg, at least 15 mg, at least 25 mg, at least 35 mg, at least 45 mg, at least 50 mg, at least 75 mg, or at least 100 mg. The lyophilized antibodies or pharmaceutical compositions should be stored at between 2° C. and 8° C. in the original container and the antibodies or pharmaceutical compositions should be administered within 1 week, for example within 5 days, within 72 hours, within 48 hours, within 24 hours, within 12 hours, within 6 hours, within 5 hours, within 3 hours, or within 1 hour after being reconstituted. In an alternative embodiment, one or more of the antibodies or pharmaceutical compositions is supplied in liquid form in a hermetically sealed container indicating the quantity and concentration of the antibody. In a further embodiment, the liquid form of the administered composition is supplied in a hermetically sealed container at least 0.25 mg/ml, for example at least 0.5 mg/ml, at least 1 mg/ml, at least 2.5 mg/ml, at least 5 mg/ml, at least 8 mg/ml, at least 10 mg/ml, at least 15 mg/kg, at least 25 mg/ml, at least 50 mg/ml, at least 75 mg/ml or at least 100 mg/ml. The liquid form should be stored at between 2° C. and 8° C. in its original container.

The antibodies can be incorporated into a pharmaceutical composition suitable for parenteral administration. In one aspect, antibodies will be prepared as an injectable solution containing 0.1-250 mg/ml antibody. The injectable solution can be composed of either a liquid or lyophilized dosage form in a flint or amber vial, ampule or pre-filled syringe. The buffer can be L-histidine (1-50 mM), optimally 5-10 mM, at pH 5.0 to 7.0 (optimally pH 6.0). Other suitable buffers include but are not limited to, sodium succinate, sodium citrate, sodium phosphate or potassium phosphate. Sodium chloride can be used to modify the toxicity of the solution at a concentration of 0-300 mM (optimally 150 mM for a liquid dosage form). Cryoprotectants can be included for a lyophilized dosage form, principally 0-10% sucrose (optimally 0.5-1.0%). Other suitable cryoprotectants include trehalose and lactose. Bulking agents can be included for a lyophilized dosage form, principally 1-10% mannitol (optimally 2-4%). Stabilizers can be used in both liquid and lyophilized dosage forms, principally 1-50 mM L-Methionine (optimally 5-10 mM). Other suitable bulking agents include glycine, arginine, can be included as 0-0.05% polysorbate-80 (optimally 0.005-0.01%). Additional surfactants include but are not limited to polysorbate 20 and BRIJ surfactants. The pharmaceutical composition comprising the antibodies prepared as an injectable solution for parenteral administration, can further comprise an agent useful as an adjuvant, such as those used to increase the absorption, or dispersion of the antibody. A particularly useful adjuvant is hyaluronidase, such as Hylenex® (recombinant human hyaluronidase). Addition of hyaluronidase in the injectable solution improves human bioavailability following parenteral administration, particularly subcutaneous administration. It also allows for greater injection site volumes (i.e. greater than 1 ml) with less pain and discomfort, and minimum incidence of injection site reactions. (See International Appln. Publication No. WO 04/078140 and U.S. Patent Appln. Publication No. US 2006104968, incorporated herein by reference.)

The compositions may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Compositions can be in the form of injectable or infusible solutions, such as compositions similar to those used for passive immunization of humans with other antibodies. In one embodiment, the antibody is administered by intravenous infusion or injection. In another embodiment, the antibody is administered by intramuscular or subcutaneous injection.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound (i.e., a binding protein, e.g. an antibody) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile, lyophilized powders for the preparation of sterile injectable solutions, methods of preparation comprise vacuum drying and spray drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including, in the composition, an agent that delays absorption, for example, monostearate salts and gelatin.

The antibodies can be administered by a variety of methods known in the art. For many therapeutic applications, the route/mode of administration may be subcutaneous injection, intravenous injection or infusion. As will be appreciated by the skilled artisan, the route and/or mode of administration will vary depending upon the desired results. In certain embodiments, the active compound may be prepared with a carrier that will protect the compound against rapid release, such as a controlled-release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978.

In certain embodiments, an antibody may be orally administered, for example, with an inert diluent or an assimilable edible carrier. The antibody (and other ingredients, if desired) may also be enclosed in a hard or soft shell gelatin capsule, compressed into tablets, or incorporated directly into the subject's diet. For oral therapeutic administration, the antibody may be incorporated with excipients and used in the form of ingestible tablets, buccal tablets, troches, capsules, elixirs, suspensions, syrups, wafers, and the like. To administer an antibody by other than parenteral administration, it may be necessary to coat the antibody with, or co-administer the antibody with, a material to prevent its inactivation.

Supplementary active compounds can also be incorporated into the compositions. In certain embodiments, an antibody is coformulated with and/or coadministered with one or more additional therapeutic agents that are useful for treating disorders or diseases described herein. For example, an anti-RGMc globulomer antibody may be coformulated and/or coadministered with one or more additional antibodies that bind other targets (e.g., antibodies that bind other soluble antigens or that bind cell surface molecules). Furthermore, one or more antibodies may be used in combination with two or more of the foregoing therapeutic agents. Such combination therapies may advantageously utilize lower dosages of the administered therapeutic agents, thus avoiding possible toxicities or complications associated with the various monotherapies.

In certain embodiments, an antibody is linked to a half-life extending vehicle known in the art. Such vehicles include, but are not limited to, the Fc domain, polyethylene glycol, and dextran. Such vehicles are described, e.g., in U.S. application Ser. No. 09/428,082 and published PCT Application No. WO 99/25044, which are hereby incorporated by reference for this purpose.

In a specific embodiment, nucleic acid sequences comprising nucleotide sequences encoding an antibody are administered to treat, prevent, manage, or ameliorate a disorder or one or more symptoms thereof by way of gene therapy. Gene therapy refers to therapy performed by the administration to a subject of an expressed or expressible nucleic acid. In this embodiment, the nucleic acid produces its encoded antibody that mediates a prophylactic or therapeutic effect.

Any of the methods for gene therapy available in the art can be used according to the present invention. For general reviews of the methods of gene therapy, see Goldspiel et al., Clinical Pharmacy 12:488-505, (1993); Wu and Wu, Biotherapy 3:87-95, (1991); Tolstoshev, Ann. Rev. Pharmacol. Toxicol. 32:573-596, (1993); Mulligan, Science 260:926-932 (1993); and Morgan and Anderson, Ann. Rev. Biochem. 62:191-217 (1993); May 1993, TIBTECH 11(5): 155-215. Methods commonly known in the art of recombinant DNA technology which can be used are described in Ausubel et al. (eds.), Current Protocols in Molecular Biology, John Wiley & Sons, N Y (1993); and Kriegler, Gene Transfer and Expression, A Laboratory Manual, Stockton Press, NY (1990). A detailed description of various methods of gene therapy are disclosed in US 20050042664 A1 which is incorporated herein by reference.

It should further be understood that the combinations are those combinations useful for their intended purpose. The agents set forth above are for illustrative purposes and not intended to be limiting. The combinations can comprise an antibody and at least one additional agent selected from the lists below. The combination can also include more than one additional agent, e.g., two or three additional agents if the combination is such that the formed composition can perform its intended function.

The pharmaceutical compositions may include a "therapeutically effective amount" or a "prophylactically effective amount" of an antibody. A "therapeutically effective amount" refers to an amount effective, at dosages and for periods of time necessary, to achieve the desired therapeutic result. A therapeutically effective amount of the antibody may be determined by a person skilled in the art and may vary according to factors such as the disease state, age, sex, and weight of the individual, and the ability of the antibody to elicit a desired response in the individual. A therapeutically effective amount is also one in which toxic or detrimental effects, if any, of the antibody are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

An exemplary, non-limiting range for a therapeutically or prophylactically effective amount of the antibody is a dose of between 0.1 and 200 mg/kg, for example between 0.1 and 10 mg/kg. The therapeutically or prophylactically effective amount of the antibody may be between 1 and 200 mg/kg, 10 and 200 mg/kg, 20 and 200 mg/kg, 50 and 200 mg/kg, 75 and 200 mg/kg, 100 and 200 mg/kg, 150 and 200 mg/kg, 50 and 100 mg/kg, 5 and 10 mg/kg, or 1 and 10 mg/kg. It is to be noted that dosage values may vary with the type and severity of the condition to be alleviated. Further, the antibody dose may be determined by a person skilled in the art and may vary according to factors such as the disease state, age, sex, and weight of the individual, and the ability of the antibody to elicit a desired response in the individual. The dose is also one in which toxic or detrimental effects, if any, of the antibody are outweighed by the therapeutically beneficial effects. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

4. Method of Treating, Preventing, Modulating or Attenuating a Disease of Iron Metabolism In any subject, an assessment may be made as to whether the subject has an iron metabolism-related disorder using routine techniques known in the art (e.g., such an assessment can include one or more blood tests to determine hemoglobin level, red blood count, reticulocyte count, serum ferritin, serum iron, saturated serum transferrin, serum hepcidin, serum RGMc, etc.). The assessment may be made as to whether the subject has an iron-related disorder related to iron deficiency or iron overload and, thus, may indicate an appropriate course of therapy, such as preventative therapy, maintenance therapy, or modulative therapy. As a reference, a haematologist may use the following reference numbers to indicate that the patient has normal levels of the corresponding parameter. See Table 2.

TABLE 3

| Serum Iron in Micrograms per deciliter (Rows 1-4) | |
|---|---|
| 1. Men | 65 to 176 |
| 2. Women | 50 to 170 |
| 3. Newborn | 100 to 250 |
| 4. Child | 50 to 120 |
| 5. Total Iron Binding Capacity ("TIBC") | 240 to 450 |
| 6. Transferrin Saturation | 20% to 50% |

Accordingly, provided herein is a method of treating, preventing, modulating or attenuating a disease of iron metabolism. The antibody may be administered to a subject in need thereof. The antibody may be administered to the subject in a therapeutically effective amount, wherein said amount can be readily determined by one skilled in the art. The method of treating, preventing, modulating or attenuating the disease may modulate up or down the level of hepcidin protein in a cell or tissue as compared to the level of hepcidin in a normal control or a calibrator. The method of treating, preventing, modulating or attenuating the disease may attenuate the level of hepcidin protein a cell or tissue as compared to a the level of hepcidin in a normal control or a calibrator.

a. Disease of Iron Metabolism

The disease or disorder of iron metabolism may be any disease or disorder in which iron homeostasis is perturbed in the subject. This homeostasis relies on the proper regulation of adequate plasma iron levels. Iron circulates in plasma bound to transferrin, which is a vehicle for iron delivery into cells. Plasma transferrin is normally about 30% saturated with iron. Accordingly, transferrin saturation must be maintained at appropriate physiological levels in response to a variety of signals from pathways involved in iron consumption.

Hepcidin coordinates systemic iron fluxes and controls plasma iron levels by binding to ferroportin and inducing its degradation. Because ferroportin is degraded, macrophages and duodenal enterocytes are no longer able to release iron into the blood and, as a consequence, iron transfer to transferrin is reduced. Accordingly, inherited and acquired disorders that upset normal hepcidin production can cause iron deficiency (high hepcidin levels) or iron overload (hepcidin deficiency).

This perturbation may result in an iron deficiency, an iron overload, or an iron overload with anemia. This perturbation may also result in anemia of chronic disease, wherein a subject with the disease exhibits high levels of blood hepcidin. The subject may have, or be at risk of, a disease or disorder such as fatigue, joint pain, bone or joint disease (osteoarthritis, osteoporosis), rheumatoid arthritis, inflammatory bowel disease, shortness of breath, irregular heart beat, liver trouble, diabetes, infertility, impotence, depression, mood or mental disorders, poor cognitive skills or neurodegenerative diseases, ACD, iron-refractory iron-deficiency anemia, anemia of chronic kidney disease, resistance to erythropoiesis-stimulating agents, aplastic anemia, myelodysplastic syndromes, sideroblastic anemia, hypoplastic anemias, paroxysmal nocturnal hemoglobinuria, von Willebrand disease, hemophilia hereditary hemorrhagic telangiectasia, red cell enzymopathies: glucose-6 phosphate dehydrogenase (G6PD) or pyruvate kinase deficiency (PKD), atransferrinemia or hypotransferrinemia, aceruloplasminemia or hypoceruloplasminia, CDAII: (congenital dyserythropoietic anemia), which is also called: HEMPAS (hereditary erythroblastic multi-nuclearity with positive acidified serum lysis test).

The suppression of hepcidin in the liver, along with the increased expression of ferroportin and reduced intracellular iron and oxidative stress within peritoneal macrophages, are associated with increased expression of the macrophage cholesterol efflux proteins ABCA1 and ABCG1, which are ABC transporters. See Saeed et al., Arterioscler. Thromb. Vasc. Biol., 32 (February 2012), Accepted on Nov. 5, 2011. The suppression of hepcidin increases the expression of ABCA1 and ABCG1, which can result in increased lipid efflux and reduced foam cell formation. Accordingly, the antibody may be administered to a subject in need thereof. The antibody may be administered to the subject in a therapeutically effective amount, wherein the formation of foam cells and atherosclerosis can be limited and/or atherosclerosis can be treated, prevented, modulated or attenuated. The antibody may reduce macrophage intracellular iron leading to enhanced ABC transporter expression and lipid efflux capacity.

The cyclic activity of hair follicles may be regulated by signaling molecules normally expressed in the dermal macro-environment. See, for example, U.S. Patent Application No. 2011/0293526, the content of which is hereby incorporated in its entirety. For example, expression of BMP may be negatively correlated with hair growth. The antibody may be used to stimulate resting hair follicles to be reactivated to grow again. The antibody may disrupt, directly or indirectly, the signaling of molecules normally expressed in the dermal macro-environment.

(1) Iron Deficiency

The disease of iron metabolism may be one in which there is too little iron in the body. For example, a subject may be diagnosed with an iron deficiency if serum iron is found to be below 60 μg/dl, below 55 μg/dl, below 50 μg/dl, below 45 μg/dl, or below 40 g/dl. A subject may be diagnosed with an iron deficiency if his/her total iron binding capacity ("TIBC") is lower than 50%, 45%, 40%, 35%, 30%, 25%, 20%, 15%, or 10%. A subject may be diagnosed with an iron deficiency if he/she has increased ferritin levels as compared to a subject that does not have an iron deficiency. A subject may be diagnosed with an iron deficiency if he/she has a hemoglobin level of lower than 15.5, 15, 14.5, 14, 13.5, 13, 12.5, 12, 11.5, 11, 10.5, 10, 9.5, 9, 8.5, 8, 7.5, 7, 6.5, or 6 g/dl. A transferrin saturation of less than 25%, less than 20%, less than 19%, 18%, 17%, 16%, 15%, 14%, 13%, 12%, 11%, 10%, 9%, 8%, or 7% may be indicative of iron deficiency. A subject may be diagnosed as having an iron deficiency based on one or more factors as set forth above.

Iron deficiency at critical times of growth and development can result in premature births, low birth weight babies, delayed growth and development, and delayed normal infant activity and movement; iron deficiency can result in poor memory or poor cognitive skills (mental function) resulting in poor performance in school, work, the military or in recreation. Lower IQs have been linked to iron deficiency occurring during critical periods of growth.

Iron Deficiency Anemia ("IDA") is a condition where a subject has inadequate amounts of iron to meet body demands. IDA results from a decrease in the amount of red cells in the blood, which is related to the subject having too little iron. IDA may be caused by a diet insufficient in iron or from blood loss. IDA is the most common form of anemia. About 20% of women, 50% of pregnant women, and 3% of men are iron-deficient.

Iron refractory iron anemia ("IRIDA") afflicted subjects suffer from microcytic anemia and do not respond to oral therapy and are partially refractory to parenteral iron, because of inappropriately high hepcidin levels. IRIDA is caused by a mutation in the matriptase-2 gene (TMPRSS6), which encodes a serine protease that negatively regulates hepcidin expression by cleaving membrane-bound RGMc.

(2) Iron Overload

Examples of disorders associated with iron overload include: chronic fatigue, joint pain, abdominal pain, liver disease (cirrhosis, liver cancer), diabetes mellitus, irregular heart rhythm, heart attack, or heart failure, skin color changes (bronze, ashen-gray green), loss of period, loss of interest in sex, osteoarthritis, osteoporosis, hair loss, enlarged liver or spleen, impotence, infertility, hypogonadism, hypothyroidism, hypopituitarism, depression, adrenal function problems, early onset neurodegenerative disease, elevated blood sugar, elevated liver enzymes, and elevated iron (serum iron, serum ferritin). For example, a subject may be diagnosed with an iron overload if serum iron is found to be above 150 μg/dl, above 155 μg/dl, above 160 μg/dl, above 165 μg/dl, or above 170 μg/dl. A subject may be diagnosed with an iron deficiency if his/her total iron binding capacity ("TIBC") is greater than 50%, 55%, 60%, 65%, 70%, 75%, or 80%. A subject may be diagnosed with an iron deficiency if he/she has increased ferritin levels as compared to a subject that does not have an iron deficiency. A subject may be diagnosed with an iron deficiency if he/she has a hemoglobin level of greater than 18.5, 18, 17.5, 17, 16.5, 16, 15.5, 15, 14.5, 14, 13.5, 13, 12.5 or 12 g/dl. A transferrin saturation of greater than 35%, 40%, 41%, 42%, 43%, 44%, 45%, 46%, 47%, 48%, 49%, 50%, 55%, 60%, 65%, or 70% may be indicative of iron overload. A subject may be diagnosed as having an iron overload based on one or more factors as set forth above.

Hemochromatosis (HH) is another disorder that results from excessive amounts of iron in the body (iron overload). Hereditary (genetic) hemochromatosis (HHC) an inherited disorder of abnormal iron metabolism. Individuals with HHC absorb too much dietary iron. Once absorbed, the body does not have an efficient way of excreting iron excesses. Over time, these excesses build to a condition of iron overload, which is a toxic to cells. Glands and organs, including the liver, heart, pituitary, thyroid, pancreas, synovium (joints) and bone marrow burdened with excess iron cannot function properly. Symptoms develop and disease progresses.

There are several types of HHC. These include: Type I or Classic (HHC); Type II a, b or Juvenile (JHC); Type III or Transferrin Receptor Mutation; and Type IV or Ferroportin Mutation.

HHC is an autosomal recessive disease that may lead to iron overload of the liver and other organs. Four genes have been implicated in hemochromatosis: the HFE (C282Y), TfR2, hemojuvelin (HJV), and HAMP genes (hepcidin). The recessive forms of the disease are a result of inappropriately low hepcidin expression, whereby the disease severity and the age of onset may correlate with the degree of hepcidin expression.

A dominant form of hereditary hemochromatosis is caused by missense mutations in the cellular iron exporter, and hepcidin receptor, ferroportin. For example, mutations that reduce ferroportin's membrane localization or its ability to export iron result in macrophage iron overload or retention, normal to low plasma iron levels, and in some cases iron-restricted erythropoiesis.

Hemochromatosis-related disorders, in which there is high plasma iron and hepatocyte iron accumulation may be caused by hepcidin-resistant ferroportin mutations, whereby hepcidin fails to bind ferroportin (C326S) or the internalization and degradation of ferroportin following hepcidin binding is impaired.

Hepcidin levels may also be inappropriately low in "iron-loading anemia," whereby erythropoietic signals suppress hepcidin transcription even when systemic iron is high. β-thalassemia intermedia is an example of such an anemia and is characterized by transfusion-independent iron overloads and low to absent hepcidin levels.

(3) Iron Overload with Anemia

Iron Overload with Anemia (IOA), also called aceruloplasminemia, is a recessive disorder and may be characterized by anemia, iron overload, and neurodegeneration. The disorder is caused by mutations in the gene coding for the copper-containing ferroxidase ceruloplasmin. Patients suffering from aceruloplasminemia have lower serum hepcidin levels and a decreased ferroportin expression in the liver, due to the lack of a stabilizing function of mutant ceruloplasmin on ferroportin.

Iron overload is regarded as the main cause of mortality and morbidity in anemias with ineffective erythropoiesis (e.g. β-thalassemias, and congenital dyserythropoietic anemias). In these disorders, high levels of erythropoietin stimulate an extensive but ineffective erythropoiesis. Severe iron overload resembling juvenile hemochromatosis can develop in a subject who rarely or never receives a blood transfusion and indicate that dietary iron is hyperabsorbed under these conditions. Those patients not receiving transfusions usually have low hepcidin levels, despite high serum ferritin levels and high liver iron overload. It may be assumed that ineffective erythropoieses produce mediators like GDF-15, which can suppress liver hepcidin synthesis. See Ganz, T., Blood, 117:4425-33, 2011, Hepcidin and Iron Regulation: 10 Years Later.

IOA is often caused by circumstances whereby subjects have very high body iron, which may be due to whole blood transfusions or blood cell disorders that cause chronic hemolytic anemia (the premature turnover, or break down, of red blood cells). This process may cause body iron accumulations similar to those found in hemochromatosis patients. Various circumstances (including high dietary consumption) can cause iron surpluses to build rapidly. The levels of erythropoietin, hepcidin, and/or growth differentiation factor-15 (GDF-15) may be used to distinguish subjects that have IOA. In β-thalassaemia, for example, subjects have dramatically elevated GDF-15 levels. A subject that has β-thalassaemia may have greater than 45,000 pg/ml of GDF-15, greater than 50,000 pg/ml of GDF-15, greater than 55,000 pg/ml of GDF-15, greater than 60,000 pg/ml of GDF-15, greater than 65,000 pg/ml of GDF-15, greater than 66,000 pg/ml of GDF-15, or greater than 70,000 pg/ml of GDF-15. For example, β-thalassaemia subjects may have mean levels of GDF-15 at or near 66,000+/−9,600 pg/ml as compared to levels at or near 450+/−50 pg/ml in healthy subjects. The red blood cells in hemoglobin may be too few to sustain life and whole blood transfusions may be needed for the subject to survive. Examples of disorders associated with iron overload with anemia include sickle cell anemia, thalassemia, sideroblastic anemia, and enzyme deficiency.

b. Subject

The subject may be a mammal, which may be a human or a non-human. The subject may be a critical care patient, undergoing chemotherapy, recovering from surgery, or may be at risk for, or have, an infection, cancer, an autoimmunce disease or disorder, chronic organ disease and/or inflammation, and/or chronic rejection of an organ after solid organ transplantation. The infection may be acute or chronic. The infection may be viral, bacterial, parasitic, or fungal. The cancer may be any cancer, such as hematologic or a solid tumor. The autoimmune disease may be any autoimmune disease, such as rheumatoid arthritis, systemic lupus erythematosus and connective tissue diseases, vasculitis, sarcoidosis, and inflammatory bowel disease. The chronic organ disease may be chronic kidney disease, in which the subject may or may not be undergoing dialysis. The viral infection may be hepatitis B or C infection, or human immunodeficiency virus infection. Any of the diseases and disorders may be an underlying cause of ACD. The surgery may be perioperative or postoperative. The surgery may be oncologic surgery.

5. Method of Diagnosis

Provided herein is a method for determining whether a subject has an iron-related disorder. The level of membrane-associated RGMc or soluble RGMc may be measured in a sample from a subject and compared to a level of RGMc in a control sample or a calibrator, such as a series of calibrators. The control sample may be from a normal tissue or a bodily fluid (such as from whole blood, serum, plasma, etc).

An altered level of RGMc as compared to the control may indicate that the subject has an iron-related disorder. For example, a decreased level of membrane-associated RGMc as compared to the level of membrane-associated RGMc in a normal control may indicate that the subject has an iron-related disorder related to iron overload. Alternatively, an increased level of membrane-associated RGMc, as compared to the level of membrane-associated RGMc in a normal control, may indicate that the subject has an iron-related disorder related to iron-deficiency. Further, an increased level of soluble RGMc, or a soluble fragment thereof, may indicate that the subject has an iron-related disorder related to iron-overload. A decreased level of soluble RGMc, or a soluble fragment thereof, may indicate that the subject has an iron-related disorder related to iron-deficiency. The level of RGMc (membrane-associated or soluble) may be measured using the herein described antibodies.

The methods for determining whether a subject has an iron-related disorder may also involve measuring the level of hepcidin in addition to measuring the level of membrane-associated RGMc or soluble RGMc in one or more samples obtained from a subject. Specifically, in one aspect, the level of membrane-associated RGMc or soluble RGMc in a sample from a subject may be measured and compared to a level of RGMc in a control sample or a calibrator, such as a series of calibrators. The control sample for the membrane-associated RGMc or soluble RGMc may be from a normal tissue or a bodily fluid (such as from whole blood, serum, plasma, etc). The method may also involve measuring the level of hepcidin in the same sample and comparing the level of hepcidin in a control sample or a calibrator, such as a series of calibrators. The control sample for the hepcidin can be from normal tissue or a bodily fluid (such as from whole blood, serum, plasma, etc). An altered level of RGMc as compared to the level of RGMc in a control may indicate that the subject has an iron-related disorder. For example, a decreased level of membrane-associated RGMc as compared to the membrane-associated RGMc in a normal control may indicate that the subject has an iron-related disorder related to iron overload. Alternatively, an increased level of membrane-associated RGMc, as compared to the level of membrane-associated RGMc in a normal control, may indicate that the subject has an iron-related disorder related to iron-deficiency. Further, an increased level of soluble RGMc, or a soluble fragment thereof, may indicate that the subject has an iron-related disorder related to iron-overload. A decreased level of soluble RGMc, or a soluble fragment thereof, may indicate that the subject has an iron-related disorder related to iron-deficiency. The level of RGMc may be measured using the herein described antibodies. An altered level of hepcidin as compared to the level of hepcidin in a normal control may indicate that the subject has an iron-related disorder. For example, a decreased level of hepcidin as compared to the level of hepcidin in a normal control may indicate that the subject has an iron-related disorder related to iron overload. Alternatively, an increased level of hepcidin, as compared to the level of hepcidin in a normal control, may indicate that the subject has an iron-related disorder related to iron-deficiency. The order in which the level of membrane-associated RGMc or soluble RGMc and hepcidin are measured is not critical. They can be measured simultaneously or sequentially in any order. In addition, the level of membrane-associated RGMc or soluble RGMc and hepcidin can be measured in the same reaction vessel or in different reaction vessel. In another aspect, the level of membrane-associated RGMc or soluble RGMc and hepcidin do not have be determined in the same sample from a subject. For example, the level of membrane-associated RGMc or soluble RGMc can be determined in a first sample obtained in a subject. The level of hepcidin can be determined in a second sample obtained in a subject. Alternatively, the level of hepcidin can be determined in a first sample obtained from a subject and the level of membrane-associated RGMc or soluble RGMc can be determined in a second sample obtained from the subject. The first and second samples obtained from the patient can be obtained at the same time or at different periods of time from one another. The level of RGMc (membrane-associated or soluble) may be measured using the herein described antibodies.

The method may further comprise assaying a test sample for the presence, amount or concentration of hepcidin, wherein either (i) the test sample assayed for hepcidin may be the same test sample assayed for RGMc or (ii) the test sample assayed for hepcidin is a different test sample from the test sample assayed for RGMc but the source of the test sample assayed for hepcidin and the source of the test sample assayed for RGMc are the same. The test sample is, or the test samples are, assayed for RGMc and hepcidin simultaneously or sequentially in either order using the same type of methodology or different types of methodology as described herein and known in the art. Alternatively, the method can further comprising using results of an assay of a test sample for the presence, amount or concentration of hepcidin, wherein either (i) the test sample assayed for hepcidin is the same test sample assayed for RGMc or (ii) the test sample assayed for hepcidin is a different test sample from the test sample assayed for RGMc but the source of the test sample assayed for hepcidin and the source of the test sample assayed for RGMc are the same. In this regard, the assay of a test sample for hepcidin, the results of which are used in the context of the above method, can be performed at a different point in time, either before or after, from the time of assay of a test sample for RGMc, such as hours (e.g., 12 hours), a day, two days, three days, a week, two weeks, three weeks, or even a month, provided that the results are still deemed representative and reliable. It can be preferred that the assay of a test sample for hepcidin enables the determination of the presence, amount or concentration of hepcidin-25. A sample, such as a plasma sample, a serum sample, or a urine sample, can be assayed for hepcidin-25 using TOF-MS and an internal standard, for example.

The level of hepicidin may be measured using hepcidin antibodies known in the art, such as those available from ABCAM® (Cambridge, MA) and BACHEM® (Torrance, CA), such as the Hepcidin-25 antibodies. The level of hepcidin in a sample can be determined using the various formats described herein (such as an immunoassay).

The level of hepcidin and the level of RGMc determined by any of the methods described herein may be compared to indicate the presence of an iron-related disorder. For example, a ratio of membrane-associated RGMc to hepcidin in a test sample that is different from the ratio of membrane-associated RGMc to hepcidin in a normal control, may indicate that the subject from which the test sample is derived has an iron-related disorder. For example, an increased ratio of soluble RGMc to hepcidin in a test sample, as compared to the ratio of the soluble RGMc to hepcidin in a normal control, may indicate that the subject from which the test sample is derived has an iron-related disorder, such as iron overload. A decreased ratio of membrane-associated RGMc to hepcidin in a test sample, as compared to the ratio of the soluble RGMc to hepcidin in a normal control, may indicate that the subject from which the test sample is derived has an iron-related disorder, such as iron deficiency.

a. Sample

The sample may be any tissue sample from the subject. The sample may comprise protein from the subject.

Any cell type, tissue, or bodily fluid may be utilized to obtain a sample. Such cell types, tissues, and fluid may include sections of tissues such as biopsy and autopsy samples, frozen sections taken for histologic purposes, blood (such as whole blood), plasma, serum sputum, stool, tears, mucus, saliva, hair, and skin. Cell types and tissues may also include lymph fluid, ascetic fluid, gynecological fluid, urine, serum, plasma, peritoneal fluid, cerebrospinal fluid, a fluid collected by vaginal rinsing, or a fluid collected by vaginal flushing. A tissue or cell type may be provided by removing a sample of cells from an animal, but can also be accomplished by using previously isolated cells (e.g., isolated by another person, at another time, and/or for another purpose). Archival tissues, such as those having treatment or outcome history, may also be used. Protein purification may not be necessary.

Methods well-known in the art for collecting, handling and processing urine, blood, serum and plasma, and other body fluids, are used in the practice of the present disclosure, for instance, when the antibodies provided herein are employed as immunodiagnostic reagents, and/or in an RGMc immunoassay kit. The test sample can comprise further moieties in addition to the RGMc analyte of interest, such as antibodies, antigens, haptens, hormones, drugs, enzymes, receptors, proteins, peptides, polypeptides, oligonucleotides or polynucleotides. For example, the sample can be a whole blood sample obtained from a subject. It can be necessary or desired that a test sample, particularly whole blood, be treated prior to immunoassay as described herein, e.g., with a pretreatment reagent. Even in cases where pretreatment is not necessary (e.g., most urine samples), pretreatment optionally can be done for mere convenience (e.g., as part of a regimen on a commercial platform). The sample may be used directly as obtained from the subject or following pretreatment to modify a characteristic of the sample. Pretreatment may include extraction, concentration, inactivation of interfering components, and/or the addition of reagents.

The pretreatment reagent can be any reagent appropriate for use with the assay, e.g., immunoassay, and kit described herein. The pretreatment optionally comprises: (a) one or more solvents (e.g., methanol and ethylene glycol) and salt, (b) one or more solvents, salt and detergent, (c) detergent, or (d) detergent and salt. Pretreatment reagents are known in the art, and such pretreatment can be employed, e.g., as used for assays on Abbott TDx, AxSYM®, and ARCHITECT® analyzers (Abbott Laboratories, Abbott Park, Ill.), as described in the literature (see, e.g., Yatscoff et al., Abbott TDx Monoclonal Antibody Assay Evaluated for Measuring Cyclosporine in Whole Blood, Clin. Chem. 36: 1969-1973 (1990), and Wallemacq et al., Evaluation of the New AxSYM Cyclosporine Assay: Comparison with TDx Monoclonal Whole Blood and EMIT Cyclosporine Assays, Clin. Chem. 45: 432-435 (1999)), and/or as commercially available. Additionally, pretreatment can be done as described in Abbott's U.S. Pat. No. 5,135,875, European Pat. Pub. No. 0 471 293, and U.S. Pat. App. Pub. No. 2008/0020401 (incorporated by reference in its entirety for its teachings regarding pretreatment). The pretreatment reagent can be a heterogeneous agent or a homogeneous agent.

With use of a heterogeneous pretreatment reagent, the pretreatment reagent precipitates analyte binding protein (e.g., protein that can bind to RGMc (membrane-associated RGMc or soluble RGMc) or a fragment thereof) present in the sample. Such a pretreatment step comprises removing any analyte binding protein by separating from the precipitated analyte binding protein the supernatant of the mixture formed by addition of the pretreatment agent to sample. In such an assay, the supernatant of the mixture absent any binding protein is used in the assay, proceeding directly to the antibody capture step.

With use of a homogeneous pretreatment reagent there is no such separation step. The entire mixture of test sample and pretreatment reagent are contacted with a labeled specific binding partner for RGMc (membrane-associated RGMc, soluble RGMc, fragments of membrane-associated RGMc, fragments of soluble RGMc, variants of RGMc (membrane-associated or soluble RGMc) or any combinations thereof), such as a labeled anti-RGMc monoclonal antibody (or an antigenically reactive fragment thereof). The pretreatment reagent employed for such an assay typically is diluted in the pretreated test sample mixture, either before or during capture by the first specific binding partner. Despite such dilution, a certain amount of the pretreatment reagent (for example, 5 M methanol and/or 0.6 M ethylene glycol) is still present (or remains) in the test sample mixture during capture.

b. RGMc Detection

The presence or amount of RGMc (membrane-associated RGMc, soluble RGMc, fragments of membrane-associated RGMc, fragments of soluble RGMc, variants of RGMc (membrane-associated or soluble RGMc) or any combinations thereof) present in a body sample may be readily determined using any suitable assay as is known in the art. Examples include, but are not limited to, immunoassay, such as sandwich immunoassay (e.g., monoclonal-polyclonal sandwich immunoassays, including radioisotope detection (radioimmunoassay (RIA)) and enzyme detection (enzyme immunoassay (EIA) or enzyme-linked immunosorbent assay (ELISA) (e.g., Quantikine ELISA assays, R&D Systems, Minneapolis, MN)), competitive inhibition immunoassay (e.g., forward and reverse), fluorescence polarization immunoassay (FPIA), enzyme multiplied immunoassay technique (EMIT), bioluminescence resonance energy transfer (BRET), and homogeneous chemiluminescent assay, etc. In a SELDI-based immunoassay, a capture reagent that specifically binds RGMc (or a fragment thereof) of interest is attached to the surface of a mass spectrometry probe, such as a pre-activated protein chip array. The RGMc (membrane-associated RGMc, soluble RGMc, fragments of membrane-associated RGMc, fragments of soluble RGMc, variants of RGMc (membrane-associated or soluble RGMc) or any combinations thereof) is then specifically captured on the biochip, and the captured RGMc (membrane-associated RGMc, soluble RGMc, fragments of membrane-associated RGMc, fragments of soluble RGMc, variants of RGMc (membrane-associated or soluble RGMc) or any combinations thereof) is detected by mass spectrometry. Alternatively, the RGMc (membrane-associated RGMc, soluble RGMc, fragments of membrane-associated RGMc, fragments of soluble RGMc, variants of RGMc (membrane-associated or soluble RGMc) or any combinations thereof) can be eluted from the capture reagent and detected by traditional MALDI (matrix-assisted laser desorption/ionization) or by SELDI. A chemiluminescent microparticle immunoassay, in particular one employing the ARCHITECT® automated analyzer (Abbott Laboratories, Abbott Park, Ill.), is an example of a preferred immunoassay. Other methods include, for example, mass spectrometry and immunohistochemistry (e.g. with sections from tissue biopsies) using the herein described antibodies (monoclonal, polyclonal, chimeric, humanized, human etc) or fragments thereof against RGMc. Anti-RGMc antibodies and fragments thereof can be produced as described above. Other methods of detection include those described in, for example, U.S. Pat. Nos. 6,143,576; 6,113,855; 6,019,944; 5,985,579; 5,947,124; 5,939,272; 5,922,615; 5,885,527; 5,851,776; 5,824,799; 5,679,526; 5,525,524; and 5,480,792, each of which is hereby incorporated by reference in its entirety.

(1) Immunoassay

RGMc, and/or peptides or fragments thereof (such as membrane-associated RGMc, soluble RGMc, fragments of membrane-associated RGMc, fragments of soluble RGMc, variants of RGMc (membrane-associated or soluble RGMc) or any combinations thereof), may be analyzed using an immunoassay. The presence or amount of RGMc (such as membrane-associated RGMc, soluble RGMc, fragments of membrane-associated RGMc, fragments of soluble RGMc, variants of RGMc (membrane-associated or soluble RGMc) or any combinations thereof) can be determined using the herein-described antibodies and detecting specific binding to RGMc. For example, the antibody, or fragment thereof, may specifically bind to a polypeptide comprising SEQ ID NO: 1, or a fragment thereof. The antibody, or fragment thereof, may specifically bind to a polypeptide comprising SEQ ID NO:2, or a fragment thereof. If desired, one or more of the antibodies described herein can be used in combination with one or more commercially available monoclonal/polyclonal antibodies. Such antibodies are available from companies such as R&D Systems, Inc. (Minneapolis, MN) and Enzo Life Sciences International, Inc. (Plymouth Meeting, PA).

Any immunoassay may be utilized. The immunoassay may be an enzyme-linked immunoassay (ELISA), radioimmunoassay (RIA), a competitive inhibition assay, such as forward or reverse competitive inhibition assays, a fluorescence polarization assay, or a competitive binding assay, for example. The ELISA may be a sandwich ELISA.

A heterogeneous format may be used. For example, after the test sample is obtained from a subject, a first mixture is prepared. The mixture contains the test sample being assessed for RGMc (such as membrane-associated RGMc, soluble RGMc, fragments of membrane-associated RGMc, fragments of soluble RGMc, variants of RGMc (membrane-associated or soluble RGMc) or any combinations thereof) and a first specific binding partner, wherein the first specific binding partner and any RGMc contained in the test sample form a first specific binding partner-RGMc complex. Preferably, the first specific binding partner is an anti-RGMc antibody or a fragment thereof. The order in which the test sample and the first specific binding partner are added to form the mixture is not critical. Preferably, the first specific binding partner is immobilized on a solid phase. The solid phase used in the immunoassay (for the first specific binding partner and, optionally, the second specific binding partner) can be any solid phase known in the art, such as, but not limited to, a magnetic particle, a bead, a test tube, a microtiter plate, a cuvette, a membrane, a scaffolding molecule, a film, a filter paper, a disc and a chip.

After the mixture containing the first specific binding partner-RGMc complex is formed, any unbound RGMc is removed from the complex using any technique known in the art. For example, the unbound RGMc can be removed by washing. Desirably, however, the first specific binding partner is present in excess of any RGMc present in the test sample, such that all RGMc that is present in the test sample is bound by the first specific binding partner.

After any unbound RGMc is removed, a second specific binding partner is added to the mixture to form a first specific binding partner-RGMc-second specific binding partner complex. The second specific binding partner is preferably an anti-RGMc antibody that binds to an epitope on RGMc that differs from the epitope on RGMc bound by the first specific binding partner. Moreover, also preferably, the second specific binding partner is labeled with or contains a detectable label as described above.

The use of immobilized antibodies or fragments thereof may be incorporated into the immunoassay. The antibodies may be immobilized onto a variety of supports, such as magnetic or chromatographic matrix particles, the surface of an assay plate (such as microtiter wells), pieces of a solid substrate material, and the like. An assay strip can be prepared by coating the antibody or plurality of antibodies in an array on a solid support. This strip can then be dipped into the test biological sample and then processed quickly through washes and detection steps to generate a measurable signal, such as a colored spot.

(a) Sandwich ELISA

The Sandwich ELISA measures the amount of antigen between two layers of antibodies (i.e., a capture antibody (i.e., at least one capture antibody) and a detection antibody (i.e. at least one detection antibody). The capture antibody and the detection antibody bind to different epitopes on the antigen, e.g., RGMc. Desirably, binding of the capture antibody to an epitope does not interfere with binding of the detection antibody to an epitope. Either monoclonal or polyclonal antibodies may be used as the capture and detection antibodies in the sandwich ELISA.

Generally, at least two antibodies are employed to separate and quantify RGMc (such as membrane-associated RGMc, soluble RGMc, fragments of membrane-associated RGMc, fragments of soluble RGMc, variants of RGMc (membrane-associated or soluble RGMc) or any combinations thereof) in a test sample. More specifically, the at least two antibodies bind to certain epitopes of RGMc or an RGMc fragment forming an immune complex which is referred to as a "sandwich". One or more antibodies can be used to capture the RGMc (such as membrane-associated RGMc, soluble RGMc, fragments of membrane-associated RGMc, fragments of soluble RGMc, variants of RGMc (membrane-associated or soluble RGMc) or any combinations thereof) in the test sample (these antibodies are frequently referred to as a "capture" antibody or "capture" antibodies) and one or more antibodies is used to bind a detectable (namely, quantifiable) label to the sandwich (these antibodies are frequently referred to as the "detection" antibody or "detection" antibodies). In a sandwich assay, the binding of an antibody to its epitope desirably is not diminished by the binding of any other antibody in the assay to its respective epitope. In other words, antibodies are selected so that the one or more first antibodies brought into contact with a test sample suspected of containing RGMc (such as membrane-associated RGMc, soluble RGMc, fragments of membrane-associated RGMc, fragments of soluble RGMc, variants of RGMc (membrane-associated or soluble RGMc) or any combinations thereof) do not bind to all or part of an epitope recognized by the second or subsequent antibodies, thereby interfering with the ability of the one or more second detection antibodies to bind to the RGMc (such as membrane-associated RGMc, soluble RGMc, fragments of membrane-associated RGMc, fragments of soluble RGMc, variants of RGMc (membrane-associated or soluble RGMc) or any combinations thereof).

The antibodies may be used as a first antibody in said immunoassay. Preferably, the antibody immunospecifically binds to an epitope comprising at least three contiguous (3) amino acids of SEQ ID NO:2 with a $K_D$ of from $4.2\times10^{-11}$ M to $7.4\times10^{-13}$ M. The immunoassay may comprise a second antibody that immunospecifically binds to an epitope comprising at least three contiguous (3) amino acids of SEQ ID NO:2, wherein the contiguous (3) amino acids to which the second antibody binds is different from the three (3) contiguous amino acids to which the first antibody binds.

In a preferred embodiment, a test sample suspected of containing RGMc (such as membrane-associated RGMc, soluble RGMc, fragments of membrane-associated RGMc, fragments of soluble RGMc, variants of RGMc (membrane-associated or soluble RGMc) or any combinations thereof) can be contacted with at least one capture antibody (or antibodies) and at least one detection antibodies either simultaneously or sequentially. In the sandwich assay format, a test sample suspected of containing RGMc (membrane-associated RGMc, soluble RGMc, fragments of membrane-associated RGMc, fragments of soluble RGMc, variants of RGMc (membrane-associated or soluble RGMc) or any combinations thereof) is first brought into contact with the at least one capture antibody that specifically binds to a particular epitope under conditions which allow the formation of a antibody-RGMc complex. If more than one capture antibody is used, a multiple capture antibody-RGMc complex is formed. In a sandwich assay, the antibodies, preferably, the at least one capture antibody, are used in molar excess amounts of the maximum amount of RGMc or the RGMc fragment expected in the test sample. For example, from about 5 μg/mL to about 1 mg/mL of antibody per mL of microparticle coating buffer may be used.

Optionally, prior to contacting the test sample with the at least one first capture antibody, the at least one capture antibody can be bound to a solid support which facilitates the separation the antibody-RGMc complex from the test sample. Any solid support known in the art can be used, including but not limited to, solid supports made out of polymeric materials in the forms of wells, tubes or beads. The antibody (or antibodies) can be bound to the solid support by adsorption, by covalent bonding using a chemical coupling agent or by other means known in the art, provided that such binding does not interfere with the ability of the antibody to bind RGMc or RGMc fragment. Moreover, if necessary, the solid support can be derivatized to allow reactivity with various functional groups on the antibody. Such derivatization requires the use of certain coupling agents such as, but not limited to, maleic anhydride, N-hydroxysuccinimide and 1-ethyl-3-(3-dimethylaminopropyl) carbodiimide.

After the test sample suspected of containing RGMc (such as membrane-associated RGMc, soluble RGMc, fragments of membrane-associated RGMc, fragments of soluble RGMc, variants of RGMc (membrane-associated or soluble RGMc) or any combinations thereof) is brought into contact with the at least one capture antibody, the test sample is incubated in order to allow for the formation of a capture antibody (or capture antibodies)-RGMc complex. The incubation can be carried out at a pH of from about 4.5 to about 10.0, at a temperature of from about 2° C. to about 45° C., and for a period from at least about one (1) minute to about eighteen (18) hours, from about 2-6 minutes, or from about 3-4 minutes.

After formation of the capture antibody (antibodies)-RGMc complex, the complex is then contacted with at least one detection antibody (under conditions which allow for the formation of a capture antibody (antibodies)-RGMc-detection antibody (antibodies) complex). If the capture antibody-RGMc complex is contacted with more than one detection antibody, then a capture antibody (antibodies)-RGMc-detection antibody (antibodies) detection complex is formed. As with the capture antibody, when the at least one detection (and subsequent) antibody is brought into contact with the capture antibody-RGMc complex, a period of incubation under conditions similar to those described above is required for the formation of the capture antibody (antibodies)-RGMc-detection antibody (antibodies) complex. Preferably, at least one detection antibody contains a detectable label. The detectable label can be bound to the at least one detection antibody prior to, simultaneously with or after the formation of the capture antibody (antibodies)-RGMc-detection antibody (antibodies) complex. Any detectable label known in the art can be used as discussed herein and known in the art.

Chemiluminescent assays can be performed in accordance with the methods described in Adamczyk et al., Anal. Chim. Acta 579(1): 61-67 (2006). While any suitable assay format can be used, a microplate chemiluminometer (Mithras LB-940, Berthold Technologies U.S.A., LLC, Oak Ridge, TN) enables the assay of multiple samples of small volumes rapidly. The chemiluminometer can be equipped with multiple reagent injectors using 96-well black polystyrene microplates (Costar #3792). Each sample can be added into a separate well, followed by the simultaneous/sequential addition of other reagents as determined by the type of assay employed. Desirably, the formation of pseudobases in neutral or basic solutions employing an acridinium aryl ester is avoided, such as by acidification. The chemiluminescent response is then recorded well-by-well. In this regard, the time for recording the chemiluminescent response will depend, in part, on the delay between the addition of the reagents and the particular acridinium employed.

The order in which the test sample and the specific binding partner(s) are added to form the mixture for chemiluminescent assay is not critical. If the first specific binding partner is detectably labeled with an acridinium compound, detectably labeled first specific binding partner-RGMc complexes form. Alternatively, if a second specific binding partner is used and the second specific binding partner is detectably labeled with an acridinium compound, detectably labeled first specific binding partner-RGMc-second specific binding partner complexes form. Any unbound specific binding partner, whether labeled or unlabeled, can be removed from the mixture using any technique known in the art, such as washing.

Hydrogen peroxide can be generated in situ in the mixture or provided or supplied to the mixture before, simultaneously with, or after the addition of an above-described acridinium compound. Hydrogen peroxide can be generated in situ in a number of ways such as would be apparent to one skilled in the art.

Alternatively, a source of hydrogen peroxide can be simply added to the mixture. For example, the source of the hydrogen peroxide can be one or more buffers or other solutions that are known to contain hydrogen peroxide. In this regard, a solution of hydrogen peroxide can simply be added.

Upon the simultaneous or subsequent addition of at least one basic solution to the sample, a detectable signal, namely, a chemiluminescent signal, indicative of the presence of RGMc or a fragment thereof is generated. The basic solution contains at least one base and has a pH greater than or equal to 10, preferably, greater than or equal to 12. Examples of basic solutions include, but are not limited to, sodium hydroxide, potassium hydroxide, calcium hydroxide, ammonium hydroxide, magnesium hydroxide, sodium carbonate, sodium bicarbonate, calcium hydroxide, calcium carbonate, and calcium bicarbonate. The amount of basic solution added to the sample depends on the concentration of the basic solution. Based on the concentration of the basic solution used, one skilled in the art can easily determine the amount of basic solution to add to the sample.

The chemiluminescent signal that is generated can be detected using routine techniques known to those skilled in the art. Based on the intensity of the signal generated, the amount of RGMc (such as membrane-associated RGMc, soluble RGMc, fragments of membrane-associated RGMc, fragments of soluble RGMc, variants of RGMc (membrane-associated or soluble RGMc) or any combinations thereof) in the sample can be quantified. Specifically, the amount of RGMc in the sample is proportional to the intensity of the signal generated. The amount of RGMc present can be quantified by comparing the amount of light generated to a standard curve for RGMc or by comparison to a reference standard. The standard curve can be generated using serial dilutions or solutions of known concentrations of RGMc by mass spectroscopy, gravimetric methods, and other techniques known in the art.

In a chemiluminescent microparticle assay employing the ARCHITECT® (or its successor) analyzer, the conjugate diluent pH should be about 6.0+/−0.2, the microparticle coating buffer should be maintained at room temperature (i.e., at about 17 to about 27° C.), the microparticle coating buffer pH should be about 6.5+/−0.2, and the microparticle diluent pH should be about 7.8+/−0.2. Solids preferably are less than about 0.2%, such as less than about 0.15%, less than about 0.14%, less than about 0.13%, less than about 0.12%, or less than about 0.11%, such as about 0.10%.

(b) Forward Competitive Inhibition

In a forward competitive format, an aliquot of labeled RGMc (such as membrane-associated RGMc peptide, soluble RGMc peptide, fragments of membrane-associated RGMc RGmc) or any combinations thereof thereof) of a known concentration is used to compete with RGMc in a test sample for binding to RGMc antibody (such as an antibody).

In a forward competition assay, an immobilized antibody (such as an antibody) can either be sequentially or simultaneously contacted with the test sample and a labeled RGMc, RGMc fragment or RGMc variant thereof. The RGMc peptide, RGMc fragment or RGMc variant can be labeled with any detectable label, including those detectable labels discussed above in connection with the anti-RGMc antibodies. In this assay, the antibody can be immobilized on to a solid support. Alternatively, the antibody can be coupled to an antibody, such as an antispecies antibody, that has been immobilized on a solid support, such as a microparticle.

The labeled RGMc (such as membrane-associated RGMc peptide, soluble RGMc peptide, fragments of membrane-associated RGMc peptide, fragments of soluble RGMc, variants of RGMc (membrane-associated or soluble RGMc) or any combinations thereof thereof), the test sample and the antibody are incubated under conditions similar to those described above in connection with the sandwich assay format. Two different species of antibody-RGMc complexes may then be generated. Specifically, one of the antibody-RGMc complexes generated contains a detectable label while the other antibody-RGMc complex does not contain a detectable label. The antibody-RGMc complex can be, but does not have to be, separated from the remainder of the test sample prior to quantification of the detectable label. Regardless of whether the antibody-RGMc complex is separated from the remainder of the test sample, the amount of detectable label in the antibody-RGMc complex is then quantified. The concentration of RGMc (such as membrane-associated RGMc, soluble RGMc, fragments of soluble RGMc, variants of RGMc (membrane-associated or soluble RGMc) or any combinations thereof) in the test sample can then be determined by comparing the quantity of detectable label in the antibody-RGMc complex to a standard curve. The standard curve can be generated using serial dilutions of RGMc (such as membrane-associated RGMc, soluble RGMc, fragments of soluble RGMc, variants of RGMc (membrane-associated or soluble RGMc) or any combinations thereof) of known concentration, by mass spectroscopy, gravimetrically and by other techniques known in the art.

The antibody-RGMc complex can be separated from the test sample by binding the antibody to a solid support, such as the solid supports discussed above in connection with the sandwich assay format, and then removing the remainder of the test sample from contact with the solid support.

(c) Reverse Competition Assay

In a reverse competition assay, an immobilized RGMc (such as membrane-associated RGMc peptide, soluble RGMc peptide, fragments of membrane-associated RGMc peptide, fragments of soluble RGMc, variants of RGMc (membrane-associated or soluble RGmc) or any combinations thereof thereof) can either be sequentially or simultaneously contacted with a test sample and at least one labeled antibody. Preferably, the antibody specifically binds to an epitope comprising at least three (3) amino acids of SEQ ID NO:2 or to an epitope comprising amino acids 5-13, 5-12, 5-11, 5-10, 5-9, 5-8, 5-7, 6-13, 6-12, 6-11, 6-10, 6-9, 6-8, 7-13, 7-13, 7-11, 7-10, 7-9, 8-13, 8-12, 8-11, 8-10, 9-13, 9-12, 9-11, 10-13, 10-12 or 11-13 of RGMc (SEQ ID NO:1).

The RGMc (such as membrane-associated RGMc peptide, soluble RGMc peptide, fragments of membrane-associated RGMc peptide, fragments of soluble RGMc, variants of RGMc (membrane-associated or soluble RGMc) or any combinations thereof thereof) can be bound to a solid support, such as the solid supports discussed above in connection with the sandwich assay format. Preferably, the RGMc (membrane-associated or soluble) peptide fragment comprises amino acids 5-13, 5-12, 5-11, 5-10, 5-9, 5-8, 5-7, 6-13, 6-12, 6-11, 6-10, 6-9, 6-8, 7-13, 7-13, 7-11, 7-10, 7-9, 8-13, 8-12, 8-11, 8-10, 9-13, 9-12, 9-11, 10-13, 10-12 or 11-13 of RGMc (SEQ ID NO:1).

The immobilized RGMc (such as membrane-associated RGMc peptide, soluble RGMc peptide, fragments of membrane-associated RGMc peptide, fragments of soluble RGMc, variants of RGMc (membrane-associated or soluble RGMc) or any combinations thereof thereof), test sample and at least one labeled antibody are incubated under conditions similar to those described above in connection with the sandwich assay format. Two different species RGMc-antibody complexes are then generated. Specifically, one of the RGMc-antibody complexes generated is immobilized and contains a detectable label while the other RGMc-antibody complex is not immobilized and contains a detectable label. The non-immobilized RGMc-antibody complex and the remainder of the test sample are removed from the presence of the immobilized RGMc-antibody complex through techniques known in the art, such as washing. Once the non-immobilized RGMc antibody complex is removed, the amount of detectable label in the immobilized RGMc-antibody complex is then quantified. The concentration of RGMc ((such as membrane-associated RGMc, soluble RGMc, fragments of membrane-associated RGMc, fragments of soluble RGMc, variants of RGMc (membrane-associated or soluble RGMc) or any combinations thereof) in the test sample can then be determined by comparing the quantity of detectable label in the RGMc-complex to a standard curve. The standard curve can be generated using serial dilutions of RGMc or RGMc fragment of known concentration, by mass spectroscopy, gravimetrically and by other techniques known in the art.

(d) Fluorescence Polarization

In a fluorescence polarization assay, an antibody or functionally active fragment thereof may be first contacted with an unlabeled test sample suspected of containing RGMc (such as membrane-associated RGMc peptide, soluble RGMc peptide, fragments of membrane-associated RGMc peptide, fragments of soluble RGMc, variants of RGMc (membrane-associated or soluble RGMc) or any combinations thereof) to form an unlabeled RGMc-antibody complex. The unlabeled RGMc-antibody complex is then contacted with a fluorescently labeled RGMc (such as membrane-associated RGMc peptide, soluble RGMc peptide, fragments of membrane-associated RGMc peptide, fragments of soluble RGMc, variants of RGMc (membrane-associated or soluble RGMc). The labeled RGMc (such as membrane-associated RGMc peptide, soluble RGMc peptide, fragments of membrane-associated RGMc peptide, fragments of soluble RGMc, variants of RGMc (membrane-associated or soluble RGMc) or any combinations thereof) competes with any unlabeled RGMc (such as membrane-associated RGMc peptide, soluble RGMc peptide, fragments of membrane-associated RGMc peptide, fragments of soluble RGMc, variants of RGMc (membrane-associated or soluble RGMc) or any combinations thereof) in the test sample for binding to the antibody or functionally active fragment thereof. The amount of labeled RGMc-antibody complex formed is determined and the amount of RGMc (such as membrane-associated RGMc peptide, soluble RGMc peptide, fragments of membrane-associated RGMc peptide, fragments of soluble RGMc, variants of RGMc (membrane-associated or soluble RGMc) or any combinations thereof) in the test sample determined via use of a standard curve.

The antibody used in a fluorescence polarization assay specifically binds to an epitope comprising at least three (3) amino acids of SEQ ID NO:2 or to an epitope comprising amino acids 5-13, 5-12, 5-11, 5-10, 5-9, 5-8, 5-7, 6-13, 6-12, 6-11, 6-10, 6-9, 6-8, 7-13, 7-13, 7-11, 7-10, 7-9, 8-13, 8-12, 8-11, 8-10, 9-13, 9-12, 9-11, 10-13, 10-12 or 11-13 of RGMc (SEQ ID NO:1).

The antibody, labeled RGMc (such as membrane-associated RGMc peptide, soluble RGMc peptide, fragments of membrane-associated RGMc peptide, fragments of soluble RGMc, variants of RGMc (membrane-associated or soluble RGMc) or any combinations thereof) and test sample and at least one labeled antibody may be incubated under conditions similar to those described above in connection with the sandwich immunoassay.

Alternatively, an antibody or functionally active fragment thereof may be simultaneously contacted with a fluorescently labeled RGMc (such as membrane-associated RGMc peptide, soluble RGMc peptide, fragments of membrane-associated RGMc peptide, fragments of soluble RGMc, variants of RGMc (membrane-associated or soluble RGMc) or any combinations thereof) and an unlabeled test sample suspected of containing RGMc (such as membrane-associated RGMc peptide, soluble RGMc peptide, fragments of membrane-associated RGMc peptide, fragments of soluble RGMc, variants of RGMc (membrane-associated or soluble RGMc) or any combinations thereof) thereof to form both labeled RGMc-antibody complexes and unlabeled RGMc-antibody complexes. The amount of labeled RGMc-antibody complex formed is determined and the amount of RGMc in the test sample determined via use of a standard curve. The antibody used in this immunoassay specifically may bind to an epitope having an amino acid sequence from SEQ ID NO: 1 or 2 to an epitope having an amino acid sequence containing amino acids 5-13, 5-12, 5-11, 5-10, 5-9, 5-8, 5-7, 6-13, 6-12, 6-11, 6-10, 6-9, 6-8, 7-13, 7-13, 7-11, 7-10, 7-9, 8-13, 8-12, 8-11, 8-10, 9-13, 9-12, 9-11, 10-13, 10-12 or 11-13 of RGMc (SEQ ID NO:1 or 2).

Alternatively, an antibody or functionally active fragment thereof is first contacted with a fluorescently labeled RGMc (such as membrane-associated RGMc peptide, soluble RGMc peptide, fragments of membrane-associated RGMc peptide, fragments of soluble RGMc, variants of RGMc (membrane-associated or soluble RGMc) or any combinations thereof) to form a labeled RGMc-antibody complex. The labeled RGMc-antibody complex is then contacted with an unlabeled test sample suspected of containing RGMc (such as membrane-associated RGMc peptide, soluble RGMc peptide, fragments of membrane-associated RGMc peptide, fragments of soluble RGMc, variants of RGMc (membrane-associated or soluble RGMc) or any combinations thereof). Any unlabeled RGMc in the test sample competes with the labeled RGMc (such as membrane-associated RGMc peptide, soluble RGMc peptide, fragments of membrane-associated RGMc peptide, fragments of soluble RGMc, variants of RGMc (membrane-associated or soluble RGMc) or any combinations thereof) for binding to the antibody or functionally active fragment thereof. The amount of labeled RGMc-antibody complex formed is determined the amount of RGMc in the test sample determined via use of a standard curve. The antibody used in this immunoassay specifically binds to an epitope comprising at least three (3) amino acids of amino acids 5-13 of RGMc (SEQ ID NO:2) or to an epitope comprising amino acids 13-20, 13-19, 13-18, 13-17, 13-16, 14-20, 14-19, 14-18, 14-17, 14-16, 15-20, 15-19, 15-18, 16-20, 16-19, 17-24, 17-23, 17-22, 17-21, 17-20, 17-19, 18-24, 18-23, 18-22, 18-21, 18-20, 19-24, 19-23, 19-22 or 19-21 of RGMc (SEQ ID NO: 1 or 2).

(e) Mass Spectrometry

Mass spectrometry (MS) analysis may be used alone or in combination with other methods. Other methods include immunoassays and those described above to detect specific polynucleotides. The mass spectrometry method may be used to determine the presence and/or quantity of one or more biomarkers. MS analysis may comprise matrix-assisted laser desorption/ionization (MALDI) time-of-flight (TOF) MS analysis, such as, for example, directed-spot MALDI-TOF or liquid chromatography MALDI-TOF analysis. In some embodiments, the MS analysis comprises electrospray ionization (ESI) MS, such as liquid chromatography (LC) ESI-MS. Mass analysis can be accomplished using commercially available spectrometers. Methods for utilizing MS analysis, including MALDI-TOF MS and ESI-MS, to detect the presence and quantity of biomarker peptides in biological samples may be used. See, for example, U.S. Pat. Nos. 6,925,389; 6,989,100; and 6,890,763 for guidance, each of which is incorporated herein by reference.

c. Control

It may be desirable to include a control sample or a calibrator, such as a series of calibrators. The control sample may be analyzed concurrently with the sample from the subject as described above. The results obtained from the subject sample can be compared to the results obtained from the control sample. Standard curves may be provided, with which asay results for the biological sample may be compared. Such standard curves present levels as a function of assay units, i.e. fluorescent signal intensity, if a fluorescent label is used. Using samples taken from multiple donors, standard curves can be provided for control levels of the RGMc in normal tissue, as well as for "at-risk" levels of the RGMc in tissue taken from donors, who may have one or more of the characteristics set forth above.

Thus, in view of the above, a method of determining the presence, amount or concentration of RGMc (such as membrane-associated RGMc peptide, soluble RGMc peptide, fragments of membrane-associated RGMc peptide, fragments of soluble RGMc, variants of RGMc (membrane-associated or soluble RGMc) or any combinations thereof) in a test sample is provided. The method comprises assaying the test sample for RGMc (such as membrane-associated RGMc peptide, soluble RGMc peptide, fragments of membrane-associated RGMc peptide, fragments of soluble RGMc, variants of RGMc (membrane-associated or soluble RGMc) or any combinations thereof) by an immunoassay, for example, employing at least one antibody and at least one detectable label and comprising comparing a signal generated by the detectable label as a direct or indirect indication of the presence, amount or concentration of RGMc in the test sample to a signal generated as a direct or indirect indication of the presence, amount or concentration of RGMc in a calibrator. The calibrator is optionally, and is preferably, part of a series of calibrators in which each of the calibrators differs from the other calibrators in the series by the concentration of RGMc. One of the at least one antibody is an isolated antibody, which specifically binds to RGMc (such as membrane-associated RGMc peptide, soluble RGMc peptide, fragments of membrane-associated RGMc peptide, fragments of soluble RGMc, variants of RGMc (membrane-associated or soluble RGMc) or any combinations thereof), wherein the antibody has a domain or region selected from (a) a variable heavy domain region comprising the amino acid sequence of SEQ ID NO:3, (b) a variable light domain region comprising the amino acid sequence of SEQ ID NO:4, (c) a variably heavy domain region comprising the amino acid sequence of SEQ ID NO:5, (d) a variable light domain region comprising the amino acid sequence of SEQ ID NO:6, (e) a variably heavy domain region comprising the amino acid sequence of SEQ ID NO:7, (f) a variable light domain region comprising the amino acid sequence of SEQ ID NO:8, (g) a variably heavy domain region comprising the amino acid sequence of SEQ ID NO:9, (h) a variable light domain region comprising the amino acid sequence of SEQ ID NO:10, (i) a variable heavy chain comprising a complementarity determining region (CDR)1 comprising the amino acid sequence of SEQ ID NO:11, a CDR2 comprising the amino acid sequence of SEQ ID NO:12, and a CDR3 comprising the amino acid sequence of SEQ ID NO: 13, (j) a variable light chain comprising a CDR1 comprising the amino acid sequence of SEQ ID NO: 14, a CDR2 comprising the amino acid sequence of SEQ ID NO: 15, and a CDR3 comprising the amino acid sequence of SEQ ID NO:16, (k) a variable heavy chain comprising a CDR1 comprising the amino acid sequence of SEQ ID NO:17, a CDR2 comprising the amino acid sequence of SEQ ID NO:18, and a CDR3 comprising the amino acid sequence of SEQ ID NO: 19, (l) a variable light chain comprising a CDR1 comprising the amino acid sequence of SEQ ID NO:20, a CDR2 comprising the amino acid sequence of SEQ ID NO:21, and a CDR3 comprising the amino acid sequence of SEQ ID NO:22, (m) a variable heavy chain comprising a CDR1 comprising the amino acid sequence of SEQ ID NO:23, a CDR2 comprising the amino acid sequence of SEQ ID NO:24, and a CDR3 comprising the amino acid sequence of SEQ ID NO:25, (n) a variable light chain comprising a CDR1 comprising the amino acid sequence of SEQ ID NO:26, a CDR2 comprising the amino acid sequence of SEQ ID NO:27, and a CDR3 comprising the amino acid sequence of SEQ ID NO:28, (o) a variable heavy chain comprising a CDR1 comprising the amino acid sequence of SEQ ID NO:29, a CDR2 comprising the amino acid sequence of SEQ ID NO:30, and a CDR3 comprising the amino acid sequence of SEQ ID NO:31, (p) a variable light chain comprising a CDR1 comprising the amino acid sequence of SEQ ID NO:32, a CDR2 comprising the amino acid sequence of SEQ ID NO:33, and a CDR3 comprising the amino acid sequence of SEQ ID NO:34, (q) a variable heavy chain comprising a complementarity determining region (CDR)1 comprising the amino acid sequence of SEQ ID NO: 11, a CDR2 comprising the amino acid sequence of SEQ ID NO: 12, and a CDR3 comprising the amino acid sequence of SEQ ID NO:13 and a variable light chain comprising a CDR1 comprising the amino acid sequence of SEQ ID NO:14, a CDR2 comprising the amino acid sequence of SEQ ID NO:15, and a CDR3 comprising the amino acid sequence of SEQ ID NO:16, (r) a variable heavy chain comprising a CDR1 comprising the amino acid sequence of SEQ ID NO:17, a CDR2 comprising the amino acid sequence of SEQ ID NO: 18, and a CDR3 comprising the amino acid sequence of SEQ ID NO:19 and a variable light chain comprising a CDR1 comprising the amino acid sequence of SEQ ID NO:20, a CDR2 comprising the amino acid sequence of SEQ ID NO:21, and a CDR3 comprising the amino acid sequence of SEQ ID NO:22, (s) a variable heavy chain comprising a CDR1 comprising the amino acid sequence of SEQ ID NO:23, a CDR2 comprising the amino acid sequence of SEQ ID NO:24, and a CDR3 comprising the amino acid sequence of SEQ ID NO:25 and a variable light chain comprising a CDR1 comprising the amino acid sequence of SEQ ID NO:26, a CDR2 comprising the amino acid sequence of SEQ ID NO:27, and a CDR3 comprising the amino acid sequence of SEQ ID NO:28, (t) a variable heavy chain comprising a CDR1 comprising the amino acid sequence of SEQ ID NO:29, a CDR2 comprising the amino acid sequence of SEQ ID NO:30, and a CDR3 comprising the amino acid sequence of SEQ ID NO:31 and a variable light chain comprising a CDR1 comprising the amino acid sequence of SEQ ID NO:32, a CDR2 comprising the amino acid sequence of SEQ ID NO:33, and a CDR3 comprising the amino acid sequence of SEQ ID NO:34.

Optionally, the antibody has a domain or region selected from the sequences provided in Table 2. For example, the antibody has a domain or region selected from (a) a variable heavy domain region comprising the amino acid sequence of SEQ ID NO:37, (b) a variable light domain region comprising the amino acid sequence of SEQ ID NO:38, (c) a variably heavy domain region comprising the amino acid sequence of SEQ ID NO:39, (d) a variable light domain region comprising the amino acid sequence of SEQ ID NO:40, (e) a variably heavy domain region comprising the amino acid sequence of SEQ ID NO:41, (f) a variable light domain region comprising the amino acid sequence of SEQ ID NO:42, (g) a variably heavy domain region comprising the amino acid sequence of SEQ ID NO:43, (h) a variable light domain region comprising the amino acid sequence of SEQ ID NO:44, (i) a variably heavy domain region comprising the amino acid sequence of SEQ ID NO:45, (j) a variable light domain region comprising the amino acid sequence of SEQ ID NO:46, (k) a variably heavy domain region comprising the amino acid sequence of SEQ ID NO:47, (l) a variable light domain region comprising the amino acid sequence of SEQ ID NO:48, (m) a variably heavy domain region comprising the amino acid sequence of SEQ ID NO:49, (n) a variable light domain region comprising the amino acid sequence of SEQ ID NO:50, (o) a variably heavy domain region comprising the amino acid sequence of SEQ ID NO:51, (p) a variable light domain region comprising the amino acid sequence of SEQ ID NO:52, (q) a variably heavy domain region comprising the amino acid sequence of SEQ ID NO:53, (r) a variable light domain region comprising the amino acid sequence of SEQ ID NO:54, (s) a variably heavy domain region comprising the amino acid sequence of SEQ ID NO:55, (t) a variable light domain region comprising the amino acid sequence of SEQ ID NO:56, (u) a variably heavy domain region comprising the amino acid sequence of SEQ ID NO:57, (v) a variable light domain region comprising the amino acid sequence of SEQ ID NO:58, (w) a variably heavy domain region comprising the amino acid sequence of SEQ ID NO:59, (x) a variable light domain region comprising the amino acid sequence of SEQ ID NO:60, (y) a variably heavy domain region comprising the amino acid sequence of SEQ ID NO:61, (z) a variable light domain region comprising the amino acid sequence of SEQ ID NO:62, (aa) a variably heavy domain region comprising the amino acid sequence of SEQ ID NO:63, (bb) a variable light domain region comprising the amino acid sequence of SEQ ID NO:64, (cc) a variably heavy domain region comprising the amino acid sequence of SEQ ID NO:65, (dd) a variable light domain region comprising the amino acid sequence of SEQ ID NO:66, (ee) a variably heavy domain region comprising the amino acid sequence of SEQ ID NO:67, (ff) a variable light domain region comprising the amino acid sequence of SEQ ID NO:68, (gg) a variably heavy domain region comprising the amino acid sequence of SEQ ID NO:69, (hh) a variable light domain region comprising the amino acid sequence of SEQ ID NO:70, (ii) a variably heavy domain region comprising the amino acid sequence of SEQ ID NO:71, (jj) a variable light domain region comprising the amino acid sequence of SEQ ID NO:72, (kk) a variably heavy domain region comprising the amino acid sequence of SEQ ID NO:73, (ll) a variable light domain region comprising the amino acid sequence of SEQ ID NO:74, (mm) a variably heavy domain region comprising the amino acid sequence of SEQ ID NO:75, (nn) a variable light domain region comprising the amino acid sequence of SEQ ID NO:76, (oo) a variable heavy chain comprising a complementarity determining region (CDR)1 comprising the amino acid sequence of SEQ ID NO:77, a CDR2 comprising the amino acid sequence of SEQ ID NO:78, and a CDR3 comprising the amino acid sequence of SEQ ID NO:79, (pp) a variable light chain comprising a CDR1 comprising the amino acid sequence of SEQ ID NO:80, a CDR2 comprising the amino acid sequence of SEQ ID NO:81, and a CDR3 comprising the amino acid sequence of SEQ ID NO:82, or (qq) a variable heavy chain comprising a complementarity determining region (CDR)1 comprising the amino acid sequence of SEQ ID NO:77, a CDR2 comprising the amino acid sequence of SEQ ID NO:78, and a CDR3 comprising the amino acid sequence of SEQ ID NO: 79 and a variable light chain comprising a CDR1 comprising the amino acid sequence of SEQ ID NO:80, a CDR2 comprising the amino acid sequence of SEQ ID NO:81, and a CDR3 comprising the amino acid sequence of SEQ ID NO:82.

The method can comprise (i) contacting the test sample with at least one capture antibody, which binds to an epitope on RGMc (such as membrane-associated RGMc peptide, soluble RGMc peptide, fragments of membrane-associated RGMc peptide, fragments of soluble RGMc, variants of RGMc (membrane-associated or soluble RGMc) or any combinations thereof), so as to form a capture antibody/RGMc (such as membrane-associated RGMc peptide, soluble RGMc peptide, fragments of membrane-associated RGMc peptide, fragments of soluble RGMc, variants of RGMc (membrane-associated or soluble RGMc) or any combinations thereof) complex, (ii) contacting the capture antibody/RGMc (such as membrane-associated RGMc peptide, soluble RGMc peptide, fragments of membrane-associated RGMc peptide, fragments of soluble RGMc, variants of RGMc (membrane-associated or soluble RGMc) or any combinations thereof) complex with at least one detection antibody, which comprises a detectable label and binds to an epitope on RGMc (such as membrane-associated RGMc peptide, soluble RGMc peptide, fragments of membrane-associated RGMc peptide, fragments of soluble RGMc, variants of RGMc (membrane-associated or soluble RGMc) or any combinations thereof) that is not bound by the capture antibody, to form a capture antibody/RGMc (such as membrane-associated RGMc peptide, soluble RGMc peptide, fragments of membrane-associated RGMc peptide, fragments of soluble RGMc, variants of RGMc (membrane-associated or soluble RGMc) or any combinations thereof)/detection antibody complex, and (iii) determining the amount of RGMc (or a fragment thereof) in the test sample based on the signal generated by the detectable label in the capture antibody/RGMc (such as membrane-associated RGMc peptide, soluble RGMc peptide, fragments of membrane-associated RGMc peptide, fragments of soluble RGMc, variants of RGMc (membrane-associated or soluble RGMc) or any combinations thereof)/detection antibody complex formed in (ii).

Alternatively, the method can comprise (i) contacting the test sample with at least one capture antibody, which binds to an epitope on RGMc (such as membrane-associated RGMc peptide, soluble RGMc peptide, fragments of membrane-associated RGMc peptide, fragments of soluble RGMc, variants of RGMc (membrane-associated or soluble RGMc) or any combinations thereof) so as to form a capture antibody/RGMc (such as membrane-associated RGMc peptide, soluble RGMc peptide, fragments of membrane-associated RGMc peptide, fragments of soluble RGMc, variants of RGMc (membrane-associated or soluble RGMc) or any combinations thereof) complex, and simultaneously or sequentially, in either order, contacting the test sample with detectably labeled RGMc (such as membrane-associated RGMc peptide, soluble RGMc peptide, fragments of membrane-associated RGMc peptide, fragments of soluble RGMc, variants of RGMc (membrane-associated or soluble RGMc) or any combinations thereof), which can compete with any RGMc (such as membrane-associated RGMc peptide, soluble RGMc peptide, fragments of membrane-associated RGMc peptide, fragments of soluble RGMc, variants of RGMc (membrane-associated or soluble RGMc) or any combinations thereof) in the test sample for binding to the at least one capture antibody. Any RGMc (such as membrane-associated RGMc peptide, soluble RGMc peptide, fragments of membrane-associated RGMc peptide, fragments of soluble RGMc, variants of RGMc (membrane-associated or soluble RGMc) or any combinations thereof) present in the test sample and the detectably labeled RGMc compete with each other to form a capture antibody/RGMc (such as membrane-associated RGMc peptide, soluble RGMc peptide, fragments of membrane-associated RGMc peptide, fragments of soluble RGMc, variants of RGMc (membrane-associated or soluble RGMc) or any combinations thereof) complex and a capture antibody/detectably labeled RGMc (such as membrane-associated RGMc peptide, soluble RGMc peptide, fragments of membrane-associated RGMc peptide, fragments of soluble RGMc, variants of RGMc (membrane-associated or soluble RGMc) or any combinations thereof) complex, respectively. The method further comprises (ii) determining the presence, amount or concentration of RGMc in the test sample based on the signal generated by the detectable label in the capture antibody/detectably labeled RGMc (such as membrane-associated RGMc peptide, soluble RGMc peptide, fragments of membrane-associated RGMc peptide, fragments of soluble RGMc, variants of RGMc (membrane-associated or soluble RGMc) or any combinations thereof) complex formed in (ii). The signal generated by the detectable label in the capture antibody/detectably labeled RGMc (such as membrane-associated RGMc peptide, soluble RGMc peptide, fragments of membrane-associated RGMc peptide, fragments of soluble RGMc, variants of RGMc (membrane-associated or soluble RGMc) or any combinations thereof) complex is inversely proportional to the amount or concentration of RGMc in the test sample.

In one embodiment, a mouse anti-RGMc Ab can be attached directly or indirectly, e.g., via a sheep (or other species) anti-mouse Ab, to a solid support. Any RGMc, which is present in a sample and brought into contact with the solid support, is bound by the mouse anti-RGMc Ab. A biotin-labeled goat anti-RGMc Ab also binds to the RGMc. Streptavidin, which is linked to horseradish peroxidase (HRPO), binds to the biotin on the goat anti-RGMc Ab. Upon being contacted with o-phenylenediamine, the HRPO converts the o-phenylenediamine to 2,3-diaminophenazine, which is orange-brown in color and can be measured spectrophotometrically at 492 nm.

The method can further comprise diagnosing, prognosticating, or assessing the efficacy of a therapeutic/prophylactic treatment of a patient from whom the test sample was obtained. If the method further comprises assessing the efficacy of a therapeutic/prophylactic treatment of the patient from whom the test sample was obtained, the method optionally further comprises modifying the therapeutic/prophylactic treatment of the patient as needed to improve efficacy. The method can be adapted for use in an automated system or a semi-automated system.

Generally, a predetermined level can be employed as a benchmark against which to assess results obtained upon assaying a test sample for RGMc (such as membrane-associated RGMc peptide, soluble RGMc peptide, fragments of membrane-associated RGMc peptide, fragments of soluble RGMc, variants of RGMc (membrane-associated or soluble RGMc) or any combinations thereof). Generally, in making such a comparison, the predetermined level is obtained by running a particular assay a sufficient number of times and under appropriate conditions such that a linkage or association of analyte presence, amount or concentration with a particular stage or endpoint of a disease, disorder or condition (e.g., an iron-related disorder, such as one related to iron overload or iron deficiency as discussed herein and/or known in the art) or with particular indicia can be made. Typically, the predetermined level is obtained with assays of reference subjects (or populations of subjects). The RGMc measured can include fragments thereof, degradation products thereof, and/or enzymatic cleavage products thereof.

In particular, with respect to a predetermined level as employed for monitoring disease progression and/or treatment, the amount or concentration of RGMc (such as membrane-associated RGMc peptide, soluble RGMc peptide, fragments of membrane-associated RGMc RGMc) or any combinations thereof) may be "unchanged," "favorable" (or "favorably altered"), or "unfavorable" (or "unfavorably altered"). "Elevated" or "increased" refers to an amount or a concentration in a test sample that is higher than a typical or normal level or range (e.g., predetermined level), or is higher than another reference level or range (e.g., earlier or baseline sample). The term "lowered" or "reduced" refers to an amount or a concentration in a test sample that is lower than a typical or normal level or range (e.g., predetermined level), or is lower than another reference level or range (e.g., earlier or baseline sample). The term "altered" refers to an amount or a concentration in a sample that is altered (increased or decreased) over a typical or normal level or range (e.g., predetermined level), or over another reference level or range (e.g., earlier or baseline sample).

The typical or normal level or range for RGMc is defined in accordance with standard practice. A so-called altered level or alteration can be considered to have occurred when there is any net change as compared to the typical or normal level or range, or reference level or range, that cannot be explained by experimental error or sample variation. Thus, the level measured in a particular sample will be compared with the level or range of levels determined in similar samples from a so-called normal subject. In this context, a "normal subject" is an individual with no detectable disease or disorder, and a "normal" (sometimes termed "control") patient or population is/are one(s) that exhibit(s) no detectable disease or disorder, respectively, for example. An "apparently normal subject" is one in which RGMc has not been or is being assessed. The level of an analyte is said to be "elevated" when the analyte is normally undetectable (e.g., the normal level is zero, or within a range of from about 25 to about 75 percentiles of normal populations), but is detected in a test sample, as well as when the analyte is present in the test sample at a higher than normal level. Thus, inter alia, the disclosure provides a method of screening for a subject having, or at risk of having, an iron-related disorder, such as one related to iron overload or iron deficiency as discussed herein and/or known in the art.

Generally, a predetermined level can be employed as a benchmark against which to assess results obtained upon assaying a test sample for hepcidin. Generally, in making such a comparison, the predetermined level is obtained by running a particular assay a sufficient number of times and under appropriate conditions such that a linkage or association of analyte presence, amount or concentration with a particular stage or endpoint of a disease, disorder or condition (e.g., an iron-related disorder, such as one related to iron overload or iron deficiency as discussed herein and/or known in the art) or with particular indicia can be made. Typically, the predetermined level is obtained with assays of reference subjects (or populations of subjects). The hepcidin measured can include fragments thereof, degradation products thereof, and/or enzymatic cleavage products thereof.

In particular, with respect to a predetermined level as employed for monitoring disease progression and/or treatment, the amount or concentration of hepcidin may be "unchanged," "favorable" (or "favorably altered"), or "unfavorable" (or "unfavorably altered"). "Elevated" or "increased" refers to an amount or a concentration in a test sample that is higher than a typical or normal level or range (e.g., predetermined level), or is higher than another reference level or range (e.g., earlier or baseline sample). The term "lowered" or "reduced" refers to an amount or a concentration in a test sample that is lower than a typical or normal level or range (e.g., predetermined level), or is lower than another reference level or range (e.g., earlier or baseline sample). The term "altered" refers to an amount or a concentration in a sample that is altered (increased or decreased) over a typical or normal level or range (e.g., predetermined level), or over another reference level or range (e.g., earlier or baseline sample).

The typical or normal level or range for hepcidin is defined in accordance with standard practice. A so-called altered level or alteration can be considered to have occurred when there is any net change as compared to the typical or normal level or range, or reference level or range that cannot be explained by experimental error or sample variation. Thus, the level measured in a particular sample will be compared with the level or range of levels determined in similar samples from a so-called normal subject. In this context, a "normal subject" is an individual with no detectable disease or disorder, and a "normal" (sometimes termed "control") patient or population is/are one(s) that exhibit(s) no detectable disease or disorder, respectively, for example. An "apparently normal subject" is one in which hepcidin has not been or is being assessed. The level of an analyte is said to be "elevated" when the analyte is normally undetectable (e.g., the normal level is zero, or within a range of from about 25 to about 75 percentiles of normal populations), but is detected in a test sample, as well as when the analyte is present in the test sample at a higher than normal level. Thus, inter alia, the disclosure provides a method of screening for a subject having, or at risk of having, an iron-related disorder, such as one related to iron overload or iron deficiency as discussed herein and/or known in the art.

The method of assay can also involve the assay of other markers and the like as discussed herein and known in the art. For example, the method of assay can also involve the assay of hepcidin (as described above), neogenin, growth differentiation factor 15 (GDF-15), neutrophil gelatinase-associated lipocalin (NGAL), interleukin 6 (IL-6), and/or BMP-6, for example.

The methods described herein also can be used to determine whether or not a subject has or is at risk of developing an iron-related disorder, such as discussed herein and known in the art. Specifically, such a method can comprise the steps of:

(a) determining the concentration or amount in a test sample from a subject of RGMc (such as membrane-associated RGMc peptide, soluble RGMc peptide, fragments of membrane-associated RGMc peptide, fragments of soluble RGMc, variants of RGMc (membrane-associated or soluble RGMc) or any combinations thereof using the methods described herein, or methods known in the art); and (b) comparing the concentration or amount of RGMc (such as membrane-associated RGMc peptide, soluble RGMc peptide, fragments of membrane-associated RGMc peptide, fragments of soluble RGMc, variants of RGMc (membrane-associated or soluble RGMc) or any combinations thereof) determined in step (a) with a predetermined level, wherein, if the concentration or amount of RGMc determined in step (a) is favorable with respect to a predetermined level, then the subject is determined not to have or be at risk for an iron-related disorder as discussed herein and known in in the art. However, if the concentration or amount of RGMc determined in step (a) is unfavorable with respect to the predetermined level, then the subject is determined to have or be at risk for an iron-related disorder as discussed herein and known in the art.

Additionally, provided herein is method of monitoring the progression of disease in a subject. Optimally, the method comprises the steps of:

(a) determining the concentration or amount in a test sample from a subject of RGMc (such as membrane-associated RGMc peptide, soluble RGMc peptide, fragments of membrane-associated RGMc peptide, fragments of soluble RGMc, variants of RGMc (membrane-associated or soluble RGMc) or any combinations thereof);

(b) determining the concentration or amount in a later test sample from the subject of RGMc; and (c) comparing the concentration or amount of RGMc as determined in step (b) with the concentration or amount of RGMc determined in step (a), wherein if the concentration or amount determined in step (b) is unchanged or is unfavorable when compared to the concentration or amount of RGMc determined in step (a), then the disease in the subject is determined to have continued, progressed or worsened. By comparison, if the concentration or amount of RGMc as determined in step (b) is favorable when compared to the concentration or amount of RGMc as determined in step (a), then the disease in the subject is determined to have discontinued, regressed or improved.

Optionally, the method further comprises comparing the concentration or amount of RGMc as determined in step (b), for example, with a predetermined level. Further, optionally the method comprises treating the subject with one or more pharmaceutical compositions for a period of time if the comparison shows that the concentration or amount of RGMc as determined in step (b), for example, is unfavorably altered with respect to the predetermined level.

Still further, the methods can be used to monitor treatment in a subject receiving treatment with one or more pharmaceutical compositions. Specifically, such methods involve providing a first test sample from a subject before the subject has been administered one or more pharmaceutical compositions. Next, the concentration or amount in a first test sample from a subject of RGMc is determined (e.g., using the methods described herein or as known in the art). After the concentration or amount of RGMc is determined, optionally the concentration or amount of RGMc is then compared with a predetermined level. If the concentration or amount of RGMc as determined in the first test sample is lower than the predetermined level, then the subject is not treated with one or more pharmaceutical compositions. However, if the concentration or amount of RGMc as determined in the first test sample is higher than the predetermined level, then the subject is treated with one or more pharmaceutical compositions for a period of time. The period of time that the subject is treated with the one or more pharmaceutical compositions can be determined by one skilled in the art (for example, the period of time can be from about seven (7) days to about two years, preferably from about fourteen (14) days to about one (1) year).

During the course of treatment with the one or more pharmaceutical compositions, second and subsequent test samples are then obtained from the subject. The number of test samples and the time in which said test samples are obtained from the subject are not critical. For example, a second test sample could be obtained seven (7) days after the subject is first administered the one or more pharmaceutical compositions, a third test sample could be obtained two (2) weeks after the subject is first administered the one or more pharmaceutical compositions, a fourth test sample could be obtained three (3) weeks after the subject is first administered the one or more pharmaceutical compositions, a fifth test sample could be obtained four (4) weeks after the subject is first administered the one or more pharmaceutical compositions, etc.

After each second or subsequent test sample is obtained from the subject, the concentration or amount of RGMc (such as membrane-associated RGMc peptide, soluble RGMc peptide, fragments of membrane-associated RGMc peptide, fragments of soluble RGMc, variants of RGMc (membrane-associated or soluble RGMc) or any combinations thereof) is determined in the second or subsequent test sample is determined (e.g., using the methods described herein or as known in the art). The concentration or amount of RGMc as determined in each of the second and subsequent test samples is then compared with the concentration or amount of RGMc as determined in the first test sample (e.g., the test sample that was originally optionally compared to the predetermined level). If the concentration or amount of RGMc as determined in step (c) is favorable when compared to the concentration or amount of RGMc as determined in step (a), then the disease in the subject is determined to have discontinued, regressed or improved, and the subject should continue to be administered the one or pharmaceutical compositions of step (b). However, if the concentration or amount determined in step (c) is unchanged or is unfavorable when compared to the concentration or amount of RGMc as determined in step (a), then the disease in the subject is determined to have continued, progressed or worsened, and the subject should be treated with a higher concentration of the one or more pharmaceutical compositions administered to the subject in step (b) or the subject should be treated with one or more pharmaceutical compositions that are different from the one or more pharmaceutical compositions administered to the subject in step (b). Specifically, the subject can be treated with one or more pharmaceutical compositions that are different from the one or more pharmaceutical compositions that the subject had previously received to decrease or lower said subject's RGMc level.

Generally, for assays in which repeat testing may be done (e.g., monitoring disease progression and/or response to treatment), a second or subsequent test sample is obtained at a period in time after the first test sample has been obtained from the subject. Specifically, a second test sample from the subject can be obtained minutes, hours, days, weeks or years after the first test sample has been obtained from the subject. For example, the second test sample can be obtained from the subject at a time period of about 1 minute, about 5 minutes, about 10 minutes, about 15 minutes, about 30 minutes, about 45 minutes, about 60 minutes, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 2 days, about 3 days, about 4 days, about 5 days, about 6 days, about 7 days, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, about 21 weeks, about 22 weeks, about 23 weeks, about 24 weeks, about 25 weeks, about 26 weeks, about 27 weeks, about 28 weeks, about 29 weeks, about 30 weeks, about 31 weeks, about 32 weeks, about 33 weeks, about 34 weeks, about 35 weeks, about 36 weeks, about 37 weeks, about 38 weeks, about 39 weeks, about 40 weeks, about 41 weeks, about 42 weeks, about 43 weeks, about 44 weeks, about 45 weeks, about 46 weeks, about 47 weeks, about 48 weeks, about 49 weeks, about 50 weeks, about 51 weeks, about 52 weeks, about 1.5 years, about 2 years, about 2.5 years, about 3.0 years, about 3.5 years, about 4.0 years, about 4.5 years, about 5.0 years, about 5.5 years, about 6.0 years, about 6.5 years, about 7.0 years, about 7.5 years, about 8.0 years, about 8.5 years, about 9.0 years, about 9.5 years or about 10.0 years after the first test sample from the subject is obtained. When used to monitor disease progression, the above assay can be used to monitor the progression of disease in subjects suffering from acute conditions. Acute conditions, also known as critical care conditions, refer to acute, life-threatening diseases or other critical medical conditions involving, for example, the cardiovascular system or excretory system. Typically, critical care conditions refer to those conditions requiring acute medical intervention in a hospital-based setting (including, but not limited to, the emergency room, intensive care unit, trauma center, or other emergent care setting) or administration by a paramedic or other field-based medical personnel. For critical care conditions, repeat monitoring is generally done within a shorter time frame, namely, minutes, hours or days (e.g., about 1 minute, about 5 minutes, about 10 minutes, about 15 minutes, about 30 minutes, about 45 minutes, about 60 minutes, about 2 hours, about 3 hours, about 4 hours, 4 about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 2 days, about 3 days, about 4 days, about 5 days, about 6 days or about 7 days), and the initial assay likewise is generally done within a shorter timeframe, e.g., about minutes, hours or days of the onset of the disease or condition.

The assays also can be used to monitor the progression of disease in subjects suffering from chronic or non-acute conditions. Non-critical care or, non-acute conditions, refers to conditions other than acute, life-threatening disease or other critical medical conditions involving, for example, the cardiovascular system and/or excretory system. Typically, non-acute conditions include those of longer-term or chronic duration. For non-acute conditions, repeat monitoring generally is done with a longer timeframe, e.g., hours, days, weeks, months or years (e.g., about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 2 days, about 3 days, about 4 days, about 5 days, about 6 days, about 7 days, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, about 21 weeks, about 22 weeks, about 23 weeks, about 24 weeks, about 25 weeks, about 26 weeks, about 27 weeks, about 28 weeks, about 29 weeks, about 30 weeks, about 31 weeks, about 32 weeks, about 33 weeks, about 34 weeks, about 35 weeks, about 36 weeks, about 37 weeks, about 38 weeks, about 39 weeks, about 40 weeks, about 41 weeks, about 42 weeks, about 43 weeks, about 44 weeks, about 45 weeks, about 46 weeks, about 47 weeks, about 48 weeks, about 49 weeks, about 50 weeks, about 51 weeks, about 52 weeks, about 1.5 years, about 2 years, about 2.5 years, about 3.0 years, about 3.5 years, about 4.0 years, about 4.5 years, about 5.0 years, about 5.5. years, about 6.0 years, about 6.5 years, about 7.0 years, about 7.5 years, about 8.0 years, about 8.5 years, about 9.0 years, about 9.5 years or about 10.0 years), and the initial assay likewise generally is done within a longer time frame, e.g., about hours, days, months or years of the onset of the disease or condition.

Furthermore, the above assays can be performed using a first test sample obtained from a subject where the first test sample is obtained from one source, such as urine, serum or plasma. Optionally the above assays can then be repeated using a second test sample obtained from the subject where the second test sample is obtained from another source. For example, if the first test sample was obtained from urine, the second test sample can be obtained from serum or plasma. The results obtained from the assays using the first test sample and the second test sample can be compared. The comparison can be used to assess the status of a disease or condition in the subject.

Moreover, the present disclosure also relates to methods of determining whether a subject predisposed to or suffering from a disease (e.g., an iron-related disorder, such as iron overload or iron deficiency, as discussed herein and known in the art) will benefit from treatment. In particular, the disclosure relates to RGMc companion diagnostic methods and products. Thus, the method of "monitoring the treatment of disease in a subject" as described herein further optimally also can encompass selecting or identifying candidates for therapy, such as therapy with erythropoietin (EPO).

Thus, in particular embodiments, the disclosure also provides a method of determining whether a subject having, or at risk for, an iron-related disorder, such as iron overload or iron deficiency, as discussed herein and known in the art) is a candidate for therapy. Generally, the subject is one who has experienced some symptom of the disease or who has actually been diagnosed as having, or being at risk for, such a disease, and/or who demonstrates an unfavorable concentration or amount of RGMc or a fragment thereof, as described herein.

The method optionally comprises an assay as described herein, where analyte is assessed before and following treatment of a subject with one or more pharmaceutical compositions (e.g., particularly with a pharmaceutical related to a mechanism of action involving RGMc), or where analyte is assessed following such treatment and the concentration or the amount of analyte is compared against a predetermined level. An unfavorable concentration of amount of analyte observed following treatment confirms that the subject will not benefit from receiving further or continued treatment, whereas a favorable concentration or amount of analyte observed following treatment confirms that the subject will benefit from receiving further or continued treatment. This confirmation assists with management of clinical studies, and provision of improved patient care.

It goes without saying that, while certain embodiments herein are advantageous when employed to assess an iron-related disorder, such as iron deficiency or iron overload, the assays and kits also optionally can be employed to assess RGMc in other diseases, disorders and conditions as appropriate.

The method of assay also can be used to identify a compound that ameliorates an iron-related disorder, such as iron deficiency or iron overload. For example, a cell that expresses RGMc can be contacted with a candidate compound. The level of expression of RGMc in the cell contacted with the compound can be compared to that in a control cell using the method of assay described herein.

6. Kits

Provided herein is a kit, which may be used for treating a subject suffering from an iron-related disorder or diagnosing a subject as having an iron-related disorder as described previously herein.

Kits to be used for treating a patient will contain an antibody specific for RGMc. The kits preferably include instructions for treating a subject using the antibodies described herein. Instructions included in kits can be affixed to packaging material or can be included as a package insert. While the instructions are typically written or printed materials they are not limited to such. Any medium capable of storing such instructions and communicating them to an end user is contemplated by this disclosure. Such media include, but are not limited to, electronic storage media (e.g., magnetic discs, tapes, cartridges, chips), optical media (e.g., CD ROM), and the like. As used herein, the term "instructions" can include the address of an internet site that provides the instructions.

Also provided is a kit for assaying a test sample for RGMc (such as membrane-associated RGMc peptide, soluble RGMc peptide, fragments of membrane-associated RGMc peptide, fragments of soluble RGMc, variants of RGMc (membrane-associated or soluble RGMc) or any combinations thereof). The kit comprises at least one component for assaying the test sample for RGMc and instructions for assaying the test sample for RGMc (such as membrane-associated RGMc peptide, soluble RGMc peptide, fragments of membrane-associated RGMc peptide, fragments of soluble RGMc, variants of RGMc (membrane-associated or soluble RGMc) or any combinations thereof). The at least one component includes at least one composition comprising an isolated antibody that specifically binds to RGMc (such as membrane-associated RGMc peptide, soluble RGMc peptide, fragments of membrane-associated RGMc peptide, fragments of soluble RGMc, variants of RGMc (membrane-associated or soluble RGMc) or any combinations thereof). The antibody may have (i) a variable heavy domain region comprising the amino acid sequence of SEQ ID NO:3 and a variable light domain region comprising the amino acid sequence of SEQ ID NO:4, (ii) a variable heavy domain region comprising the amino acid sequence of SEQ ID NO:5 and a variable light domain region comprising the amino acid sequence of SEQ ID NO:6, (iii) a variable heavy domain region comprising the amino acid sequence of SEQ ID NO:7 and a variable light domain region comprising the amino acid sequence of SEQ ID NO:8, (iv) a variable heavy domain region comprising the amino acid sequence of SEQ ID NO:9 and a variable light domain region comprising the amino acid sequence of SEQ ID NO: 10, (vi) a variable heavy chain comprising a complementarity determining region (CDR)1 comprising the amino acid sequence of SEQ ID NO:11, a CDR2 comprising the amino acid sequence of SEQ ID NO: 12, and a CDR3 comprising the amino acid sequence of SEQ ID NO:13 and a variable light chain comprising a CDR1 comprising the amino acid sequence of SEQ ID NO: 14, a CDR2 comprising the amino acid sequence of SEQ ID NO:15, and a CDR3 comprising the amino acid sequence of SEQ ID NO:16, (r) a variable heavy chain comprising a CDR1 comprising the amino acid sequence of SEQ ID NO:17, a CDR2 comprising the amino acid sequence of SEQ ID NO: 18, and a CDR3 comprising the amino acid sequence of SEQ ID NO: 19 and a variable light chain comprising a CDR1 comprising the amino acid sequence of SEQ ID NO:20, a CDR2 comprising the amino acid sequence of SEQ ID NO:21, and a CDR3 comprising the amino acid sequence of SEQ ID NO:22, (s) a variable heavy chain comprising a CDR1 comprising the amino acid sequence of SEQ ID NO:23, a CDR2 comprising the amino acid sequence of SEQ ID NO:24, and a CDR3 comprising the amino acid sequence of SEQ ID NO:25 and a variable light chain comprising a CDR1 comprising the amino acid sequence of SEQ ID NO:26, a CDR2 comprising the amino acid sequence of SEQ ID NO:27, and a CDR3 comprising the amino acid sequence of SEQ ID NO:28, (t) a variable heavy chain comprising a CDR1 comprising the amino acid sequence of SEQ ID NO:29, a CDR2 comprising the amino acid sequence of SEQ ID NO:30, and a CDR3 comprising the amino acid sequence of SEQ ID NO:31 and a variable light chain comprising a CDR1 comprising the amino acid sequence of SEQ ID NO:32, a CDR2 comprising the amino acid sequence of SEQ ID NO:33, and a CDR3 comprising the amino acid sequence of SEQ ID NO:34. The antibody is optionally detectably labeled.

Optionally, the antibody may have a domain or region selected from the sequences provided in Table 2. For example, the antibody may have (a) a variable heavy domain region comprising the amino acid sequence of SEQ ID NO:37, (b) a variable light domain region comprising the amino acid sequence of SEQ ID NO:38, (c) a variably heavy domain region comprising the amino acid sequence of SEQ ID NO:39, (d) a variable light domain region comprising the amino acid sequence of SEQ ID NO:40, (e) a variably heavy domain region comprising the amino acid sequence of SEQ ID NO:41, (f) a variable light domain region comprising the amino acid sequence of SEQ ID NO:42, (g) a variably heavy domain region comprising the amino acid sequence of SEQ ID NO:43, (h) a variable light domain region comprising the amino acid sequence of SEQ ID NO:44, (i) a variably heavy domain region comprising the amino acid sequence of SEQ ID NO:45, (j) a variable light domain region comprising the amino acid sequence of SEQ ID NO:46, (k) a variably heavy domain region comprising the amino acid sequence of SEQ ID NO:47, (l) a variable light domain region comprising the amino acid sequence of SEQ ID NO:48, (m) a variably heavy domain region comprising the amino acid sequence of SEQ ID NO:49, (n) a variable light domain region comprising the amino acid sequence of SEQ ID NO:50, (o) a variably heavy domain region comprising the amino acid sequence of SEQ ID NO:51, (p) a variable light domain region comprising the amino acid sequence of SEQ ID NO:52, (q) a variably heavy domain region comprising the amino acid sequence of SEQ ID NO:53, (r) a variable light domain region comprising the amino acid sequence of SEQ ID NO:54, (s) a variably heavy domain region comprising the amino acid sequence of SEQ ID NO:55, (t) a variable light domain region comprising the amino acid sequence of SEQ ID NO:56, (u) a variably heavy domain region comprising the amino acid sequence of SEQ ID NO:57, (v) a variable light domain region comprising the amino acid sequence of SEQ ID NO:58, (w) a variably heavy domain region comprising the amino acid sequence of SEQ ID NO:59, (x) a variable light domain region comprising the amino acid sequence of SEQ ID NO:60, (y) a variably heavy domain region comprising the amino acid sequence of SEQ ID NO:61, (z) a variable light domain region comprising the amino acid sequence of SEQ ID NO:62, (aa) a variably heavy domain region comprising the amino acid sequence of SEQ ID NO:63, (bb) a variable light domain region comprising the amino acid sequence of SEQ ID NO:64, (cc) a variably heavy domain region comprising the amino acid sequence of SEQ ID NO:65, (dd) a variable light domain region comprising the amino acid sequence of SEQ ID NO:66, (ee) a variably heavy domain region comprising the amino acid sequence of SEQ ID NO:67, (ff) a variable light domain region comprising the amino acid sequence of SEQ ID NO:68, (gg) a variably heavy domain region comprising the amino acid sequence of SEQ ID NO:69, (hh) a variable light domain region comprising the amino acid sequence of SEQ ID NO:70, (ii) a variably heavy domain region comprising the amino acid sequence of SEQ ID NO:71, (jj) a variable light domain region comprising the amino acid sequence of SEQ ID NO:72, (kk) a variably heavy domain region comprising the amino acid sequence of SEQ ID NO:73, (ll) a variable light domain region comprising the amino acid sequence of SEQ ID NO:74, (mm) a variably heavy domain region comprising the amino acid sequence of SEQ ID NO:75, (nn) a variable light domain region comprising the amino acid sequence of SEQ ID NO:76, (oo) a variable heavy chain comprising a complementarity determining region (CDR)1 comprising the amino acid sequence of SEQ ID NO:77, a CDR2 comprising the amino acid sequence of SEQ ID NO:78, and a CDR3 comprising the amino acid sequence of SEQ ID NO:79, (pp) a variable light chain comprising a CDR1 comprising the amino acid sequence of SEQ ID NO:80, a CDR2 comprising the amino acid sequence of SEQ ID NO:81, and a CDR3 comprising the amino acid sequence of SEQ ID NO:82, or (qq) a variable heavy chain comprising a complementarity determining region (CDR)1 comprising the amino acid sequence of SEQ ID NO:77, a CDR2 comprising the amino acid sequence of SEQ ID NO:78, and a CDR3 comprising the amino acid sequence of SEQ ID NO:79 and a variable light chain comprising a CDR1 comprising the amino acid sequence of SEQ ID NO:80, a CDR2 comprising the amino acid sequence of SEQ ID NO:81, and a CDR3 comprising the amino acid sequence of SEQ ID NO:82. The antibody is optionally detectably labeled.

For example, the kit can comprise instructions for assaying the test sample for RGMc (such as membrane-associated RGMc peptide, soluble RGMc peptide, fragments of membrane-associated RGMc peptide, fragments of soluble RGMc, variants of RGMc (membrane-associated or soluble RGMc) or any combinations thereof) by immunoassay, e.g., chemiluminescent microparticle immunoassay. The instructions can be in paper form or computer-readable form, such as a disk, CD, DVD, or the like. The antibody can be an RGMc capture antibody and/or a RGMc detection antibody. Alternatively or additionally, the kit can comprise a calibrator or control, e.g., purified, and optionally lyophilized, RGMc (such as membrane-associated RGMc peptide, soluble RGMc peptide, fragments of membrane-associated RGMc peptide, fragments of soluble RGMc, variants of RGMc (membrane-associated or soluble RGMc) or any combinations thereof), and/or at least one container (e.g., tube, microtiter plates or strips, which can be already coated with an anti-RGMc monoclonal antibody) for conducting the assay, and/or a buffer, such as an assay buffer or a wash buffer, either one of which can be provided as a concentrated solution, a substrate solution for the detectable label (e.g., an enzymatic label), or a stop solution. Preferably, the kit comprises all components, i.e., reagents, standards, buffers, diluents, etc., which are necessary to perform the assay. The instructions also can include instructions for generating a standard curve or a reference standard for purposes of quantifying RGMc.

Any antibodies, which are provided in the kit, such as recombinant antibodies specific for RGMc, can incorporate a detectable label, such as a fluorophore, radioactive moiety, enzyme, biotin/avidin label, chromophore, chemiluminescent label, or the like, or the kit can include reagents for labeling the antibodies or reagents for detecting the antibodies (e.g., detection antibodies) and/or for labeling the analytes or reagents for detecting the analyte. The antibodies, calibrators and/or controls can be provided in separate containers or pre-dispensed into an appropriate assay format, for example, into microtiter plates.

Optionally, the kit includes quality control components (for example, sensitivity panels, calibrators, and positive controls). Preparation of quality control reagents is well-known in the art and is described on insert sheets for a variety of immunodiagnostic products. Sensitivity panel members optionally are used to establish assay performance characteristics, and further optionally are useful indicators of the integrity of the immunoassay kit reagents, and the standardization of assays.

The kit can also optionally include other reagents required to conduct a diagnostic assay or facilitate quality control evaluations, such as buffers, salts, enzymes, enzyme co-factors, substrates, detection reagents, and the like. Other components, such as buffers and solutions for the isolation and/or treatment of a test sample (e.g., pretreatment reagents), also can be included in the kit. The kit can additionally include one or more other controls. One or more of the components of the kit can be lyophilized, in which case the kit can further comprise reagents suitable for the reconstitution of the lyophilized components.

The various components of the kit optionally are provided in suitable containers as necessary, e.g., a microtiter plate. The kit can further include containers for holding or storing a sample (e.g., a container or cartridge for a plasma, serum, or urine sample). Where appropriate, the kit optionally also can contain reaction vessels, mixing vessels, and other components that facilitate the preparation of reagents or the test sample. The kit can also include one or more instrument for assisting with obtaining a test sample, such as a syringe, pipette, forceps, measured spoon, or the like.

If the detectable label is at least one acridinium compound, the kit can comprise at least one acridinium-9-carboxamide, at least one acridinium-9-carboxylate aryl ester, or any combination thereof. If the detectable label is at least one acridinium compound, the kit also can comprise a source of hydrogen peroxide, such as a buffer, solution, and/or at least one basic solution. If desired, the kit can contain a solid phase, such as a magnetic particle, bead, test tube, microtiter plate, cuvette, membrane, scaffolding molecule, film, filter paper, disc or chip.

If desired, the kit can further comprise one or more components, alone or in further combination with instructions, for assaying the test sample for another analyte, which can be a biomarker, such as a biomarker of an iron-related disorder, such as iron deficiency or iron overload. Examples of other analytes include, but are not limited to, hepcidin, neogenin, growth differentiation factor 15 (GDF-15), neutrophil gelatinase-associated lipocalin (NGAL), interleukin 6 (IL-6), and/or BMP-6, as well as other analytes and biomarkers discussed herein. It can be preferred that one or more components for assaying a test sample for hepcidin enable the determination of the presence, amount or concentration of hepcidin-25. A sample, such as a serum sample, a plasma sample, or a urine sample, can be assayed for hepcidin-25 using TOF-MS and an internal standard.

a. Adaptation of Kit and Method

The kit (or components thereof), as well as the method of determining the concentration of RGMc in a test sample by an immunoassay as described herein, can be adapted for use in a variety of automated and semi-automated systems (including those wherein the solid phase comprises a microparticle), as described, e.g., in U.S. Pat. Nos. 5,089,424 and 5,006,309, and as commercially marketed, e.g., by Abbott Laboratories (Abbott Park, Ill.) as ARCHITECT®.

Some of the differences between an automated or semi-automated system as compared to a non-automated system (e.g., ELISA) include the substrate to which the first specific binding partner (e.g., analyte antibody or capture antibody) is attached (which can impact sandwich formation and analyte reactivity), and the length and timing of the capture, detection and/or any optional wash steps. Whereas a non-automated format such as an ELISA may require a relatively longer incubation time with sample and capture reagent (e.g., about 2 hours), an automated or semi-automated format (e.g., ARCHITECT® and any successor platform, Abbott Laboratories) may have a relatively shorter incubation time (e.g., approximately 18 minutes for ARCHITECT®). Similarly, whereas a non-automated format such as an ELISA may incubate a detection antibody such as the conjugate reagent for a relatively longer incubation time (e.g., about 2 hours), an automated or semi-automated format (e.g., ARCHITECT® and any successor platform) may have a relatively shorter incubation time (e.g., approximately 4 minutes for the ARCHITECT® and any successor platform).

Other platforms available from Abbott Laboratories include, but are not limited to, AxSYM®, IMx® (see, e.g., U.S. Pat. No. 5,294,404, which is hereby incorporated by reference in its entirety), PRISM®, EIA (bead), and Quantum™ II, as well as other platforms. Additionally, the assays, kits and kit components can be employed in other formats, for example, on electrochemical or other hand-held or point-of-care assay systems. The present disclosure is, for example, applicable to the commercial Abbott Point of Care (i-STAT®, Abbott Laboratories) electrochemical immunoassay system that performs sandwich immunoassays. Immunosensors and their methods of manufacture and operation in single-use test devices are described, for example in, U.S. Pat. No. 5,063,081, U.S. Pat. App. Pub. No. 2003/0170881, U.S. Pat. App. Pub. No. 2004/0018577, U.S. Pat. App. Pub. No. 2005/0054078, and U.S. Pat. App. Pub. No. 2006/0160164, which are incorporated in their entireties by reference for their teachings regarding same.

In particular, with regard to the adaptation of an assay to the I-STAT® system, the following configuration is preferred. A microfabricated silicon chip is manufactured with a pair of gold amperometric working electrodes and a silver-silver chloride reference electrode. On one of the working electrodes, polystyrene beads (0.2 mm diameter) with immobilized capture antibody are adhered to a polymer coating of patterned polyvinyl alcohol over the electrode. This chip is assembled into an I-STAT® cartridge with a fluidics format suitable for immunoassay. On a portion of the wall of the sample-holding chamber of the cartridge there is a layer comprising the detection antibody labeled with alkaline phosphatase (or other label). Within the fluid pouch of the cartridge is an aqueous reagent that includes p-aminophenol phosphate.

In operation, a sample suspected of containing RGMc is added to the holding chamber of the test cartridge and the cartridge is inserted into the I-STAT® reader. After the second antibody (detection antibody) has dissolved into the sample, a pump element within the cartridge forces the sample into a conduit containing the chip. Here it is oscillated to promote formation of the sandwich between the first capture antibody, RGMc, and the labeled second detection antibody. In the penultimate step of the assay, fluid is forced out of the pouch and into the conduit to wash the sample off the chip and into a waste chamber. In the final step of the assay, the alkaline phosphatase label reacts with p-aminophenol phosphate to cleave the phosphate group and permit the liberated p-aminophenol to be electrochemically oxidized at the working electrode. Based on the measured current, the reader is able to calculate the amount of analyte RGMc in the sample by means of an embedded algorithm and factory-determined calibration curve.

It further goes without saying that the methods and kits as described herein necessarily encompass other reagents and methods for carrying out the immunoassay. For instance, encompassed are various buffers such as are known in the art and/or which can be readily prepared or optimized to be employed, e.g., for washing, as a conjugate diluent, and/or as a calibrator diluent. An exemplary conjugate diluent is ARCHITECT® conjugate diluent employed in certain kits (Abbott Laboratories, Abbott Park, Ill.) and containing 2-(N-morpholino)ethanesulfonic acid (MES), a salt, a protein blocker, an antimicrobial agent, and a detergent. An exemplary calibrator diluent is ARCHITECT® human calibrator diluent employed in certain kits (Abbott Laboratories, Abbott Park, Ill.), which comprises a buffer containing MES, other salt, a protein blocker, and an antimicrobial agent. Additionally, as described in U.S. Patent Application No. 61/142,048 filed Dec. 31, 2008, improved signal generation may be obtained, e.g., in an I-STAT® cartridge format, using a nucleic acid sequence linked to the signal antibody as a signal amplifier.

The present invention has multiple aspects, illustrated by the following non-limiting examples. It will be readily apparent to those skilled in the art that other suitable modifications and adaptations of the methods described herein are obvious and may be made using suitable equivalents without departing from the scope of the present disclosure or the embodiments disclosed herein. Having now described the present disclosure in detail, the same will be more clearly understood by reference to the following examples, which are included for purposes of illustration only and are not intended to limit the scope of the claimed invention. The disclosures of all journal references, U.S. patents and publications referred to herein are hereby incorporated by reference in their entireties to the same extent as if each individual publication were specifically and individually indicated to be incorporated by reference. The terms and expressions, which have been employed, are used as terms of description and not of limitation. In this regard, where certain terms are defined under "Definitions" and are otherwise defined, described, or discussed elsewhere in the "Detailed Description," all such definitions, descriptions, and discussions are intended to be attributed to such terms. There also is no intention in the use of such terms and expressions of excluding any equivalents of the features shown and described or portions thereof. Furthermore, while subheadings, e.g., "Definitions," are used in the "Detailed Description," such use is solely for ease of reference and is not intended to limit any disclosure made in one section to that section only; rather, any disclosure made under one subheading is intended to constitute a disclosure under each and every other subheading.

EXAMPLES

Example 1

Affinity Maturation of Antibodies and Method for Determining Binding Characteristics Sequence alignment shows that the RGMA antibody h5F9.23 shares the highest identity to human germlines VH3-23/JH3 and A17/Jk2 (see figures from h5F9 affinity maturation design document). To improve the affinity of h5F9.23 to RGMA, hypermutated CDR residues were identified from other human antibody sequences in the IgBLAST database that also shared high identity to germlines VH3-23 and A17. The corresponding h5F9.23 CDR residues were then subjected to limited mutagenesis by PCR with primers having low degeneracy at these positions to create two antibody libraries in the scFv format suitable for surface display.

The first library contained mutations at residues 31, 35, 50, 52, 52a, 53, 55, 56, 95, 96, 97 and 102 in the VH CDR1, 2 and 3 (Kabat numbering); and the second library at residues 27c, 27d, 30, 34, 50, 53, 89, 91, 93, 94, 96 and 97 in the three VL CDRs. To further increase the identity of hMAK195 to the human germline framework sequences, a binary degeneracy at VH positions 37 (V/I), 48 (V/I), 49 (S/G), were introduced into the first library. Also, a binary degeneracy at VL positions 4 (M/L), and 46 (R/L) were introduced into the second library.

These h5F9.23 libraries were displayed on cell surfaces to be selected against a low concentration of biotinylated RGMA by magnetic then fluorescence activated cell sorting. Selection for improved on-rate, off-rate, or both were carried out and antibody protein sequences of affinity-modulated h5F9.23 clones were recovered for convertion from scFv back to IgG format for further characterization. These are the affinity matured h5F9.23 antibodies. See Table 1.

Eleven h5F9.23 affinity matured clones were expressed in 293-6E cells. The expression level was recorded and antibodies were purified by ProteinA affinity column. H5F9 affinity matured antibody showed good physical chemical property in SEC and MS analysis.

The binding characteristics of affinity-matured h5F9.23 affinity matured antibodies were evaluated in h RGMa Indirect ELISA. This is an anti-human Fc capturing ELISA. Briefly, dilute the anti-h Fc in 0.2 molar sodium bicarbonate buffer (pH 9.4) to 0.5 µg/ml, coat at 100 ul per well and incubate plate at room temperature for 2 hours. Add 200 ul of 5% non-fat dry milk in PBS to each well and block it at room temperature for an hour. After washing plate, add 100 µl of 0.2 µg/ml of diluted individual antibodies to each well in duplicates. Incubate for 1 hour at the room temperature and then wash the plate. 100 µl of 1 to 6 serially diluted biotin hRGMa from 10 nM to 0.001 nM was added to each well, then plate was incubated at room temperature for an hour. After washing, 1:10000 diluted SA-HRP was 120 µl per well, incubate at room temperature for 15 minutes. Finally, after washing the plate, 120 µl of TMB substrate from Invitrogen (CAT #00-2023 Lot #425820A) was added to each well, wait 5-10 minutes for the color to develop. Stop the reaction with 60 μl of 2N sulfuric acid. Proceed to read the plate at 450 nm and collect the data to do data analysis. We were able to rank affinity matured h5F9.23 antibodies' binding to human RGMa in this format of ELISA. The binding of human RGMc was evaluated in human RGMc Direct ELISA due the format of human RGMc, The data concludes the h5F9.23 AM antibodies have improved human RGMa and RGMc binding in reference to h5F9.23 parental antibody.

Example 2

Competitive Binding Data

With respect to Table 3, "(a) MSD" corresponds to using biotinylated hRGMa-Fc complexed with streptavidin-Sulfo-Tag, and incubation with cells at room temperature. "bHCS" corresponds to using hRGMa-Fc complexed with Cy3-labeled anti-Fc antibody, and incubation with cells at 37° C.

TABLE 4

| | Clone | | | |
|---|---|---|---|---|
| | H5F9AM.4 | H5F9AM.8 | H5F9AM.9 | H5F9AM.11 |
| hRGMa binding (ELISA) | +++ | +++ | +++ | +++ |
| Rat RGMa binding (ELISA) | +++ | +++ | +++ | +++ |
| Cyno RGMa binding (ELISA) | | | | |
| R &D hRGMc-His ELISA | +++ | +++ | +++ | +++ |
| hRGMa-His (Affinity $K_D$ (nM)) | 0.015 | 0.031 | 0.47 | 0.11 |
| Rat RGMa-His (Affinity $K_D$ (nM)) | <0.00094 | <0.0015 | 0.31 | 0.074 |
| hRGMc-His (Affinity $K_D$ (nM)) | 0.12 | 0.08 | 0.69 | 0.25 |
| Compete with biot-hRGMa-Fc for binding to neo-His (ELISA) | ++ | ? | ++ | ? |
| Compete with RGMa Fr 0-Fc for binding to Neo-His (ELISA) | ++ | ++ | ++ | ++ |
| $a$ Block hRGMa-Fc binding to SH-SY5Y cells (MSD) | ++ | ++ | ++ | ++ |
| $b$ Block hRGMa-Fc binding to SH-SY5Y cells (HCS) | +++ | +++ | +++ | +++ |
| Block hRGMa-Fc binding to A172 cells (HCS) | +++ | +++ | +++ | +++ |
| Block hRGMa-Fc binding to primary neurons (HCS) | +++ | +/− | − | ++ |
| Compete with FL-RGMa-Fc for binding to BMP-2 (ELISA) | ++ | ++ | ++ | +++ |
| Compete with FL-RGMa-Fc for binding to BMP-4 (ELISA) | ++ | ++ | ++ | ++ |
| RGMa mediated BRE luc assay | ++ | +/− | − | ++ |
| RGMc mediated BRE luc assay | − | ++ | ++ | ++ | capacity). UIBC was calculated with the measured parameters ion and TIBC. Ferritin was determined using an in-house immunoturbimetric assay adapted to a cobas system (Roche Diagnostics GmBH, Germany).

Figure 3:
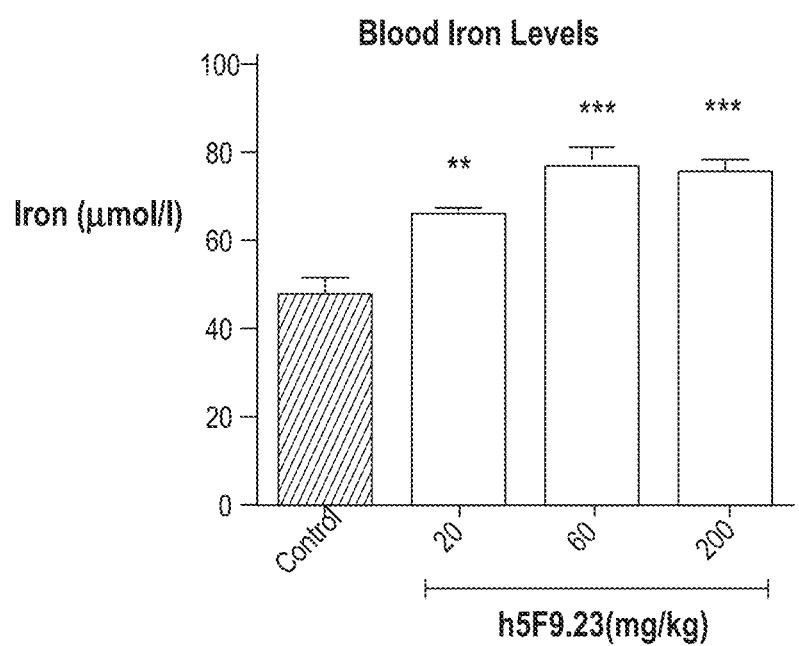
FIG. 3 is a histogram that shows humanized 5F9.23 (h5F9.23) increases blood iron levels in rats.
Figure 4:
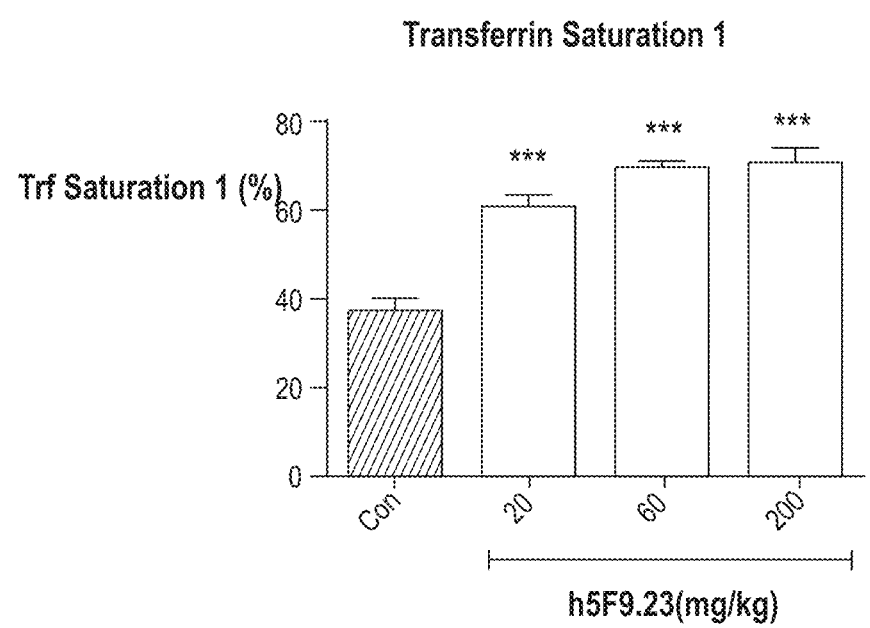
FIG. 4 is a histogram that shows h5F9.23 increases saturated transferrin 1 levels (%) in rats. Saturated transferrin 1 levels were measured in rats that were treated once weekly by IV injection of 0, 20, 60 or 200 mg/kg of h5F9.23. Saturated transferrin 1 levels were significantly increased at all h5F9.23 doses (significance: ***p<0.001).
Figure 5:
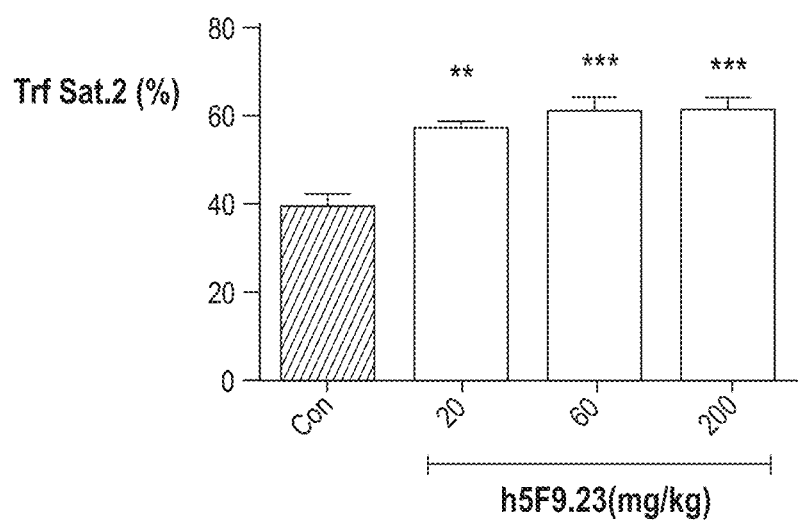
FIG. 5 is a histogram that shows h5F9.23 increases saturated transferrin 2 levels (%) in rats. Saturated transferrin 2 levels were measured in rats that were treated once weekly by IV injection of 0, 20, 60 or 200 mg/kg of h5F9.23. Saturated transferrin 2 levels were significantly increased at all h5F9.23 doses (significance: p<0.01; *p<0.001).
Figure 6:
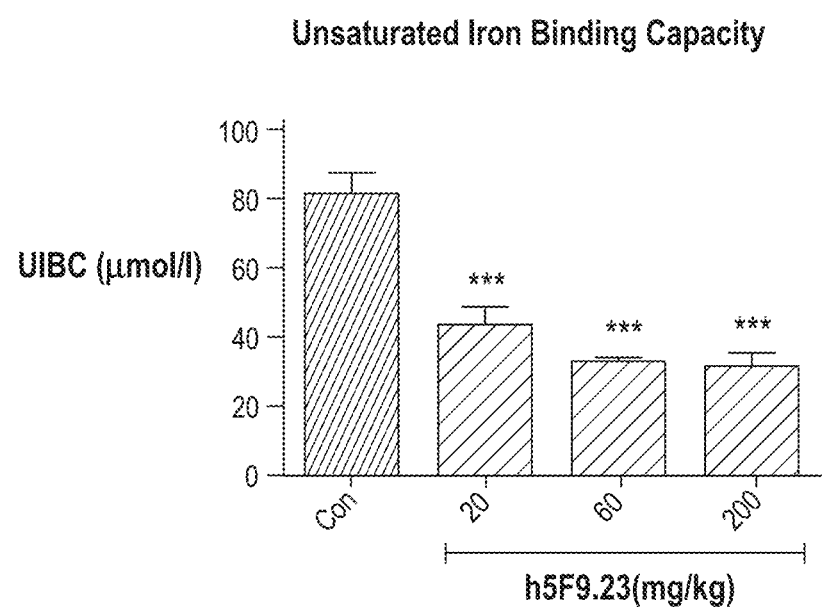
FIG. 6 is a histogram that shows h5F9.23 decreases unsaturated iron binding capacity (UIBC) in rats. Unsaturated iron binding capacity (UIBC) was also measured in rates that were treated one weekly by IV injection of 0, 20, 60 or 200 mg/kg of h5F9.23. UIBC levels were significantly decreased at all h5F9.23 doses (significance: ***p<0.001).
Figure 7:
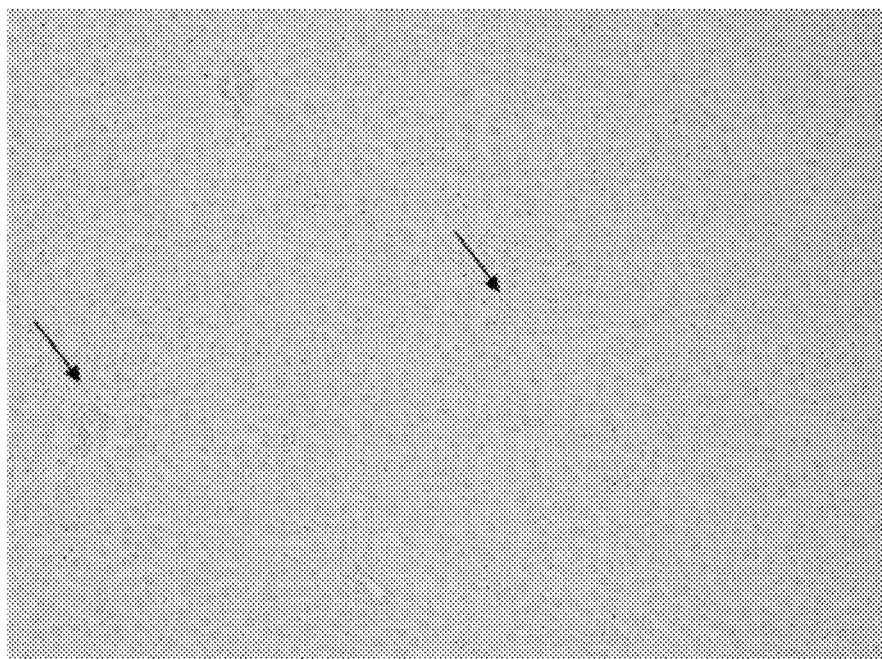
FIG. 7 shows a fixed rat liver sample (control) stained with Prussian Blue (×100 magnification). Arrows are directed to the periportal region of the liver lobe.
Figure 8:
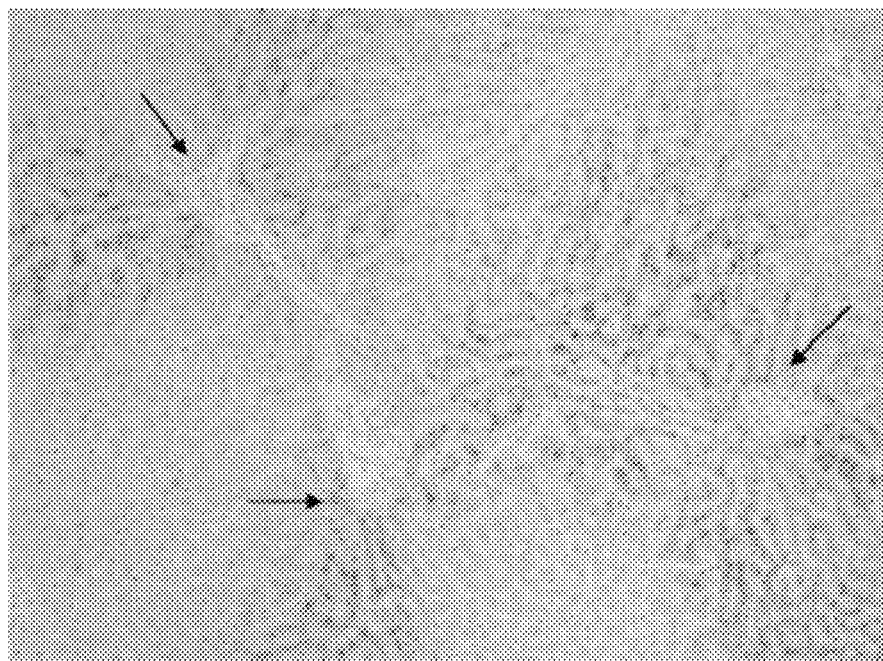
FIG. 8 shows a fixed rat liver sample (treated-200 mg/kg/week of h5F9.23) stained with Prussian Blue (×100 magnification). Arrows are directed to the periportal region of the liver lobe. Black colored granules represent iron.

The rats tolerated treatment with h5F9 without any change of animal behaviour, clinical signs, food consumption, body and organ weights, hematology, blood coagulation and clinical chemistry. Serum iron levels (FIG. 3) and transferrin saturation (FIGS. 4 and 5) were dose dependently increased and unsaturated iron binding capacity (UIBC) was dose dependently decreased (FIG. 6).

h5F9.23 leads to a dose dependent periportal accumulation of iron in the liver of rats treated once weekly by iv injection of 0, 20, 60 or 200 mg/kg. After four weekly treatments with 200 mg/kg h5F9, iron granules in hepatocytes accumulate and can be demonstrated using Prussian Blue stain (Compare FIGS. 7 and 8). In contrast, iron storage Example 3

Humanized 5F9.23 Affects Iron Metabolism in Healthy Rats

Various assays were undertaken to understand the effects of h5F9.23 on iron metabolism in rats. 5 female Sprague-Dawley rats per dose were treated intravenously (IV) with h5F9.23 once weekly with 0, 20, 60 or 200 mg/kg/week for a period of 4 weeks. The animals were sacrificed 7 days after last treatment. Blood for clinical pathology evaluation including iron metabolism parameters (namely free serum iron, saturated transferrin, unsaturated iron binding capacity (UIBC)) were taken and organs (liver, spleen, brain, pancreas, heart, kidneys) were fixed for histopathological examination. Specifically, the iron metabolism parameters (namely, free serum iron, saturated transferring, unsaturated iron binding capacity (UIBC)) were determined using commercially available colorimetric assays from RANDOX Lab, Ltd. Crumlin, UK (for the iron and total iron binding of macrophages in the spleen (FIG. 9, Control) is reduced after 4 weekly treatments with 200 mg/kg 5F9. See FIG. 10.

Figure 9:
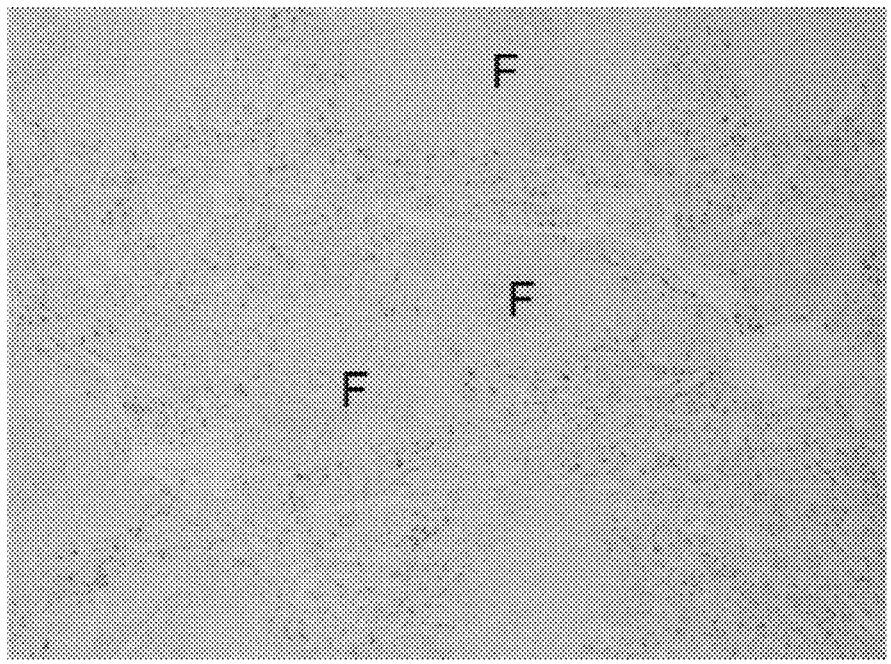
FIG. 9 shows a fixed rat spleen sample (control) stained with Prussian Blue (×40 magnification). Iron loaded macrophages are shown in the red pulp between lymph follicles (F).
Figure 10:
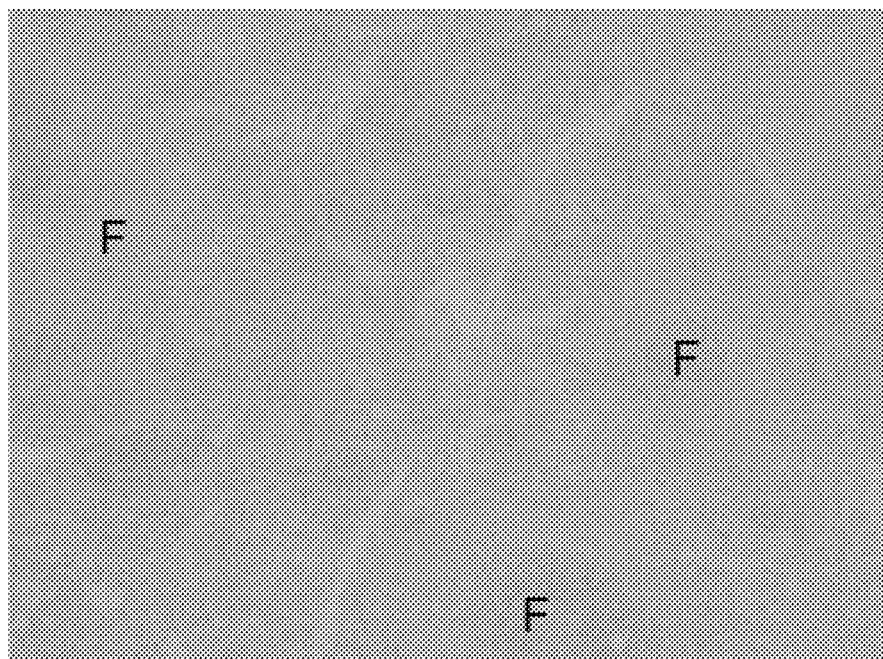
FIG. 10 shows a fixed rat spleen sample (treated-200 mg/kg/week of h5F9.23) stained with Prussian Blue (×40 magnification). Macrophages in the red pulp between lymph follicles (F) released iron into serum.

In the spleen, iron loaded macrophages are localized in the red pulp between lymphfollicles (FIG. 9). In contrast, the macrophages in the spleen of animals treated with 200 mg/kg/week showed reduced or no iron accumulation indicative for an increase of iron release into blood as a result of the binding to RGMc (FIG. 10).

Example 4

Characterization of h5F9.23 Affinity Matured mAbs by RGMc-Mediated BMP Reporter Assay RGMc regulates iron regulating hormone hepcidin through the BMP/Smad1/5/8 signaling pathway. As a co-receptor for BMPs, membrane bound RGMc enhances BMP signaling. To test if h5F9.23 affinity matured Abs block BMP/Smad signaling, an RGMc-mediated BMP reporter assay was developed.

A BMP responsive luciferase (luc) reporter construct was built by cloning a BMP responsive element (BRE) (Korchynskyi et al, 2002) to upstream of a luc gene in a basic reporter vector pGL4.27 [luc2P/minP/Hygro] (Promega). In RGMc BMP reporter assay, 293HEK cells were transiently transfected with the BRE-luc reporter and a hRGMc expressing vector in a 10 cm dish, and 24 h later split into a 96-well plate at a cell density of 105 per well. After 24 h incubation, cells were serum-starved in MEM with 1% FBS for 6 h, followed by the addition of serially diluted testing Ab. Following additional 16 h incubation, cells were lysed and measured for luc activity using Promega luciferase assay system.

Figure 11A:
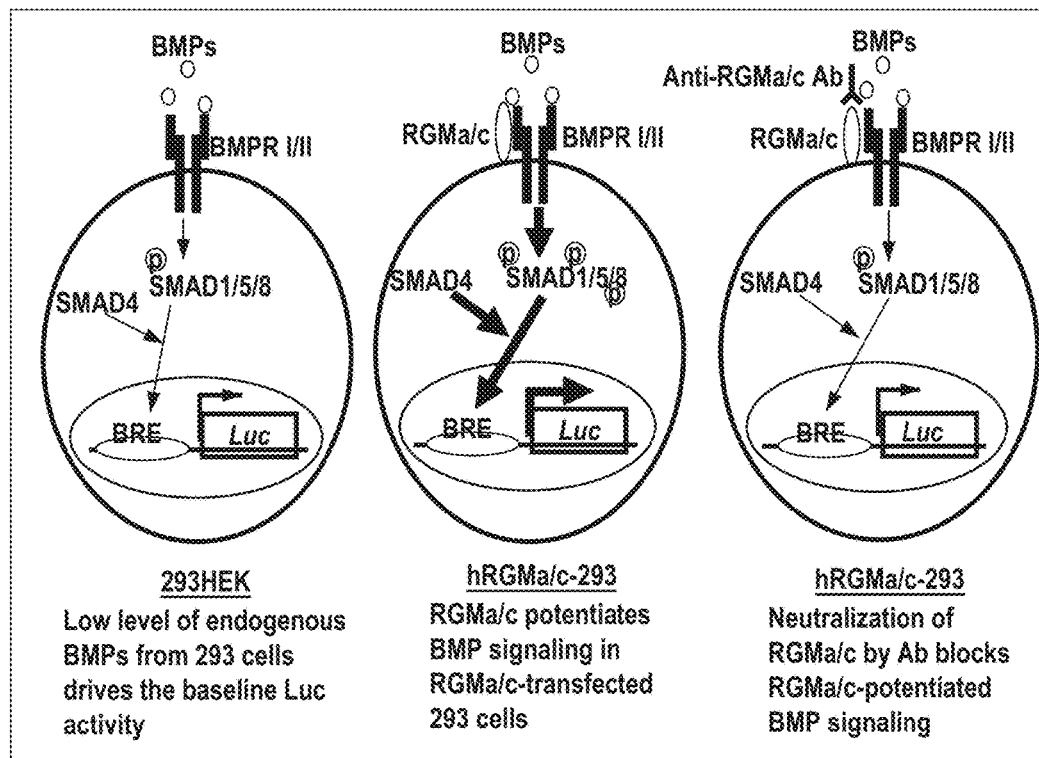
FIGS. 11A and 11B show an RGMc-mediated BMP reporter assay in 293HEK cells for evaluating select h5F9 affinity matured Abs for blocking RGMc function.
Figure 11B:
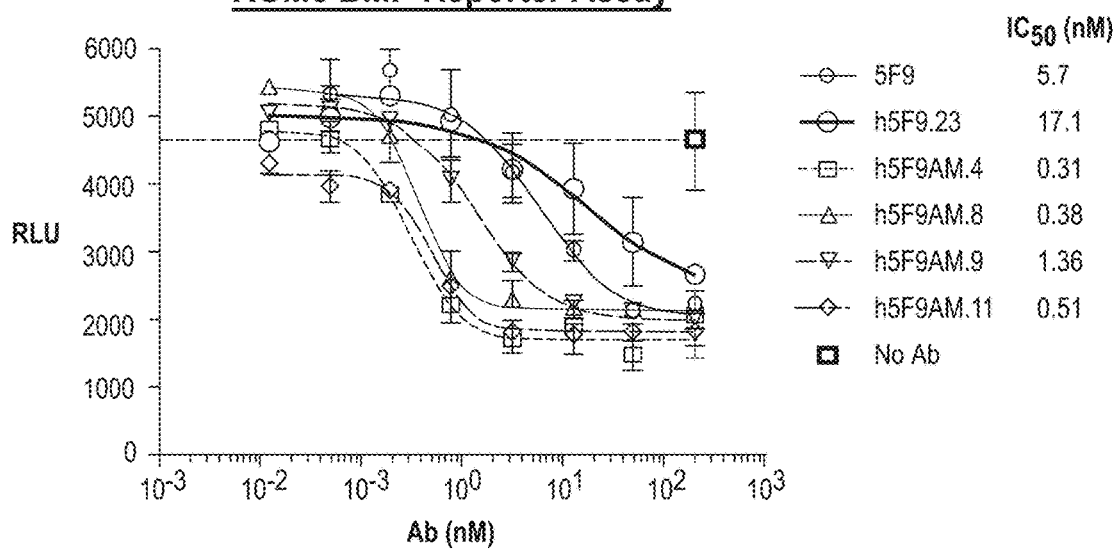

The results are shown in FIGS. 11A and 11B. The h5F9.23 affinity matured Abs (AM.4, 8, 9, 11) showed much improved potency in blocking hRGMc activity with IC50 values ranging from 0.3 to 1.4 nM, as compared to h5F9.23 with IC50 of 17 nM. The potency data correlates with the affinity data (see Table 5). The affinity of h5F9.23 affinity matured Abs towards human RGMa, rat RGMa, and human RGMc were determined by BIAcore analysis (Table 5). Testing Abs were captured to the surface of a CM5 chip via anti-hIgG Fc Ab, and serially diluted antigens were injected. Association and dissociation rates were monitored for 5 and 10 min respectively. Sensorgrams were fitted by global analysis using the BIAevaluation 4.0.1 software for a 1:1 Langmuir binding model. The equilibrium dissociation constants (KD) were calculated from kinetic rate constants (off rate kd and on rate ka): KD–kd/ka.

Example 5

Use of RGM A/C and RGM C Selective Antibodies in the Treatment of Anemia of Chronic Disease in Monkeys Female cyno monkeys were intravenously administered 20 mg/kg, 60 mg/kg, 200 mg/kg or subcutaneously 60 mg/kg of humanized antibody 5F9.23 (which as discussed previously herein is disclosed in U.S. Patent Publication No. 2010/0028340, the contents of which are herein incorporated by reference), once per week for a period of 4 weeks. At day 22, primate blood serum was collected at 0.5 hours, 4 hours, 24 hours and post-antibody application ($4^{th}$ dose). Hepcidin levels were measured using a time-of-flight mass spectrometric method as described in Kroot, J. J. C, et al., Clinical Chemistry, 57:12:1650-1669 (2011) and Kroot, J. J. C., et al., American Journal of Hematology, 87:977-983 (2012). As shown in FIG. 12, humanized antibody 5F9.23 (h5F9.23) decreases blood hepcidin levels in a dose dependent manner.

Example 6

Use of RGM A/C and RGM C Selective Antibodies in the Treatment of Anemia of Chronic Disease in Rats Female Sprague Dawley rats were intravenously administered 2.5 mg/kg, 5 mg/kg, 10 mg/kg or 20 mg/kg of h5F9.AM8, once per week for a period of 4 weeks. After the 4 week treatment period, serum was collected and iron parameters (namely, free serum iron, saturated transferrin,-

TABLE 5

Affinity Measurement of h5F9.23 Affinity Matured Antibodies by BIAcore Analysis

Figure 13A:
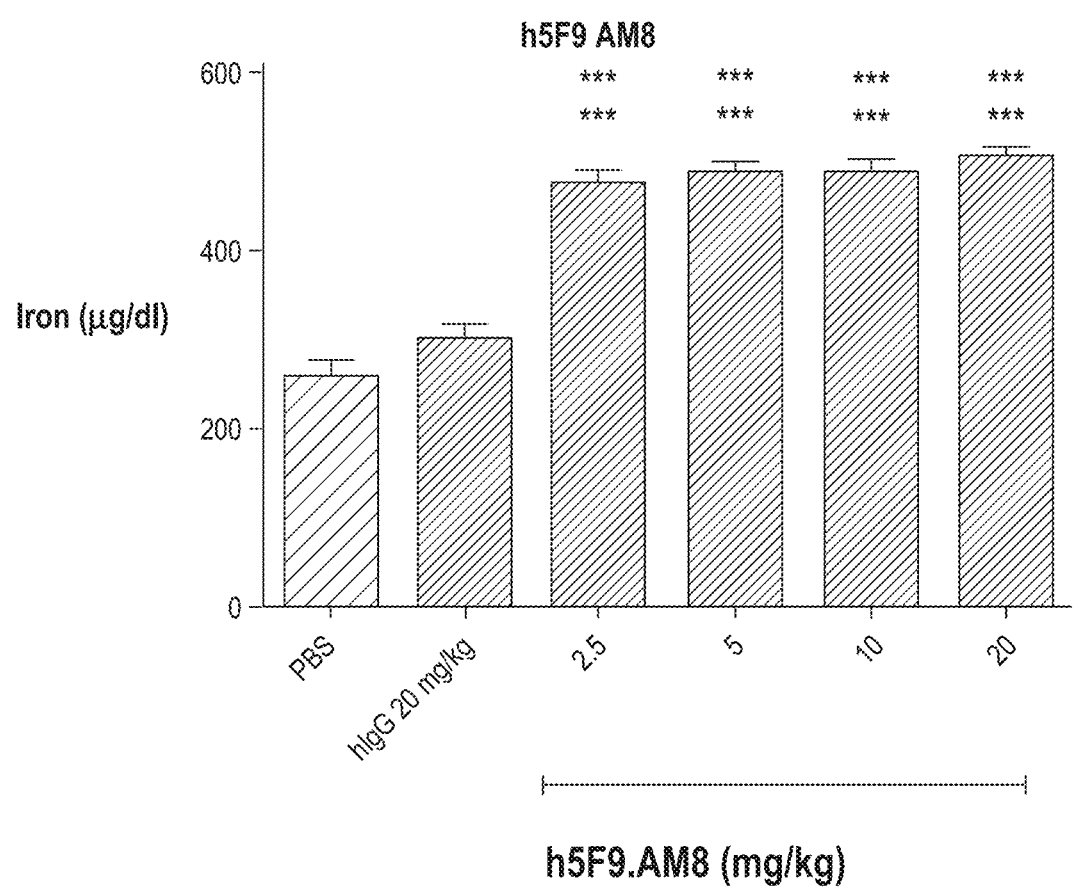
FIGS. 13A and 13B are histograms that show the results of Example 6, where Female Sprague Dawley rats were treated with different doses of antibody h5F923.AM8. Rats were injected intraveneously 2.5 mg/kg, 5 mg/kg 10 mg/kg or 20 mg/kg once per week for 4 weeks. At the end of week, 4, serum was collected and the following determined: (1) free blood iron levels (FIG. 13A) and (2) unsaturated iron binding capacity (FIG. 13B). *significance versus phosphate buffered saline (PBS) (light grey), *p<0.01: significance versus monoclonal antibody human IgG (black). The control is a human IgG antibody directed against IL-18 that was obtained from Abbott Laboratories, Worcestser, MA. The control was not cross reactive with the rat IL-18 protein.
Figure 13B:
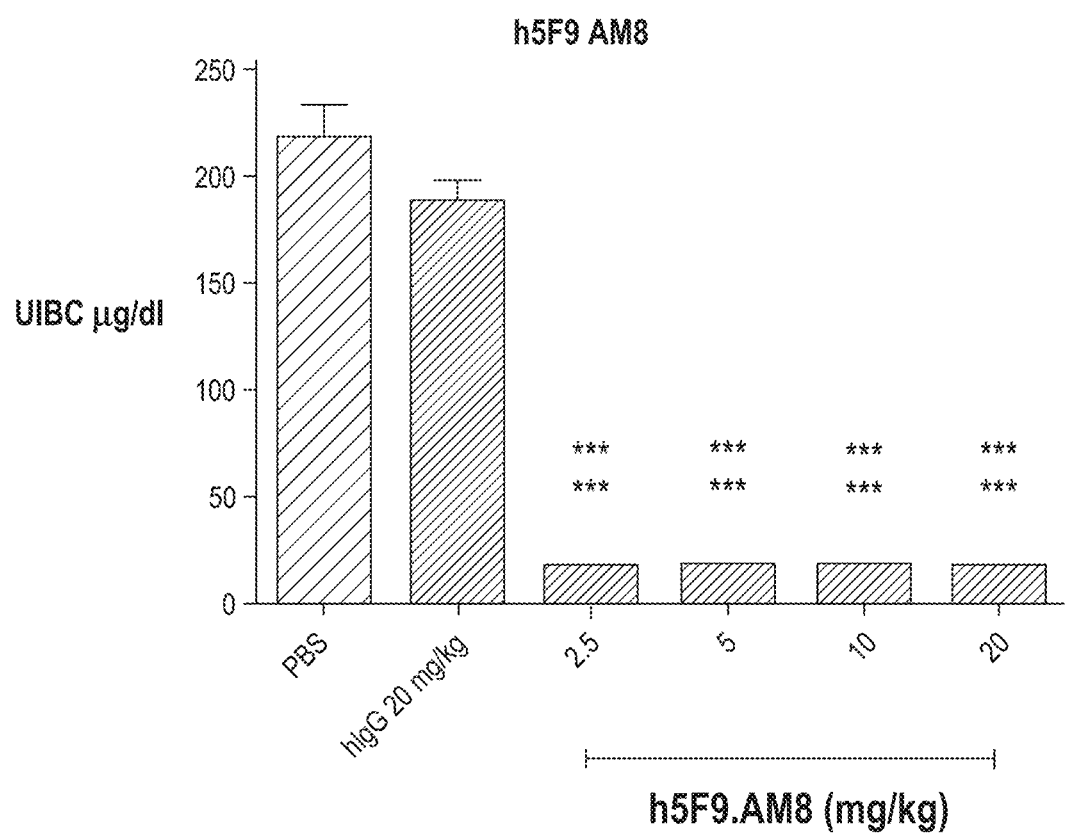

| Ab Name | Other Ab Name | Human RGMa $K_a$ (1/MS) | $K_d$ (1/s) | $K_D$ (M) | Rat RGMa $K_a$ (1/MS) | $K_d$ (1/s) | $K_D$ (M) | Human RGMc $K_a$ (1/MS) | $K_d$ (1/s) | $K_D$ (M) |
|---|---|---|---|---|---|---|---|---|---|---|
| RGMA-h5F9Vh7a/pJP288 hIgG1/K mut | RGMA-h5F9AM.1 | 1.8E+06 | 6.7E−05 | 3.8E−11 | 1.2E+06 | 3.6E−05 | 3.1E−11 | 1.08E+07 | 1.65E−03 | 1.6E−10 |
| RGMA-h5F9Vh7a/pJP289 hIgG1/K mut | RGMA-h5F9AM.2 | 1.4E+06 | 5.0E−05 | 3.7E−11 | 1.0E+06 | 5.5E−05 | 5.3E−11 | 7.65E+06 | 1.70E−03 | 2.25E−10 |
| RGMA-h5F9Vh7a/pJP290 hIgG1/K mut | RGMA-h5F9AM.3 | 1.1E+06 | 1.4E−04 | 1.2E−10 | 8.7E+05 | 3.1E−05 | 3.6E−11 | 8.10E+06 | 2.40E−03 | 3E−10 |
| RGMA-h5F9Vh7a/pJP291 hIgG1/K mut | RGMA-h5F9AM.4 | 1.4E+06 | 2.2E−05 | 1.5E−11 | 1.1E+06 | <1e−6 | <9.4e−13 | 7.85E+06 | 1.04E−03 | 1.3E−10 |
| RGMA-h5F9Vh7a/pJP292 hIgG1/K mut | RGMA-h5F9AM.5 | 1.9E+06 | 2.5E−04 | 1.3E−10 | 1.4E+06 | 2.1E−04 | 1.5E−10 | 4.15E+07 | 1.36E−02 | 3.2E−10 |
| RGMA-h5F9pJP293/pJP294 hIgG1/K mut | RGMA-h5F9AM.6 | 1.2E+06 | 1.4E−04 | 1.2E−10 | 9.4E+05 | 3.0E−05 | 3.2E−11 | 6.65E+06 | 2.55E−03 | 3.85E−10 |
| RGMA-h5F9pJP295/pJP296 hIgG1/K mut | RGMA-h5F9AM.7 | 5.9E+05 | 8.9E−05 | 1.5E−10 | 5.1E+05 | <1e−6 | <2.0e−12 | 5.05E+06 | 2.15E−03 | 4.25E−10 |
| RGMA-h5F9pJP297/pJP298 hIgG1/K mut | RGMA-h5F9AM.8 | 8.7E+05 | 2.7E−05 | 3.1E−11 | 6.6E+05 | <1e−6 | <1.5e−12 | 3.95E+06 | 3.90E−04 | 1.05E−10 |
| RGMA-h5F9pJP297/pJP299 hIgG1/K mut | RGMA-h5F9AM.9 | 8.6E+05 | 4.0E−04 | 4.7E−10 | 6.8E+05 | 2.1E−04 | 3.1E−10 | 1.55E+07 | 1.07E−02 | 7.1E−10 |
| RGMA-h5F9pJP300/pJP301 hIgG1/K mut | RGMA-h5F9AM.10 | 8.5E+05 | 1.0E−04 | 1.2E−10 | 6.6E+05 | 2.6E−05 | 3.9E−11 | 9.90E+06 | 4.40E−03 | 4.45E−10 |
| RGMA-h5F9pJP302/pJP303 hIgG1/K mut | RGMA-h5F9AM.11 | 9.3E+05 | 9.9E−05 | 1.1E−10 | 7.0E+05 | 5.2E−05 | 7.4E−11 | 5.05E+06 | 1.40E−03 | 2.85E−10 |
| H5F9.23* | | 6.0E+06 | 2.2E−03 | 3.7E−09 | 8.3E+05 | 1.7E−03 | 2.1E−09 | 8.3E+05 | | 2.9E−08 | unsaturated iron binding capacity) were determined. Specifically, the iron metabolism parameters (namely, free serum iron, saturated transferring, unsaturated iron binding capacity (UIBC)) were determined using commercially available colorimetric assays from RANDOX Lab, Ltd. Crumlin, UK (for the iron and total iron binding capacity). UIBC was calculated with the measured parameters ion and TIBC. Transferrin was determined using an in-house immunoturbimetric assay adapted to a cobas system (Roche Diagnostics GmBH, Germany). Antibody AM8 increased free iron levels and decreased unsaturated iron binding capacity (UIBC), as shown in FIG. 13A and FIG. 13B.

Example 7

Figure 14A:
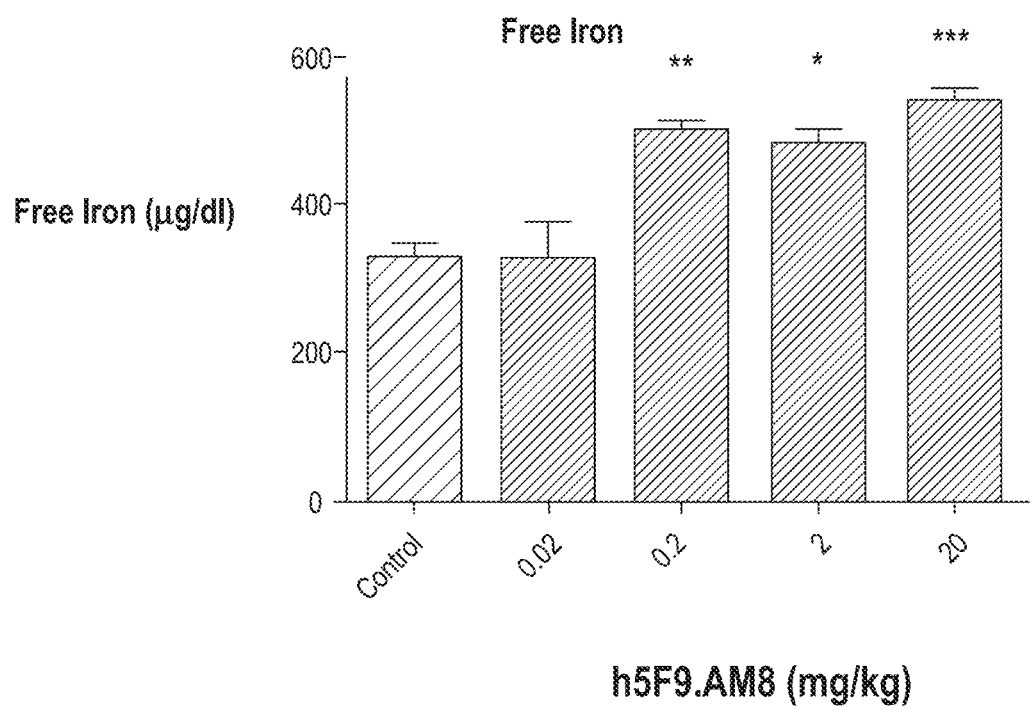
FIGS. 14A and 14B are histograms that show the results of Example 7, where Female Sprague Dawley rats were treated with different doses of antibody h5F923.AM8. Rats were injected intraveneously 0.02 mg/kg, 0.2 mg/kg 2.0 mg/kg or 20 mg/kg once per week for 4 weeks. At the end of week 4, serum was collected and the following determined: (1) free blood iron levels (FIG. 14A) and (2) unsaturated iron binding capacity (FIG. 14B). *p<0.001 significance versus vehicle control; p<0.01 significance versus vehicle control; *p<0.05 significance versus vehicle control. The vehicle control comprises a solution of 30 mM Histidine, 8% w/v of sucrose, pH 6.0 plus 0.02% Tween 80 in water.
Figure 14B:
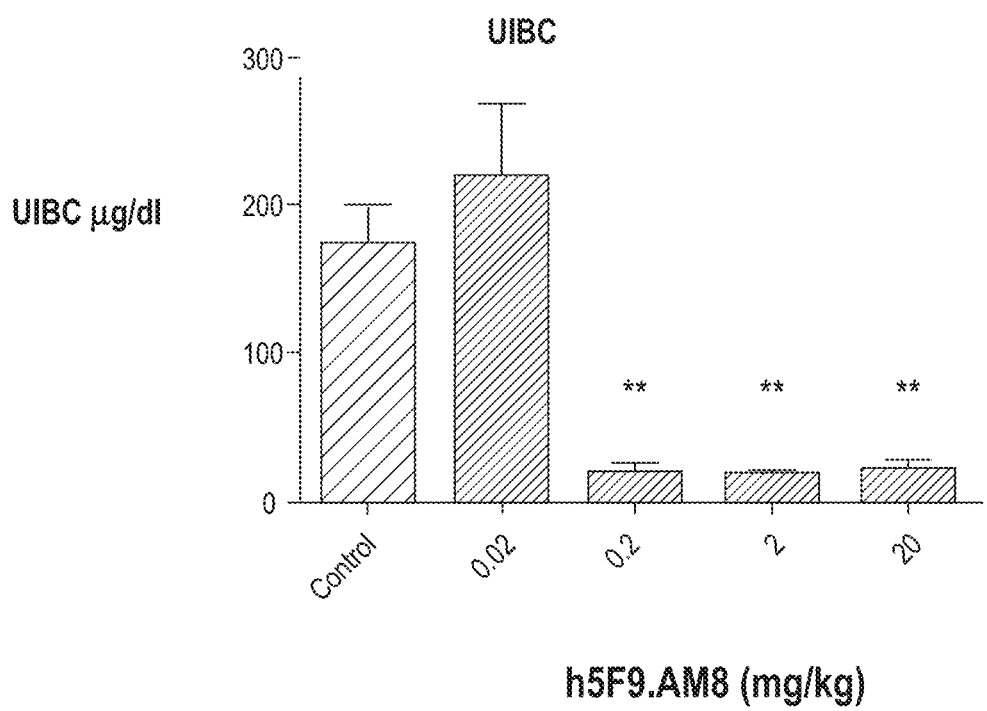

Use of RGM A/C and RGM C Selective Antibodies in the Treatment of Anemia of Chronic Disease in Rats Female Sprague Dawley rats were intravenously administered 0.02 mg/kg, 0.2 mg/kg, 2.0 mg/kg or 20 mg/kg of h5F9.AM8, once per week for a period of 4 weeks. After the 4 week treatment period, serum was collected and iron parameters (serum iron, transferrin and UIBC) were determined using commercially available colorimetric assays from Roche Diagnostics GmbH, Germany (for the iron and UIBC). Transferrin was determined using an immunoturbimetric assay on the cobas system (Roche Diagnostics GmBH, Germany). Antibody AM8 increased free iron levels and decreased unsaturated iron binding capacity (UIBC), as shown in FIG. 14A and FIG. 14B beginning at 0.2 mg/kg/week. At 0.02 mg/kg/week, no effect was observed.

Example 8

Use of RGM A/C and RGM C Selective Antibodies in the Treatment of Anemia of Chronic Disease (ACD) in Rats In this example, a rat arthritis model as described by Theurl et al. (Theurl et al. *Blood*, 118: 4977-94 (2011)), the contents of which are herein incorporated by reference, was used. Female Lewis rats, aged 8-10 weeks, (obtained from the Charles River Laboratories, Germany, Sulzfeld), kept on a standard rodent diet (namely, 180 mg iron/kg, C1000 from Altromin, Lage, Germany) received an intraparental injection of peptidoglycan-polysaccharide fragments (PG-APS) (adapted from Theurl et al., supra). Rats had free access to food and water and were housed according to institutional and governmental guidelines with a 12 hour light-dark cycle and a temperature of 20° C.±1° C. Female Lewis rats were inoculated on day 0 with a single interparental. injection of Group A Streptococcal Peptidoglycan-Polysaccharide (PG-APS) (Lee Laboratories, Grayson, GA) suspended in 0.85% saline with a total dose of 15 μg rhamnose/g body weight. Three weeks after PG-APS administration, animals were tested for the development of anemia and randomized into groups with similar hemoglobulin levels. Rats which developed anemia (namely, exhibited greater than a 2 g/dL drop from baseline range) were designated as anemic ACD rats.

For long-term treatment experiments, ACD rats were injected at 21 days post PG-APS administration with:
 (a) one of two control antibodies, namely either a (i) humanized monoclonal antibody that was selective for RGM A or (ii) human IgG isotype (hIgG) control antibody;
 (b) 20 mg/kg intravenously for 28 days (n=10) of one of: (i) humanized antibody 5F9.23 (h5F9.23; described in U.S. Patent Publication 2010/0028340, the contents of which are herein incorporated by reference); (ii) humanized antibody 5F923.AM8 (h5F923.AM8) which is a humanized affinity-matured monoclonal antibody that is selective for both RGM A and RGM C; (iii) mouse monoclonal antibody 1A-2989 which is selective for RGM C and is described in U.S. Application No. 61/570,499, filed on Dec. 14, 2011 and U.S. Application No. 61/578,122 filed on Dec. 20, 2011 the contents of each of which are herein incorporated by reference; and
 (c) 2 mg/kg intraperitonealy, every second day, of dorsomorphin (n=8), a small molecule inhibitor of the BMP receptors I and II.

Throughout the treatment period, a total of 500 μL blood was collected weekly by puncture of the tail veins for complete blood counts (CBC) and serum iron analysis. CBC analysis was performed using Vet-ABC Animal blood counter (Scil Animal Care Company, Viernheim, Germany) Serum iron was determined using commercially available colorimetric assay (Cobas system; Roche Diagnostics Deutschland GmbH).

Figure 15:
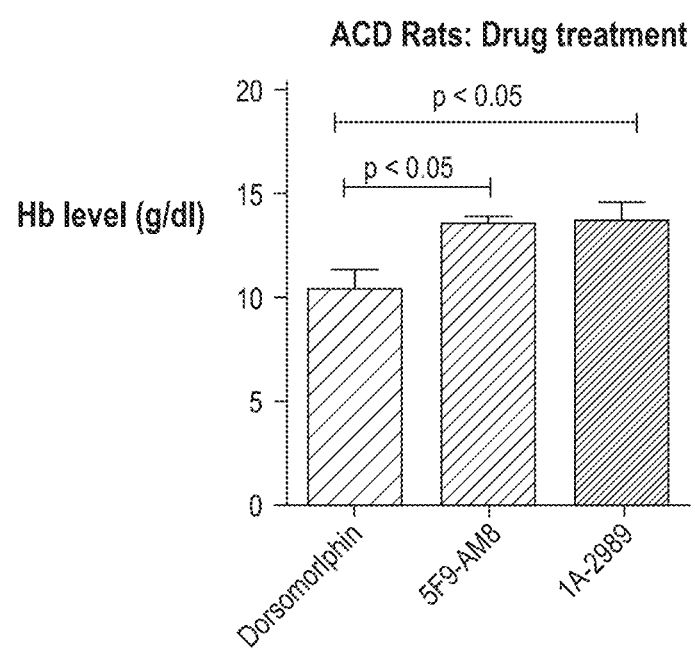
FIG. 15 is a histogram that shows the results of a first set of experiments described in Example 8, demonstrating that h5F923.AM8 and 1A-2989 improved anemia in ACD rates at day 30 by increasing the haemoglobin level. As also shown in this figure, dorsomorphin was inactive.

After 28 days of treatment (49 days after induction of ACD), all rats were euthanized and tissues were harvested for necropsy, histopathology, gene expression and protein analysis. As shown in FIG. 15, h5F923.AM8 and 1A-2989 improved anemia in ACD rates at day 30 by increasing the haemoglobin level. Dorsomorphin was inactive.

Figure 16A:
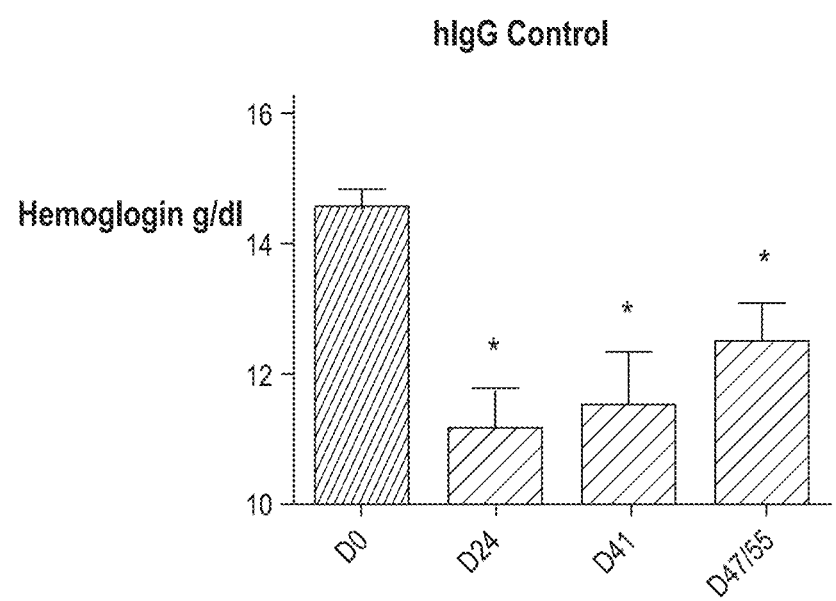
FIGS. 16A, 16B, 16C, and 16D are histograms that show the results of a second series of experiments described in Example 8. Specifically.
Figure 16B:
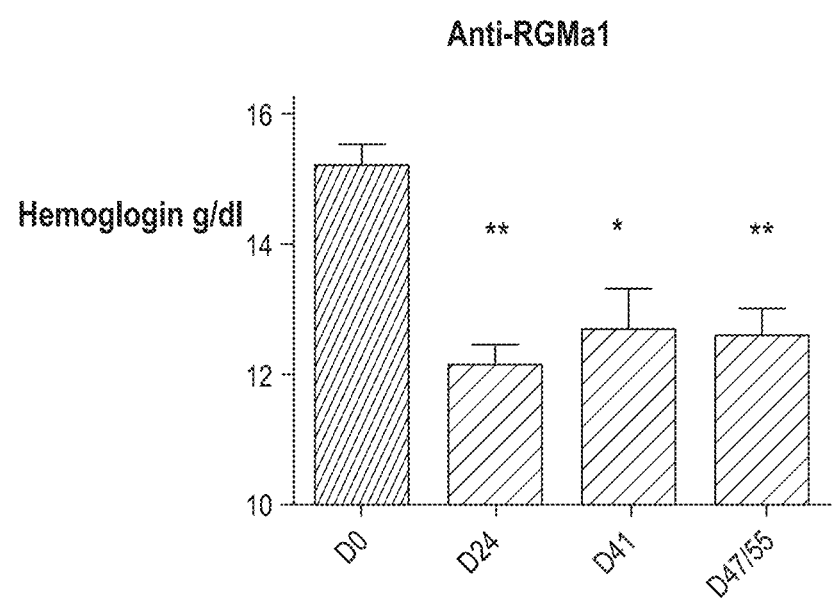
Figure 16C:
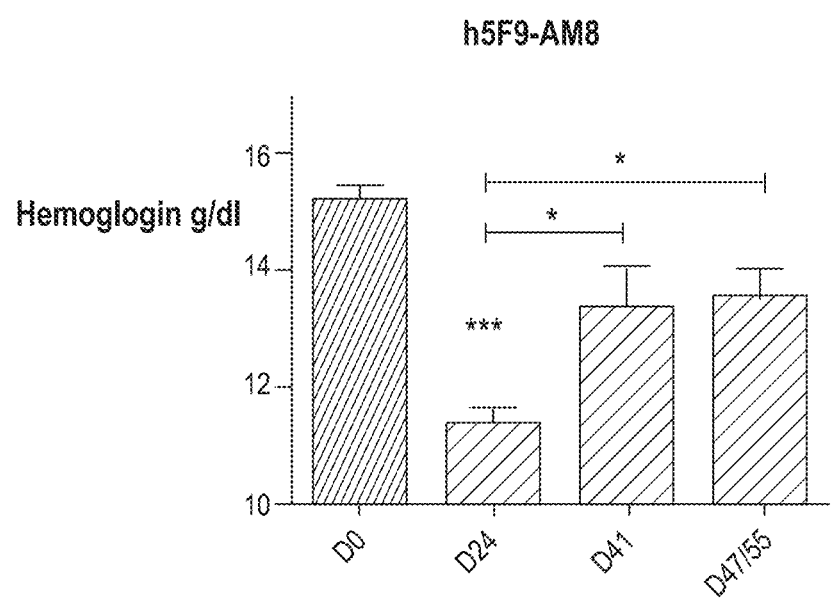
Figure 16D:
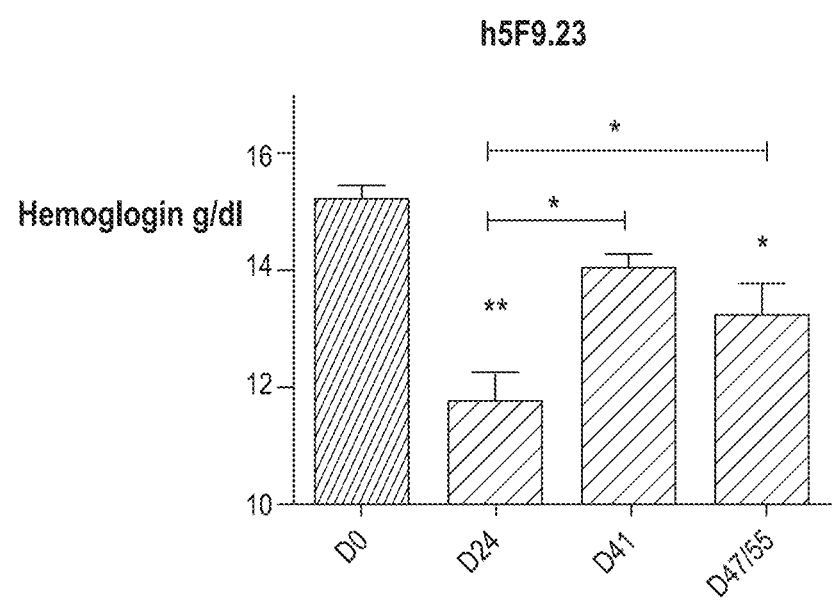

In a second set of experiments, the hIgG control antibody, h5F9.23 and h5F923.AM8 and were tested in anemic ACD rats (obtained from the Charles River Laboratories, Germany, Sulzfeld) The rats were classified as anemic, when the hemoglobin level dropped by greater than 2 g/dL at day 24 as determined using hepicidin assay techniques known in the art such as those described in Kroot, J. J. C, et al., *Clinical Chemistry*, 57:12:1650-1669 (2011) and Kroot, J. J. C., et al., *American Journal of Hematology*, 87:977-983 (2012). Starting with 20 mg/kg antibody treatment intraveneously once weekly for 28 weeks, hemoglobin levels were analysed on days 41 and 47 and 51 As shown in FIG. 16A, the control antibody hIgG does not change significantly the low hemoglobin level of the anemic rats on days 41 47 and 51. FIG. 16B shows that a humanized monoclonal antibody that was selective for RGM A, called anti-RGMa 1, does not change significantly the low haemoglobin level of the anemic rates on days 41, 47 and 51. FIG. 16C shows that antibody h5F9.AM8 significantly increases the low hemoglobin level (D24) of the anemic rats on days 41, 47 and 51. FIG. 16D shows that antibody h5F9.23, increases the low hemoglobin level (day 24 (D24) of the anemic rats on days 41, 47 and 51.

SEQUENCE LISTING

```
Sequence total quantity: 199
SEQ ID NO: 1            moltype = AA   length = 426
FEATURE                 Location/Qualifiers
source                  1..426
                        mol_type = protein
                        organism = Homo sapiens
SEQUENCE: 1
MGEPGQSPSP RSSHGSPPTL STLTLLLLLC GHAHSQCKIL RCNAEYVSST LSLRGGGSSG   60
ALRGGGGGGR GGGVGSGGLC RALRSYALCT RRTARTCRGD LAFHSAVHGI EDLMIQHNCS  120
RQGPTAPPPP RGPALPGAGS GLPAPDPCDY EGRFSRLHGR PPGFLHCASF GDPHVRSFHH  180
HPHTCRVQGA WPLLDNDFLF VQATSSPMAL GANATATRKL TIIFKNMQEC IDQKVYQAEV  240
DNLPVAFEDG SINGGDRPGG SSLSIQTANP GNHVEIQAAY IGTTIIIRQT AGQLSFSIKV  300
AEDVAMAFSA EQDLQLCVGG CPPSQRLSRS ERNRRGAITI DTARRLCKEG LPVEDAYFHS  360
CVFDVLISGD PNFTVAAQAA LEDARAFLPD LEKLHLFPSD AGVPLSSATL LAPLLSGLFV  420
LWLCIQ                                                            426

SEQ ID NO: 2            moltype = AA   length = 359
FEATURE                 Location/Qualifiers
source                  1..359
                        mol_type = protein
                        organism = Homo sapiens
SEQUENCE: 2
AHSQCKILRC NAEYVSSTLS LRGGGSSGAL RGGGGGGRGG GVGSGGLCRA LRSYALCTRR   60
TARTCRGDLA FHSAVHGIED LMIQHNCSRQ GPTAPPPPRG PALPGAGSGL PAPDPCDYEG  120
RFSRLHGRPP GFLHCASFGD PHVRSFHHHP HTCRVQGAWP LLDNDFLVQ ATSSPMALGA  180
NATATRKLTI IFKNMQECID QKVYQAEVDN LPVAFEDGSI NGGDRPGGSS LSIQTANPGN  240
HVEIQAAYIG TTIIIRQTAG QLSFSIKVAE DVAMAFSAEQ DLQLCVGGCP PSQRLSRSER  300
NRRGAITIDT ARRLCKEGLP VEDAYFHSCV FDVLISGDPN FTVAAQAALE DARAFLPDL   359

SEQ ID NO: 3            moltype = AA   length = 115
FEATURE                 Location/Qualifiers
REGION                  1..115
                        note = Description of Artificial Sequence: Synthetic
                        polypeptide
source                  1..115
                        mol_type = protein
                        organism = synthetic construct
SEQUENCE: 3
EVQLVESGGG LVQPGGSLRL SCAASGFTFS NYGMNWIRQA PGKGLEWIGM IYYDSSEKHY   60
ADSVKGRFTI SRDNSKNTLY LQMNSLRAED TAVYYCAKGT TPDYWGQGTM VTVSS       115

SEQ ID NO: 4            moltype = AA   length = 112
FEATURE                 Location/Qualifiers
REGION                  1..112
                        note = Description of Artificial Sequence: Synthetic
                        polypeptide
source                  1..112
                        mol_type = protein
                        organism = synthetic construct
SEQUENCE: 4
DVVLTQSPLS LPVTLGQPAS ISCRSSQSLE SSDGDTFLEW FQQRPGQSPR LLIYDVSTRF   60
SGVPDRFSGS GSGTDFTLKI SRVEAEDVGV YYCFQVTHDP VTFGQGTKLE IK          112

SEQ ID NO: 5            moltype = AA   length = 115
FEATURE                 Location/Qualifiers
REGION                  1..115
                        note = Description of Artificial Sequence: Synthetic
                        polypeptide
source                  1..115
                        mol_type = protein
                        organism = synthetic construct
SEQUENCE: 5
EVQLVESGGG LVQPGGSLRL SCAASGFTFS NYGMNWIRQA PGKGLEWIGM IYYDSSEKHY   60
ADSVKGRFTI SRDNSKNTLY LQMNSLRAED TAVYYCAKGT TPDYWGQGTM VTVSS       115

SEQ ID NO: 6            moltype = AA   length = 112
FEATURE                 Location/Qualifiers
REGION                  1..112
                        note = Description of Artificial Sequence: Synthetic
                        polypeptide
source                  1..112
                        mol_type = protein
                        organism = synthetic construct
SEQUENCE: 6
DVVLTQSPLS LPVTLGQPAS ISCRSSQSLE ESDGYTFLHW FQQRPGQSPR LLIYEVSTRF   60
SGVPDRFSGS GSGTDFTLKI SRVEAEDVGV YYCFQATHDP LTFGQGTKLE IK          112

SEQ ID NO: 7            moltype = AA   length = 115
```

```
                        -continued

FEATURE             Location/Qualifiers
REGION              1..115
                    note = Description of Artificial Sequence: Synthetic
                     polypeptide
source              1..115
                    mol_type = protein
                    organism = synthetic construct
SEQUENCE: 7
EVQLVESGGG VVQPGRSLRL SCAASGFTFS NYGMNWVRQA PGKGLEWVAM IYYDSSEKHY   60
ADSVKGRFTI SRDNSKNTLY LQMNSLRAED TAVYYCARGT TPDYWGQGTM VTVSS       115

SEQ ID NO: 8        moltype = AA  length = 112
FEATURE             Location/Qualifiers
REGION              1..112
                    note = Description of Artificial Sequence: Synthetic
                     polypeptide
source              1..112
                    mol_type = protein
                    organism = synthetic construct
SEQUENCE: 8
DVVLTQSPLS LPVTLGQPAS ISCRSSQSLA DSDGDTFLHW FQQRPGQSPR LLIYAVSHRF   60
SGVPDRFSGS GSGTDFTLKI SRVEAEDVGV YYCFQATHDP VTFGQGTKLE IK          112

SEQ ID NO: 9        moltype = AA  length = 115
FEATURE             Location/Qualifiers
REGION              1..115
                    note = Description of Artificial Sequence: Synthetic
                     polypeptide
source              1..115
                    mol_type = protein
                    organism = synthetic construct
SEQUENCE: 9
EVQLVESGGG LVQPGGSLRL SCAASGFTFS NYGMNWVRQA PGKGLEWVSM IYYDSSEKHY   60
ADSVKGRFTI SRDNSKNTLY LQMNSLRAED TAVYYCAKGT TPDYWGQGTM VTVSS       115

SEQ ID NO: 10       moltype = AA  length = 112
FEATURE             Location/Qualifiers
REGION              1..112
                    note = Description of Artificial Sequence: Synthetic
                     polypeptide
source              1..112
                    mol_type = protein
                    organism = synthetic construct
SEQUENCE: 10
DVVLTQSPLS LPVTLGQPAS ISCRSSQSLE DSDGGTFLEW FQQRPGQSPR LLIYDVSSRF   60
SGVPDRFSGS GSGTDFTLKI SRVEAEDVGV YYCFQATHDP LSFGQGTKLE IK          112

SEQ ID NO: 11       moltype = AA  length = 5
FEATURE             Location/Qualifiers
REGION              1..5
                    note = Description of Artificial Sequence: Synthetic peptide
source              1..5
                    mol_type = protein
                    organism = synthetic construct
SEQUENCE: 11
NYGMN                                                               5

SEQ ID NO: 12       moltype = AA  length = 17
FEATURE             Location/Qualifiers
REGION              1..17
                    note = Description of Artificial Sequence: Synthetic peptide
source              1..17
                    mol_type = protein
                    organism = synthetic construct
SEQUENCE: 12
MIYYDSSEKH YADSVKG                                                  17

SEQ ID NO: 13       moltype = AA  length = 6
FEATURE             Location/Qualifiers
REGION              1..6
                    note = Description of Artificial Sequence: Synthetic peptide
source              1..6
                    mol_type = protein
                    organism = synthetic construct
SEQUENCE: 13
GTTPDY                                                              6

SEQ ID NO: 14       moltype = AA  length = 16
FEATURE             Location/Qualifiers
```

```
REGION              1..16
                    note = Description of Artificial Sequence: Synthetic peptide
source              1..16
                    mol_type = protein
                    organism = synthetic construct
SEQUENCE: 14
RSSQSLESSD GDTFLE                                                             16

SEQ ID NO: 15       moltype = AA  length = 7
FEATURE             Location/Qualifiers
REGION              1..7
                    note = Description of Artificial Sequence: Synthetic peptide
source              1..7
                    mol_type = protein
                    organism = synthetic construct
SEQUENCE: 15
DVSTRFS                                                                        7

SEQ ID NO: 16       moltype = AA  length = 9
FEATURE             Location/Qualifiers
REGION              1..9
                    note = Description of Artificial Sequence: Synthetic peptide
source              1..9
                    mol_type = protein
                    organism = synthetic construct
SEQUENCE: 16
FQVTHDPVT                                                                      9

SEQ ID NO: 17       moltype = AA  length = 5
FEATURE             Location/Qualifiers
REGION              1..5
                    note = Description of Artificial Sequence: Synthetic peptide
source              1..5
                    mol_type = protein
                    organism = synthetic construct
SEQUENCE: 17
NYGMN                                                                          5

SEQ ID NO: 18       moltype = AA  length = 17
FEATURE             Location/Qualifiers
REGION              1..17
                    note = Description of Artificial Sequence: Synthetic peptide
source              1..17
                    mol_type = protein
                    organism = synthetic construct
SEQUENCE: 18
MIYYDSSEKH YADSVKG                                                            17

SEQ ID NO: 19       moltype = AA  length = 6
FEATURE             Location/Qualifiers
REGION              1..6
                    note = Description of Artificial Sequence: Synthetic peptide
source              1..6
                    mol_type = protein
                    organism = synthetic construct
SEQUENCE: 19
GTTPDY                                                                         6

SEQ ID NO: 20       moltype = AA  length = 16
FEATURE             Location/Qualifiers
REGION              1..16
                    note = Description of Artificial Sequence: Synthetic peptide
source              1..16
                    mol_type = protein
                    organism = synthetic construct
SEQUENCE: 20
RSSQSLEESD GYTFLH                                                             16

SEQ ID NO: 21       moltype = AA  length = 7
FEATURE             Location/Qualifiers
REGION              1..7
                    note = Description of Artificial Sequence: Synthetic peptide
source              1..7
                    mol_type = protein
                    organism = synthetic construct
SEQUENCE: 21
EVSTRFS                                                                        7

SEQ ID NO: 22       moltype = AA  length = 9
```

-continued

| FEATURE | Location/Qualifiers |
| --- | --- |
| REGION | 1..9 |
| | note = Description of Artificial Sequence: Synthetic peptide |
| source | 1..9 |
| | mol_type = protein |
| | organism = synthetic construct |

SEQUENCE: 22
FQATHDPLT                                                                          9

SEQ ID NO: 23         moltype = AA   length = 5
FEATURE               Location/Qualifiers
REGION                1..5
                      note = Description of Artificial Sequence: Synthetic peptide
source                1..5
                      mol_type = protein
                      organism = synthetic construct
SEQUENCE: 23
NYGMN                                                                              5

SEQ ID NO: 24         moltype = AA   length = 17
FEATURE               Location/Qualifiers
REGION                1..17
                      note = Description of Artificial Sequence: Synthetic peptide
source                1..17
                      mol_type = protein
                      organism = synthetic construct
SEQUENCE: 24
MIYYDSSEKH YADSVKG                                                                17

SEQ ID NO: 25         moltype = AA   length = 6
FEATURE               Location/Qualifiers
REGION                1..6
                      note = Description of Artificial Sequence: Synthetic peptide
source                1..6
                      mol_type = protein
                      organism = synthetic construct
SEQUENCE: 25
GTTPDY                                                                             6

SEQ ID NO: 26         moltype = AA   length = 16
FEATURE               Location/Qualifiers
REGION                1..16
                      note = Description of Artificial Sequence: Synthetic peptide
source                1..16
                      mol_type = protein
                      organism = synthetic construct
SEQUENCE: 26
RSSQSLADSD GDTFLH                                                                 16

SEQ ID NO: 27         moltype = AA   length = 7
FEATURE               Location/Qualifiers
REGION                1..7
                      note = Description of Artificial Sequence: Synthetic peptide
source                1..7
                      mol_type = protein
                      organism = synthetic construct
SEQUENCE: 27
AVSHRFS                                                                            7

SEQ ID NO: 28         moltype = AA   length = 9
FEATURE               Location/Qualifiers
REGION                1..9
                      note = Description of Artificial Sequence: Synthetic peptide
source                1..9
                      mol_type = protein
                      organism = synthetic construct
SEQUENCE: 28
FQATHDPVT                                                                          9

SEQ ID NO: 29         moltype = AA   length = 5
FEATURE               Location/Qualifiers
REGION                1..5
                      note = Description of Artificial Sequence: Synthetic peptide
source                1..5
                      mol_type = protein
                      organism = synthetic construct
SEQUENCE: 29
NYGMN                                                                              5

```
SEQ ID NO: 30            moltype = AA  length = 17
FEATURE                  Location/Qualifiers
REGION                   1..17
                         note = Description of Artificial Sequence: Synthetic peptide
source                   1..17
                         mol_type = protein
                         organism = synthetic construct
SEQUENCE: 30
MIYYDSSEKH YADSVKG                                                      17

SEQ ID NO: 31            moltype = AA  length = 6
FEATURE                  Location/Qualifiers
REGION                   1..6
                         note = Description of Artificial Sequence: Synthetic peptide
source                   1..6
                         mol_type = protein
                         organism = synthetic construct
SEQUENCE: 31
GTTPDY                                                                  6

SEQ ID NO: 32            moltype = AA  length = 16
FEATURE                  Location/Qualifiers
REGION                   1..16
                         note = Description of Artificial Sequence: Synthetic peptide
source                   1..16
                         mol_type = protein
                         organism = synthetic construct
SEQUENCE: 32
RSSQSLEDSD GGTFLE                                                       16

SEQ ID NO: 33            moltype = AA  length = 7
FEATURE                  Location/Qualifiers
REGION                   1..7
                         note = Description of Artificial Sequence: Synthetic peptide
source                   1..7
                         mol_type = protein
                         organism = synthetic construct
SEQUENCE: 33
DVSSRFS                                                                 7

SEQ ID NO: 34            moltype = AA  length = 9
FEATURE                  Location/Qualifiers
REGION                   1..9
                         note = Description of Artificial Sequence: Synthetic peptide
source                   1..9
                         mol_type = protein
                         organism = synthetic construct
SEQUENCE: 34
FQATHDPLS                                                               9

SEQ ID NO: 35            moltype = AA  length = 434
FEATURE                  Location/Qualifiers
source                   1..434
                         mol_type = protein
                         organism = Homo sapiens
SEQUENCE: 35
MGMGRGAGRS ALGFWPTLAF LLCSFPAATS PCKILKCNSE FWSATSGSHA PASDDTPEFC        60
AALRSYALCT RRTARTCRGD LAYHSAVHGI EDLMSQHNCS KDGPTSQPRL RTLPPAGDSQ        120
ERSDSPEICH YEKSFPHKHSA TPNYTHCGLF GDPHLRTFTD RFQTCKVQGA WPLIDNNYLN       180
VQVTNTPVLP GSAATATSKL TIIFKNFQEC VDQKVYQAEM DELPAAFVDG SKNGGDKHGA        240
NSLKITEKVS GQHVEIQAKY IGTTIVVRQV GRYLTFAVRM PEEVVNAVED WDSQGLYLCL        300
RGCPLNQQID FQAFHTNAEG TGARRLAAAS PAPTAPETFP YETAVAKCKE KLPVEDLYYQ        360
ACVFDLLTTG DVNFTLAAYY ALEDVKMLHS NKDKLHLYER TRDLPGRAAA GLPLAPRPLL        420
GALVPLLALL PVFC                                                         434

SEQ ID NO: 36            moltype = AA  length = 200
FEATURE                  Location/Qualifiers
source                   1..200
                         mol_type = protein
                         organism = Homo sapiens
SEQUENCE: 36
MGMGRGAGRS ALGFWPTLAF LLCSFPAATS PCKILKCNSE FWSATSGSHA PASDDTPEFC        60
AALRSYALCT RRTARTCRGD LAYHSAVHGI EDLMSQHNCS KDGPTSQPRL RTLPPAGDSQ        120
ERSDSPEICH YEKSFPHKHSA TPNYTHCGLF GDPHLRTFTD RFQTCKVQGA WPLIDNNYLN       180
VQVTNTPVLP GSAATATSKL                                                   200

SEQ ID NO: 37            moltype = AA  length = 115
FEATURE                  Location/Qualifiers
REGION                   1..115
```

```
                    note = Description of Artificial Sequence: Synthetic
                          polypeptide
source              1..115
                    mol_type = protein
                    organism = synthetic construct
SEQUENCE: 37
EVQLVESGGG VVQPGRSLRL SCAASGFTFS NYGMNWVRQA PGKGLEWVAM IYYDSSEKHY      60
ADSVKGRFTI SRDNSKNTLY LQMNSLRAED TAVYYCARGT TPDYWGQGTM VTVSS          115

SEQ ID NO: 38           moltype = AA   length = 113
FEATURE                 Location/Qualifiers
REGION                  1..113
                        note = Description of Artificial Sequence: Synthetic
                              polypeptide
source                  1..113
                        mol_type = protein
                        organism = synthetic construct
SEQUENCE: 38
DIVMTQTPLS LSVTPGQPAS ISCRSSQSLE YSDGYTFLEW YLQKPGQSPQ LLIYEVSNRF      60
SGVPDRFSGS GSGTDFTLKI SRVEAEDVGV YYCFQATHDP LTFGQGTKLE IKR            113

SEQ ID NO: 39           moltype = AA   length = 115
FEATURE                 Location/Qualifiers
REGION                  1..115
                        note = Description of Artificial Sequence: Synthetic
                              polypeptide
source                  1..115
                        mol_type = protein
                        organism = synthetic construct
SEQUENCE: 39
EVQLVESGGG VVQPGRSLRL SCAASGFTFS NYGMNWIRQA PGKGLEWIGM IYYDSSEKHY      60
ADSVKGRFTI SRDNSKNTLY LQMNSLRAED TAVYYCAKGT TPDYWGQGTM VTVSS          115

SEQ ID NO: 40           moltype = AA   length = 113
FEATURE                 Location/Qualifiers
REGION                  1..113
                        note = Description of Artificial Sequence: Synthetic
                              polypeptide
source                  1..113
                        mol_type = protein
                        organism = synthetic construct
SEQUENCE: 40
DIVMTQTPLS LSVTPGQPAS ISCRSSQSLE YSDGYTFLEW YLQKPGQSPQ LLIYEVSNRF      60
SGVPDRFSGS GSGTDFTLKI SRVEAEDVGV YYCFQATHDP LTFGQGTKLE IKR            113

SEQ ID NO: 41           moltype = AA   length = 115
FEATURE                 Location/Qualifiers
REGION                  1..115
                        note = Description of Artificial Sequence: Synthetic
                              polypeptide
source                  1..115
                        mol_type = protein
                        organism = synthetic construct
SEQUENCE: 41
EVQLVESGGG LVQPGGSLRL SCAASGFTFS NYGMNWVRQA PGKGLEWVSM IYYDSSEKHY      60
ADSVKGRFTI SRDNSKNTLY LQMNSLRAED TAVYYCAKGT TPDYWGQGTM VTVSS          115

SEQ ID NO: 42           moltype = AA   length = 113
FEATURE                 Location/Qualifiers
REGION                  1..113
                        note = Description of Artificial Sequence: Synthetic
                              polypeptide
source                  1..113
                        mol_type = protein
                        organism = synthetic construct
SEQUENCE: 42
DIVMTQTPLS LSVTPGQPAS ISCRSSQSLE YSDGYTFLEW YLQKPGQSPQ LLIYEVSNRF      60
SGVPDRFSGS GSGTDFTLKI SRVEAEDVGV YYCFQATHDP LTFGQGTKLE IKR            113

SEQ ID NO: 43           moltype = AA   length = 115
FEATURE                 Location/Qualifiers
REGION                  1..115
                        note = Description of Artificial Sequence: Synthetic
                              polypeptide
source                  1..115
                        mol_type = protein
                        organism = synthetic construct
SEQUENCE: 43
EVQLVESGGG LVQPGGSLRL SCAASGFTFS NYGMNWIRQA PGKGLEWIGM IYYDSSEKHY      60
```

```
ADSVKGRFTI SRDNSKNTLY LQMNSLRAED TAVYYCAKGT TPDYWGQGTM VTVSS          115

SEQ ID NO: 44           moltype = AA  length = 113
FEATURE                 Location/Qualifiers
REGION                  1..113
                        note = Description of Artificial Sequence: Synthetic
                        polypeptide
source                  1..113
                        mol_type = protein
                        organism = synthetic construct
SEQUENCE: 44
DIVMTQTPLS LSVTPGQPAS ISCRSSQSLE YSDGYTFLEW YLQKPGQSPQ LLIYEVSNRF     60
SGVPDRFSGS GSGTDFTLKI SRVEAEDVGV YYCFQATHDP LTFGQGTKLE IKR           113

SEQ ID NO: 45           moltype = AA  length = 115
FEATURE                 Location/Qualifiers
REGION                  1..115
                        note = Description of Artificial Sequence: Synthetic
                        polypeptide
source                  1..115
                        mol_type = protein
                        organism = synthetic construct
SEQUENCE: 45
EVQLVESGGG VVQPGRSLRL SCAASGFTFS NYGMNWVRQA PGKGLEWVAM IYYDSSEKHY     60
ADSVKGRFTI SRDNSKNTLY LQMNSLRAED TAVYYCARGT TPDYWGQGTM VTVSS          115

SEQ ID NO: 46           moltype = AA  length = 113
FEATURE                 Location/Qualifiers
REGION                  1..113
                        note = Description of Artificial Sequence: Synthetic
                        polypeptide
source                  1..113
                        mol_type = protein
                        organism = synthetic construct
SEQUENCE: 46
DVVMTQSPLS LPVTLGQPAS ISCRSSQSLE YSDGYTFLEW FQQRPGQSPR RLIYEVSNRF     60
SGVPDRFSGS GSGTDFTLKI SRVEAEDVGV YYCFQATHDP LTFGQGTKLE IKR           113

SEQ ID NO: 47           moltype = AA  length = 115
FEATURE                 Location/Qualifiers
REGION                  1..115
                        note = Description of Artificial Sequence: Synthetic
                        polypeptide
source                  1..115
                        mol_type = protein
                        organism = synthetic construct
SEQUENCE: 47
EVQLVESGGG VVQPGRSLRL SCAASGFTFS NYGMNWIRQA PGKGLEWIGM IYYDSSEKHY     60
ADSVKGRFTI SRDNSKNTLY LQMNSLRAED TAVYYCAKGT TPDYWGQGTM VTVSS          115

SEQ ID NO: 48           moltype = AA  length = 113
FEATURE                 Location/Qualifiers
REGION                  1..113
                        note = Description of Artificial Sequence: Synthetic
                        polypeptide
source                  1..113
                        mol_type = protein
                        organism = synthetic construct
SEQUENCE: 48
DVVMTQSPLS LPVTLGQPAS ISCRSSQSLE YSDGYTFLEW FQQRPGQSPR RLIYEVSNRF     60
SGVPDRFSGS GSGTDFTLKI SRVEAEDVGV YYCFQATHDP LTFGQGTKLE IKR           113

SEQ ID NO: 49           moltype = AA  length = 115
FEATURE                 Location/Qualifiers
REGION                  1..115
                        note = Description of Artificial Sequence: Synthetic
                        polypeptide
source                  1..115
                        mol_type = protein
                        organism = synthetic construct
SEQUENCE: 49
EVQLVESGGG LVQPGGSLRL SCAASGFTFS NYGMNWVRQA PGKGLEWVSM IYYDSSEKHY     60
ADSVKGRFTI SRDNSKNTLY LQMNSLRAED TAVYYCAKGT TPDYWGQGTM VTVSS          115

SEQ ID NO: 50           moltype = AA  length = 113
FEATURE                 Location/Qualifiers
REGION                  1..113
                        note = Description of Artificial Sequence: Synthetic
                        polypeptide
```

```
source                  1..113
                        mol_type = protein
                        organism = synthetic construct
SEQUENCE: 50
DVVMTQSPLS LPVTLGQPAS ISCRSSQSLE YSDGYTFLEW FQQRPGQSPR RLIYEVSNRF    60
SGVPDRFSGS GSGTDFTLKI SRVEAEDVGV YYCFQATHDP LTFGQGTKLE IKR          113

SEQ ID NO: 51           moltype = AA   length = 115
FEATURE                 Location/Qualifiers
REGION                  1..115
                        note = Description of Artificial Sequence: Synthetic
                        polypeptide
source                  1..115
                        mol_type = protein
                        organism = synthetic construct
SEQUENCE: 51
EVQLVESGGG LVQPGGSLRL SCAASGFTFS NYGMNWIRQA PGKGLEWIGM IYYDSSEKHY    60
ADSVKGRFTI SRDNSKNTLY LQMNSLRAED TAVYYCAKGT TPDYWGQGTM VTVSS        115

SEQ ID NO: 52           moltype = AA   length = 113
FEATURE                 Location/Qualifiers
REGION                  1..113
                        note = Description of Artificial Sequence: Synthetic
                        polypeptide
source                  1..113
                        mol_type = protein
                        organism = synthetic construct
SEQUENCE: 52
DVVMTQSPLS LPVTLGQPAS ISCRSSQSLE YSDGYTFLEW FQQRPGQSPR RLIYEVSNRF    60
SGVPDRFSGS GSGTDFTLKI SRVEAEDVGV YYCFQATHDP LTFGQGTKLE IKR          113

SEQ ID NO: 53           moltype = AA   length = 115
FEATURE                 Location/Qualifiers
REGION                  1..115
                        note = Description of Artificial Sequence: Synthetic
                        polypeptide
source                  1..115
                        mol_type = protein
                        organism = synthetic construct
SEQUENCE: 53
EVQLVESGGG VVQPGRSLRL SCAASGFTFS NYGMNWVRQA PGKGLEWVAM IYYDSSEKHY    60
ADSVKGRFTI SRDNSKNTLY LQMNSLRAED TAVYYCARGT TPDYWGQGTM VTVSS        115

SEQ ID NO: 54           moltype = AA   length = 113
FEATURE                 Location/Qualifiers
REGION                  1..113
                        note = Description of Artificial Sequence: Synthetic
                        polypeptide
source                  1..113
                        mol_type = protein
                        organism = synthetic construct
SEQUENCE: 54
DVVMTQSPLS LPVTLGQPAS ISCRSSQSLE YSDGYTFLEW YLQKPGQSPQ LLIYEVSNRF    60
SGVPDRFSGS GSGTDFTLKI SRVEAEDVGV YYCFQATHDP LTFGQGTKLE IKR          113

SEQ ID NO: 55           moltype = AA   length = 115
FEATURE                 Location/Qualifiers
REGION                  1..115
                        note = Description of Artificial Sequence: Synthetic
                        polypeptide
source                  1..115
                        mol_type = protein
                        organism = synthetic construct
SEQUENCE: 55
EVQLVESGGG VVQPGRSLRL SCAASGFTFS NYGMNWIRQA PGKGLEWIGM IYYDSSEKHY    60
ADSVKGRFTI SRDNSKNTLY LQMNSLRAED TAVYYCAKGT TPDYWGQGTM VTVSS        115

SEQ ID NO: 56           moltype = AA   length = 113
FEATURE                 Location/Qualifiers
REGION                  1..113
                        note = Description of Artificial Sequence: Synthetic
                        polypeptide
source                  1..113
                        mol_type = protein
                        organism = synthetic construct
SEQUENCE: 56
DVVMTQSPLS LPVTLGQPAS ISCRSSQSLE YSDGYTFLEW YLQKPGQSPQ LLIYEVSNRF    60
SGVPDRFSGS GSGTDFTLKI SRVEAEDVGV YYCFQATHDP LTFGQGTKLE IKR          113
```

```
SEQ ID NO: 57              moltype = AA   length = 115
FEATURE                    Location/Qualifiers
REGION                     1..115
                           note = Description of Artificial Sequence: Synthetic
                           polypeptide
source                     1..115
                           mol_type = protein
                           organism = synthetic construct
SEQUENCE: 57
EVQLVESGGG LVQPGGSLRL SCAASGFTFS NYGMNWVRQA PGKGLEWVSM IYYDSSEKHY   60
ADSVKGRFTI SRDNSKNTLY LQMNSLRAED TAVYYCAKGT TPDYWGQGTM VTVSS       115

SEQ ID NO: 58              moltype = AA   length = 113
FEATURE                    Location/Qualifiers
REGION                     1..113
                           note = Description of Artificial Sequence: Synthetic
                           polypeptide
source                     1..113
                           mol_type = protein
                           organism = synthetic construct
SEQUENCE: 58
DVVMTQSPLS LPVTLGQPAS ISCRSSQSLE YSDGYTFLEW YLQKPGQSPQ LLIYEVSNRF   60
SGVPDRFSGS GSGTDFTLKI SRVEAEDVGV YYCFQATHDP LTFGQGTKLE IKR         113

SEQ ID NO: 59              moltype = AA   length = 115
FEATURE                    Location/Qualifiers
REGION                     1..115
                           note = Description of Artificial Sequence: Synthetic
                           polypeptide
source                     1..115
                           mol_type = protein
                           organism = synthetic construct
SEQUENCE: 59
EVQLVESGGG LVQPGGSLRL SCAASGFTFS NYGMNWIRQA PGKGLEWIGM IYYDSSEKHY   60
ADSVKGRFTI SRDNSKNTLY LQMNSLRAED TAVYYCAKGT TPDYWGQGTM VTVSS       115

SEQ ID NO: 60              moltype = AA   length = 113
FEATURE                    Location/Qualifiers
REGION                     1..113
                           note = Description of Artificial Sequence: Synthetic
                           polypeptide
source                     1..113
                           mol_type = protein
                           organism = synthetic construct
SEQUENCE: 60
DVVMTQSPLS LPVTLGQPAS ISCRSSQSLE YSDGYTFLEW YLQKPGQSPQ LLIYEVSNRF   60
SGVPDRFSGS GSGTDFTLKI SRVEAEDVGV YYCFQATHDP LTFGQGTKLE IKR         113

SEQ ID NO: 61              moltype = AA   length = 115
FEATURE                    Location/Qualifiers
REGION                     1..115
                           note = Description of Artificial Sequence: Synthetic
                           polypeptide
source                     1..115
                           mol_type = protein
                           organism = synthetic construct
SEQUENCE: 61
EVQLVESGGG VVQPGRSLRL SCAASGFTFS NYGMNWIRQA PGKGLEWIGM IYYDSSEKHY   60
ADSVKGRFTI SRDNSKNTLY LQMNSLRAED TAVYYCAKGT TPDYWGQGTM VTVSS       115

SEQ ID NO: 62              moltype = AA   length = 113
FEATURE                    Location/Qualifiers
REGION                     1..113
                           note = Description of Artificial Sequence: Synthetic
                           polypeptide
source                     1..113
                           mol_type = protein
                           organism = synthetic construct
SEQUENCE: 62
DVVLTQSPLS LPVTLGQPAS ISCRSSQSLE YSDGYTFLEW FQQRPGQSPR LLIYEVSNRF   60
SGVPDRFSGS GSGTDFTLKI SRVEAEDVGV YYCFQATHDP LTFGQGTKLE IKR         113

SEQ ID NO: 63              moltype = AA   length = 115
FEATURE                    Location/Qualifiers
REGION                     1..115
                           note = Description of Artificial Sequence: Synthetic
                           polypeptide
source                     1..115
                           mol_type = protein
```

```
                         organism = synthetic construct
SEQUENCE: 63
EVQLVESGGG VVQPGRSLRL SCAASGFTFS NYGMNWIRQA PGKGLEWIGM IYYDSSEKHY    60
ADSVKGRFTI SRDNSKNTLY LQMNSLRAED TAVYYCAKGT TPDYWGQGTM VTVSS        115

SEQ ID NO: 64            moltype = AA   length = 113
FEATURE                  Location/Qualifiers
REGION                   1..113
                         note = Description of Artificial Sequence: Synthetic
                          polypeptide
source                   1..113
                         mol_type = protein
                         organism = synthetic construct
SEQUENCE: 64
DVVLTQSPLS LPVTLGQPAS ISCRSSQSLE YSDGYTFLEW FQQRPGQSPR RLIYEVSNRF    60
SGVPDRFSGS GSGTDFTLKI SRVEAEDVGV YYCFQATHDP LTFGQGTKLE IKR          113

SEQ ID NO: 65            moltype = AA   length = 115
FEATURE                  Location/Qualifiers
REGION                   1..115
                         note = Description of Artificial Sequence: Synthetic
                          polypeptide
source                   1..115
                         mol_type = protein
                         organism = synthetic construct
SEQUENCE: 65
EVQLVESGGG VVQPGRSLRL SCAASGFTFS NYGMNWIRQA PGKGLEWIGM IYYDSSEKHY    60
ADSVKGRFTI SRDNSKNTLY LQMNSLRAED TAVYYCAKGT TPDYWGQGTM VTVSS        115

SEQ ID NO: 66            moltype = AA   length = 113
FEATURE                  Location/Qualifiers
REGION                   1..113
                         note = Description of Artificial Sequence: Synthetic
                          polypeptide
source                   1..113
                         mol_type = protein
                         organism = synthetic construct
SEQUENCE: 66
DVVLTQSPLS LPVTLGQPAS ISCRSSQSLE YSDGYTFLEW FLQKPGQSPQ LLIYEVSNRF    60
SGVPDRFSGS GSGTDFTLKI SRVEAEDVGV YYCFQATHDP LTFGQGTKLE IKR          113

SEQ ID NO: 67            moltype = AA   length = 115
FEATURE                  Location/Qualifiers
REGION                   1..115
                         note = Description of Artificial Sequence: Synthetic
                          polypeptide
source                   1..115
                         mol_type = protein
                         organism = synthetic construct
SEQUENCE: 67
EVQLVESGGG VVQPGRSLRL SCAASGFTFS NYGMNWIRQA PGKGLEWIGM IYYDSSEKHY    60
ADSVKGRFTI SRDNSKNTLY LQMNSLRAED TAVYYCAKGT TPDYWGQGTM VTVSS        115

SEQ ID NO: 68            moltype = AA   length = 113
FEATURE                  Location/Qualifiers
REGION                   1..113
                         note = Description of Artificial Sequence: Synthetic
                          polypeptide
source                   1..113
                         mol_type = protein
                         organism = synthetic construct
SEQUENCE: 68
DVVLTQSPLS LPVTLGQPAS ISCRSSQSLE YSDGYTFLEW YLQKPGQSPQ LLIYEVSNRF    60
SGVPDRFSGS GSGTDFTLKI SRVEAEDVGV YYCFQATHDP LTFGQGTKLE IKR          113

SEQ ID NO: 69            moltype = AA   length = 115
FEATURE                  Location/Qualifiers
REGION                   1..115
                         note = Description of Artificial Sequence: Synthetic
                          polypeptide
source                   1..115
                         mol_type = protein
                         organism = synthetic construct
SEQUENCE: 69
EVQLVESGGG LVQPGGSLRL SCAASGFTFS NYGMNWIRQA PGKGLEWIGM IYYDSSEKHY    60
ADSVKGRFTI SRDNSKNTLY LQMNSLRAED TAVYYCAKGT TPDYWGQGTM VTVSS        115

SEQ ID NO: 70            moltype = AA   length = 113
FEATURE                  Location/Qualifiers
```

```
REGION                      1..113
                            note = Description of Artificial Sequence: Synthetic
                             polypeptide
source                      1..113
                            mol_type = protein
                            organism = synthetic construct
SEQUENCE: 70
DVVLTQSPLS LPVTLGQPAS ISCRSSQSLE YSDGYTFLEW FQQRPGQSPR LLIYEVSNRF   60
SGVPDRFSGS GSGTDFTLKI SRVEAEDVGV YYCFQATHDP LTFGQGTKLE IKR         113

SEQ ID NO: 71               moltype = AA  length = 115
FEATURE                     Location/Qualifiers
REGION                      1..115
                            note = Description of Artificial Sequence: Synthetic
                             polypeptide
source                      1..115
                            mol_type = protein
                            organism = synthetic construct
SEQUENCE: 71
EVQLVESGGG LVQPGGSLRL SCAASGFTFS NYGMNWIRQA PGKGLEWIGM IYYDSSEKHY   60
ADSVKGRFTI SRDNSKNTLY LQMNSLRAED TAVYYCAKGT TPDYWGQGTM VTVSS       115

SEQ ID NO: 72               moltype = AA  length = 113
FEATURE                     Location/Qualifiers
REGION                      1..113
                            note = Description of Artificial Sequence: Synthetic
                             polypeptide
source                      1..113
                            mol_type = protein
                            organism = synthetic construct
SEQUENCE: 72
DVVLTQSPLS LPVTLGQPAS ISCRSSQSLE YSDGYTFLEW FQQRPGQSPR RLIYEVSNRF   60
SGVPDRFSGS GSGTDFTLKI SRVEAEDVGV YYCFQATHDP LTFGQGTKLE IKR         113

SEQ ID NO: 73               moltype = AA  length = 115
FEATURE                     Location/Qualifiers
REGION                      1..115
                            note = Description of Artificial Sequence: Synthetic
                             polypeptide
source                      1..115
                            mol_type = protein
                            organism = synthetic construct
SEQUENCE: 73
EVQLVESGGG LVQPGGSLRL SCAASGFTFS NYGMNWIRQA PGKGLEWIGM IYYDSSEKHY   60
ADSVKGRFTI SRDNSKNTLY LQMNSLRAED TAVYYCAKGT TPDYWGQGTM VTVSS       115

SEQ ID NO: 74               moltype = AA  length = 113
FEATURE                     Location/Qualifiers
REGION                      1..113
                            note = Description of Artificial Sequence: Synthetic
                             polypeptide
source                      1..113
                            mol_type = protein
                            organism = synthetic construct
SEQUENCE: 74
DVVLTQSPLS LPVTLGQPAS ISCRSSQSLE YSDGYTFLEW FLQKPGQSPQ LLIYEVSNRF   60
SGVPDRFSGS GSGTDFTLKI SRVEAEDVGV YYCFQATHDP LTFGQGTKLE IKR         113

SEQ ID NO: 75               moltype = AA  length = 115
FEATURE                     Location/Qualifiers
REGION                      1..115
                            note = Description of Artificial Sequence: Synthetic
                             polypeptide
source                      1..115
                            mol_type = protein
                            organism = synthetic construct
SEQUENCE: 75
EVQLVESGGG LVQPGGSLRL SCAASGFTFS NYGMNWIRQA PGKGLEWIGM IYYDSSEKHY   60
ADSVKGRFTI SRDNSKNTLY LQMNSLRAED TAVYYCAKGT TPDYWGQGTM VTVSS       115

SEQ ID NO: 76               moltype = AA  length = 113
FEATURE                     Location/Qualifiers
REGION                      1..113
                            note = Description of Artificial Sequence: Synthetic
                             polypeptide
source                      1..113
                            mol_type = protein
                            organism = synthetic construct
SEQUENCE: 76
```

```
DVVLTQSPLS LPVTLGQPAS ISCRSSQSLE YSDGYTFLEW YLQKPGQSPQ LLIYEVSNRF    60
SGVPDRFSGS GSGTDFTLKI SRVEAEDVGV YYCFQATHDP LTFGQGTKLE IKR          113

SEQ ID NO: 77            moltype = AA  length = 5
FEATURE                  Location/Qualifiers
REGION                   1..5
                         note = Description of Artificial Sequence: Synthetic peptide
source                   1..5
                         mol_type = protein
                         organism = synthetic construct
SEQUENCE: 77
NYGMN                                                                5

SEQ ID NO: 78            moltype = AA  length = 17
FEATURE                  Location/Qualifiers
REGION                   1..17
                         note = Description of Artificial Sequence: Synthetic peptide
source                   1..17
                         mol_type = protein
                         organism = synthetic construct
SEQUENCE: 78
MIYYDSSEKH YADSVKG                                                  17

SEQ ID NO: 79            moltype = AA  length = 6
FEATURE                  Location/Qualifiers
REGION                   1..6
                         note = Description of Artificial Sequence: Synthetic peptide
source                   1..6
                         mol_type = protein
                         organism = synthetic construct
SEQUENCE: 79
GTTPDY                                                               6

SEQ ID NO: 80            moltype = AA  length = 16
FEATURE                  Location/Qualifiers
REGION                   1..16
                         note = Description of Artificial Sequence: Synthetic peptide
source                   1..16
                         mol_type = protein
                         organism = synthetic construct
SEQUENCE: 80
RSSQSLEYSD GYTFLE                                                   16

SEQ ID NO: 81            moltype = AA  length = 7
FEATURE                  Location/Qualifiers
REGION                   1..7
                         note = Description of Artificial Sequence: Synthetic peptide
source                   1..7
                         mol_type = protein
                         organism = synthetic construct
SEQUENCE: 81
EVSNRFS                                                              7

SEQ ID NO: 82            moltype = AA  length = 9
FEATURE                  Location/Qualifiers
REGION                   1..9
                         note = Description of Artificial Sequence: Synthetic peptide
source                   1..9
                         mol_type = protein
                         organism = synthetic construct
SEQUENCE: 82
FQATHDPLT                                                            9

SEQ ID NO: 83            moltype = AA  length = 5
FEATURE                  Location/Qualifiers
REGION                   1..5
                         note = Description of Artificial Sequence: Synthetic peptide
source                   1..5
                         mol_type = protein
                         organism = synthetic construct
SEQUENCE: 83
NYGMN                                                                5

SEQ ID NO: 84            moltype = AA  length = 17
FEATURE                  Location/Qualifiers
REGION                   1..17
                         note = Description of Artificial Sequence: Synthetic peptide
source                   1..17
                         mol_type = protein
```

```
                              organism = synthetic construct
SEQUENCE: 84
MIYYDSSEKH YADSVKG                                                          17

SEQ ID NO: 85          moltype = AA  length = 6
FEATURE                Location/Qualifiers
REGION                 1..6
                       note = Description of Artificial Sequence: Synthetic peptide
source                 1..6
                       mol_type = protein
                       organism = synthetic construct
SEQUENCE: 85
GTTPDY                                                                       6

SEQ ID NO: 86          moltype = AA  length = 16
FEATURE                Location/Qualifiers
REGION                 1..16
                       note = Description of Artificial Sequence: Synthetic peptide
source                 1..16
                       mol_type = protein
                       organism = synthetic construct
SEQUENCE: 86
RSSQSLEYSD GYTFLE                                                           16

SEQ ID NO: 87          moltype = AA  length = 7
FEATURE                Location/Qualifiers
REGION                 1..7
                       note = Description of Artificial Sequence: Synthetic peptide
source                 1..7
                       mol_type = protein
                       organism = synthetic construct
SEQUENCE: 87
EVSNRFS                                                                      7

SEQ ID NO: 88          moltype = AA  length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 88
FQATHDPLT                                                                    9

SEQ ID NO: 89          moltype = AA  length = 5
FEATURE                Location/Qualifiers
REGION                 1..5
                       note = Description of Artificial Sequence: Synthetic peptide
source                 1..5
                       mol_type = protein
                       organism = synthetic construct
SEQUENCE: 89
NYGMN                                                                        5

SEQ ID NO: 90          moltype = AA  length = 17
FEATURE                Location/Qualifiers
REGION                 1..17
                       note = Description of Artificial Sequence: Synthetic peptide
source                 1..17
                       mol_type = protein
                       organism = synthetic construct
SEQUENCE: 90
MIYYDSSEKH YADSVKG                                                          17

SEQ ID NO: 91          moltype = AA  length = 6
FEATURE                Location/Qualifiers
REGION                 1..6
                       note = Description of Artificial Sequence: Synthetic peptide
source                 1..6
                       mol_type = protein
                       organism = synthetic construct
SEQUENCE: 91
GTTPDY                                                                       6

SEQ ID NO: 92          moltype = AA  length = 16
FEATURE                Location/Qualifiers
REGION                 1..16
                       note = Description of Artificial Sequence: Synthetic peptide
source                 1..16
```

```
SEQUENCE: 92
RSSQSLEYSD GYTFLE                                                16

SEQ ID NO: 93          moltype = AA   length = 7
FEATURE                Location/Qualifiers
REGION                 1..7
                       note = Description of Artificial Sequence: Synthetic peptide
source                 1..7
                       mol_type = protein
                       organism = synthetic construct
SEQUENCE: 93
EVSNRFS                                                          7

SEQ ID NO: 94          moltype = AA   length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 94
FQATHDPLT                                                        9

SEQ ID NO: 95          moltype = AA   length = 5
FEATURE                Location/Qualifiers
REGION                 1..5
                       note = Description of Artificial Sequence: Synthetic peptide
source                 1..5
                       mol_type = protein
                       organism = synthetic construct
SEQUENCE: 95
NYGMN                                                            5

SEQ ID NO: 96          moltype = AA   length = 17
FEATURE                Location/Qualifiers
REGION                 1..17
                       note = Description of Artificial Sequence: Synthetic peptide
source                 1..17
                       mol_type = protein
                       organism = synthetic construct
SEQUENCE: 96
MIYYDSSEKH YADSVKG                                               17

SEQ ID NO: 97          moltype = AA   length = 6
FEATURE                Location/Qualifiers
REGION                 1..6
                       note = Description of Artificial Sequence: Synthetic peptide
source                 1..6
                       mol_type = protein
                       organism = synthetic construct
SEQUENCE: 97
GTTPDY                                                           6

SEQ ID NO: 98          moltype = AA   length = 16
FEATURE                Location/Qualifiers
REGION                 1..16
                       note = Description of Artificial Sequence: Synthetic peptide
source                 1..16
                       mol_type = protein
                       organism = synthetic construct
SEQUENCE: 98
RSSQSLEYSD GYTFLE                                                16

SEQ ID NO: 99          moltype = AA   length = 7
FEATURE                Location/Qualifiers
REGION                 1..7
                       note = Description of Artificial Sequence: Synthetic peptide
source                 1..7
                       mol_type = protein
                       organism = synthetic construct
SEQUENCE: 99
EVSNRFS                                                          7

SEQ ID NO: 100         moltype = AA   length = 9
FEATURE                Location/Qualifiers
REGION                 1..9
                       note = Description of Artificial Sequence: Synthetic peptide
```

```
                    -continued source              1..9
                    mol_type = protein
                    organism = synthetic construct
SEQUENCE: 100
FQATHDPLT                                                              9

SEQ ID NO: 101      moltype = AA   length = 5
FEATURE             Location/Qualifiers
REGION              1..5
                    note = Description of Artificial Sequence: Synthetic peptide
source              1..5
                    mol_type = protein
                    organism = synthetic construct
SEQUENCE: 101
NYGMN                                                                  5

SEQ ID NO: 102      moltype = AA   length = 17
FEATURE             Location/Qualifiers
REGION              1..17
                    note = Description of Artificial Sequence: Synthetic peptide
source              1..17
                    mol_type = protein
                    organism = synthetic construct
SEQUENCE: 102
MIYYDSSEKH YADSVKG                                                     17

SEQ ID NO: 103      moltype = AA   length = 6
FEATURE             Location/Qualifiers
REGION              1..6
                    note = Description of Artificial Sequence: Synthetic peptide
source              1..6
                    mol_type = protein
                    organism = synthetic construct
SEQUENCE: 103
GTTPDY                                                                 6

SEQ ID NO: 104      moltype = AA   length = 16
FEATURE             Location/Qualifiers
REGION              1..16
                    note = Description of Artificial Sequence: Synthetic peptide
source              1..16
                    mol_type = protein
                    organism = synthetic construct
SEQUENCE: 104
RSSQSLEYSD GYTFLE                                                      16

SEQ ID NO: 105      moltype = AA   length = 7
FEATURE             Location/Qualifiers
REGION              1..7
                    note = Description of Artificial Sequence: Synthetic peptide
source              1..7
                    mol_type = protein
                    organism = synthetic construct
SEQUENCE: 105
EVSNRFS                                                                7

SEQ ID NO: 106      moltype = AA   length = 9
FEATURE             Location/Qualifiers
REGION              1..9
                    note = Description of Artificial Sequence: Synthetic peptide
source              1..9
                    mol_type = protein
                    organism = synthetic construct
SEQUENCE: 106
FQATHDPLT                                                              9

SEQ ID NO: 107      moltype = AA   length = 5
FEATURE             Location/Qualifiers
REGION              1..5
                    note = Description of Artificial Sequence: Synthetic peptide
source              1..5
                    mol_type = protein
                    organism = synthetic construct
SEQUENCE: 107
NYGMN                                                                  5

SEQ ID NO: 108      moltype = AA   length = 17
FEATURE             Location/Qualifiers
REGION              1..17
```

```
                      note = Description of Artificial Sequence: Synthetic peptide
source                1..17
                      mol_type = protein
                      organism = synthetic construct
SEQUENCE: 108
MIYYDSSEKH YADSVKG                                                          17

SEQ ID NO: 109        moltype = AA   length = 6
FEATURE               Location/Qualifiers
REGION                1..6
                      note = Description of Artificial Sequence: Synthetic peptide
source                1..6
                      mol_type = protein
                      organism = synthetic construct
SEQUENCE: 109
GTTPDY                                                                       6

SEQ ID NO: 110        moltype = AA   length = 16
FEATURE               Location/Qualifiers
REGION                1..16
                      note = Description of Artificial Sequence: Synthetic peptide
source                1..16
                      mol_type = protein
                      organism = synthetic construct
SEQUENCE: 110
RSSQSLEYSD GYTFLE                                                           16

SEQ ID NO: 111        moltype = AA   length = 7
FEATURE               Location/Qualifiers
REGION                1..7
                      note = Description of Artificial Sequence: Synthetic peptide
source                1..7
                      mol_type = protein
                      organism = synthetic construct
SEQUENCE: 111
EVSNRFS                                                                      7

SEQ ID NO: 112        moltype = AA   length = 9
FEATURE               Location/Qualifiers
REGION                1..9
                      note = Description of Artificial Sequence: Synthetic peptide
source                1..9
                      mol_type = protein
                      organism = synthetic construct
SEQUENCE: 112
FQATHDPLT                                                                    9

SEQ ID NO: 113        moltype = AA   length = 5
FEATURE               Location/Qualifiers
REGION                1..5
                      note = Description of Artificial Sequence: Synthetic peptide
source                1..5
                      mol_type = protein
                      organism = synthetic construct
SEQUENCE: 113
NYGMN                                                                        5

SEQ ID NO: 114        moltype = AA   length = 17
FEATURE               Location/Qualifiers
REGION                1..17
                      note = Description of Artificial Sequence: Synthetic peptide
source                1..17
                      mol_type = protein
                      organism = synthetic construct
SEQUENCE: 114
MIYYDSSEKH YADSVKG                                                          17

SEQ ID NO: 115        moltype = AA   length = 6
FEATURE               Location/Qualifiers
REGION                1..6
                      note = Description of Artificial Sequence: Synthetic peptide
source                1..6
                      mol_type = protein
                      organism = synthetic construct
SEQUENCE: 115
GTTPDY                                                                       6

SEQ ID NO: 116        moltype = AA   length = 16
FEATURE               Location/Qualifiers
```

```
REGION                  1..16
                        note = Description of Artificial Sequence: Synthetic peptide
source                  1..16
                        mol_type = protein
                        organism = synthetic construct
SEQUENCE: 116
RSSQSLEYSD GYTFLE                                                           16

SEQ ID NO: 117          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 117
EVSNRFS                                                                      7

SEQ ID NO: 118          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 118
FQATHDPLT                                                                    9

SEQ ID NO: 119          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 119
NYGMN                                                                        5

SEQ ID NO: 120          moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 120
MIYYDSSEKH YADSVKG                                                          17

SEQ ID NO: 121          moltype = AA  length = 6
FEATURE                 Location/Qualifiers
REGION                  1..6
                        note = Description of Artificial Sequence: Synthetic peptide
source                  1..6
                        mol_type = protein
                        organism = synthetic construct
SEQUENCE: 121
GTTPDY                                                                       6

SEQ ID NO: 122          moltype = AA  length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 122
RSSQSLEYSD GYTFLE                                                           16

SEQ ID NO: 123          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 123
EVSNRFS                                                                      7

SEQ ID NO: 124          moltype = AA  length = 9
```

|   |   |   |
|---|---|---|
| FEATURE | Location/Qualifiers | |
| REGION | 1..9 | |
|  | note = Description of Artificial Sequence: Synthetic peptide | |
| source | 1..9 | |
|  | mol_type = protein | |
|  | organism = synthetic construct | |
| SEQUENCE: 124 | | |
| FQATHDPLT | | 9 |
| | | |
| SEQ ID NO: 125 | moltype = AA   length = 5 | |
| FEATURE | Location/Qualifiers | |
| REGION | 1..5 | |
|  | note = Description of Artificial Sequence: Synthetic peptide | |
| source | 1..5 | |
|  | mol_type = protein | |
|  | organism = synthetic construct | |
| SEQUENCE: 125 | | |
| NYGMN | | 5 |
| | | |
| SEQ ID NO: 126 | moltype = AA   length = 17 | |
| FEATURE | Location/Qualifiers | |
| REGION | 1..17 | |
|  | note = Description of Artificial Sequence: Synthetic peptide | |
| source | 1..17 | |
|  | mol_type = protein | |
|  | organism = synthetic construct | |
| SEQUENCE: 126 | | |
| MIYYDSSEKH YADSVKG | | 17 |
| | | |
| SEQ ID NO: 127 | moltype = AA   length = 6 | |
| FEATURE | Location/Qualifiers | |
| REGION | 1..6 | |
|  | note = Description of Artificial Sequence: Synthetic peptide | |
| source | 1..6 | |
|  | mol_type = protein | |
|  | organism = synthetic construct | |
| SEQUENCE: 127 | | |
| GTTPDY | | 6 |
| | | |
| SEQ ID NO: 128 | moltype = AA   length = 16 | |
| FEATURE | Location/Qualifiers | |
| REGION | 1..16 | |
|  | note = Description of Artificial Sequence: Synthetic peptide | |
| source | 1..16 | |
|  | mol_type = protein | |
|  | organism = synthetic construct | |
| SEQUENCE: 128 | | |
| RSSQSLEYSD GYTFLE | | 16 |
| | | |
| SEQ ID NO: 129 | moltype = AA   length = 7 | |
| FEATURE | Location/Qualifiers | |
| REGION | 1..7 | |
|  | note = Description of Artificial Sequence: Synthetic peptide | |
| source | 1..7 | |
|  | mol_type = protein | |
|  | organism = synthetic construct | |
| SEQUENCE: 129 | | |
| EVSNRFS | | 7 |
| | | |
| SEQ ID NO: 130 | moltype = AA   length = 9 | |
| FEATURE | Location/Qualifiers | |
| REGION | 1..9 | |
|  | note = Description of Artificial Sequence: Synthetic peptide | |
| source | 1..9 | |
|  | mol_type = protein | |
|  | organism = synthetic construct | |
| SEQUENCE: 130 | | |
| FQATHDPLT | | 9 |
| | | |
| SEQ ID NO: 131 | moltype = AA   length = 5 | |
| FEATURE | Location/Qualifiers | |
| REGION | 1..5 | |
|  | note = Description of Artificial Sequence: Synthetic peptide | |
| source | 1..5 | |
|  | mol_type = protein | |
|  | organism = synthetic construct | |
| SEQUENCE: 131 | | |
| NYGMN | | 5 |

-continued

| | | |
|---|---|---|
| SEQ ID NO: 132<br>FEATURE<br>REGION<br><br>source | moltype = AA   length = 17<br>Location/Qualifiers<br>1..17<br>note = Description of Artificial Sequence: Synthetic peptide<br>1..17<br>mol_type = protein<br>organism = synthetic construct | |
| SEQUENCE: 132<br>MIYYDSSEKH YADSVKG | | 17 |
| SEQ ID NO: 133<br>FEATURE<br>REGION<br><br>source | moltype = AA   length = 6<br>Location/Qualifiers<br>1..6<br>note = Description of Artificial Sequence: Synthetic peptide<br>1..6<br>mol_type = protein<br>organism = synthetic construct | |
| SEQUENCE: 133<br>GTTPDY | | 6 |
| SEQ ID NO: 134<br>FEATURE<br>REGION<br><br>source | moltype = AA   length = 16<br>Location/Qualifiers<br>1..16<br>note = Description of Artificial Sequence: Synthetic peptide<br>1..16<br>mol_type = protein<br>organism = synthetic construct | |
| SEQUENCE: 134<br>RSSQSLEYSD GYTFLE | | 16 |
| SEQ ID NO: 135<br>FEATURE<br>REGION<br><br>source | moltype = AA   length = 7<br>Location/Qualifiers<br>1..7<br>note = Description of Artificial Sequence: Synthetic peptide<br>1..7<br>mol_type = protein<br>organism = synthetic construct | |
| SEQUENCE: 135<br>EVSNRFS | | 7 |
| SEQ ID NO: 136<br>FEATURE<br>REGION<br><br>source | moltype = AA   length = 9<br>Location/Qualifiers<br>1..9<br>note = Description of Artificial Sequence: Synthetic peptide<br>1..9<br>mol_type = protein<br>organism = synthetic construct | |
| SEQUENCE: 136<br>FQATHDPLT | | 9 |
| SEQ ID NO: 137<br>FEATURE<br>REGION<br><br>source | moltype = AA   length = 5<br>Location/Qualifiers<br>1..5<br>note = Description of Artificial Sequence: Synthetic peptide<br>1..5<br>mol_type = protein<br>organism = synthetic construct | |
| SEQUENCE: 137<br>NYGMN | | 5 |
| SEQ ID NO: 138<br>FEATURE<br>REGION<br><br>source | moltype = AA   length = 17<br>Location/Qualifiers<br>1..17<br>note = Description of Artificial Sequence: Synthetic peptide<br>1..17<br>mol_type = protein<br>organism = synthetic construct | |
| SEQUENCE: 138<br>MIYYDSSEKH YADSVKG | | 17 |
| SEQ ID NO: 139<br>FEATURE<br>REGION<br><br>source | moltype = AA   length = 6<br>Location/Qualifiers<br>1..6<br>note = Description of Artificial Sequence: Synthetic peptide<br>1..6<br>mol_type = protein<br>organism = synthetic construct | |
| SEQUENCE: 139<br>GTTPDY | | 6 |

```
SEQ ID NO: 140          moltype = AA  length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 140
RSSQSLEYSD GYTFLE                                                           16

SEQ ID NO: 141          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 141
EVSNRFS                                                                     7

SEQ ID NO: 142          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 142
FQATHDPLT                                                                   9

SEQ ID NO: 143          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 143
NYGMN                                                                       5

SEQ ID NO: 144          moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 144
MIYYDSSEKH YADSVKG                                                          17

SEQ ID NO: 145          moltype = AA  length = 6
FEATURE                 Location/Qualifiers
REGION                  1..6
                        note = Description of Artificial Sequence: Synthetic peptide
source                  1..6
                        mol_type = protein
                        organism = synthetic construct
SEQUENCE: 145
GTTPDY                                                                      6

SEQ ID NO: 146          moltype = AA  length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 146
RSSQSLEYSD GYTFLE                                                           16

SEQ ID NO: 147          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 147
```

EVSNRFS                                                                                      7

SEQ ID NO: 148          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 148
FQATHDPLT                                                                                    9

SEQ ID NO: 149          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 149
NYGMN                                                                                        5

SEQ ID NO: 150          moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 150
MIYYDSSEKH YADSVKG                                                                           17

SEQ ID NO: 151          moltype = AA  length = 6
FEATURE                 Location/Qualifiers
REGION                  1..6
                        note = Description of Artificial Sequence: Synthetic peptide
source                  1..6
                        mol_type = protein
                        organism = synthetic construct
SEQUENCE: 151
GTTPDY                                                                                       6

SEQ ID NO: 152          moltype = AA  length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 152
RSSQSLEYSD GYTFLE                                                                           16

SEQ ID NO: 153          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 153
EVSNRFS                                                                                      7

SEQ ID NO: 154          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 154
FQATHDPLT                                                                                    9

SEQ ID NO: 155          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct

```
SEQUENCE: 155
NYGMN                                                                    5

SEQ ID NO: 156          moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 156
MIYYDSSEKH YADSVKG                                                       17

SEQ ID NO: 157          moltype = AA  length = 6
FEATURE                 Location/Qualifiers
REGION                  1..6
                        note = Description of Artificial Sequence: Synthetic peptide
source                  1..6
                        mol_type = protein
                        organism = synthetic construct
SEQUENCE: 157
GTTPDY                                                                   6

SEQ ID NO: 158          moltype = AA  length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 158
RSSQSLEYSD GYTFLE                                                        16

SEQ ID NO: 159          moltype = AA  length = 6
FEATURE                 Location/Qualifiers
REGION                  1..6
                        note = Description of Artificial Sequence: Synthetic peptide
source                  1..6
                        mol_type = protein
                        organism = synthetic construct
SEQUENCE: 159
EVSNRF                                                                   6

SEQ ID NO: 160          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 160
FQATHDPLT                                                                9

SEQ ID NO: 161          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 161
NYGMN                                                                    5

SEQ ID NO: 162          moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 162
MIYYDSSEKH YADSVKG                                                       17

SEQ ID NO: 163          moltype = AA  length = 6
FEATURE                 Location/Qualifiers
REGION                  1..6
                        note = Description of Artificial Sequence: Synthetic peptide
source                  1..6
                        mol_type = protein
```

```
                        organism = synthetic construct
SEQUENCE: 163
GTTPDY                                                                          6

SEQ ID NO: 164          moltype = AA   length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 164
RSSQSLEYSD GYTFLE                                                               16

SEQ ID NO: 165          moltype = AA   length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 165
EVSNRFS                                                                         7

SEQ ID NO: 166          moltype = AA   length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 166
FQATHDPLT                                                                       9

SEQ ID NO: 167          moltype = AA   length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 167
NYGMN                                                                           5

SEQ ID NO: 168          moltype = AA   length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 168
MIYYDSSEKH YADSVKG                                                              17

SEQ ID NO: 169          moltype = AA   length = 6
FEATURE                 Location/Qualifiers
REGION                  1..6
                        note = Description of Artificial Sequence: Synthetic peptide
source                  1..6
                        mol_type = protein
                        organism = synthetic construct
SEQUENCE: 169
GTTPDY                                                                          6

SEQ ID NO: 170          moltype = AA   length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 170
RSSQSLEYSD GYTFLE                                                               16

SEQ ID NO: 171          moltype = AA   length = 7
FEATURE                 Location/Qualifiers
REGION                  1..7
                        note = Description of Artificial Sequence: Synthetic peptide
source                  1..7
```

```
                        mol_type = protein
                        organism = synthetic construct
SEQUENCE: 171
EVSNRFS                                                                  7

SEQ ID NO: 172          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 172
FQATHDPLT                                                                9

SEQ ID NO: 173          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 173
NYGMN                                                                    5

SEQ ID NO: 174          moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 174
MIYYDSSEKH YADSVKG                                                       17

SEQ ID NO: 175          moltype = AA  length = 6
FEATURE                 Location/Qualifiers
REGION                  1..6
                        note = Description of Artificial Sequence: Synthetic peptide
source                  1..6
                        mol_type = protein
                        organism = synthetic construct
SEQUENCE: 175
GTTPDY                                                                   6

SEQ ID NO: 176          moltype = AA  length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 176
RSSQSLEYSD GYTFLE                                                        16

SEQ ID NO: 177          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 177
EVSNRFS                                                                  7

SEQ ID NO: 178          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 178
FQATHDPLT                                                                9

SEQ ID NO: 179          moltype = AA  length = 5
FEATURE                 Location/Qualifiers
REGION                  1..5
                        note = Description of Artificial Sequence: Synthetic peptide
```

```
                        source                    1..5
                                                  mol_type = protein
                                                  organism = synthetic construct
       SEQUENCE: 179
       NYGMN                                                                                  5

SEQ ID NO: 180            moltype = AA   length = 17
       FEATURE                   Location/Qualifiers
       REGION                    1..17
                                 note = Description of Artificial Sequence: Synthetic peptide
       source                    1..17
                                 mol_type = protein
                                 organism = synthetic construct
       SEQUENCE: 180
       MIYYDSSEKH YADSVKG                                                                    17

SEQ ID NO: 181            moltype = AA   length = 6
       FEATURE                   Location/Qualifiers
       REGION                    1..6
                                 note = Description of Artificial Sequence: Synthetic peptide
       source                    1..6
                                 mol_type = protein
                                 organism = synthetic construct
       SEQUENCE: 181
       GTTPDY                                                                                 6

SEQ ID NO: 182            moltype = AA   length = 16
       FEATURE                   Location/Qualifiers
       REGION                    1..16
                                 note = Description of Artificial Sequence: Synthetic peptide
       source                    1..16
                                 mol_type = protein
                                 organism = synthetic construct
       SEQUENCE: 182
       RSSQSLEYSD GYTFLE                                                                     16

SEQ ID NO: 183            moltype = AA   length = 7
       FEATURE                   Location/Qualifiers
       REGION                    1..7
                                 note = Description of Artificial Sequence: Synthetic peptide
       source                    1..7
                                 mol_type = protein
                                 organism = synthetic construct
       SEQUENCE: 183
       EVSNRFS                                                                                7

SEQ ID NO: 184            moltype = AA   length = 9
       FEATURE                   Location/Qualifiers
       REGION                    1..9
                                 note = Description of Artificial Sequence: Synthetic peptide
       source                    1..9
                                 mol_type = protein
                                 organism = synthetic construct
       SEQUENCE: 184
       FQATHDPLT                                                                              9

SEQ ID NO: 185            moltype = AA   length = 5
       FEATURE                   Location/Qualifiers
       REGION                    1..5
                                 note = Description of Artificial Sequence: Synthetic peptide
       source                    1..5
                                 mol_type = protein
                                 organism = synthetic construct
       SEQUENCE: 185
       NYGMN                                                                                  5

SEQ ID NO: 186            moltype = AA   length = 17
       FEATURE                   Location/Qualifiers
       REGION                    1..17
                                 note = Description of Artificial Sequence: Synthetic peptide
       source                    1..17
                                 mol_type = protein
                                 organism = synthetic construct
       SEQUENCE: 186
       MIYYDSSEKH YADSVKG                                                                    17

SEQ ID NO: 187            moltype = AA   length = 6
       FEATURE                   Location/Qualifiers
       REGION                    1..6
```

```
                        note = Description of Artificial Sequence: Synthetic peptide
source                  1..6
                        mol_type = protein
                        organism = synthetic construct
SEQUENCE: 187
GTTPDY                                                                         6

SEQ ID NO: 188          moltype = AA   length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 188
RSSQSLEYSD GYTFLE                                                             16

SEQ ID NO: 189          moltype = AA   length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 189
EVSNRFS                                                                        7

SEQ ID NO: 190          moltype = AA   length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 190
FQATHDPLT                                                                      9

SEQ ID NO: 191          moltype = AA   length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 191
NYGMN                                                                          5

SEQ ID NO: 192          moltype = AA   length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 192
MIYYDSSEKH YADSVKG                                                            17

SEQ ID NO: 193          moltype = AA   length = 6
FEATURE                 Location/Qualifiers
REGION                  1..6
                        note = Description of Artificial Sequence: Synthetic peptide
source                  1..6
                        mol_type = protein
                        organism = synthetic construct
SEQUENCE: 193
GTTPDY                                                                         6

SEQ ID NO: 194          moltype = AA   length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 194
RSSQSLEYSD GYTFLE                                                             16

SEQ ID NO: 195          moltype = AA   length = 7
FEATURE                 Location/Qualifiers
```

```
                        -continued
REGION              1..7
                    note = Description of Artificial Sequence: Synthetic peptide
source              1..7
                    mol_type = protein
                    organism = synthetic construct
SEQUENCE: 195
EVSNRFS                                                                        7

SEQ ID NO: 196      moltype = AA  length = 9
FEATURE             Location/Qualifiers
REGION              1..9
                    note = Description of Artificial Sequence: Synthetic peptide
source              1..9
                    mol_type = protein
                    organism = synthetic construct
SEQUENCE: 196
FQATHDPLT                                                                      9

SEQ ID NO: 197      moltype = AA  length = 6
FEATURE             Location/Qualifiers
REGION              1..6
                    note = Description of Artificial Sequence: Synthetic 6xHis
                     tag
source              1..6
                    mol_type = protein
                    organism = synthetic construct
SEQUENCE: 197
HHHHHH                                                                         6

SEQ ID NO: 198      moltype = AA  length = 5
FEATURE             Location/Qualifiers
REGION              1..5
                    note = Description of Artificial Sequence: Synthetic peptide
source              1..5
                    mol_type = protein
                    organism = synthetic construct
SEQUENCE: 198
DDDDK                                                                          5

SEQ ID NO: 199      moltype = AA  length = 6
FEATURE             Location/Qualifiers
REGION              1..6
                    note = Description of Artificial Sequence: Synthetic peptide
source              1..6
                    mol_type = protein
                    organism = synthetic construct
SEQUENCE: 199
ADDDDK                                                                         6
```

We claim:

1. A composition comprising an anti-Repulsive Guidance Molecule c (RGMc) antibody that comprises:
   (i) a variable heavy chain region comprising a complementary determining region (CDR)1 with the amino acid sequence set forth in SEQ ID NO: 17, a CDR2 with the amino acid sequence set forth in SEQ ID NO: 18, a CDR3 with the amino acid sequence set forth in SEQ ID NO: 19, and a variable light chain region comprising a CDR1 with the amino acid sequence set forth in SEQ ID NO: 20, a CDR2 with the amino acid sequence set forth in SEQ ID NO: 21, and a CDR3 with the amino acid sequence set forth in SEQ ID NO:22; and
   (ii) a human IgG1 constant domain.

2. The composition of claim 1, wherein the antibody is affinity matured.

3. The composition of claim 1, wherein the variable light chain region has the amino acid sequence set forth in SEQ ID NO: 6.

4. The composition of claim 1, wherein the variable heavy chain region has the amino acid sequence set forth in SEQ ID NO: 5 with up to one amino acid difference in a framework region.

5. The composition of claim 3, wherein the variable heavy chain region has the amino acid sequence set forth in SEQ ID NO: 5 with up to one amino acid difference in a framework region.

6. The composition of claim 1, further comprising a pharmaceutically acceptable carrier.

7. The composition of claim 1, wherein the composition is in a lyophilized form.

8. The composition of claim 1, wherein the composition is in a solution form.

9. The composition of claim 5, wherein the composition is in a lyophilized form.

10. The composition of claim 5, wherein the composition is in a solution form.

11. A composition comprising an anti-Repulsive Guidance Molecule c (RGMc) antibody that comprises:
   a variable heavy chain region linked to a heavy chain constant domain, the heavy chain variable region comprises a complementary determining region (CDR)1 comprising the amino acid sequence set forth in SEQ ID NO: 17, a CDR2 comprising the amino acid sequence set forth in SEQ ID NO: 18, a CDR3 comprising the amino acid sequence set forth in SEQ ID NO: 19, and
   a variable light chain region linked to a light chain constant domain, the light chain variable region comprises a CDR1 comprising the amino acid sequence set forth in SEQ ID NO: 20, a CDR2 comprising the amino acid sequence set forth in SEQ ID NO: 21, and a CDR3 comprising the amino acid sequence set forth in SEQ ID NO:22.

12. The composition of claim 11, wherein the antibody is affinity matured.

13. The composition of claim 11, wherein the variable light chain region has the amino acid sequence set forth in SEQ ID NO: 6.

14. The composition of claim 11, wherein the variable heavy chain region has the amino acid sequence set forth in SEQ ID NO: 5 with up to one amino acid difference in a framework region.

15. The composition of claim 13, wherein the variable heavy chain region has the amino acid sequence set forth in SEQ ID NO: 5 with up to one amino acid difference in a framework region.

16. The composition of claim 11, further comprising a pharmaceutically acceptable carrier.

17. The composition of claim 11, wherein the composition is in a lyophilized form.

18. The composition of claim 11, wherein the composition is in a solution form.

19. The composition of claim 15, wherein the composition is in a lyophilized form.

20. The composition of claim 15, wherein the composition is in a solution form.

\* \* \* \* \*